(12) United States Patent
Melander et al.

(10) Patent No.: US 8,367,713 B2
(45) Date of Patent: *Feb. 5, 2013

(54) INHIBITION AND DISPERSION OF BACTERIAL BIOFILMS WITH IMIDAZOLE-TRIAZOLE DERIVATIVES

(75) Inventors: Christian Melander, Raleigh, NC (US); Steven A. Rogers, Raleigh, NC (US); Robert W. Huigens, III, Apex, NC (US); Catherine S. Reed, Raleigh, NC (US)

(73) Assignee: North Carolina State University, Raleigh, NC (US)

(*) Notice: Subject to any disclaimer, the term of this patent is extended or adjusted under 35 U.S.C. 154(b) by 0 days.

This patent is subject to a terminal disclaimer.

(21) Appl. No.: 13/011,532

(22) Filed: Jan. 21, 2011

(65) Prior Publication Data

US 2011/0117158 A1    May 19, 2011

Related U.S. Application Data

(63) Continuation of application No. 12/426,742, filed on Apr. 20, 2009, now Pat. No. 7,897,631.

(60) Provisional application No. 61/046,674, filed on Apr. 21, 2008, provisional application No. 61/092,145, filed on Aug. 27, 2008.

(51) Int. Cl.
C07D 403/06 (2006.01)
A61K 31/4192 (2006.01)

(52) U.S. Cl. ........................ 514/392; 548/255
(58) Field of Classification Search ............. 514/392; 548/255
See application file for complete search history.

(56) References Cited

U.S. PATENT DOCUMENTS

| | | | |
|---|---|---|---|
| 3,575,929 A | 4/1971 | Jones | |
| 4,514,382 A | 4/1985 | Gaffar et al. | |
| 5,358,960 A | 10/1994 | Ulrich et al. | |
| 5,670,055 A | 9/1997 | Yu et al. | |
| 5,814,668 A | 9/1998 | Whittemore et al. | |
| 5,834,411 A | 11/1998 | Bolkan et al. | |
| 6,143,774 A | 11/2000 | Heckmann et al. | |
| 7,087,661 B1 | 8/2006 | Alberte et al. | |
| 7,132,567 B2 | 11/2006 | Alberte et al. | |
| 7,160,879 B2 | 1/2007 | DeSimone et al. | |
| 7,514,458 B2 | 4/2009 | Cogan et al. | |
| 7,897,631 B2 * | 3/2011 | Melander et al. | 514/392 |
| 2003/0171421 A1 | 9/2003 | Davies et al. | |
| 2003/0229000 A1 | 12/2003 | Merritt et al. | |
| 2004/0024037 A1 | 2/2004 | Ryu et al. | |
| 2004/0249441 A1 | 12/2004 | Miller et al. | |
| 2005/0161859 A1 | 7/2005 | Miller et al. | |
| 2006/0018945 A1 | 1/2006 | Britigan et al. | |
| 2006/0228384 A1 | 10/2006 | Eldridge | |
| 2006/0276468 A1 | 12/2006 | Blow | |
| 2007/0231291 A1 | 10/2007 | Huang et al. | |
| 2008/0181923 A1 | 7/2008 | Melander et al. | |
| 2009/0143230 A1 | 6/2009 | Melander et al. | |
| 2009/0270475 A1 | 10/2009 | Melander et al. | |

FOREIGN PATENT DOCUMENTS

WO    WO 2005/012263 A1    2/2005

OTHER PUBLICATIONS

Musk et al. Curr. Med. Chem. 2006, 13, 2163.*
Wang B et al. Drug Delivery: Principles and Applications, 2005 John Wiley & Sons, Inc. Publication, Section 8.3, pp. 136-137.
Rautio J et al. Prodrugs: design and clinical applications. Nature Reviews Drug Discovery. Mar. 2008; 7: 255-270.
Smith DA. Do prodrugs deliver? Current Opinion in Drug Discovery & Development. 2007; 10(5): 550-559.
Testa B. Current Opinion in Chemical Biology. 2009; 13: 338-344.
International Search Report and Written Opinion for PCT/US08/01045, dated May 9, 2008.
Foley L and Büchi G. Biomimetic synthesis of dibromophakellin. J. Am. Chem. Soc. 1982; 104: 1776-1777.
Yamada A et al. Development of chemical substances regulating biofilm formation. Bull. Chem. Soc. Jpn. 1997; 70: 3061-3069.
Mourabit AA and Potter P. Sponge's molecular diversity through the ambivalent reactivity of 2-aminoimidazole: a universal chemical pathway to the oroidin-based pyrrole-imidazole alkaloids and their palau'amine congeners. Eur. J. Org. Chem. 2001: 237-243.
Hoffmann H and Lindel T. Synthesis of the pyrrole-imidazolealkaloids. Synthesis. 2003; 12: 1753-1783.
Kelly SR et al. Effects of Caribbean sponge extracts on bacterial attachment. Aquatic Microbial Ecology. Mar. 13, 2003; 31: 175-182.
Kelly SR et al. Effects of Caribbean sponge secondary metabolites on bacterial colonization. Aquatic Microbial Ecology. Sep. 6, 2005; 40: 191-203.
Musk Jr. D.J. and Hergenrother P.J. Chemical countermeasures for the control of bacterial biofilms: effective compounds and promising targets. Current Medicinal Chemistry 2006; 13: 2163-2177.
Huigens RW 3rd et al. Inhibition of *Pseudomonas aeruginosa* biofilm formation with bromoageliferin analogues. J. Am. Chem. Soc. 2007; 129: 6966-6967.

(Continued)

*Primary Examiner* — Joseph Kosack
*Assistant Examiner* — Matthew Coughlin
(74) *Attorney, Agent, or Firm* — Myers Bigel Sibley & Sajovec, P.A.

(57) ABSTRACT

Disclosure is provided for imidazole-triazole derivative compounds such as those given in Formulas (I)-(VI) that prevent, remove and/or inhibit the formation of biofilms, compositions comprising these compounds, devices comprising these compounds, and methods of using the same.

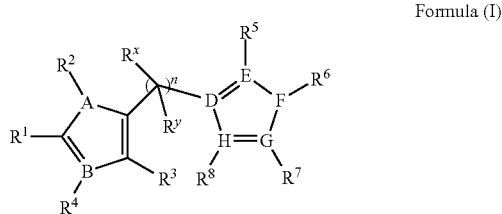

Formula (I)

27 Claims, 17 Drawing Sheets

OTHER PUBLICATIONS

Shore D. College Profile: Dr. John Cavanagh shows that in scientific collaboration—as in a community of molecules—the product is more powerful than the sum of its parts. Perspectives Online. North Carolina State University. Summer 2007: 4 pp.

Fishing for seafood safety. Scope. North Carolina State University College of Physical and Mathematical Sciences. Fall 2007: 11.

Ballard TE et al. Synthesis and antibiofilm activity of a second-generation reverse-amide oroidin library: a structure-activity relationship study. Chemistry. 2008; 14(34): 10745-61.

Galvin F. Marine inspiration for biofilm break up. Chemical Biology. RCS Publishing. Mar. 5, 2008: 2 pp.

Huigens RW 3rd et al. Control of bacterial biofilms with marine alkaloid derivatives. Molecular BioSystems. 2008; 4: 614-621.

Richards JJ et al. Inhibition and dispersion of *Pseudomonas aeruginosa* biofilms with reverse amide 2-aminoimidazole oroidin analogues. Organic & Biomolecular Chemistry. Apr. 21, 2008; 6(8): 1356-1363.

Richards JJ et al. Effects of N-pyrrole substitution on the anti-biofilm activities of oroidin derivatives against *Acinetobacter baumannii*. Bioorganic & Medicinal Chemistry Letters. 2008; 18: 4325-4327.

Richards JJ and Melander C. Synthesis of a 2-aminoimidazole library for antibiofilm screening utilizing the Sonogashira reaction. J. Org. Chem. 2008; 73(13): 5191-5193.

Richards JJ et al. Inhibition and dispersion of proteobacterial biofilms. Chem. Comm. 2008; 1698-1700.

Richards JJ et al. Synthesis and screening of an oroidin library against *Pseudomonas aeruginosa* biofilms. ChemBioChem. 2008; 9: 1267-1279.

Rogers SA and Melander C. Construction and screening of a 2-aminoimidazole library identifies a small molecule capable of inhibiting and dispersing bacterial biofilms across order, class, and phylum. Angew. Chem. Int. Ed. 2008; 47: 5229-5231.

Ballard TE et al. Antibiofilm activity of a diverse oroidin library generated through reductive acylation. J. Org. Chem. 2009; 74(4): 1755-1758.

Huigens RW 3rd et al. Inhibition of *Acinetobacter baumannii*, *Staphylococcus aureus* and *Pseudomonas aeruginosa* biofilm formation with a class of TAGE-triazole conjugates. Org. Biomol. Chem. 2009; 7: 794-802.

Melander C et al. Evaluation of dihydrooroidin as an antifouling additive in marine paint. International Biodeterioration & Biodegradation. 2009; 53: 529-532.

Rogers SA et al. Tandem dispersion and killing of bacteria from a biofilm. Organic & Biomolecular Chemistry. 2009; 7: 603-606.

Stokstad E. Sponging away antibiotic resistance. Findings. The Science Magazine News Biog. Feb. 14, 2009: 1 p.

Lydersen K. Scientists learning to target bacteria where they live. washingtonpost.com. The Washington Post. Mar. 9, 2009; A05: 3 pp.

Taking the Resistance out of drug-resistant infections. PhysOrg.com. Apr. 10, 2009: 2 pp.

Avery S. Slime-fighting molecule may rearm antibiotics. newsobserver.com. The News and Observer. Raleigh, NC. Apr. 22, 2009: 2 pp.

International Search Report and Written Opinion, PCT/US09/02101, mailed Jul. 13, 2009.

International Search Report and Written Opinion, PCT/US09/02446, mailed Aug. 31, 2009.

Casalinuovo IA et al. Fluconazole resistance in *Candida abicans*: a review of mechanisms. European Review for Medical and Pharmacological Sciences, 2004; 8(2): 69-77.

Rogers SA et al. A 2-aminobenzimidazole that inhibits and disperses gram-positive biofilms through a zinc-dependent mechanism. J. Am. Chem. Soc. 2009; 131(29): 9868-9869.

Richards JJ et al. Amide isosteres of oroidin: assessment of antibiofilm activity and *C. elegans* toxicity. Journal of Medicinal Chemistry. 2009; 52(15): 4582-4585.

Richards JJ and Melander C. Controlling bacterial biofilms. ChemBioChem. Epub ahead of print: Aug. 13, 2009; 9 pp.

Ginsburg I. The role of bacteriolysis in the pathophysiology of inflammation, infection and post-infectious sequelae. APMIS. 2002; 110: 753-770.

Salvatori M et al. Versatile access to C-4 substituted 2-amino-1,3-azoles from hydropyridines in oxidative conditions. J. Org. Chem. 2005; 70: 8208-8211.

Rice LB. Unmet medical needs in antibacterial therapy. Biochemical Pharmacology. 2006; 71: 991-995.

Canadian Paedriatric Society. Antimicrobial products in the home: The evolving problem of antibiotic resistance. Paediatrics & Child Health. 2006; 11(3): 169-173.

Breckle G et al. Document No. 139:164905 retrieved from CAPLUS on Jan. 3, 2010.

Kirk KL et al. Document No. 80:15172 retrieved from CAPLUS on Jan. 3, 2010.

Finn FM and Hofmann K. Document No. 62:66837 retrieved from CAPLUS on Jan. 3, 2010.

Rogers SA et al. Chemical synthesis and biological screening of 2-aminoimidazole-based bacterial and fungal antibiofilm agents. Chembiochem. Feb. 2010; 11: 396-410.

Rogers SA et al. Synergistic effects between conventional antibiotics and 2-aminoimidazole-derived antibiofilm agents. Antimicrob. Agents Chemother. Mar. 8, 2010: 1-34.

* cited by examiner

INHIBITION AND DISPERSION OF BACTERIAL BIOFILMS WITH IMIDAZOLE-TRIAZOLE DERIVATIVES

RELATED APPLICATIONS

This application is a continuation of U.S. patent application Ser. No. 12/426,742, filed Apr. 20, 2009, now U.S. Pat. No. 7,897,631, and claims the benefit under 35 U.S.C. §119 (e) of U.S. Application No. 61/046,674, filed Apr. 21, 2008, and of U.S. Application No. 61/092,145, filed Aug. 27, 2008, the disclosure of each of which is incorporated herein by reference in its entirety. This application is related to U.S. application Ser. No. 12/020,112, filed Jan. 25, 2008, and published Jul. 31, 2008, as publication no. 2008/0181923, now U.S. Pat. No. 7,906,544, the disclosure of which is incorporated herein by reference in its entirety.

FIELD OF THE INVENTION

This invention relates to compounds, compositions and methods useful for controlling biofilms and other microorganisms.

BACKGROUND OF THE INVENTION

Biofilms are complex communities of microorganisms that are commonly found on a variety of substrates or surfaces that are moist or submerged (Musk et al., *Curr. Med. Chem.*, 2006, 13, 2163; Donlan et al., *Clin. Microbiol. Rev.*, 2002, 15, 167). Though primarily populated by bacteria, biofilms can also contain many different individual types of microorganisms, e.g., bacteria, archaea, protozoa and algae. The formation of biofilms can be thought of as a developmental process in which a few free-swimming (planktonic) bacteria adhere to a solid surface and, in response to appropriate signals, initiate the formation of a complex sessile microcolony existing as a community of bacteria and other organisms. Bacteria within biofilms are usually embedded within a matrix, which can consist of protein, polysaccharide, nucleic acids, or combinations of these macromolecules. The matrix is a critical feature of the biofilm that protects the inhabiting organisms from antiseptics, microbicides, and host cells. It has been estimated that bacteria within biofilms are upwards of 1,000-fold more resistant to conventional antibiotics (Rasmussen et al., *Int. J. Med. Microbiol.*, 2006, 296, 149).

Biofilms play a significant role in infectious disease. It is estimated that biofilms account for between 50-80% of microbial infections in the body, and that the cost of these infections exceeds $1 billion annually. For example, persistent infections of indwelling medical devices remain a serious problem for patients, because eradication of these infections is virtually impossible. A few diseases in which biofilms have been implicated include endocarditis, otitis media, chronic prostatitis, periodontal disease, chronic urinary tract infections, and cystic fibrosis. The persistence of biofilm populations is linked to their inherent insensitivity to antiseptics, antibiotics, and other antimicrobial compounds or host cells.

Cystic fibrosis (CF), with 7 million asymptomatic heterozygous carriers, is one of the most common genetic diseases in the United States. Despite significant progress in the management of the symptoms of CF, virtually all CF patients succumb to chronic pulmonary infections. For reasons that are not entirely clear, the airways of CF patients are particularly susceptible to bacterial colonization. CF patients typically become infected with *Staphylococcus aureus*, *Streptococcus pneumoniae*, *Haemophilus influenzae*, *Burkholderia cepacia* complex, and nonmucoid *Pseudomonas aeruginosa*. However, as the patients age, *Pseudomona aeruginosa* becomes the predominant pulmonary pathogen, present in up to 85% of cultures from patients with advanced disease. Once colonized by *Pseudomonas aeruginosa*, the organism persists for many years or decades and is never eradicated. This persistence of *Pseudomonas aeruginosa* has been linked to its ability to form biofilms Complications arising from *Pseudomonas aeruginosa* infections are the leading cause of death among CF patents.

Deleterious effects of biofilms are also found in non-medical settings. For example, biofilms are a major problem in the shipping industry. Biofilms form on and promote the corrosion of ship hulls and also increase the roughness of the hulls, increasing the drag on the ships and thereby increasing fuel costs. The biofilms can also promote the attachment of larger living structures, such as barnacles, to the hull. Fuel can account for half of the cost of marine shipping, and the loss in fuel efficiency due to biofilm formation is substantial. One method of controlling biofilms is to simply scrape the films off of the hulls. However, this method is costly and time-consuming, and can promote the spread of troublesome non-native species in shipping waters. Another method involves the use of antifouling coatings containing tin. However, tin-based coatings are now disfavored due to toxicity concerns.

Given the breadth of detrimental effects caused by bacterial biofilms, there has been an effort to develop small molecules that will inhibit their formation (Musk et al., *Curr. Med. Chem.*, 2006, 13, 2163). The underlying principle is that if bacteria can be maintained in the planktonic state, they will either not attach to a target surface and/or they can be killed by a lower dose of microbicide.

Despite the extent of biofilm driven problems, examples of structural scaffolds that inhibit biofilm formation are rare (Musk et al., *Curr. Med. Chem.*, 2006, 13, 2163). The few known examples include the homoserine lactones (Geske et al., *J. Am. Chem. Soc.*, 2005, 127, 12762), which are naturally-occurring bacterial signaling molecules that bacteria use in quorum sensing (Dong et al., *J. Microbiol.*, 2005, 43, 101; Nealson et al., *J. Bacteria*, 1970, 104, 313), brominated furanones isolated from the macroalga *Delisea pulchra* (Hentzer et al., *Microbiology-Sgm*, 2002, 148, 87), and ursene triterpenes from the plant *Diospyros dendo* (Hu et al., *J. Nat. Prod.*, 2006, 69, 118). While the focus has predominantly been on designing small molecules that inhibit the formation of biofilms, one of the more significant challenges is the development of a small molecule that disperses pre-formed biofilms. None of the small molecules noted above have been previously reported to disperse an existing biofilm.

In addition, bacteria have an unparalleled ability to overcome foreign chemical insult. For example, resistance to vancomycin, "the antibiotic of last resort," has become more prevalent, and strains of vancomycin-resistant *Staphylococcus aureus* have become a serious health risk. It has been predicted that it is simply a matter of time before different bacterial strains develop vancomycin resistance, and the safety net that vancomycin has provided for decades in antibiotic therapy will no longer be available. Therefore, the identification of chemical architectures useful to inhibit biofilm development is needed.

Because of their natural resistance to antibiotics, phagocytic cells, and other biocides, biofilms are difficult, if not impossible, to eradicate. Therefore, the identification of compounds that control biofilm formation is of critical need.

SUMMARY OF THE INVENTION

Provided herein are compounds of Formula (I):

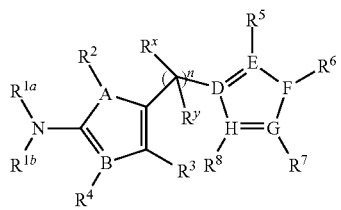

wherein:

each occurrence of $R^1$, $R^2$, $R^3$, $R^4$, $R^5$, $R^6$, $R^7$ and $R^8$ (depending upon valence requirement) is independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

each occurrence of $R^x$ and $R^y$ is present or absent (depending upon chain saturation), and is independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide; and A, B, D, E, F, G and H are each independently selected from carbon, N, S and O, wherein at least one of D, E, F, G and H is carbon; and n=0 to 20, saturated or unsaturated;

or a pharmaceutically acceptable salt or prodrug thereof. This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

In some embodiments of Formula (I), $R^1$ is a substituted amino, A, B, F, G and H are each N, and D and E are each carbon, generally depicted by Formulas (I)(a)(1)-(I)(a)(2):

Formula (I)(a)(1):

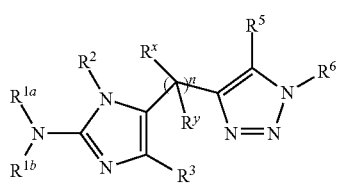

wherein:

$R^{1a}$, $R^{1b}$, $R^2$, $R^3$, $R^5$ and $R^6$ are each independently selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide; and each occurrence of $R^x$ and $R^y$ is present or absent (depending upon chain saturation), and is independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide; and n=0 to 20;

or a pharmaceutically acceptable salt or prodrug thereof. This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

Formula (I)(a)(2):

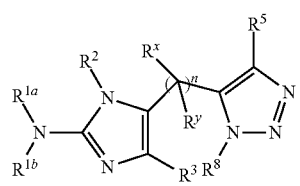

wherein:

$R^{1a}$, $R^{1b}$, $R^2$, $R^3$, $R^5$ and $R^8$ are each independently selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide; and each occurrence of $R^x$ and $R^y$ is present or absent (depending upon chain saturation), and is independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide; and n=0 to 20;

or a pharmaceutically acceptable salt or prodrug thereof. This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

In some embodiments of Formula (I), $R^1$ is a substituted amino, A, B, F, G and D are each N, and E and H are each carbon, generally depicted by Formula (I)(b)(2):

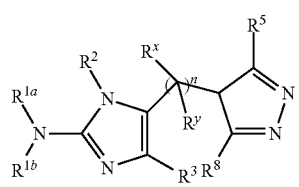

wherein:

$R^{1a}$, $R^{1b}$, $R^2$, $R^3$, $R^5$ and $R^8$ are each independently selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide;

each occurrence of $R^x$ and $R^y$ is present or absent (depending upon chain saturation), and is independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide; and n=0 to 20;

or a pharmaceutically acceptable salt or prodrug thereof. This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

Also provided are compounds of Formula (I)(i):

$$(I)(i)$$

wherein:

each occurrence of $R^1$, $R^2$, $R^3$, $R^4$, $R^5$, $R^6$, $R^7$ and $R^8$ (depending upon valence requirement) is independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

A, B, D, E, F, G and H are each independently selected from carbon, N, S and O, wherein at least one of D, E, F, G and H is carbon; and n=0 to 20, saturated or unsaturated;

or a pharmaceutically acceptable salt or prodrug thereof. This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

In some embodiments of Formula (I)(i), $R^1$ is a substituted amino; $R^2$, $R^3$, $R^4$, $R^5$, $R^7$ and $R^8$=H; A, B, F, G and H are each N, and D and E are each carbon, generally depicted by Formula (I)(i)(a):

$$(I)(i)(a)$$

wherein:

$R^6$ is selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide; and n=0 to 20, saturated or unsaturated;

or a pharmaceutically acceptable salt or prodrug thereof. This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

Further provided are compounds of Formula (II):

$$(II)$$

wherein:

each occurrence of $R^1$, $R^2$, $R^3$, $R^4$, $R^5$, $R^6$, $R^7$ and $R^8$ (depending upon valence requirement) is independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

each occurrence of $R^x$, $R^y$, $R^u$ and $R^v$ is present or absent (depending upon chain saturation), and is independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

A, B, D, E, F, G and H are each independently selected from carbon, N, S and O, wherein at least one of D, E, F, G and H is carbon; and n=0 to 20; and
m=0 to 20;

or a pharmaceutically acceptable salt or prodrug thereof. This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

In some embodiments of Formula (II), $R^1$ is a substituted amino, A, B, F, G and H are each N, and D and E are each carbon, generally depicted by Formula (II)(a):

$$(II)(a)$$

wherein:

$R^{1a}$, $R^{1b}$, $R^2$, $R^3$, $R^5$ and $R^6$ are each independently selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide;

each occurrence of $R^x$, $R^y$, $R^u$ and $R^v$ is present or absent (depending upon chain saturation), and is independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

n=0 to 20; and m=0 to 20;

or a pharmaceutically acceptable salt or prodrug thereof. This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

In some embodiments of Formula (II)(a), $R^{1a}$, $R^{1b}$, $R^2$, $R^3$ and $R^5$ are each H and $R^6$ is phenyl, e.g., Formula (II)(a)(5)(D), wherein n=5; m=3, and $R^u$=methyl at C2:

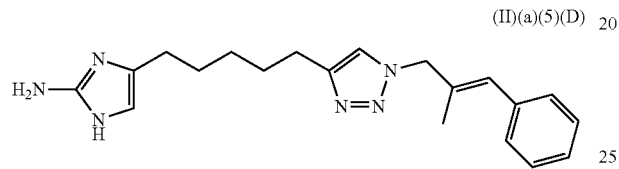

Also provided are compounds of Formula (II)(i):

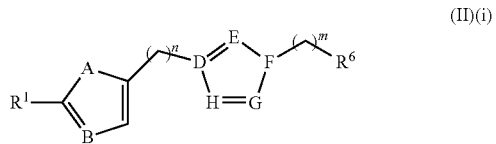

wherein:

$R^1$ and $R^6$ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

A, B, D, E, F, G and H are each independently selected from carbon, N, S and O, wherein at least one of D, E, F, G and H is carbon;

n=0 to 20, saturated or unsaturated; and m=0 to 20, saturated or unsaturated;

or a pharmaceutically acceptable salt or prodrug thereof. This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

In some embodiments of Formula (II)(i), $R^1$ is a substituted amino, A, B, F, G and H are each N, and D and E are each carbon, generally depicted by Formula (II)(i)(a):

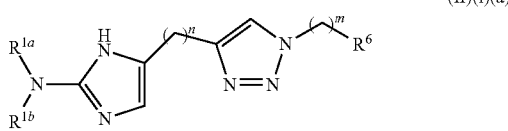

wherein:

$R^{1a}$, $R^{1b}$ and $R^6$ are each independently selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide;

n=0 to 20, saturated or unsaturated; and m=0 to 20, saturated or unsaturated;

or a pharmaceutically acceptable salt or prodrug thereof. This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

In some embodiments of Formula (II)(i)(a), $R^{1a}$ and $R^{1b}$ are each H, and $R^6$ is heteroaryl.

Further provided are compounds of Formula (III):

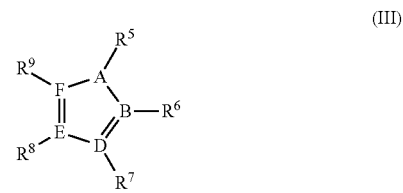

wherein:

each occurrence of $R^5$, $R^6$, $R^7$, $R^8$ and $R^9$ (depending upon valence requirement) is independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide; and A, B, D, E and F are each independently selected from carbon, N, S and O, wherein at least one of A, B, D, E and F is carbon;

or a pharmaceutically acceptable salt or prodrug thereof. This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

In some embodiments of Formula (III), B, D and E are each N, and A and F are each carbon, generally depicted as Formula (III)(a):

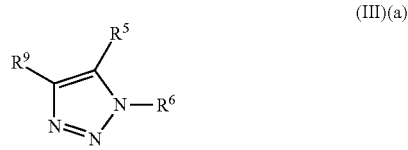

wherein:

$R^5$, $R^6$ and $R^9$ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

or a pharmaceutically acceptable salt or prodrug thereof. This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

In some embodiments of Formula (III), A, D and E are each N, and B and F are each carbon, generally depicted as Formula (III)(b):

$$\text{(III)(b)}$$

wherein:

$R^5$, $R^6$ and $R^9$ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide; and or a pharmaceutically acceptable salt or prodrug thereof. This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

In some embodiments of Formula (III)(b), $R^6$ and $R^9$ are each H, generally depicted by Formula (III)(b)(i):

$$\text{(III)(b)(i)}$$

wherein:

$R^5$ is selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide; and or a pharmaceutically acceptable salt or prodrug thereof. This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

In some embodiments of Formula (III)(b), $R^5$ and $R^6$ are each H, generally depicted by Formula (III)(b)(ii):

$$\text{(III)(b)(ii)}$$

wherein:

$R^9$ is selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide; and or a pharmaceutically acceptable salt or prodrug thereof. This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

Also provided are compounds of Formula (IV):

$$\text{(IV)}$$

wherein:

$R^1$, $R^2$, $R^3$, $R^4$, $R^5$, $R^6$, $R^7$ and $R^8$ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

each occurrence of $R^x$, $R^y$, $R^u$, $R^v$, $R^z$ and $R^w$ is present or absent (depending upon chain saturation), and is independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

A, B, D, E, F, G and H are each independently selected from carbon, N, S and O, wherein at least one of D, E, F, G and H is carbon; and n=0 to 20;

m=0 to 20; and p=0 to 20 or a pharmaceutically acceptable salt or prodrug thereof. This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

In some embodiments of Formula (IV), $R^1$ is a substituted amino, A, B, F, G and H are each N, and D and E are each carbon, generally depicted by Formula (IV)(a):

$$\text{(IV)(a)}$$

wherein:

$R^{1a}$, $R^{1b}$, $R^2$, $R^3$, $R^5$ and $R^6$ are each independently selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide;

each occurrence of $R^x$, $R^y$, $R^u$, $R^v$, $R^z$ and $R^w$ is present or absent (depending upon chain saturation), and is independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

n=0 to 20;

m=0 to 20; and p=0 to 20 or a pharmaceutically acceptable salt or prodrug thereof. This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

In some embodiments, $R^6$ is a group:

(i)

wherein:

X, Y and Z are each independently selected from the group consisting of: H, methyl, Br and Cl.

In some embodiments, $R^6$ is a group:

(ii)

wherein:

$R^{20}$, $R^{21}$, $R^{22}$ and $R^{23}$ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

Further provided are compounds of Formula (IV)(i):

(IV)(i)

wherein:

$R^1$ and $R^6$ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

A, B, D, E, F, G and H are each independently selected from carbon, N, S and O, wherein at least one of D, E, F, G and H is carbon;

n=0 to 20, saturated or unsaturated;

m=0 to 20, saturated or unsaturated; and p=0 to 20, saturated or unsaturated;

or a pharmaceutically acceptable salt or prodrug thereof. This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

In some embodiments of Formula (IV)(i), $R^1$ is a substituted amino, A, B, F, G and H are each N, and D and E are each carbon, generally depicted by Formula (IV)(i)(a):

(IV)(i)(a)

wherein:

$R^{1a}$, $R^{1b}$ and $R^6$ are each independently selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide;

n=0 to 20, saturated or unsaturated;

m=0 to 20, saturated or unsaturated; and p=0 to 20, saturated or unsaturated;

or a pharmaceutically acceptable salt or prodrug thereof. This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

In some embodiments of Formula (IV)(i)(a), $R^{1a}$, $R^{1b}$ and $R^6$ are each H. In some embodiments of Formula (IV)(i)(a), $R^{1a}$ and $R^{1b}$ are each H, and $R^6$ is aryl or heteroaryl.

Also provided are compounds of Formula (V):

(V)

wherein:

$R^1$, $R^2$, $R^3$, $R^4$, $R^5$, $R^6$, $R^7$ and $R^8$ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

each occurrence of $R^x$, $R^y$, $R^u$, $R^v$, $R^z$ and $R^w$ is present or absent (depending upon chain saturation), and is independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

A, B, D, E, F, G and H are each independently selected from carbon, N, S and O, wherein at least one of D, E, F, G and H is carbon; and n=0 to 20;

m=0 to 20; and p=0 to 20 or a pharmaceutically acceptable salt or prodrug thereof. This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

In some embodiments of Formula (V), $R^1$ is a substituted amino, A, B, F, G and H are each N, and D and E are each carbon, generally depicted by Formula (V)(a):

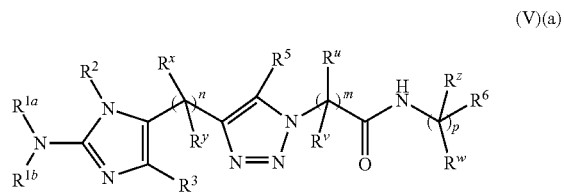

(V)(a)

wherein:

$R^{1a}$, $R^{1b}$, $R^2$, $R^3$, $R^5$ and $R^6$ are each independently selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide;

each occurrence of $R^x$, $R^y$, $R^u$, $R^v$, $R^z$ and $R^w$ is present or absent (depending upon chain saturation), and is independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

n=0 to 20;

m=0 to 20; and p=0 to 20 or a pharmaceutically acceptable salt or prodrug thereof. This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

Further provided are compounds of Formula (V)(i):

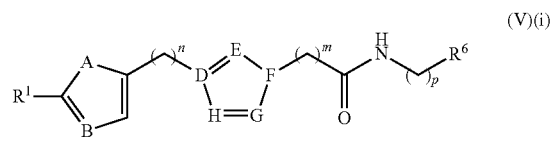

(V)(i)

wherein:

$R^1$ and $R^6$ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

A, B, D, E, F, G and H are each independently selected from carbon, N, S and O, wherein at least one of D, E, F, G and H is carbon;

n=0 to 20, saturated or unsaturated;

m=0 to 20, saturated or unsaturated; and p=0 to 20, saturated or unsaturated;

or a pharmaceutically acceptable salt or prodrug thereof. This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

In some embodiments of Formula (V)(i), $R^1$ is a substituted amino, A, B, F, G and H are each N, and D and E are each carbon, generally depicted by Formula (V)(i)(a):

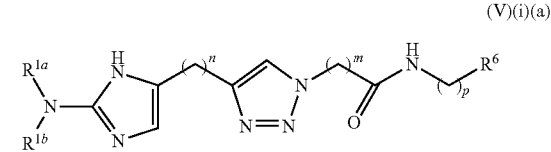

(V)(i)(a)

wherein:

$R^{1a}$, $R^{1b}$ and $R^6$ are each independently selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide;

n=0 to 20, saturated or unsaturated;

m=0 to 20, saturated or unsaturated; and p=0 to 20, saturated or unsaturated;

or a pharmaceutically acceptable salt or prodrug thereof. This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

In some embodiments of Formula (V)(i)(a), $R^{1a}$, $R^{1b}$ and $R^6$ are each H, alkyl, cycloalkyl or heterocyclo. In some embodiments of Formula (V)(i)(a), $R^{1a}$ and $R^{1b}$ are each H, and $R^6$ is aryl.

Also provided are compounds of Formula (VI):

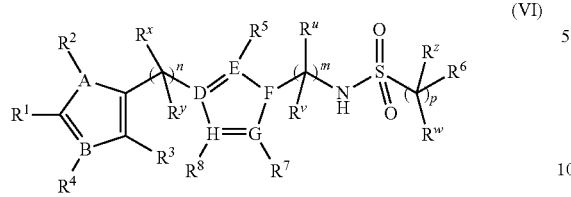

wherein:
R$^1$, R$^2$, R$^3$, R$^4$, R$^5$, R$^6$, R$^7$ and R$^8$ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

each occurrence of R$^x$, R$^y$, R$^u$, R$^v$, R$^z$ and R$^w$ is present or absent (depending upon chain saturation), and is independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

A, B, D, E, F, G and H are each independently selected from carbon, N, S and O, wherein at least one of D, E, F, G and H is carbon; and n=0 to 20;
m=0 to 20; and
p=0 to 20;
or a pharmaceutically acceptable salt or prodrug thereof.
This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

In some embodiments of Formula (VI), R$^1$ is a substituted amino, A, B, F, G and H are each N, and D and E are each carbon, generally depicted by Formula (VI)(a):

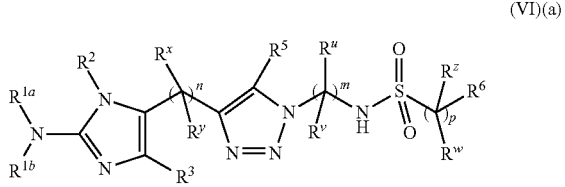

wherein:
R$^{1a}$, R$^{1b}$, R$^2$, R$^3$, R$^5$ and R$^6$ are each independently selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide;

each occurrence of R$^x$, R$^y$, R$^u$, R$^v$, R$^z$ and R$^w$ is present or absent (depending upon chain saturation), and is independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

n=0 to 20;
m=0 to 20; and
p=0 to 20;
or a pharmaceutically acceptable salt or prodrug thereof.
This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

Further provided are compounds of Formula (VI)(i):

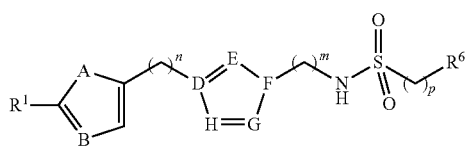

wherein:
R$^1$ and R$^6$ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

A, B, D, E, F, G and H are each independently selected from carbon, N, S and O, wherein at least one of D, E, F, G and H is carbon;

n=0 to 20, saturated or unsaturated;
m=0 to 20, saturated or unsaturated; and
p=0 to 20, saturated or unsaturated;
or a pharmaceutically acceptable salt or prodrug thereof.
This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

In some embodiments of Formula (VI)(i), R$^1$ is a substituted amino, A, B, F, G and H are each N, and D and E are each carbon, generally depicted by Formula (VI)(i)(a):

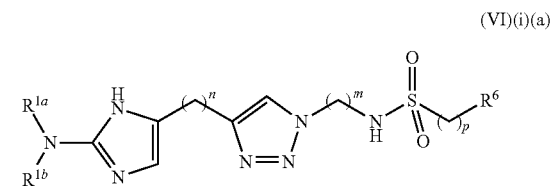

wherein:
R$^{1a}$, R$^{1b}$ and R$^6$ are each independently selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide;

n=0 to 20, saturated or unsaturated;
m=0 to 20, saturated or unsaturated; and
p=0 to 20, saturated or unsaturated;
or a pharmaceutically acceptable salt or prodrug thereof.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

In some embodiments of Formula (VI)(i)(a), $R^{1a}$ and $R^{1b}$ are each H, and $R^6$ is aryl or heteroaryl.

Biofilm preventing, removing or inhibiting compositions are provided, which include a carrier and an effective amount of a compound disclosed herein. In some embodiments, the composition is a dentifrice composition that promotes dental hygiene by preventing, reducing, inhibiting or removing a biofilm. In some embodiments, the dentifrice composition comprises a toothpaste, mouthwash, chewing gum, dental floss, or dental cream.

Compositions are also provided that include a compound disclosed herein in a pharmaceutically acceptable carrier.

Compositions are further provided that include a compound disclosed herein covalently coupled to a substrate. In some embodiments, the substrate includes a polymeric material. In some embodiments, the substrate includes a solid support. In some embodiments, the substrate includes a drainpipe, glaze ceramic, porcelain, glass, metal, wood, chrome, plastic, vinyl, and Formica® brand laminate (The Diller Corporation, Cincinnati, Ohio). In some embodiments, the substrate includes shower curtains or liners, upholstery, laundry, and carpeting. In some embodiments, the substrate includes a ship hull or a portion thereof. In some embodiments, the substrate includes a food contact surface.

Biofilm preventing, removing or inhibiting coating compositions are provided, including: (a) a film-forming resin; (b) a solvent that disperses said resin; (c) an effective amount of the compounds or compositions disclosed herein, wherein said effective amount prevents or inhibits the growth of a biofilm thereon; and (d) optionally, at least one pigment. In some embodiments, the compound is covalently coupled to the resin. In some embodiments, the resin includes a polymeric material.

Substrates coated with coating composition disclosed herein are also provided. In some embodiments, the substrate includes a polymeric material. In some embodiments, the substrate includes a solid support. In some embodiments, the substrate includes a drainpipe, glaze ceramic, porcelain, glass, metal, wood, chrome, plastic, vinyl, and Formica® brand laminate. In some embodiments, the substrate includes shower curtains or liners, upholstery, laundry, and carpeting. In some embodiments, the substrate includes a ship hull or a portion thereof. In some embodiments, the substrate includes a food contact surface.

Methods of controlling biofilm formation on a substrate are provided, including the step of contacting the substrate with a compound and/or composition disclosed herein in an amount effective to inhibit biofilm formation. In some embodiments, controlling biofilm formation includes clearing a preformed biofilm from said substrate by administering an effective amount of the compound and/or composition disclosed herein to said substrate, wherein said effective amount will reduce the amount of said biofilm on said substrate. In some embodiments, the substrate may include a drainpipe, glaze ceramic, porcelain, glass, metal, wood, chrome, plastic, vinyl, and Formica® brand laminate. In some embodiments, the substrate may include a food product (e.g., seafood). In some embodiments, the biofilm includes Gram-negative bacteria.

Methods for treating and/or preventing a bacterial infection (e.g., chronic bacterial infection) in a subject in need thereof are provided, including administering to said subject a compound and/or composition disclosed herein in an amount effective to inhibit, reduce, or remove a biofilm component of said bacterial infection. The bacterial infection may include urinary tract infection, gastritis, respiratory infection, cystitis, pyelonephritis, osteomyelitis, bacteremia, skin infection, rosacea, acne, chronic wound infection, infectious kidney stones, bacterial endocarditis, and sinus infection.

Also provided are medical devices, including (a) a medical device substrate; and (b) an effective amount of a compound disclosed herein, either coating the substrate, or incorporated into the substrate, wherein said effective amount prevents or inhibits the growth of a biofilm thereon. In some embodiments, the medical device substrate may include stents, fasteners, ports, catheters, scaffolds and grafts. In some embodiments, the compound is covalently coupled to said substrate.

Compounds and/or compositions for use in a method to control a biofilm are further provided. Also provided is the use of compounds and/or compositions disclosed herein for the preparation of a medicament for the treatment and/or prevention of a bacterial infection (e.g., chronic bacterial infection).

DETAILED DESCRIPTION OF THE PREFERRED EMBODIMENTS

Figure 1A:
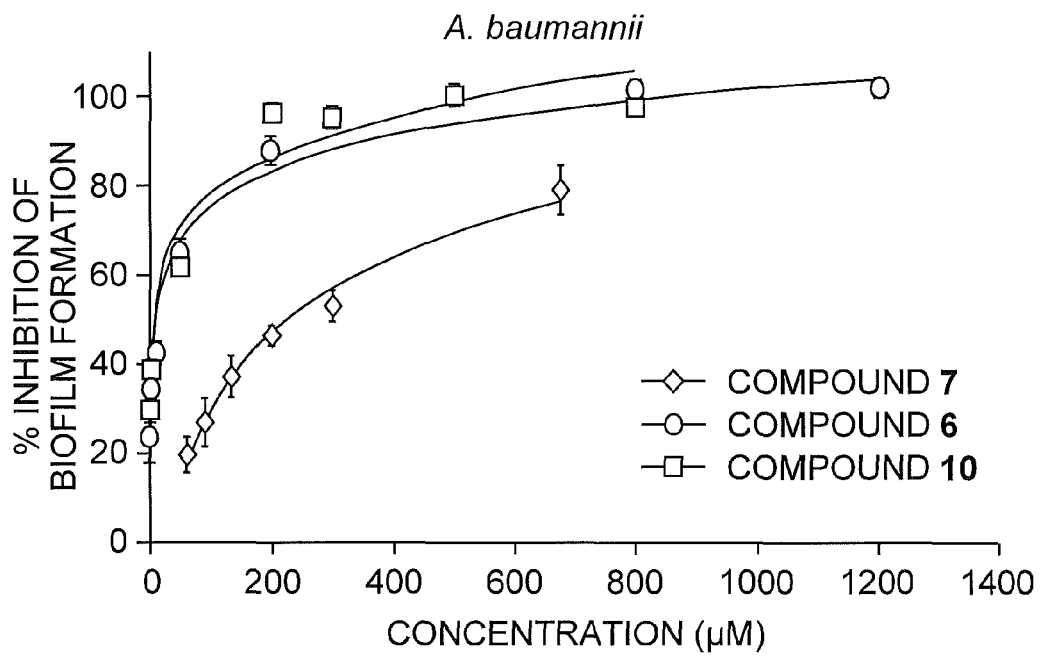
FIG. 1A-1D. Bacterial biofilm inhibition dose response curves for compounds 7, 6, 10, 11 and 12. 1A: Dose response curves for 7, 6 and 10 inhibition of *A. baumannii*. 1B: Dose response curves for 10 inhibition of *A. baumannii, P. aeruginosa*:PA14, *P. aeruginosa*:PAO1, *B. bronchiseptica*:RB50, and *S. aureus:*29213. 1C: Dose response curves for 11 inhibition of *A. baumannii, P. aeruginosa*:PA14, *P. aeruginosa*: PAO1, *B. bronchiseptica*:RB50, and *S. aureus:*29213. 1D: Dose response curves for 12 inhibition of *A. baumannii, P. aeruginosa*:PA14, *P. aeruginosa*:PAO1, *B. bronchiseptica*: RB50, and *S. aureus:*29213.

The present invention is further described below. All patent references referred to in this patent application are hereby incorporated by reference in their entirety as if set forth fully herein.

A. Definitions

"Triazole" refers to the commonly known structures:

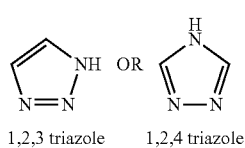

1,2,3 triazole     1,2,4 triazole

"Imidazole" refers to the commonly known structure:

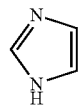

"H" refers to a hydrogen atom. "C" refers to a carbon atom. "N" refers to a nitrogen atom. "O" refers to an oxygen atom. "Halo" refers to F, Cl, Br or I. The term "hydroxy," as used herein, refers to an —OH moiety. "Br" refers to a bromine atom. "Cl" refers to a chlorine atom. "I" refers to an iodine atom. "F" refers to a fluorine atom.

An "acyl group" is intended to mean a group —C(O)—R, where R is a suitable substituent (for example, an acetyl group, a propionyl group, a butyroyl group, a benzoyl group, or an alkylbenzoyl group).

"Alkyl," as used herein, refers to a straight or branched chain hydrocarbon containing from 1 or 2 to 10 or 20 or more carbon atoms (e.g., C2, C3, C4, C5, C6, C7, C8, C9, C10, C11, C12, C13, C14, C15, etc.). Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, and the like. In some embodiments, alkyl groups as described herein are optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

As generally understood by those of ordinary skill in the art, "saturation" refers to the state in which all available valence bonds of an atom (e.g., carbon) are attached to other atoms. Similarly, "unsaturation" refers to the state in which not all the available valence bonds are attached to other atoms; in such compounds the extra bonds usually take the form of double or triple bonds (usually with carbon). For example, a carbon chain is "saturated" when there are no double or triple bonds present along the chain or directly connected to the chain (e.g., a carbonyl), and is "unsaturated" when at least one double or triple bond is present along the chain or directly connected to the chain (e.g., a carbonyl). Further, the presence or absence of a substituent depending upon chain saturation will be understood by those of ordinary skill in the art to depend upon the valence requirement of the atom or atoms to which the substituent binds (e.g., carbon).

The term "optionally substituted" indicates that the specified group is either unsubstituted, or substituted by one or more suitable substituents. A "substituent" is an atom or atoms substituted in place of a hydrogen atom on the parent chain or cycle of an organic molecule, for example, H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

"Alkenyl," as used herein, refers to a straight or branched chain hydrocarbon containing from 1 or 2 to 10 or 20 or more carbons, and containing at least one carbon-carbon double bond, formed structurally, for example, by the replacement of two hydrogens. Representative examples of "alkenyl" include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl and the like. In some embodiments, alkenyl groups as described herein are optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

"Alkynyl," as used herein, refers to a straight or branched chain hydrocarbon group containing from 1 or 2 to 10 or 20 or more carbon atoms, and containing at least one carbon-carbon triple bond. Representative examples of alkynyl include, but are not limited, to acetylenyl, 1-propynyl, 2-propynyl, 3-butynyl, 2-pentynyl, 1-butynyl and the like. In some embodiments, alkynyl groups as described herein are optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

The term "cycloalkyl," as used herein, refers to a saturated cyclic hydrocarbon group containing from 3 to 8 carbons or more. Representative examples of cycloalkyl include, cyclopropyl, cyclobutyl, cyclopentyl, cyclohexyl, cycloheptyl, and cyclooctyl. In some embodiments, cycloalkyl groups as described herein are optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

"Heterocyclo," as used herein, refers to a monocyclic or a bicyclic ring system. Monocyclic heterocycle ring systems are exemplified by any 5 or 6 member ring containing 1, 2, 3, or 4 heteroatoms independently selected from the group consisting of: O, N, and S. The 5 member ring has from 0 to 2 double bonds, and the 6 member ring has from 0-3 double bonds. Representative examples of monocyclic ring systems include, but are not limited to, azetidine, azepine, aziridine, diazepine, 1,3-dioxolane, dioxane, dithiane, furan, imidazole, imidazoline, imidazolidine, isothiazole, isothiazoline, isothiazolidine, isoxazole, isoxazoline, isoxazolidine, morpholine, oxadiazole, oxadiazoline, oxadiazolidine, oxazole, oxazoline, oxazolidine, piperazine, piperidine, pyran, pyrazine, pyrazole, pyrazoline, pyrazolidine, pyridine, pyrimidine, pyridazine, pyrrole, pyrroline, pyrrolidine, tetrahydrofuran, tetrahydrothiophene, tetrazine, tetrazole, thiadiazole, thiadiazoline, thiadiazolidine, thiazole, thiazoline, thiazolidine, thiophene, thiomorpholine, thiomorpholine sulfone, sulfoxide, thiopyran, triazine, triazole, trithiane, and the like. Bicyclic ring systems are exemplified by any of the above monocyclic ring systems fused to an aryl group as defined herein, a cycloalkyl group as defined herein, or another monocyclic ring system as defined herein. Representative examples of bicyclic ring systems include but are not limited to, for example, benzimidazole, benzothiazole, benzothiadiazole, benzothiophene, benzoxadiazole, benzoxazole, benzofuran, benzopyran, benzothiopyran, benzodioxine, 1,3-benzodioxole, cinnoline, indazole, indole, indoline, indolizine, naphthyridine, isobenzofuran, isobenzothiophene, isoindole, isoindoline, isoquinoline, phthalazine, pyranopyridine, quinoline, quinolizine, quinoxaline, quinazoline, tetrahydroisoquinoline, tetrahydroquinoline, thiopyranopyridine, and the like. In some embodiments, heterocyclo groups as described herein are optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

"Aryl" as used herein refers to a fused ring system having one or more aromatic rings. Representative examples of aryl include, azulenyl, indanyl, indenyl, naphthyl, phenyl, tetrahydronaphthyl, and the like. The aryl groups of this invention can be substituted with 1, 2, 3, 4, or 5 substituents independently selected from alkenyl, alkenyloxy, alkoxy, alkoxyalkoxy, alkoxycarbonyl, alkyl, alkylcarbonyl, alkylcarbonyloxy, alkylsulfinyl, alkylsulfonyl, alkylthio, alkynyl, aryl, aryloxy, azido, arylalkoxy, arylalkyl, aryloxy, carboxy, cyano, formyl, halogen, haloalkyl, haloalkoxy, hydroxy, hydroxyalkyl, mercapto, nitro, sulfamyl, sulfo, sulfonate, —NR'R" (wherein, R' and R" are independently selected from hydrogen, alkyl, alkylcarbonyl, aryl, arylalkyl and formyl), and —C(O)NR'R" (wherein R' and R" are independently selected from hydrogen, alkyl, alkylcarbonyl, aryl, arylalkyl, and formyl). In some embodiments, aryl groups as described herein are optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

"Heteroaryl" means a cyclic, aromatic hydrocarbon in which one or more carbon atoms have been replaced with heteroatoms. If the heteroaryl group contains more than one heteroatom, the heteroatoms may be the same or different. Examples of heteroaryl groups include pyridyl, pyrimidinyl, imidazolyl, thienyl, furyl, pyrazinyl, pyrrolyl, pyranyl, isobenzofuranyl, chromenyl, xanthenyl, indolyl, isoindolyl, indolizinyl, triazolyl, pyridazinyl, indazolyl, purinyl, quinolizinyl, isoquinolyl, quinolyl, phthalazinyl, naphthyridinyl, quinoxalinyl, isothiazolyl, and benzo[b]thienyl. Preferred heteroaryl groups are five and six membered rings and contain from one to three heteroatoms independently selected from the group consisting of: O, N, and S. The heteroaryl group, including each heteroatom, can be unsubstituted or substituted with from 1 to 4 suitable substituents, as chemically feasible. For example, the heteroatom S may be substituted with one or two oxo groups, which may be shown as =O. In some embodiments, heteroaryl groups as described herein are optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

"Alkoxy," as used herein, refers to an alkyl group, as defined herein, appended to the parent molecular moiety through an oxy group, as defined herein. Representative examples of alkoxy include, but are not limited to, methoxy, ethoxy, propoxy, 2-propoxy, butoxy, tert-butoxy, pentyloxy, hexyloxy and the like. In some embodiments, alkoxy groups as described herein are optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

An "amine" or "amino" is intended to mean, the group —NH$_2$. "Optionally substituted" amines refers to —NH$_2$ groups wherein none, one or two of the hydrogens is replaced by a suitable substituent as described herein, such as alkyl, alkenyl, alkynyl, cycloalkyl, heterocyclo, aryl, heteroaryl, alkoxy, carbonyl, carboxy, etc. In some embodiments, one or two of the hydrogens are optionally substituted with independently selected, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide. Disubstituted amines may have substituents that are bridging, i.e., form a heterocyclic ring structure that includes the amine nitrogen.

An "amide" as used herein refers to an organic functional group having a carbonyl group (C=O) linked to a nitrogen atom (N), or a compound that contains this group, generally depicted as:

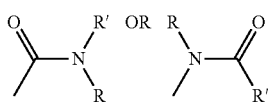

wherein, R and R' can independently be any covalently-linked atom or atoms, for example, H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

A "thiol" or "mercapto" refers to an —SH group or to its tautomer =S.

A "sulfone" as used herein refers to a sulfonyl functional group, generally depicted as:

wherein, R can be any covalently-linked atom or atoms, for example, H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

A "sulfoxide" as used herein refers to a sulfinyl functional group, generally depicted as:

wherein, R can be any covalently-linked atom or atoms, for example, H, halohydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

The term "oxo," as used herein, refers to a =O moiety. The term "oxy," as used herein, refers to a —O— moiety.

"Nitro" refers to the organic compound functional group —NO$_2$.

"Carbonyl" is a functional group having a carbon atom double-bonded to an oxygen atom (—C=O). "Carboxy" as used herein refers to a —COOH functional group, also written as —(C=O)—OH.

"Amino acid sidechain" as used herein refers to any of the 20 commonly known groups associated with naturally-occurring amino acids, or any natural or synthetic homologue thereof. An "amino acid" includes the sidechain group and the amino group, alpha-carbon atom, and carboxy groups, as commonly described in the art. Examples of amino acids include glycine, and glycine that is substituted with a suitable substituent as described herein, such as alkyl, alkenyl, alkynyl, cycloalkyl, heterocyclo, aryl, heteroaryl, alkoxy, carbonyl, carboxy, etc., or a pharmaceutically acceptable salt or prodrug thereof. For example, "Histidine" is one of the 20 most commonly known amino acids found naturally in proteins. It contains an imidazole side chain substituent. Other examples of naturally-occurring amino acids include lysine, arginine, aspartic acid, glutamic acid, asparagine, glutamine, serine, threonine, tyrosine, alanine, valine, leucine, isoleucine, phenylalanine, methionine, cryptophane, and cysteine. Also included in the definitions of "amino acid sidechain" and "amino acid" is proline, which is commonly included in the definition of an amino acid, but is technically an imino acid. As used in this application, both the naturally-occurring L-, and the non-natural D-amino acid enantiomers are included. The single letter code for amino acids is A (Ala), C (Cys), D (Asp), E (Glu), F (Phe), G (Gly), H (His), I (Ile), K (Lys), L (Leu), M (Met), N (Asn), P (Pro), Q (Gln), R (Arg), S (Ser), T (Thr), V (Val), W (Trp), and Y (Tyr). A "peptide" is a linear chain of amino acids covalently linked together, typically through an amide linkage, and contains from 1 or 2 to 10 or 20 or more amino acids, and is also optionally substituted and/or branched.

A "pharmaceutically acceptable salt" is intended to mean a salt that retains the biological effectiveness of the free acids and bases of a specified compound and that is not biologically or otherwise undesirable. Examples of pharmaceutically acceptable salts include sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycollates, tartrates, methanesulfonates, propanesulfonates, naphthalene-1-sulfonates, naphthalene-2-sulfonates, and mandelates.

A "prodrug" is intended to mean a compound that is converted under physiological conditions or by solvolysis or metabolically to a specified compound that is pharmaceutically active. A thorough discussion is provided in T. Higuchi and V. Stella, Prodrugs as Novel delivery Systems, Vol. 14 of the A.C.S. Symposium Series and in Edward B. Roche, ed., Bioreversible Carriers in Drug Design, American Pharmaceutical Association and Pergamon Press, 1987, both of which are incorporated by reference herein in their entirety.

B. Active Compounds

Active compounds are provided below. In some of the embodiments provided in the present invention, active compounds are derivatives of triazole. In some embodiments, active compounds include imidazole-triazole conjugates. In some embodiments, active compounds include 2-aminoimidazole-triazole conjugates ("2-AIT"). Active compounds as described herein can be prepared as detailed below or in accordance with known procedures or variations thereof that will be apparent to those skilled in the art.

As will be appreciated by those of skill in the art, the active compounds of the various formulas disclosed herein may contain chiral centers, e.g. asymmetric carbon atoms. Thus, the present invention is concerned with the synthesis of both: (i) racemic mixtures of the active compounds, and (ii) enantiomeric forms of the active compounds. The resolution of racemates into enantiomeric forms can be done in accordance with known procedures in the art. For example, the racemate may be converted with an optically active reagent into a diastereomeric pair, and the diastereomeric pair subsequently separated into the enantiomeric forms, Geometric isomers of double bonds and the like may also be present in the compounds disclosed herein, and all such stable isomers are included within the present invention unless otherwise specified. Also included in active compounds of the invention are tautomers (e.g., tautomers of triazole and/or imidazole) and rotamers.

All chains defined by the formulas herein which include three or more carbons may be saturated or unsaturated unless otherwise indicated.

Carbons or other atoms along a chain identified by the Formulas herein may be identified by number, and when identified by number shall be numbered from left to right. For example:

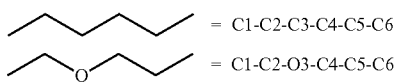

To illustrate where there are two or more discrete chains, for Formula (II)(i)(a) described below, wherein $R^2$, $R^3$, $R^4$, $R^5$, $R^7$ and $R^8$=H, and $R^6$=phenyl:

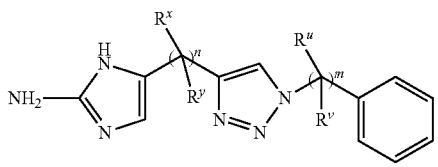

the exemplary structure below shows n=5, saturated, one of either $R^x$ or $R^y$=methyl at C4; m=3, unsaturated, $R^u$=methyl at C2 ($R^v$ is absent at C2); and $R^x$, $R^y$, $R^u$ and $R^v$=H at all other occurrences:

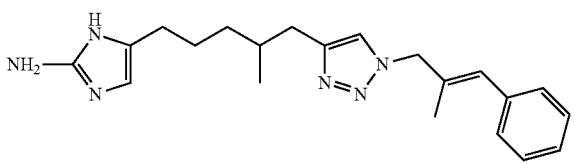 [SMILES: C/C(=C\c1ccccc1)Cn1cc(CC(C)CCCc2cnc(N)[nH]2)nn1]

Active compounds include compounds of Formula (I):

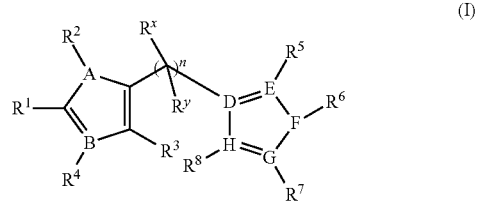

(I)

wherein:

$R^1$, $R^2$, $R^3$, $R^4$, $R^5$, $R^6$, $R^7$ and $R^8$ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

each occurrence of $R^x$ and $R^y$ is present or absent (depending upon chain saturation), and is independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide; and A, B, D, E, F, G and H are each independently selected from carbon, N, S and O, wherein at least one of D, E, F, G and H is carbon; and n=0 to 20, saturated or unsaturated;

or a pharmaceutically acceptable salt or prodrug thereof.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

As will be appreciated by those of skill in the art, a given substituent ($R^1$-$R^8$) may be present or absent depending upon the valence requirement of the atom or atoms to which the substituent binds (e.g., carbon versus nitrogen).

In some embodiments of Formula (I), R is a substituted amino, A, B, F, G and H are each N, and D and E are each carbon, generally depicted by Formulas (I)(a)(1)-(I)(a)(2):

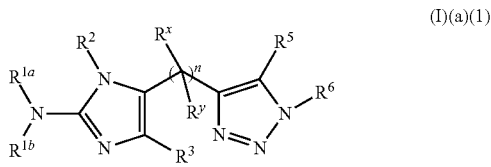

(I)(a)(1)

wherein:

$R^{1a}$, $R^{1b}$, $R^2$, $R^3$, $R^5$ and $R^6$ are each independently selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide; and each occurrence of $R^x$ and $R^y$ is present or absent (depending upon chain saturation), and is independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide; and n=0 to 20;

or a pharmaceutically acceptable salt or prodrug thereof.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

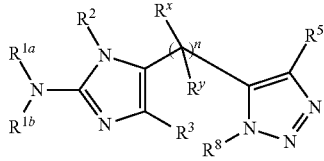

(I)(a)(2)

wherein:

$R^{1a}, R^{1b}, R^2, R^3, R^5$ and $R^8$ are each independently selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide; and each occurrence of $R^x$ and $R^y$ is present or absent (depending upon chain saturation), and is independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide; and n=0 to 20;

or a pharmaceutically acceptable salt or prodrug thereof.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

In some embodiments of Formula (I), $R^1$ is a substituted amino, A, B, F, G and D are each N, and E and H are each carbon, generally depicted by Formula (I)(b)(2):

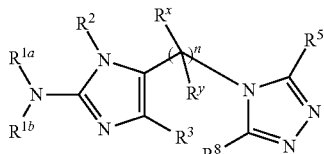

(I)(b)(2)

wherein:

$R^{1a}, R^{1b}, R^2, R^3, R^5$ and $R^8$ are each independently selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide;

each occurrence of $R^x$ and $R^y$ is present or absent (depending upon chain saturation), and is independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide; and n=0 to 20;

or a pharmaceutically acceptable salt or prodrug thereof.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

Active compounds further include compounds of Formula (I)(i):

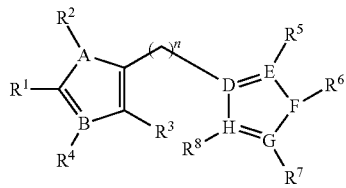

(I)(i)

wherein:

$R^1, R^2, R^3, R^4, R^5, R^6, R^7$ and $R^8$ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

A, B, D, E, F, G and H are each independently selected from carbon, N, S and O, wherein at least one of D, E, F, G and H is carbon; and n=0 to 20, saturated or unsaturated;

or a pharmaceutically acceptable salt or prodrug thereof.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

As will be appreciated by those of skill in the art, a given substituent ($R^1$-$R^8$) may be present or absent depending upon the valence requirement of the atom or atoms to which the substituent binds (e.g., carbon versus nitrogen).

In some embodiments of Formula (I)(i), $R^1$ is a substituted amino; $R^2, R^3, R^4, R^5, R^7$ and $R^8$=H; A, B, F, G and H are each N, and D and E are each carbon, generally depicted by Formula (I)(i)(a):

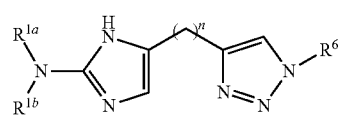

(I)(i)(a)

wherein:

$R^6$ is selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide; and n=0 to 20, saturated or unsaturated;

or a pharmaceutically acceptable salt or prodrug thereof.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

Active compounds also include compounds of Formula (II):

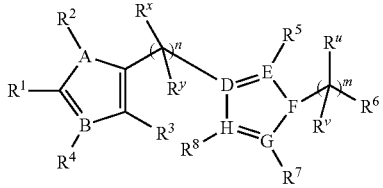

wherein:

$R^1$, $R^2$, $R^3$, $R^4$, $R^5$, $R^6$, $R^7$ and $R^8$ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

each occurrence of $R^x$, $R^y$, $R^u$ and $R^v$ is present or absent (depending upon chain saturation), and is independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

A, B, D, E, F, G and H are each independently selected from carbon, N, S and O, wherein at least one of D, E, F, G and H is carbon; and n=0 to 20; and m=0 to 20;

or a pharmaceutically acceptable salt or prodrug thereof. This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

As will be appreciated by those of skill in the art, a given substituent ($R^1$-$R^8$) may be present or absent depending upon the valence requirement of the atom or atoms to which the substituent binds (e.g., carbon versus nitrogen).

In some embodiments of Formula (II), $R^1$ is a substituted amino, A, B, F, G and H are each N, and D and E are each carbon, generally depicted by Formula (II)(a):

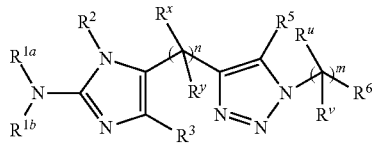

wherein:

$R^{1a}$, $R^{1b}$, $R^2$, $R^3$, $R^5$ and $R^6$ are each independently selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide;

each occurrence of $R^x$, $R^y$, $R^u$ and $R^v$ is present or absent (depending upon chain saturation), and is independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

n=0 to 20; and m=0 to 20;

or a pharmaceutically acceptable salt or prodrug thereof. This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

In some embodiments of Formula (II)(a), $R^{1a}$, $R^{1b}$, $R^2$, $R^3$ and $R^5$ are each H and $R^6$ is phenyl, examples of which include, but are not limited to, the following exemplary Formulas. Each occurrence of $R^x$, $R^y$, $R^u$ and $R^v$ present is H unless otherwise indicated.

Formulas (II)(a)(1)(A)-(II)(a)(1)(D), wherein n=1:

m = 1:

(II)(a)(1)(A)

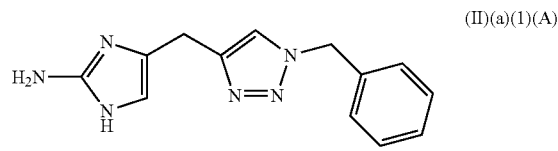

m = 2:

(II)(a)(1)(B)

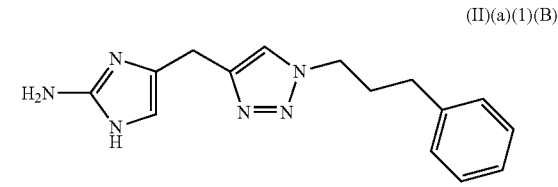

m = 3:

(II)(a)(1)(C)

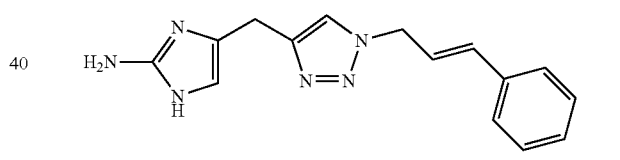

m = 3, $R^u$ = methyl at C2

(II)(a)(1)(D)

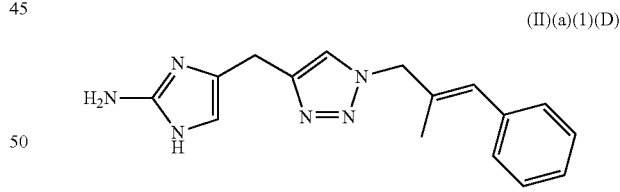

Formulas (II)(a)(2)(A)-(II)(a)(2)(D), wherein n=2:

m = 1:

(II)(a)(2)(A)

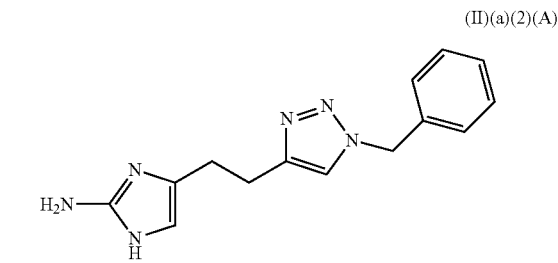

m = 2:

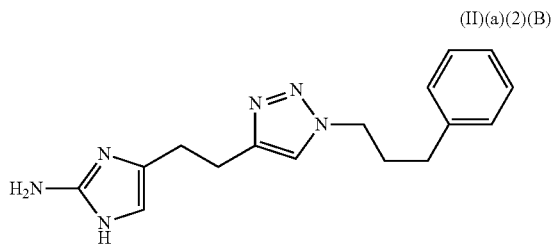
(II)(a)(2)(B)

m = 3:

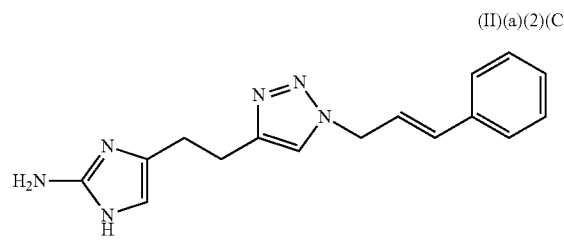
(II)(a)(2)(C)

m = 3, R$^u$ = methyl at C2:

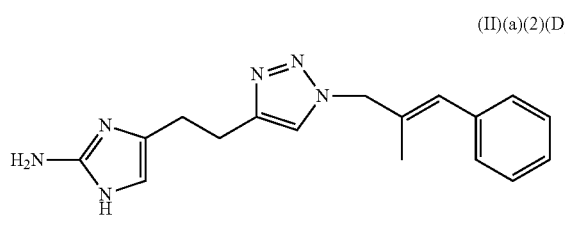
(II)(a)(2)(D)

Formulas (II)(a)(3)(A)-(II)(a)(3)(D), wherein n=3:

m = 1:

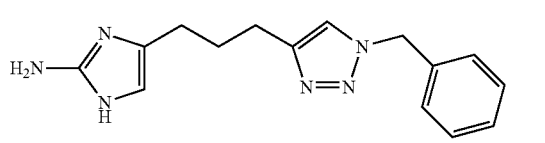
(II)(a)(3)(A)

m = 2:

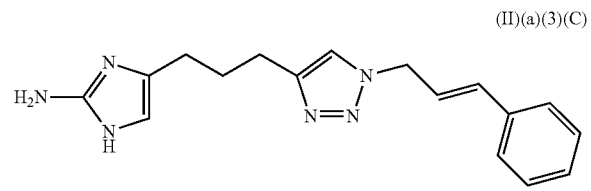
(II)(a)(3)(B)

m = 3:

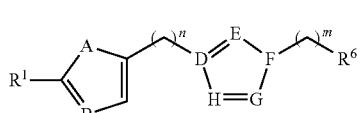
(II)(a)(3)(C)

m = 3, R$^u$ = methyl at C2:

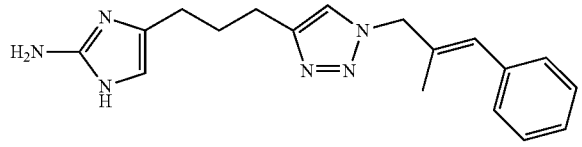
(II)(a)(3)(D)

Formula (II)(a)(4)(D), wherein n=4; m=3, R$^u$=methyl at C2:

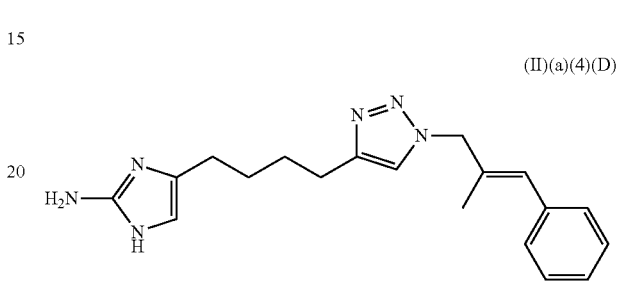
(II)(a)(4)(D)

Formula (II)(a)(5)(D), wherein n=5; m=3, R$^u$=methyl at C2:

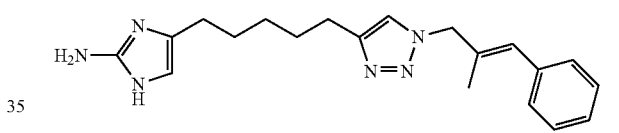
(II)(a)(5)(D)

Formula (II)(a)(6)(D), wherein n=6; m=3, R$^u$=methyl at C2:

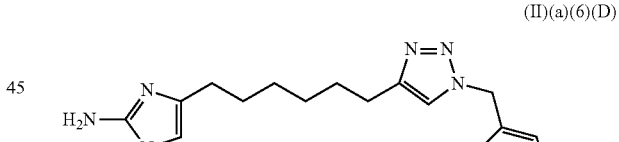
(II)(a)(6)(D)

Active compounds further include compounds of Formula (II)(i):

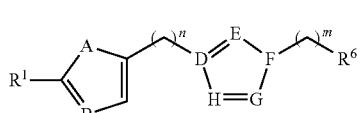
(II)(i)

wherein:

R$^1$ and R$^6$ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

A, B, D, E, F, G and H are each independently selected from carbon, N, S and O, wherein at least one of D, E, F, G and H is carbon;

n=0 to 20, saturated or unsaturated; and m=0 to 20, saturated or unsaturated;

or a pharmaceutically acceptable salt or prodrug thereof.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

In some embodiments of Formula (II)(i), $R^1$ is a substituted amino, A, B, F, G and H are each N, and D and E are each carbon, generally depicted by Formula (II)(i)(a):

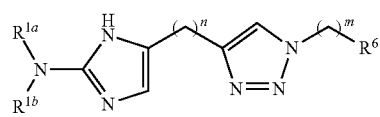
(II)(i)(a)

wherein:

$R^{1a}$, $R^{1b}$ and $R^6$ are each independently selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide;

n=0 to 20, saturated or unsaturated; and m=0 to 20, saturated or unsaturated;

or a pharmaceutically acceptable salt or prodrug thereof.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

In some embodiments of Formula (II)(i)(a), $R^{1a}$ and $R^{1b}$ are each H, and $R^6$ is heteroaryl, examples of which include, but are not limited to, the following exemplary Formulas:

Formulas (II)(i)(a)(1)(E)-(II)(i)(a)(1)(L), wherein n=1:

m = 1; $R^4$ is thiophenyl:

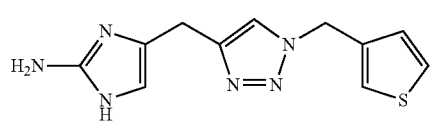
(II)(i)(a)(1)(E)

m = 2; $R^4$ is thiophenyl:

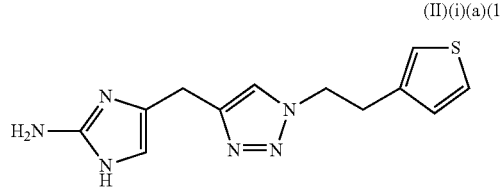
(II)(i)(a)(1)(F)

m = 1; $R^4$ is furyl:

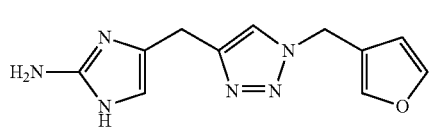
(II)(i)(a)(1)(G)

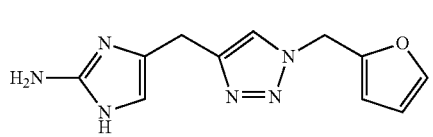
(II)(i)(a)(1)(H)

m = 1; $R^4$ is indolyl:

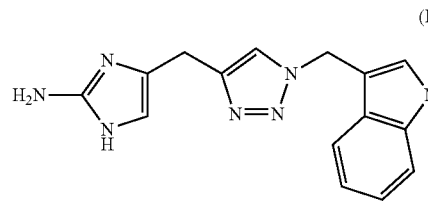
(II)(i)(a)(1)(I)

m = 2; $R^4$ is indolyl:

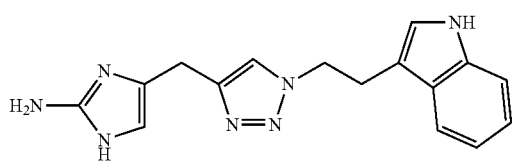
(II)(i)(a)(1)(J)

m = 1; $R^4$ is benzimidazolyl:

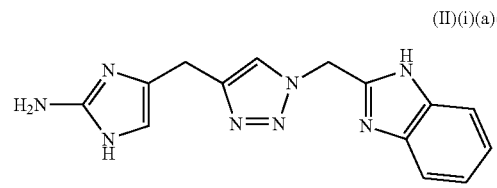
(II)(i)(a)(1)(K)

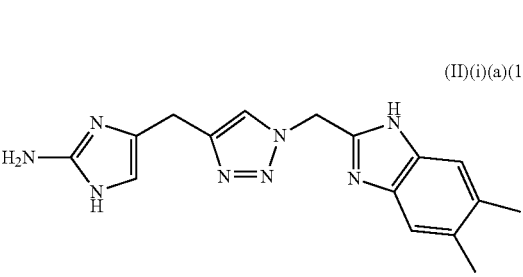
(II)(i)(a)(1)(L)

Further embodiments include Formulas (II)(i)(a)(2)(E)-(II)(i)(a)(2)(L), wherein n=2; Formulas (II)(i)(a)(3)(E)-(II)(i)(a)(3)(L), wherein n=3; Formulas (II)(i)(a)(4)(E)-(II)(i)(a)(4)(L), wherein n=4; Formulas (II)(i)(a)(5)(E)-(II)(i)(a)(5)(L), wherein n=5; Formulas (II)(i)(a)(6)(E)-(II)(i)(a)(6)(L), wherein n=6; and so on.

These formulas may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

Also provided are compounds of Formula (III):

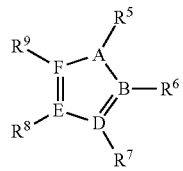

(III)

wherein:

$R^5$, $R^6$, $R^7$, $R^8$ and $R^9$ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide; and A, B, D, E and F are each independently selected from carbon, N, S and O, wherein at least one of A, B, D, E and F is carbon;

or a pharmaceutically acceptable salt or prodrug thereof.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

As will be appreciated by those of skill in the art, a given substituent ($R^5$-$R^9$) may be present or absent depending upon the valence requirement of the atom or atoms to which the substituent binds (e.g., carbon versus nitrogen).

In some embodiments of Formula (III), B, D and E are each N, and A and F are each carbon, generally depicted as Formula (III)(a):

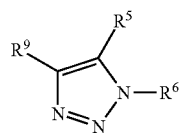

(III)(a)

wherein:

$R^5$, $R^6$ and $R^9$ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

or a pharmaceutically acceptable salt or prodrug thereof.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

In some embodiments of Formula (III), A, D and E are each N, and B and F are each carbon, generally depicted as Formula (III)(b):

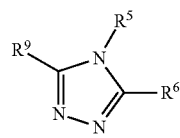

(III)(b)

wherein:

$R^5$, $R^6$ and $R^9$ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone; sulfoxide, oxo, oxy, nitro, carbonyl, carboxy, amino acid sidechain, amino acid and peptide; and or a pharmaceutically acceptable salt or prodrug thereof.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

In some embodiments of Formula (III)(b), $R^6$ and $R^9$ are each H, generally depicted by Formula (III)(b)(i):

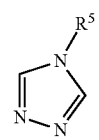

(III)(b)(i)

wherein:

$R^5$ is selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide; and or a pharmaceutically acceptable salt or prodrug thereof.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

In some embodiments of Formula (III)(b), $R^5$ and $R^6$ are each H, generally depicted by Formula (III)(b)(ii):

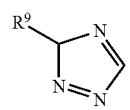

(III)(b)(ii)

wherein:

$R^9$ is selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide; and or a pharmaceutically acceptable salt or prodrug thereof.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

Active compounds for carrying out the present invention include compounds of Formula (IV):

$$(IV)$$

wherein:

$R^1$, $R^2$, $R^3$, $R^4$, $R^5$, $R^6$, $R^7$ and $R^8$ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

each occurrence of $R^x$, $R^y$, $R^u$, $R^v$, $R^z$ and $R^w$ is present or absent (depending upon chain saturation), and is independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

A, B, D, E, F, G and H are each independently selected from carbon, N, S and O, wherein at least one of D, E, F, G and H is carbon; and n=0 to 20;

m=0 to 20; and p=0 to 20 or a pharmaceutically acceptable salt or prodrug thereof. This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

As will be appreciated by those of skill in the art, a given substituent ($R^1$-$R^8$) may be present or absent depending upon the valence requirement of the atom or atoms to which the substituent binds (e.g., carbon versus nitrogen).

In some embodiments of Formula (IV), $R^1$ is a substituted amino, A, B, F, G and H are each N, and D and E are each carbon, generally depicted by Formula (IV)(a):

$$(IV)(a)$$

wherein:

$R^{1a}$, $R^{1b}$, $R^2$, $R^3$, $R^5$ and $R^6$ are each independently selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide;

each occurrence of $R^x$, $R^y$, $R^u$, $R^v$, $R^z$ and $R^w$ is present or absent (depending upon chain saturation), and is independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

n=0 to 20;

m=0 to 20; and p=0 to 20 or a pharmaceutically acceptable salt or prodrug thereof. This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

Active compounds further include compounds of Formula (IV)(i):

$$(IV)(i)$$

wherein:

$R^1$ and $R^6$ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

A, B, D, E, F, G and H are each independently selected from carbon, N, S and O, wherein at least one of D, E, F, G and H is carbon;

n=0 to 20, saturated or unsaturated;

m=0 to 20, saturated or unsaturated; and p=0 to 20, saturated or unsaturated;

or a pharmaceutically acceptable salt or prodrug thereof. This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

In some embodiments of Formula (IV)(i), $R^1$ is a substituted amino, A, B, F, G and H are each N, and D and E are each carbon, generally depicted by Formula (IV)(i)(a):

$$(IV)(i)(a)$$

wherein:

$R^{1a}$, $R^{1b}$ and $R^6$ are each independently selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide;

n=0 to 20, saturated or unsaturated;

m=0 to 20, saturated or unsaturated; and p=0 to 20, saturated or unsaturated;

or a pharmaceutically acceptable salt or prodrug thereof.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

In some embodiments of Formula (IV)(i)(a), $R^{1a}$, $R^{1b}$ and $R^6$ are each H, examples of which include, but are not limited to, the following exemplary Formulas, in which n=5 and m=2:

In some embodiments, $R^6$ is a group:

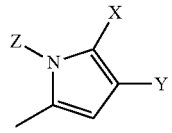

(i)

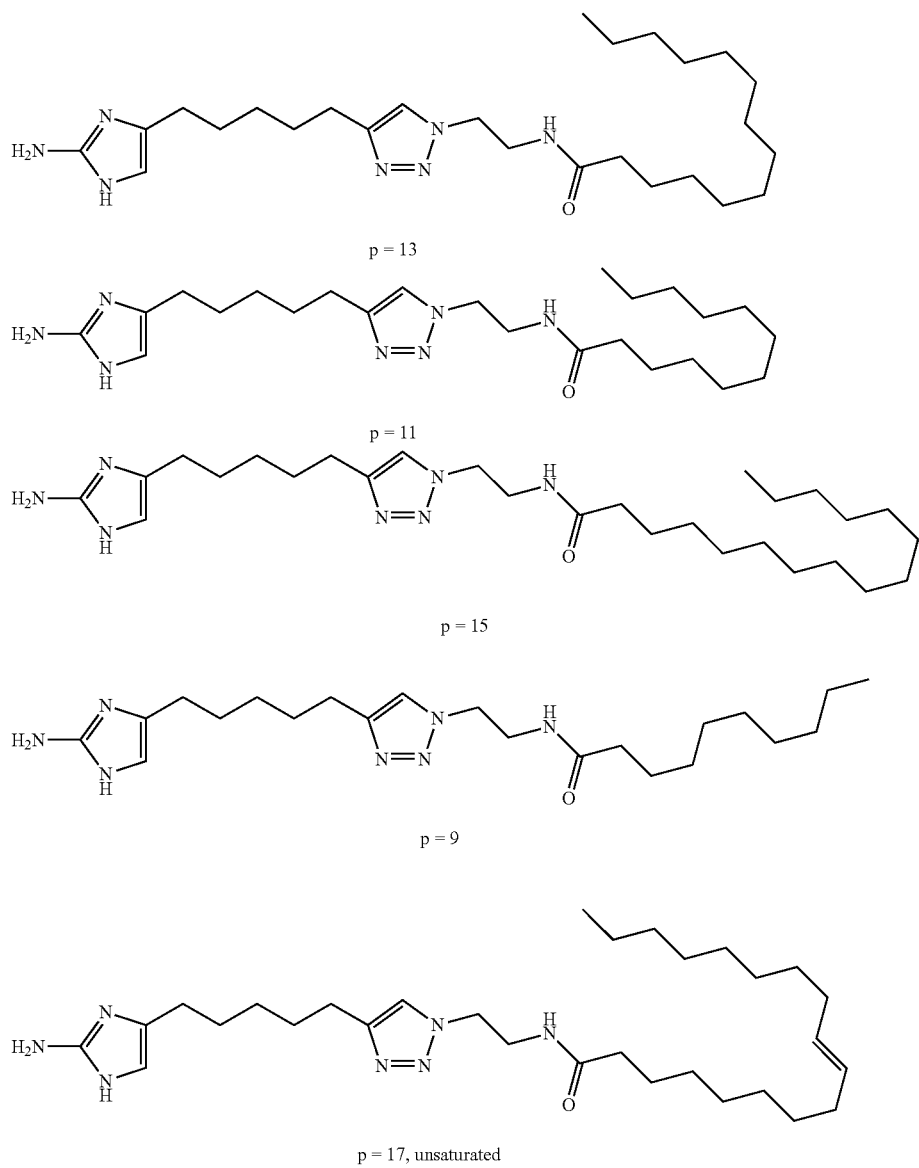

In some embodiments, $R^6$ is aryl or heteroaryl, e.g.:

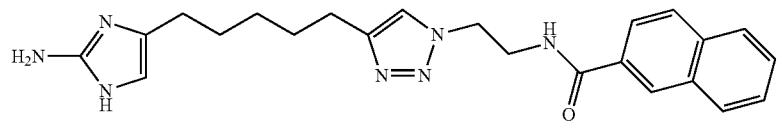

wherein:

X, Y and Z are each independently selected from the group consisting of: H, methyl, Br and Cl. Examples include, but are not limited to, the following exemplary Formulas:

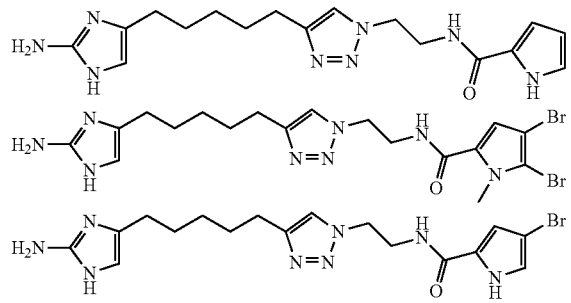

In some embodiments, $R^6$ is a group:

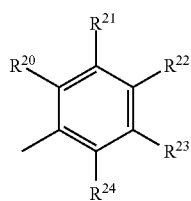

(ii)

wherein:

$R^{20}$, $R^{21}$, $R^{22}$ and $R^{23}$ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide. Examples include, but are not limited to, the following exemplary Formulas:

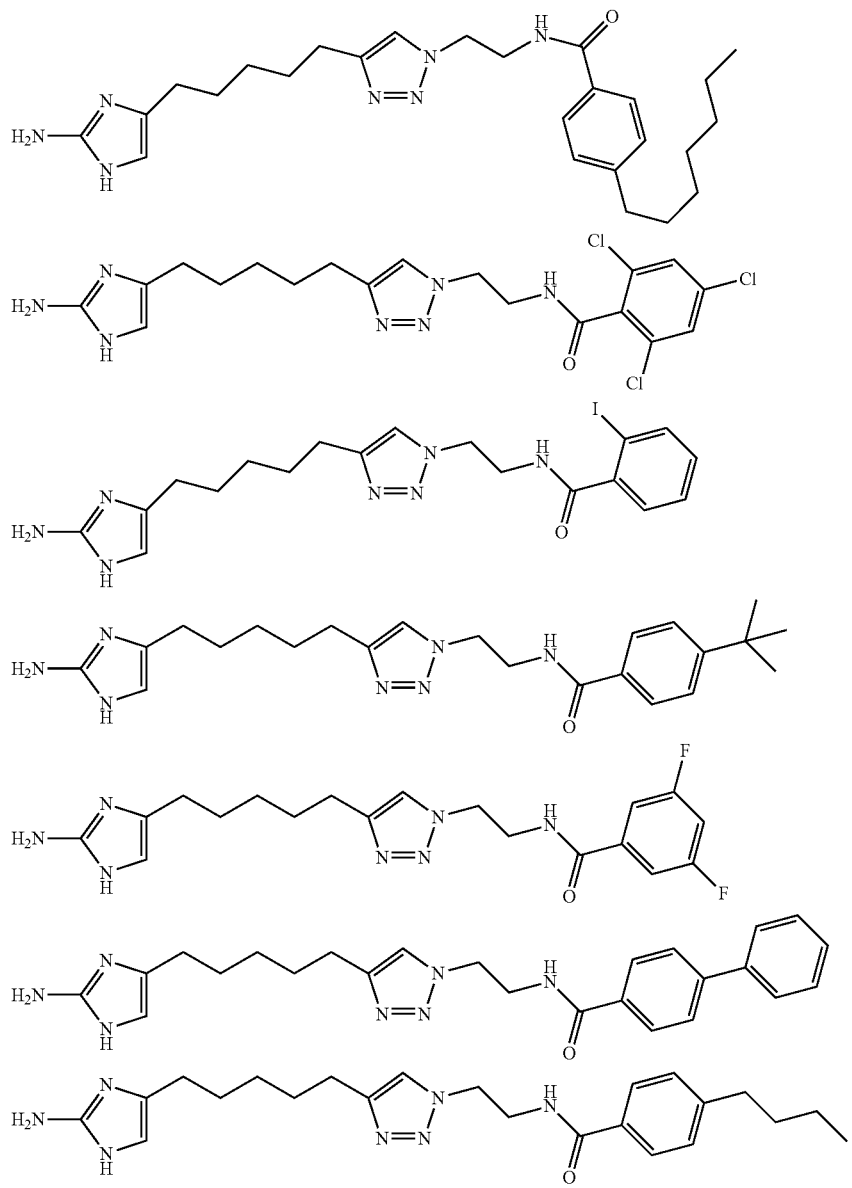

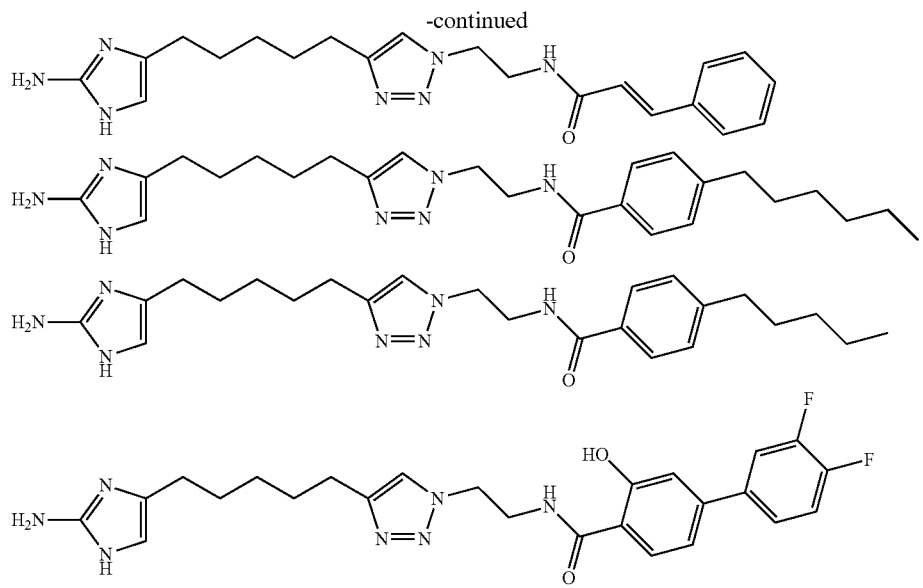

These formulas may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

Active compounds for carrying out the present invention include compounds of Formula (V):

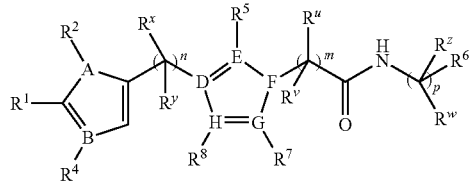

wherein:

$R^1$, $R^2$, $R^3$, $R^4$, $R^5$, $R^6$, $R^7$ and $R^8$ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

each occurrence of $R^x$, $R^y$, $R^u$, $R^v$, $R^z$ and $R^w$ is present or absent (depending upon chain saturation), and is independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

A, B, D, E, F, G and H are each independently selected from carbon, N, S and O, wherein at least one of D, E, F, G and H is carbon; and n=0 to 20;
m=0 to 20; and
p=0 to 20 or a pharmaceutically acceptable salt or prodrug thereof. This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

As will be appreciated by those of skill in the art, a given substituent ($R^1$-$R^8$) may be present or absent depending upon the valence requirement of the atom or atoms to which the substituent binds (e.g., carbon versus nitrogen).

In some embodiments of Formula (V), $R^1$ is a substituted amino, A, B, F, G and H are each N, and D and E are each carbon, generally depicted by Formula (V)(a):

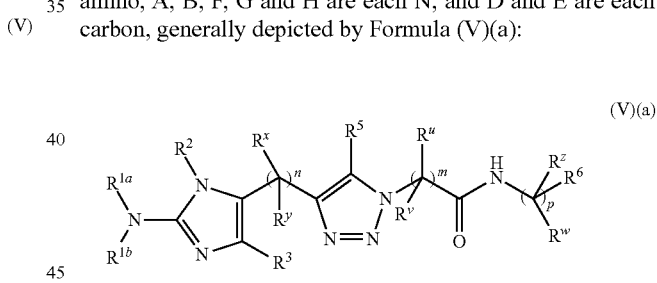

wherein:

$R^{1a}$, $R^{1b}$, $R^2$, $R^3$, $R^5$ and $R^6$ are each independently selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide;

each occurrence of $R^x$, $R^y$, $R^u$, $R^v$, $R^z$ and $R^w$ is present or absent (depending upon chain saturation), and is independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

n=0 to 20;
m=0 to 20; and
p=0 to 20 or a pharmaceutically acceptable salt or prodrug thereof. This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

Active compounds further include compounds of Formula (V)(i):

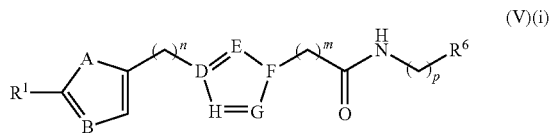

(V)(i)

wherein:

R$^1$ and R$^6$ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

A, B, D, E, F, G and H are each independently selected from carbon, N, S and O, wherein at least one of D, E, F, G and H is carbon;

n=0 to 20, saturated or unsaturated;

m=0 to 20, saturated or unsaturated; and p=0 to 20, saturated or unsaturated;

or a pharmaceutically acceptable salt or prodrug thereof.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

In some embodiments of Formula (V)(i), R$^1$ is a substituted amino, A, B, F, G and H are each N, and D and E are each carbon, generally depicted by Formula (V)(i)(a):

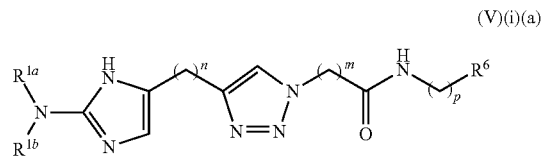

(V)(i)(a)

wherein:

R$^{1a}$, R$^{1b}$ and R$^6$ are each independently selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide;

n=0 to 20, saturated or unsaturated;

m=0 to 20, saturated or unsaturated; and p=0 to 20, saturated or unsaturated;

or a pharmaceutically acceptable salt or prodrug thereof.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

In some embodiments of Formula (V)(i)(a), R$^{1a}$, R$^{1b}$ and R$^6$ are each H, alkyl, cycloalkyl or heterocyclo, examples of which include, but are not limited to, the following exemplary Formulas:

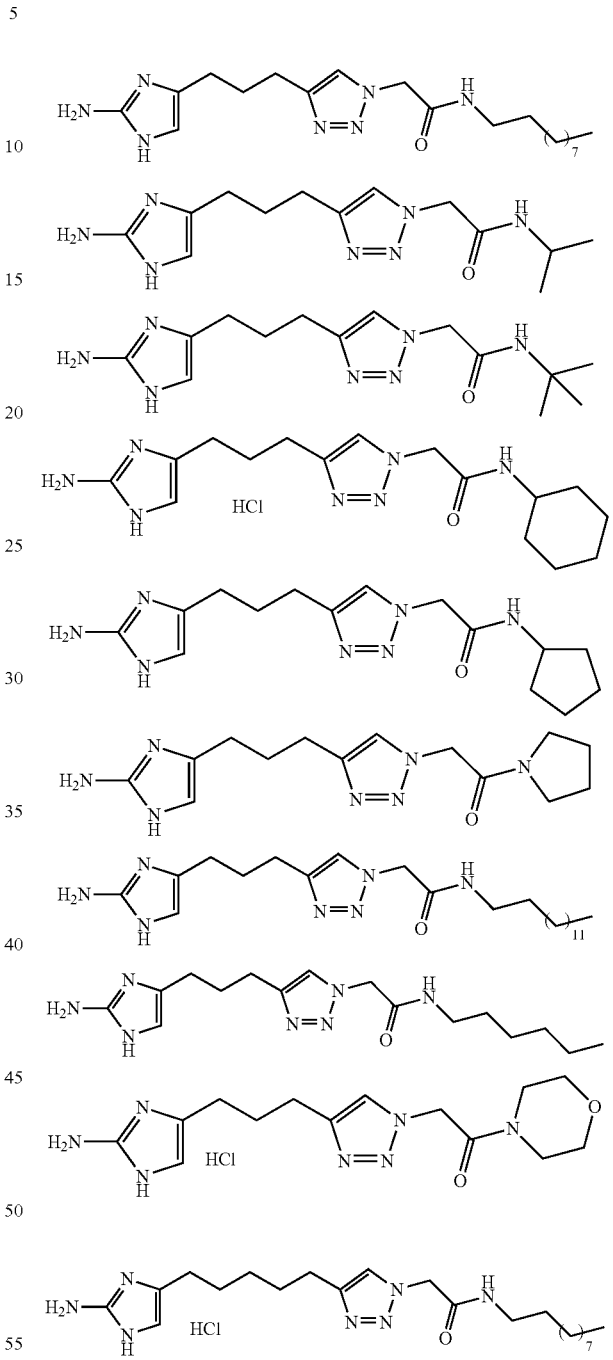

These formulas may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

In some embodiments of Formula (V)(i)(a), R$^{1a}$ and R$^{1b}$ are each H, and R$^6$ is aryl, examples of which include, but are not limited to, the following exemplary Formulas:

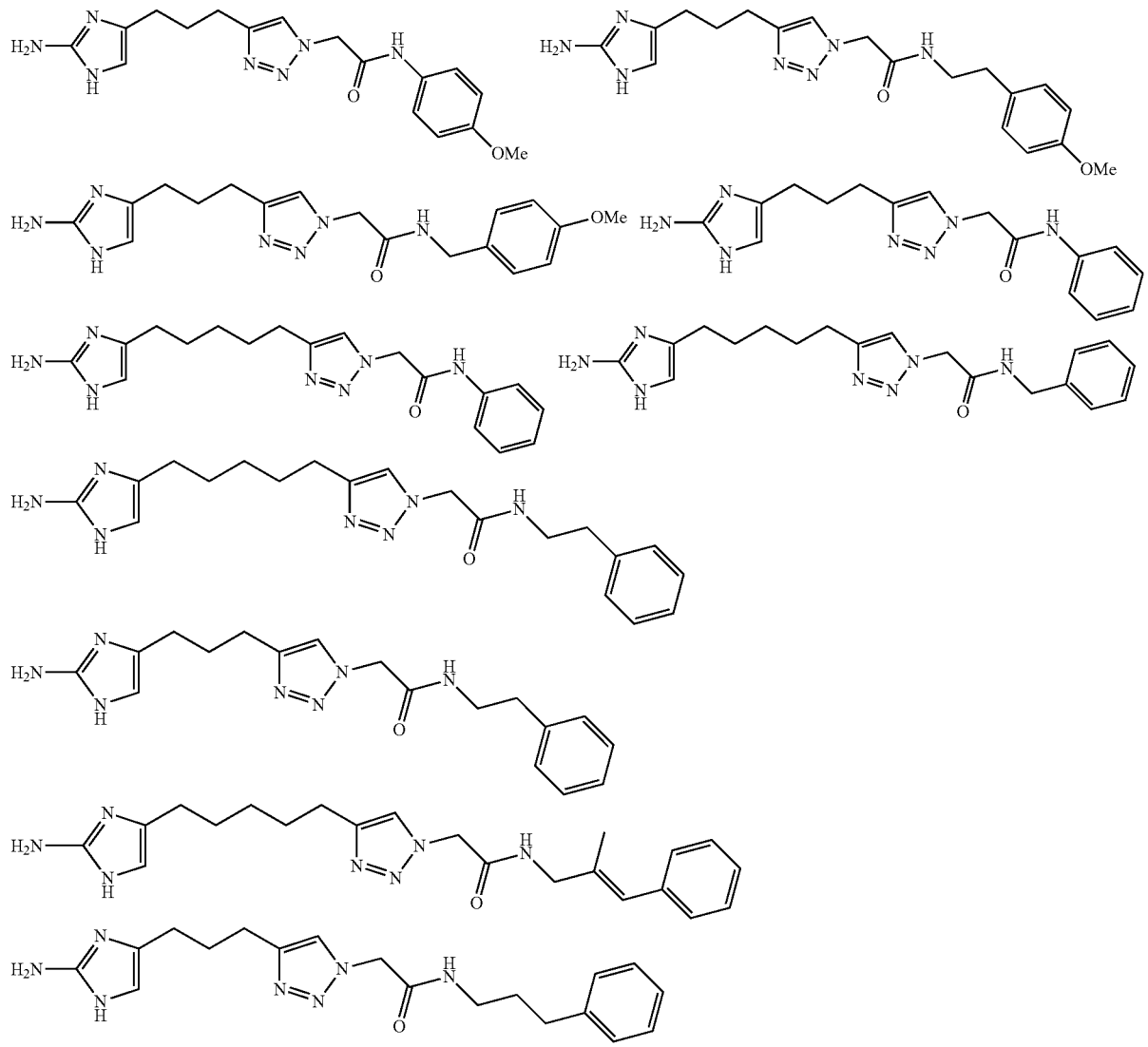

These formulas may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

Active compounds for carrying out the present invention also include compounds of Formula (VI):

(VI)

wherein:

$R^1$, $R^2$, $R^3$, $R^4$, $R^5$, $R^6$, $R^7$ and $R^8$ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

each occurrence of $R^x$, $R^y$, $R^u$, $R^v$, $R^z$ and $R^w$ is present or absent (depending upon chain saturation), and is independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

A, B, D, E, F, G and H are each independently selected from carbon, N, S and O, wherein at least one of D, E, F, G and H is carbon; and n=0 to 20;

m=0 to 20; and p=0 to 20;

or a pharmaceutically acceptable salt or prodrug thereof.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

As will be appreciated by those of skill in the art, a given substituent ($R^1$-$R^8$) may be present or absent depending upon the valence requirement of the atom or atoms to which the substituent binds (e.g., carbon versus nitrogen).

In some embodiments of Formula (VI), R is a substituted amino, A, B, F, G and H are each N, and D and E are each carbon, generally depicted by Formula (VI)(a):

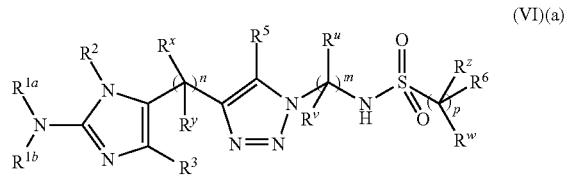

wherein:
$R^{1a}$, $R^{1b}$, $R^2$, $R^3$, $R^5$ and $R^6$ are each independently selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide;

each occurrence of $R^x$, $R^y$, $R^u$, $R^v$, $R^z$ and $R^w$ is present or absent (depending upon chain saturation), and is independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

n=0 to 20;
m=0 to 20; and
p=0 to 20;
or a pharmaceutically acceptable salt or prodrug thereof.
This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

Active compounds further include compounds of Formula (VI)(i):

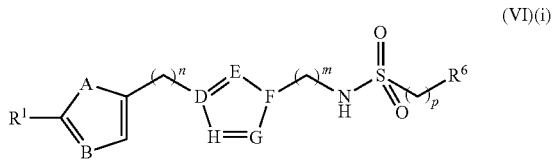

wherein:
$R^1$ and $R^6$ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

A, B, D, E, F, G and H are each independently selected from carbon, N, S and O, wherein at least one of D, E, F, G and H is carbon;

n=0 to 20, saturated or unsaturated;
m=0 to 20, saturated or unsaturated; and
p=0 to 20, saturated or unsaturated;
or a pharmaceutically acceptable salt or prodrug thereof.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

In some embodiments of Formula (VI)(i), $R^1$ is a substituted amino, A, B, F, G and H are each N, and D and E are each carbon, generally depicted by Formula (VI)(i)(a):

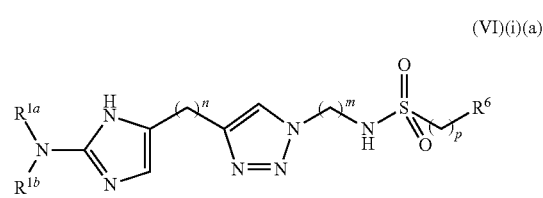

wherein:
$R^{1a}$, $R^{1b}$ and $R^6$ are each independently selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide;

n=0 to 20, saturated or unsaturated;
m=0 to 20, saturated or unsaturated; and
p=0 to 20, saturated or unsaturated;
or a pharmaceutically acceptable salt or prodrug thereof.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

In some embodiments of Formula (VI)(i)(a), $R^{1a}$ and $R^{1b}$ are each H, and $R^6$ is aryl or heteroaryl, examples of which include, but are not limited to, the following exemplary Formulas:

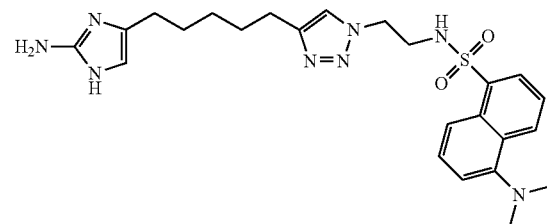

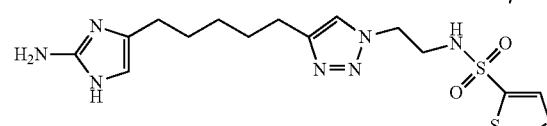

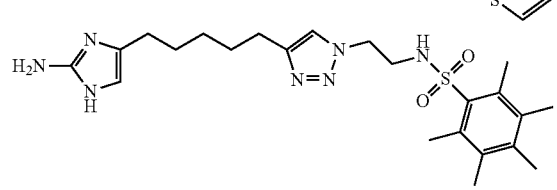

-continued

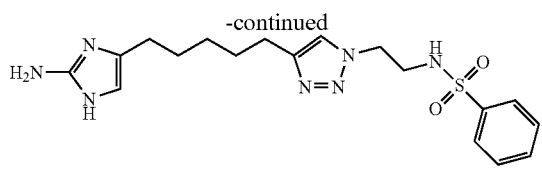

These formulas may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

C. Compositions

In some embodiments, biofilm preventing, removing or inhibiting compositions are provided, comprising a carrier and an effective amount of active compound. "Biofilm" or "biofilms" refer to communities of microorganisms that are attached to a substrate. The microorganisms often excrete a protective and adhesive matrix of polymeric compounds. They often have structural heterogeneity, genetic diversity, and complex community interactions. "Biofilm preventing", "biofilm removing", "biofilm inhibiting", "biofilm reducing", "biofilm resistant", "biofilm controlling" or "antifouling" refer to prevention of biofilm formation, inhibition of the establishment or growth of a biofilm, or decrease in the amount of organisms that attach and/or grow upon a substrate, up to and including the complete removal of the biofilm. As used herein, a "substrate" can include any living or nonliving structure. For example, biofilms often grow on synthetic materials submerged in an aqueous solution or exposed to humid air, but they also can form as floating mats on a liquid surface, in which case the microorganisms are adhering to each other or to the adhesive matrix characteristic of a biofilm. An "effective amount" of a biofilm preventing, removing or inhibiting composition is that amount which is necessary to carry out the composition's function of preventing, removing or inhibiting a biofilm.

In some embodiments, the carrier is a pharmaceutically acceptable carrier. A "pharmaceutically acceptable carrier" as used herein refers to a carrier that, when combined with an active compound of the present invention, facilitates the application or administration of that active compound for its intended purpose to prevent or inhibit biofilm formation, or remove an existing biofilm. The active compounds may be formulated for administration in a pharmaceutically acceptable carrier in accordance with known techniques. See, e.g., Remington, *The Science And Practice of Pharmacy* (9th Ed. 1995). The pharmaceutically acceptable carrier must, of course, also be acceptable in the sense of being compatible with any other ingredients in the composition. The carrier may be a solid or a liquid, or both, and is preferably formulated with the compound as a unit-dose composition, for example, a tablet, which may contain from 0.01 or 0.5% to 95% or 99% by weight of the active compound. One or more active compounds may be included in the compositions of the invention, which may be prepared by any of the well-known techniques of pharmacy comprising admixing the components, optionally including one or more accessory ingredients.

In general, compositions may be prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

The compositions of the invention include those suitable for oral, rectal, topical, buccal (e.g., sub-lingual), vaginal, parenteral (e.g., subcutaneous, intramuscular, intradermal, or intravenous), topical (i.e., both skin and mucosal surfaces, including airway surfaces) and transdermal administration, although the most suitable route in any given case will depend on the nature and severity of the condition being treated and on the nature of the particular active compound that is being used. Preferred routes of parenteral administration include intrathecal injection and intraventricular injection into a ventricle of the brain.

Compositions suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such compositions may be prepared by any suitable method of pharmacy, which includes the step of bringing into association the active compound and a suitable carrier (which may contain one or more accessory ingredients as noted above).

Compositions suitable for buccal (sub-lingual) administration include lozenges comprising the active compound in a flavored base, usually sucrose and acacia or tragacanth; and pastilles comprising the compound in an inert base such as gelatin and glycerin or sucrose and acacia.

Compositions of the present invention suitable for parenteral administration comprise sterile aqueous and non-aqueous injection solutions of the active compound, which preparations are preferably isotonic with the blood of the intended recipient. These preparations may contain anti-oxidants, buffers, bacteriostats and solutes that render the composition isotonic with the blood of the intended recipient. Aqueous and non-aqueous sterile suspensions may include suspending agents and thickening agents. The compositions may be presented in unit/dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described.

For example, in one aspect of the present invention, there is provided an injectable, stable, sterile composition comprising a compound of Formula (I), Formula (II) or Formula (III), or a salt or prodrug thereof, in a unit dosage form in a sealed container. The compound or salt is provided in the form of a lyophilizate that is capable of being reconstituted with a suitable pharmaceutically acceptable carrier to form a liquid composition suitable for injection thereof into a subject. The unit dosage form typically comprises from about 10 mg to about 10 grams of the compound or salt. When the compound or salt is substantially water-insoluble, a sufficient amount of emulsifying agent that is physiologically acceptable may be employed in sufficient quantity to emulsify the compound or salt in an aqueous carrier. One such useful emulsifying agent is phosphatidyl choline.

Compositions suitable for rectal administration are preferably presented as unit dose suppositories. These may be prepared by mixing the active compound with one or more conventional solid carriers, for example, cocoa butter, and then shaping the resulting mixture.

Compositions suitable for topical application to the skin preferably take the form of an ointment, cream, lotion, paste, gel, spray, aerosol, or oil. Carriers that may be used include petroleum jelly, lanoline, polyethylene glycols, alcohols, transdermal enhancers, and combinations of two or more thereof.

Compositions suitable for transdermal administration may be presented as discrete patches adapted to remain in intimate contact with the epidermis of the recipient for a prolonged period of time. Compositions suitable for transdermal administration may also be delivered by iontophoresis (see, for example, *Pharmaceutical Research* 3 (6):318 (1986)) and typically take the form of an optionally buffered aqueous solution of the active compound.

Also provided in some embodiments are compositions comprising an active compound and a biocide. A "biocide" as used herein refers to a substance with the ability to kill or to inhibit the growth of microorganisms (e.g., bacteria, fungal cells, protozoa, etc.), which substance is not an active compound give above in Section B. Common biocides include oxidizing and non-oxidizing chemicals. Examples of oxidizing biocides include chlorine, chlorine dioxide, and ozone. Examples of non-oxidizing biocides include quaternary ammonium compounds, formaldehyde, and anionic and non-anionic surface agents. Chlorine is the most common biocide used in sanitizing water systems.

An "antibiotic" as used herein is a type of "biocide." Common antibiotics include aminoglycosides, carbacephems (e.g., loracarbef), carbapenems, cephalosporins, glycopeptides (e.g., teicoplanin and vancomycin), macrolides, monobactams (e.g., aztreonam) penicillins, polypeptides (e.g., bacitracin, colistin, polymyxin B), quinolones, sulfonamides, tetracyclines, etc. Antibiotics treat infections by either killing or preventing the growth of microorganisms. Many act to inhibit cell wall synthesis or other vital protein synthesis of the microorganisms.

Aminoglycosides are commonly used to treat infections caused by Gram-negative bacteria such as *Escherichia coli* and *Klebsiella*, particularly *Pseudomonas aeroginosa*. Examples of aminoglycosides include, but are not limited to amikacin, gentamicin, kanamycin, neomycin, netilmicin, streptomycin, tobramycin, and paromomycin.

Carbapenems are broad-spectrum antibiotics, and include, but are not limited to, ertapenem, doripenem, imipenem/cilstatin, and meropenem.

Cephalosporins include, but are not limited to, cefadroxil, cefazolin, cefalotin (cefalothin), cefalexin, cefaclor, cefamandole, cefoxitin, cefprozil, loracarbef, cefuroxime, cefixime, cefdinir, cefditoren, cefoperazone, cefotaxime, cefpodoxime, ceftazidime, ceftibuten, ceftizoxime, ceftriaxone, cefepime, cefpirome, and ceftobiprole.

Macrolides include, but are not limited to, azithromycin, clarithromycin, dirithromycin, erythromycin, roxithromycin, troleandomycin, telithromycin and spectinomycin.

Penicillins include, but are not limited to, amoxicillin, ampicillin, azlocillin, bacampicillin, carbenicillin, cloxacillin, dicloxacillin, flucloxacillin, mezlocillin, meticillin, nafcillin, oxacillin, penicillin, piperacillin and ticarcillin.

Quinolones include, but are not limited to, ciprofloxacin, enoxacin, gatifloxacin, gemifloxacin, levofloxacin, lomefloxacin, moxifloxacin, norfloxacin, ofloxacin and trovafloxacin.

Sulfonamides include, but are not limited to, mafenide, prontosil, sulfacetamide, sulfamethizole, sulfanilamide, sulfasalazine, sulfisoxazole, trimethoprim, and co-trimoxazole (trimethoprim-sulfamethoxazole).

Tetracyclines include, but are not limited to, demeclocycline, doxycycline, minocycline, oxytetracycline and tetracycline.

Other antibiotics include arsphenamine, chloramphenicol, clindamycin, lincomycin, ethambutol, fosfomycin, fusidic acid, furazolidone, isoniazid, linezolid, metronidazole, mupirocin, nitrofurantoin, platensimycin, pyrazinamide, quinupristin/dalfopristin, rifampin (rifampicin), tinidazole, etc.

In some embodiments, a dentifrice composition is provided comprising the active compounds. A "dentifrice" is a substance that is used to clean the teeth. It may be in the form of, e.g., a paste or powder. Commonly known dentifrices include toothpaste, mouthwash, chewing gum, dental floss, and dental cream. Other examples of dentifrices include toothpowder, mouth detergent, troches, dental or gingival massage cream, dental strips, dental gels, and gargle tablets. Examples of dentifrice compositions comprising toothpaste and mouthwash are found in U.S. Pat. Nos. 6,861,048 (Yu et al.); 6,231,836 (Takhtalian et al.); and 6,331,291 (Glace et al.); each incorporated by reference herein in their entirety.

A coating composition is also provided. A "coating" as used herein is generally known. Any of a variety of organic and aqueous coating compositions, with or without pigments, may be modified to contain biofilm inhibiting compositions as described herein, including but not limited to those described in U.S. Pat. Nos. 7,109,262, 6,964,989, 6,835,459, 6,677,035, 6,528,580, 6,235,812, etc., each incorporated by reference herein in their entirety.

In general, the coatings comprise a film-forming resin, an aqueous or organic solvent that disperses the resin; and, optionally, at least one pigment. Other ingredients such as colorants, secondary pigments, stabilizers and the like can be included if desired. However, for use in the present invention the compositions further comprise one or more biofilm inhibiting compounds as described herein, which may be carried by or dispersed in the solvent and/or resin, so that the biofilm inhibiting compounds are dispersed or distributed on the substrate an article coated. A resin may carry the biofilm inhibiting compounds through covalent attachment through means well known in the art. The resin may comprise, for example, a polymeric material. A polymeric material is a material that is comprised of large molecules made from associated smaller repeating structural units, often covalently linked. Common examples of polymeric materials are unsaturated polyester resins, and epoxy resins.

Any suitable article can be coated, in whole or in part, with a composition of the invention. Suitable articles include, but are not limited to, automobiles and airplanes (including substrates such as wing and propeller surfaces for aerodynamic testing), vessel hulls (including interior and exterior surfaces thereof), pressure vessels (including interior and exterior surfaces thereof) medical implants, windmills, etc. Coating of the article with the composition can be carried out by any suitable means, such as by brushing, spraying, electrostatic deposition, dip coating, doctor blading, etc.

D. Methods of Use

Methods of controlling biofilm formation on a substrate are disclosed, comprising the step of administering an active compound to a substrate in an amount effective to inhibit biofilm formation. A "substrate" as used herein is a base on which an organism, such as those commonly found in biofilms, may live. The term "substrate," as used herein, refers to any substrate, whether in an industrial or a medical setting, that provides or can provide an interface between an object and a fluid, permitting at least intermittent contact between the object and the fluid. A substrate, as understood herein, further provides a plane whose mechanical structure, without further treatment, is compatible with the adherence of microorganisms. Substrates compatible with biofilm formation may be natural or synthetic, and may be smooth or irregular. Fluids contacting the substrates can be stagnant or flowing, and can flow intermittently or continuously, with laminar or turbulent or mixed flows. A substrate upon which a biofilm forms can be dry at times with sporadic fluid contact, or can have any degree of fluid exposure including total immersion. Fluid contact with the substrate can take place via aerosols or other means for air-borne fluid transmission.

Biofilm formation with health implications can involve those substrates in all health-related environments, including substrates found in medical environments and those substrates in industrial or residential environments that are involved in those functions essential to human well being, for example, nutrition, sanitation and the prevention of disease. Substrates found in medical environments include the inner and outer aspects of various instruments and devices, whether disposable or intended for repeated uses. Examples include the entire spectrum of articles adapted for medical use, including scalpels, needles, scissors and other devices used in invasive surgical, therapeutic or diagnostic procedures; implantable medical devices, including artificial blood vessels, catheters and other devices for the removal or delivery of fluids to patients, artificial hearts, artificial kidneys, orthopedic pins, plates and implants; catheters and other tubes (including urological and biliary tubes, endotracheal tubes, peripherably insertable central venous catheters, dialysis catheters, long term tunneled central venous catheters, peripheral venous catheters, short term central venous catheters, arterial catheters, pulmonary catheters, Swan-Ganz catheters, urinary catheters, peritoneal catheters), urinary devices (including long term urinary devices, tissue bonding urinary devices, artificial urinary sphincters, urinary dilators), shunts (including ventricular or arterio-venous shunts); prostheses (including breast implants, penile prostheses, vascular grafting prostheses, heart valves, artificial joints, artificial larynxes, otological implants), vascular catheter ports, wound drain tubes, hydrocephalus shunts, pacemakers and implantable defibrillators, and the like. Other examples will be readily apparent to practitioners in these arts. Substrates found in the medical environment also include the inner and outer aspects of pieces of medical equipment, medical gear worn or carried by personnel in the health care setting. Such substrates can include counter tops and fixtures in areas used for medical procedures or for preparing medical apparatus, tubes and canisters used in respiratory treatments, including the administration of oxygen, of solubilized drugs in nebulizers and of anesthetic agents. Also included are those substrates intended as biological barriers to infectious organisms in medical settings, such as gloves, aprons and faceshields. Commonly used materials for biological barriers may be latex-based or non-latex based. Vinyl is commonly used as a material for non-latex surgical gloves. Other such substrates can include handles and cables for medical or dental equipment not intended to be sterile. Additionally, such substrates can include those non-sterile external substrates of tubes and other apparatus found in areas where blood or body fluids or other hazardous biomaterials are commonly encountered.

Substrates in contact with liquids are particularly prone to biofilm formation. As an example, those reservoirs and tubes used for delivering humidified oxygen to patients can bear biofilms inhabited by infectious agents. Dental unit waterlines similarly can bear biofilms on their substrates, providing a reservoir for continuing contamination of the system of flowing an aerosolized water used in dentistry. Sprays, aerosols and nebulizers are highly effective in disseminating biofilm fragments to a potential host or to another environmental site. It is especially important to health to prevent biofilm formation on those substrates from where biofilm fragments can be carried away by sprays, aerosols or nebulizers contacting the substrate.

Other substrates related to health include the inner and outer aspects of those articles involved in water purification, water storage and water delivery, and articles involved in food processing. Substrates related to health can also include the inner and outer aspects of those household articles involved in providing for nutrition, sanitation or disease prevention. Examples can include food processing equipment for home use, materials for infant care, tampons and toilet bowls. "Substrate" as used herein also refers to a living substrate, such as the inner ear of a patent.

Substrates can be smooth or porous, soft or hard. Substrates can include a drainpipe, glaze ceramic, porcelain, glass, metal, wood, chrome, plastic, vinyl, Formica® brand laminate, or any other material that may regularly come in contact with an aqueous solution in which biofilms may form and grow. The substrate can be a substrate commonly found on household items such as shower curtains or liners, upholstery, laundry, and carpeting.

A substrate on which biofilm preventing, removing or inhibiting is important is that of a ship hull. Biofilms, such as those of *Halomonas pacifica*, promote the corrosion of the hull of ships and also increase the roughness of the hull, increasing the drag on the ship and thereby increasing fuel costs. The biofilm can also promote the attachment of larger living structures such as barnacles on the ship hull. Fuel can account for half of the cost of marine shipping, and the loss in fuel efficiency due to biofilm formation is substantial.

Substrates on which biofilms can adhere include those of living organisms, as in the case of humans with chronic infections caused by biofilms, as discussed above. Biofilms can also form on the substrates of food contact surfaces, such as those used for processing seafood, and also on food products themselves. Examples of seafood products that may have biofilm contamination include oysters. Human infections caused by the ingestion of raw oysters has been linked to *Vibrio vulnificus* bacterium. *Vibrio* bacteria attach to algae and plankton in the water and transfer to the oysters and fish that feed on these organisms.

Other examples of substrates or devices on which biofilms can adhere can be found in U.S. Pat. Nos. 5,814,668 and 7,087,661; and U.S. Pat. Appln. Publication Nos. 2006/0228384 and 2006/0018945, each of which is incorporated herein by reference in its entirety.

In some embodiments, methods of enhancing the effects of a biocide are disclosed, comprising the step of administering an active compound in combination with a biocide, the active compound being administered in an amount effective to enhance the effects of the biocide.

"Administering" or "administration of" an active compound and/or biocide as used herein in inclusive of contacting, applying, etc. (e.g., contacting with an aqueous solution, contacting with a surface (e.g., a hospital surface such as a table, instrumentation, etc.)), in addition to providing to a subject (for example, to a human subject in need of treatment for a microbial infection).

"Enhancing" the effects of a biocide by administering an active compound in combination with the biocide refers to increasing the effectiveness of the biocide, such that the microorganism killing and/or growth inhibition is higher at a certain concentration of the biocide administered in combination with the active compound than without. In some embodiments, a bacteria or other microorganism is "sensitized" to the effects of a biocide, such that the bacteria or other microorganism that was resistant to the biocide prior to administering the active compound (e.g., little to none, or less than 20, 10, 5 or 1% are killed upon application) is rendered vulnerable to that biocide upon or after administering the active compound (e.g., greater than 20, 30, 40, 50, 60, 70, 80, 90, or 95% or more are killed).

As used herein, the administration of two or more compounds (inclusive of active compounds and biocides) "in combination" means that the two compounds are administered closely enough in time that the administration of or presence of one alters the biological effects of the other. The two compounds may be administered simultaneously (concurrently) or sequentially.

Simultaneous administration of the compounds may be carried out by mixing the compounds prior to administration, or by administering the compounds at the same point in time but at different anatomic sites or using different routes of administration, or administered at times sufficiently close that the results observed are indistinguishable from those achieved when the compounds are administered at the same point in time.

Sequential administration of the compounds may be carried out by administering, e.g., an active compound at some point in time prior to administration of a biocide, such that the prior administration of active compound enhances the effects of the biocide (e.g., percentage of microorganisms killed and/or slowing the growth of microorganisms). In some embodiments, an active compound is administered at some point in time prior to the initial administration of a biocide. Alternatively, the biocide may be administered at some point in time prior to the administration of an active compound, and optionally, administered again at some point in time after the administration of an active compound.

Also disclosed is a method of controlling biofilm formation wherein the biofilm comprises Gram-negative bacteria. "Gram-negative" bacteria are those that do not retain crystal violet dye after an alcohol wash in the Gram staining protocol. This is due to structural properties in the cell walls of the bacteria. Many genera and species of Gram-negative bacteria are pathogenic. Gram-negative bacteria include members of the phylum proteobacteria, which include genus members *Escherichia, Salmonella, Vibrio*, and *Helicobacter*. A "genus" is a category of biological classification ranking between the family and the species, comprising structurally or phylogenetically related species, or an isolated species exhibiting unusual differentiation. It is usually designated by a Latin or latinized capitalized singular noun. Examples of genera of biofilm-forming bacteria affected by active compounds of this invention include, but are not limited to, *Pseudomonas, Bordetella, Vibrio, Haemophilus, Halomonas*, and *Acinetobacter*. "Species" refer to a category of biological classification ranking below the genus, and comprise members that are structurally or phylogenetically related, or an isolated member exhibiting unusual differentiation. Species are commonly designated by a two-part name, which name includes the capitalized and italicized name of the genus in which the species belongs as the first word in the name, followed by the second word that more specifically identifies the member of the genus, which is not capitalized. Examples of species of bacteria capable of forming biofilms that are affected by active compounds of the present invention include *Pseudomonas aeuroginosa, Bordetella bronchiseptica, Bordetella pertussis, Staphylococcus aureus, Vibrio vulnificus, Haemophilus influenzae, Halomonas pacifica*, and *Acinetobacter baumannii*.

Other examples of Gram-negative bacteria affected by active compounds of the present invention include, but are not limited to, bacteria of the genera *Klebsiella, Proteus, Neisseria, Helicobacter, Brucella, Legionella, Campylobacter, Francisella, Pasteurella, Yersinia, Bartonella, Bacteroides, Streptobacillus, Spirillum, Moraxella* and *Shigella*.

Examples of Gram-positive bacteria affected by active compounds of the present invention include, but are not limited to, bacteria of the genera *Listeria, Staphylococcus, Streptococcus, Bacillus, Corynebacterium, Peptostreptococcus*, and *Clostridium*. Examples include, but are not limited to, *Listeria monocytogenes, Staphylococcus aureus, Streptococcus pyogenes, Streptococcus pneumoniae, Bacillus cereus, Bacillus anthracis, Clostridium botulinum, Clostridium perfringens, Clostridium difficile, Clostridium tetani, Corynebacterium diphtheriae, Corynebacterium ulcerans*, and *Peptostreptococcus anaerobius*.

Additional bacteria affected by active compounds of the present invention also include bacterial genera including, but not limited to, *Actinomyces, Propionibacterium, Nocardia* and *Streptomyces*.

A method for treating a chronic bacterial infection in a subject in need thereof is disclosed, comprising administering active compound to said subject in an amount effective to inhibit, reduce, or remove a biofilm component of said chronic bacterial infection. "Treating" as used herein refers to any type of activity that imparts a benefit to a patient afflicted with a disease, including improvement in the condition of the patient (e.g., in one or more symptoms), delay in the progression of the disease, delay in onset of the disease, etc. The present invention is primarily concerned with the treatment of human subjects, but the invention may also be carried out on animal subjects, particularly mammalian subjects (e.g., mice, rats, dogs, cats, rabbits, and horses), avian subjects (e.g., parrots, geese, quail, pheasant), livestock (e.g., pigs, sheep, goats, cows, chickens, turkey, duck, ostrich, emu), reptile and amphibian subjects, for veterinary purposes or animal husbandry, and for drug screening and drug development purposes.

A "chronic bacterial infection" is a bacterial infection that is of a long duration or frequent recurrence. For example, a chronic middle ear infection, or otitis media, can occur when the Eustachian tube becomes blocked repeatedly due to allergies, multiple infections, ear trauma, or swelling of the adenoids. The definition of "long duration" will depend upon the particular infection. For example, in the case of a chronic middle ear infection, it may last for weeks to months. Other known chronic bacterial infections include urinary tract infection (most commonly caused by *Escherichia coli* and/or *Staphylococcus saprophyticus*), gastritis (most commonly caused by *Helicobacter pylori*), respiratory infection (such as those commonly afflicting patents with cystic fibrosis, most commonly caused by *Pseudomonas aeuroginosa*), cystitis (most commonly caused by *Escherichia coli*), pyelonephritis (most commonly caused by *Proteus* species, *Escherichia coli* and/or *Pseudomonas* species), osteomyelitis (most commonly caused by *Staphylococcus aureus*, but also by *Escherichia coli*), bacteremia, skin infection, rosacea, acne, chronic wound infection, infectious kidney stones (can be caused by *Proteus mirabilis*), bacterial endocarditis, and sinus infection. A common infection afflicting pigs is atrophic rhinitis (caused by *Bordatella* species, e.g. *Bordatella bronchiseptica*, *Bordatella rhinitis*, etc.).

Various nosocomial infections that are especially prevalent in intensive care units implicate *Acinetobacter* species such as *Acinetobacter baumannii* and *Acinetobacter lwoffi*. *Acinetobacter baumanni* is a frequent cause of nosocomial pneumonia, and can also cause skin and wound infections and bacteremia. *Acinetobacter lwoffi* causes meningitis. The *Acinetobacter* species are resistant to many classes of antibiotics. The CDC has reported that bloodstream infections implicating *Acinetobacter baumanni* were becoming more prevalent among service members injured during the military action in Iraq and Afghanistan.

*Staphylococcus aureus* is a common cause of nosocomial infections, often causing post-surgical wound infections. *Staphylococcus aureus* can also cause variety of other infections in humans (e.g., skin infections), and can contribute to mastitis in dairy cows. *Staphylococcus aureus* has become resistant to many of the commonly used antibiotics.

Also disclosed is a method of clearing a preformed biofilm from a substrate comprising the step of administering an effective amount of compound to said substrate, wherein said effective amount will reduce the amount of said biofilm on said substrate. "Preformed biofilm" is a biofilm that has begun to adhere to a substrate. The biofilm may or may not yet be fully formed.

E. Devices

Medical devices comprising a substrate and an effective amount of active compound are also disclosed. "Medical device" as used herein refers to an object that is inserted or implanted in a subject or applied to a surface of a subject. Common examples of medical devices include stents, fasteners, ports, catheters, scaffolds and grafts. A "medical device substrate" can be made of a variety of biocompatible materials, including, but not limited to, metals, ceramics, polymers, gels, and fluids not normally found within the human body. Examples of polymers useful in fabricating medical devices include such polymers as silicones, rubbers, latex, plastics, polyanhydrides, polyesters, polyorthoesters, polyamides, polyacrylonitrile, polyurethanes, polyethylene, polytetrafluoroethylene, polyethylenetetraphthalate, etc. Medical devices can also be fabricated using naturally-occurring materials or treated with naturally-occurring materials. Medical devices can include any combination of artificial materials, e.g., combinations selected because of the particular characteristics of the components. Medical devices can be intended for short-term or long-term residence where they are positioned. A hip implant is intended for several decades of use, for example. By contrast, a tissue expander may only be needed for a few months, and is removed thereafter.

Some examples of medical devices are found in U.S. Pat. Nos. 7,081,133 (Chinn et al.); 6,562,295 (Neuberger); and 6,387,363 (Gruskin); each incorporated by reference herein in its entirety.

F. Covalent Coupling of Active Compounds

In some embodiments, active compounds as described herein are covalently coupled to substrates. Examples of substrates include solid supports and polymers. The polymers, typically organic polymers, may be in solid form, liquid form, dispersed or solubilized in a solvent (e.g., to form a coating composition as described above), etc. The solid support may include the substrate examples as described above to be coated with or treated with active compounds of the invention.

Covalent coupling can be carried out by any suitable technique. Active compounds of the present invention may be appended to a substrate via aldehyde condensation, amide or peptide bond, carbon-carbon bond, or any suitable technique commonly used in the art.

For example, active compounds containing a terminal alkyne can be covalently linked to a substrate containing a terminal azide via click reaction conditions as shown (with the dark bar representing the substrate):

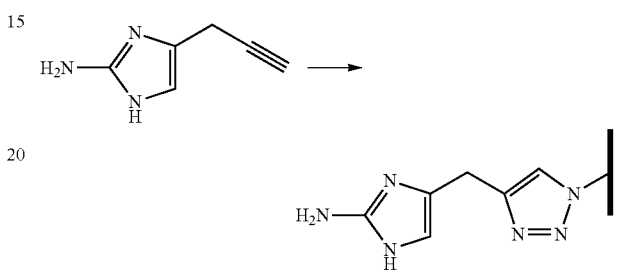

Similarly, active compounds containing a terminal azide can be covalently linked to a substrate containing a terminal alkyne employing the click reaction as shown:

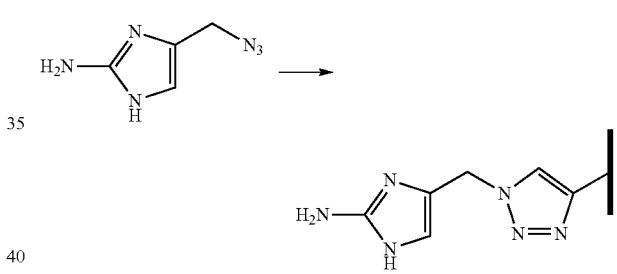

This listing of examples of reactions that can be used to append active compounds of the present invention to a substrate is not intended to be exhaustive. Those skilled in the art will readily appreciate various other methods of carrying out these teachings. See also U.S. Patent Application Publication No. 2008/0181923 to Melander et al., which is incorporated by reference herein. Further examples and explanations of these types of reactions can be found in U.S. Pat. No. 6,136,157 (Lindeberg et al.) and U.S. Pat. No. 7,115,653 (Baxter et al.), which are each hereby incorporated by reference in their entirety.

Some aspects of the present invention are described in more detail in the following non-limiting examples.

Example 1

Herein we report the development of 2-aminoimidazole/triazole conjugates that inhibit and disperse biofilms from bacteria across order and phylum without inducing bacterial death.

Our recent work has identified imidazole derivative compounds that prevent, remove, and/or inhibit the formation of biofilms, including TAGE, dihydrosventrin (DHS), and RA-11. See U.S. Patent Application Publication No. 2008/0181923 to Melander et al.

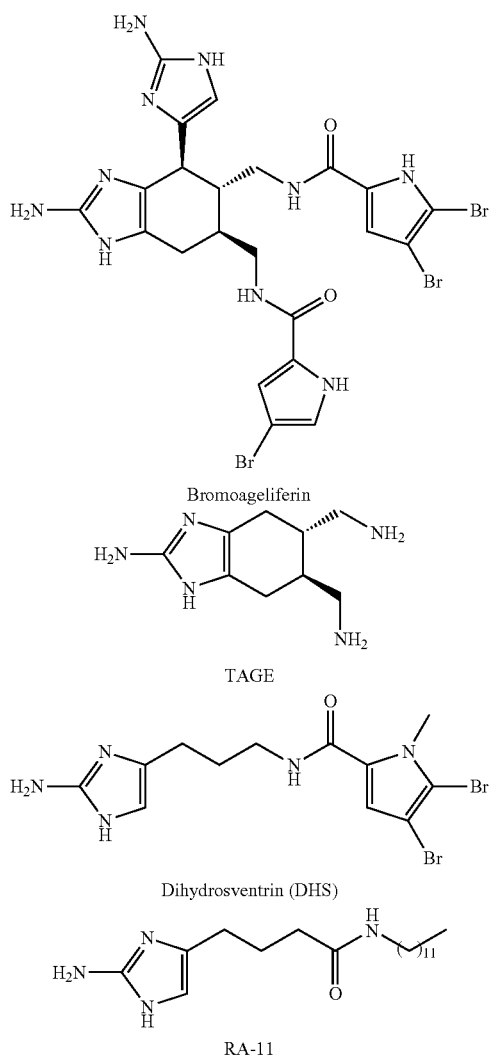

Bromoageliferin

TAGE

Dihydrosventrin (DHS)

RA-11

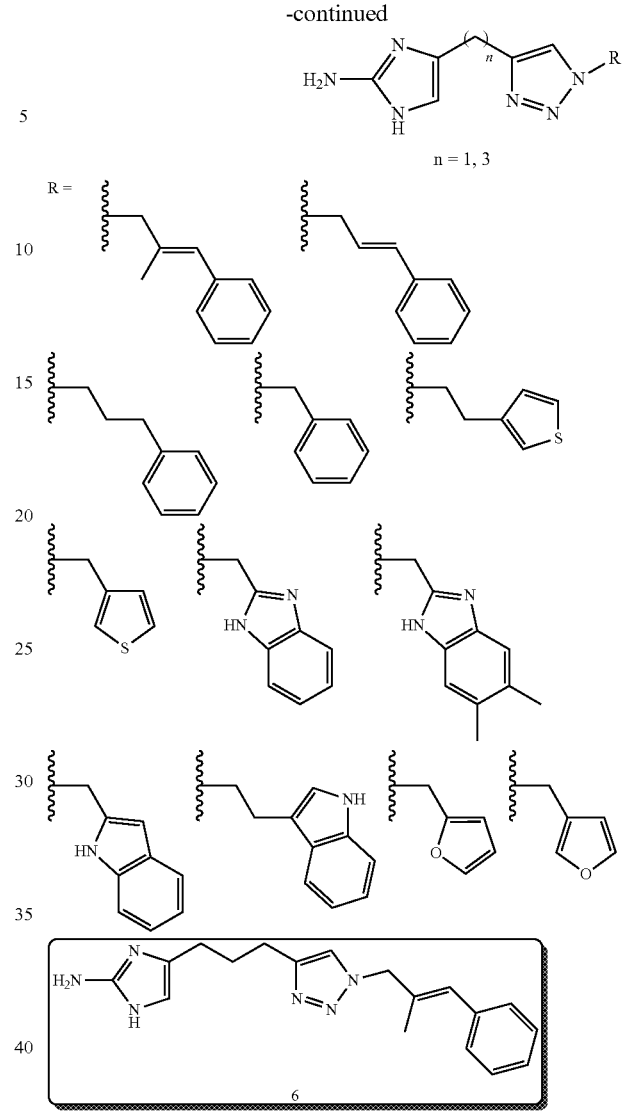

n = 1, 3

We have begun to investigate if modifications to the core DHS structure will deliver derivatives with enhanced anti-biofilm activities (J. J. Richards, T. E. Ballard, C. Melander, *Organic and Biomolecular Chemistry* 2008, 6, 1356-1363). One of the first structural variations we have studied is replacement of the pyrrole subunit with a triazole subunit.

Herein we detail the development of the synthetic protocols necessary to access 2-aminoimidazole/triazole (2-AIT) conjugates, the application of these methods to the synthesis of a focused 2-AIT library, and the discovery small molecules that inhibit and disperse bacterial biofilms across both order and phylum.

We first developed synthetic protocols necessary to access 2-AIT conjugates. There is a paucity of reactions that have been reported to be compatible with 2-aminoimidazoles. To test the applicability of the Cu(I)-catalyzed [3+2] alkyne/azide cycloaddition (Click reaction) (H. C. Kolb, M. G. Finn, K. B. Sharpless, *Angewandte Chemie-International Edition* 2001, 11, 2004-2021; V. O. Rodionov, V. V. Fokin, M. G. Finn, *Angewandte Chemie-International Edition* 2005, 15, 2210-2215), we synthesized the alkyne derived 2-aminoimidzole 1 and tested its ability to participate in a Cu(I)-catalyzed [3+2] cycloaddition with benzyl azide.

Scheme 1. Construction of the initial 2-AIT library.

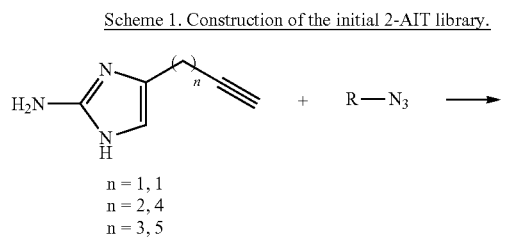

n = 1, 1
n = 2, 4
n = 3, 5

Scheme 2. Synthesis of alkyne 2-aminoimidazole 1.

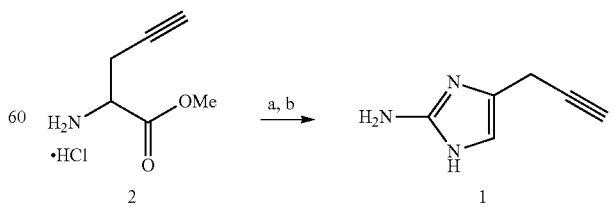

a) 5% Na/Hg, H₂0, pH = 1.5-2.0, 0-5° C.
b) cyanamide, H₂0, pH = 4.3, 95° C.

The alkyne derived 2-aminoimidazole (2-AI) was synthesized as outlined in Scheme 1. Amino acid 2 (S. Kotha, S. Halder, E. Brahmachary, *Tetrahedron* 2002, 45, 9203-9208) was subjected to small scale Akabori reduction (S. Akabori, *Berichte Der Deutschen Chemischen Gesellschaft* 1933, 66, 151-158), which, followed by condensation with cyanamide (Y. Xu K. Yakushijin, D. A. Horne, *J Org Chem* 1997, 3, 456-464) delivered the target alkyne 2-AI 1 in 88% yield. With 1 in hand, we explored various conditions to elicit the Cu-catalyzed [3+2] cycloaddition between 1 and benzyl azide (Table 1).

TABLE 1

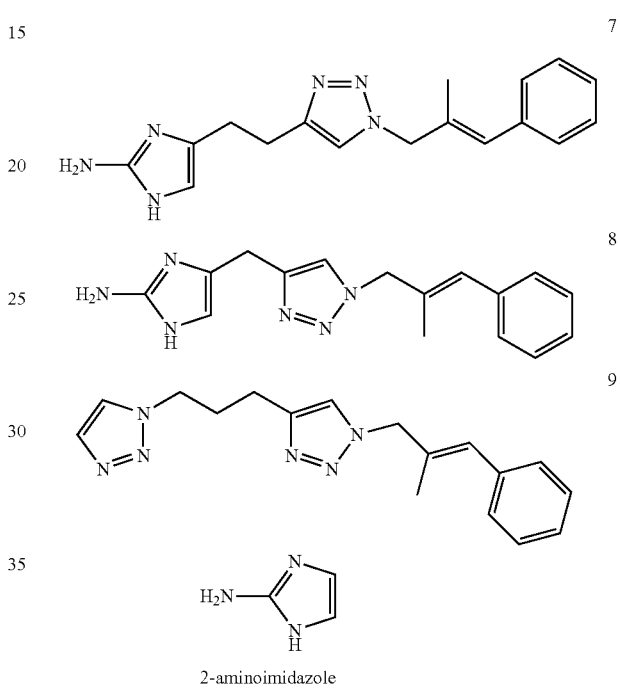

| Scale (mg) | Cu(I) Source[a] | Solvent | Base | Temp | Yield |
|---|---|---|---|---|---|
| 20 | CuI | THF | DIEA | RT | NR |
| 20 | CuI | THF | DIEA | 40° C. | NR |
| 20 | CuSO$_4$/NaAsc | EtOH/H$_2$O (1:1) | — | RT | NR |
| 20 | CuSO$_4$/NaAsc | EtOH/H$_2$O (1:1) | — | 40° C. | 86% |
| 100 | CuSO$_4$/NaAsc | EtOH/H$_2$O (1:1) | — | 40° C. | Decomp |
| 100 | CuSO$_4$/NaAsc | t-BuOH/H$_2$O/CH$_2$Cl$_2$ (1:1:1) | — | RT | 93% |

[a]NaAsc = Sodium Ascorbate

Reactions in THF using Cu(I) yielded no reaction and only returned starting material. We then switched to using CuSO$_4$ and sodium ascorbate in a 1:1 solvent mixture of H$_2$O/EtOH. Again, no reaction was noted. However, when the reaction was heated to 40° C. we noted clean conversion to the desired 2-AIT conjugate 3 in 86% yield. Unfortunately, when the reaction was scaled up, we observed a significant amount of decomposition. Room temperature click reactions have been noted when a 1:1:1 solvent mixture of H$_2$O/EtOH/CH$_2$Cl$_2$ (B. Y. Lee, S. R. Park, H. B. Jeon, K. S. Kim, *Tetrahedron Letters* 2006, 29, 5105-5109) is employed instead of the 1:1 H$_2$O/EtOH mixture. When these reaction conditions were tested, we observed conversion to 3 in 93% yield.

With the methodology established to access 2-AIT conjugates, we employed the synthetic approach outlined in Scheme 1 to synthesize 2-AI alkynes 4 and 5, in which we systematically extended the methylene space between the alkyne and the 2-AI. The click reaction was then performed between each of the 2-AI alkynes and 12 azides to yield an initial 2-AIT library (shown below). Each compound was characterized ($^1$H NMR, $^{13}$C NMR, HRMS) prior to screening.

Figure 2A:
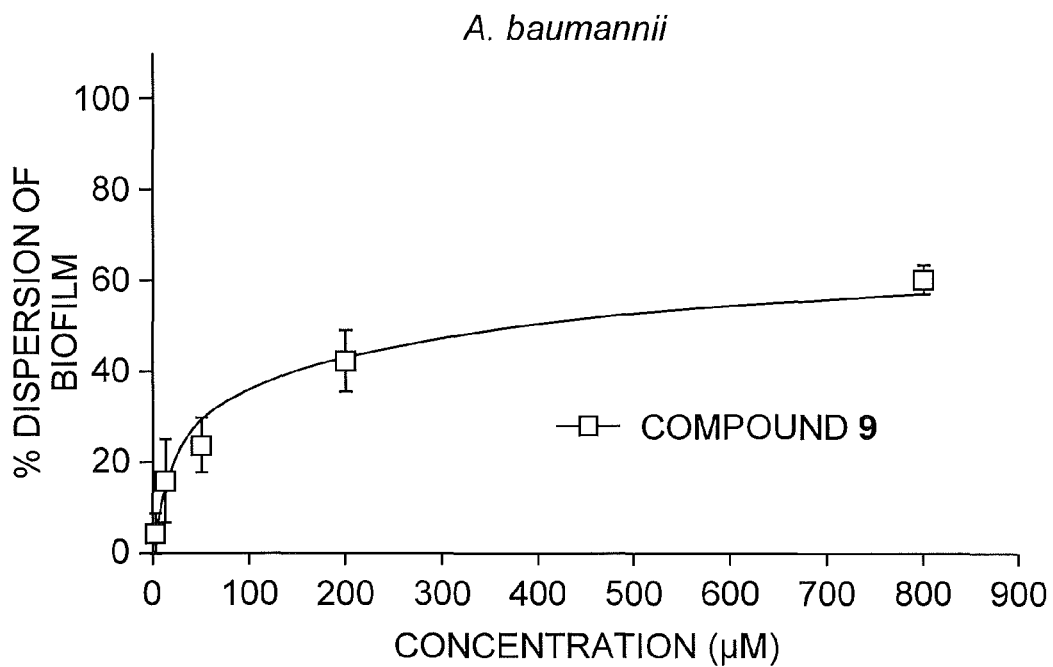
FIG. 2A-2D. Bacterial biofilm dispersion dose response curves for compounds 9, 10, 11 and 12. 2A: Dose response curves for 7, 6 and 10 dispersion of *A. baumannii*. 2B: Dose response curves for 10 dispersion of *A. baumannii, P. aeruginosa*:PA14, *P. aeruginosa*:PAO1, *B. bronchiseptica*:RB50, and *S. aureus:*29213. 2C: Dose response curves for 11 dispersion of *A. baumannii, P. aeruginosa*:PA14, *P. aeruginosa*: PAO1, *B. bronchiseptica*:RB50, and *S. aureus:*29213. 2D: Dose response curves for 12 dispersion of *A. baumannii, P. aeruginosa*:PA14, *P. aeruginosa*:PAO1, *B. bronchiseptica*: RB50, and *S. aureus:*29213.
Figure 3A:
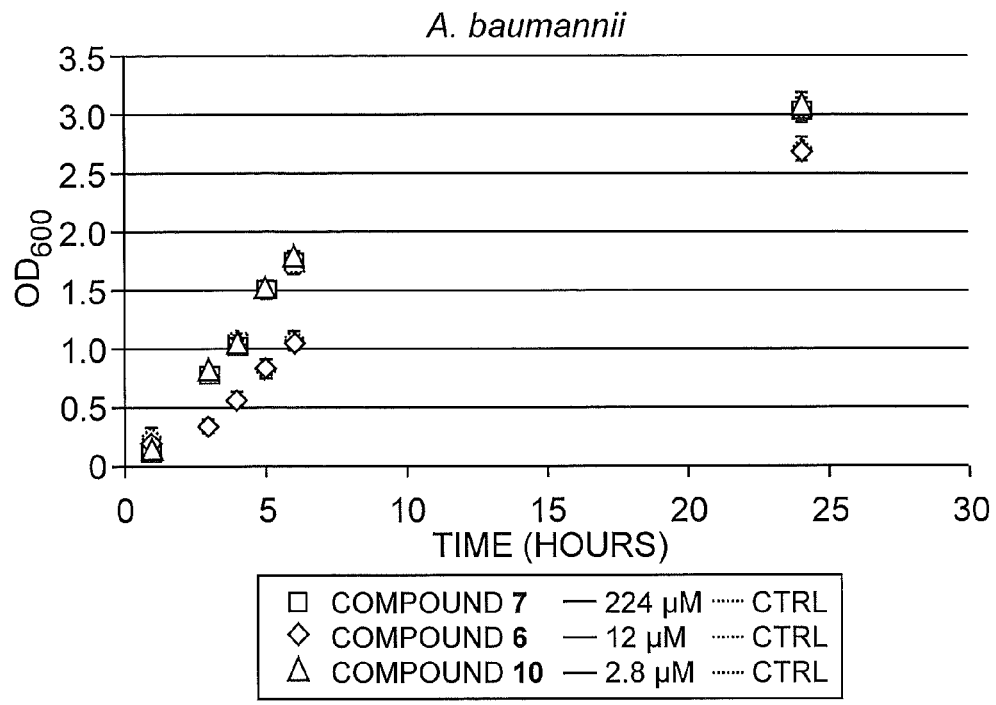
FIG. 3A-3D. Planktonic growth curves for bacteria grown in the presence or absence of compounds 7, 6, 10, 11 and 12. 3A: Planktonic growth curves for *A. baumannii* in the presence or absence of 7, 6 and 10 at 224 µM, 12 µM, and 2.8 µM, respectively. 3B: In the presence or absence of 10, planktonic growth curves for *A. baumannii* (2.8 µM), *P. aeruginosa*: PA14 (4.0 µM), *P. aeruginosa*:PAO1 (15 µM), *B. bronchiseptica*:RB50 (23 µM), and *S. aureus:*29213 (7.0 µM). 3C: In the presence or absence of 11, planktonic growth curves for *A. baumannii* (0.98 µM), *P. aeruginosa*:PA14 (0.53 µM), *P. aeruginosa*:PAO1 (5.6 µM), *B. bronchiseptica*:RB50 (9.5 µM), and *S. aureus:*29213 (0.81 µM). 3D: In the presence or absence of 12, planktonic growth curves for *A. baumannii* (6.8 µM), *P. aeruginosa*:PA14 (22 µM), *P. aeruginosa*:PAO1 (2.7 µM), *B. bronchiseptica*:RB50 (70 µM), and *S. aureus:* 29213 (4.6 µM).
Figure 4A:
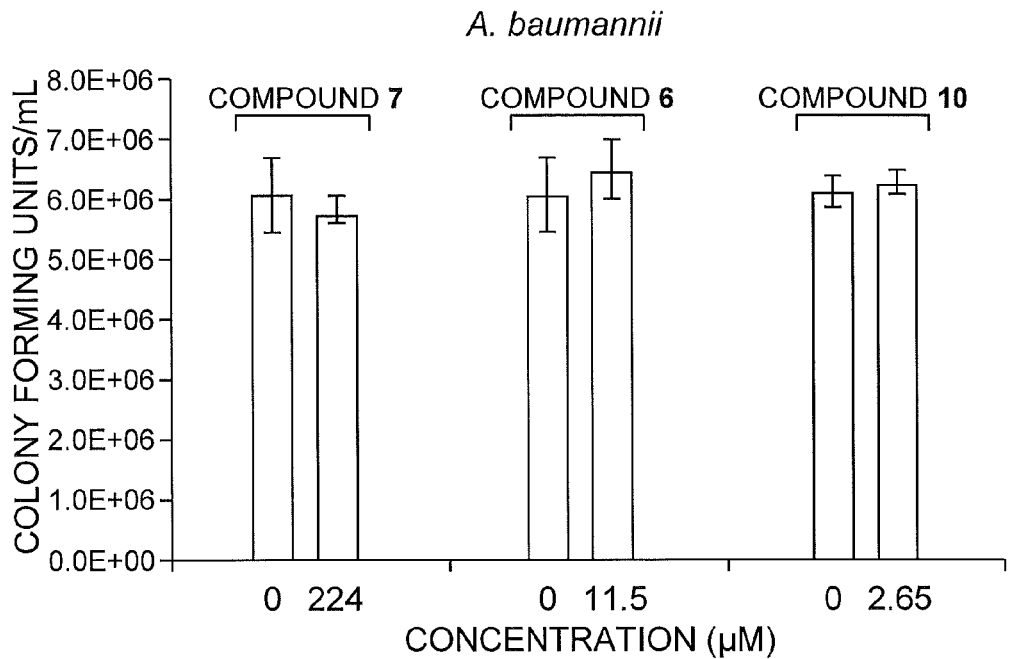
FIG. 4A-4D. Colony counts for bacteria grown in the presence or absence of compounds 7, 6, 10, 11 and 12. 4A: Colony counts for *A. baumannii* in the presence or absence of 7, 6 and 10 at 224 µM, 11.5 µM, and 2.65 µM, respectively. 4B: In the presence or absence of 10, colony counts for *A. baumannii* (2.65 µM), *P. aeruginosa*:PA14 (4.5 µM), *P. aeruginosa*: PAO1 (14.9 µM), *S. aureus:*29213 (7.26 µM) and *B. bronchiseptica*:RB50 (22.9 µM). 4C: In the presence or absence of 11, colony counts for *A. baumannii* (2.65 µM), *P. aeruginosa*: PA14 (0.53 µM), *P. aeruginosa*:PAO1 (5.6 µM), *S. aureus*: 29213 (0.811 µM) and *B. bronchiseptica*:RB50 (9.5 µM). 4D: In the presence or absence of 12, colony counts for *A. baumannii* (6.77 µM), *P. aeruginosa*:PA14 (21.5 µM), *P. aeruginosa*:PAO1 (2.67 µM), *S. aureus*:29213 (4.56 µM) and *B. bronchiseptica*:RB50 (69.8 µM).

Each 2-AIT conjugate was initially screened at 300 μM for their ability to inhibit *P. aeruginosa* PAO1 and PA14 biofilms, *A. baumannii* biofilms and *B. bronchiseptica* Rb50 biofilms using a crystal violet reporter assay (G. A. O'Toole, R. Kolter, *Molecular Microbiology* 1998, 2, 295-304). From this initial library screen, we observed that 2-AIT conjugate 6 showed the most promise, and was most active against *A. baumanii*, with an observed IC$_{50}$ of 12 μM. This is an order of magnitude increase in activity when compared to DHS (J. J. Richards, R. W. Huigens, T. E. Ballard, A. Basso, J. Cavanagh, C. Melander, *Chemical Communications* 2008, 14, 1698-1700). Follow up growth curves and colony counts indicated that 6 had no effect on planktonic growth (FIGS. 3A, 4A), indicating that inhibition of biofilm development was not due to microbicidal activity. 6 also dispersed pre-formed *A. baumanni* biofilms with an EC$_{50}$ of 400 μM (FIG. 2A).

The effect of tether length between the 2-AI and triazole on activity was addressed by determining the IC$_{50}$ of biofilm inhibition for 7 and 8 against *A. baumannii*.

Dose response studies revealed that the IC$_{50}$ of 7 was 220 μM (FIG. 1A). 8 did not inhibit *A. baumannii* biofilm development in a significant fashion (<50%) at 800 M (highest concentration tested, data not shown). Thus, increasing tether length appears to correlate with increased activity.

Within the context of the 2-AIT conjugate, we also tested the necessity of the 2-AI subunit by synthesizing compound 9 and assaying for its ability to inhibit *A. baumannii* biofilm development. 9 was synthesized by alkylating commercially available 1-H-1,2,3-triazole with 5-iodo-pent-1-yne, followed by subjecting the resulting triazole alkyne to the click reaction. Compound 9 revealed minimal activity (<30% inhibition) at the highest concentration studied (800 μM, data not shown). 2-Aminomidazole was also screened and found to be devoid of activity up to 800 μM (highest concentration tested, data not shown).

As indicated above, as the number of methylene units between the 2-AI group and the triazole are increased in the context of 6-8, we see an increase in anti-biofilm activity in the context of *A. baumannii*. Therefore, we synthesized 2-AIT conjugates 10-12, where we systematically extended the methylene linker to investigate if additional methylenes unit would deliver a 2-AIT conjugate with even greater biological activity than 6.

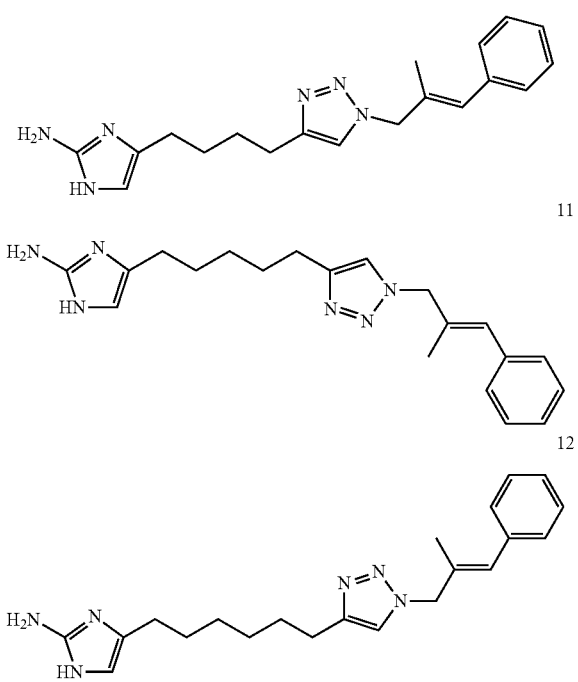

Figure 1B:
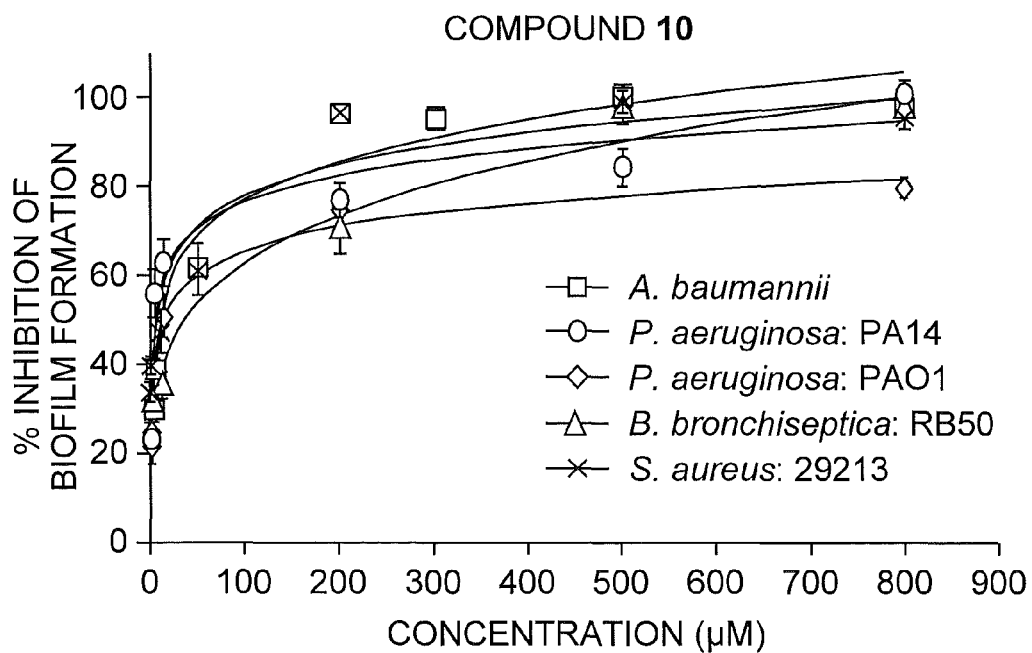
Figure 3B:
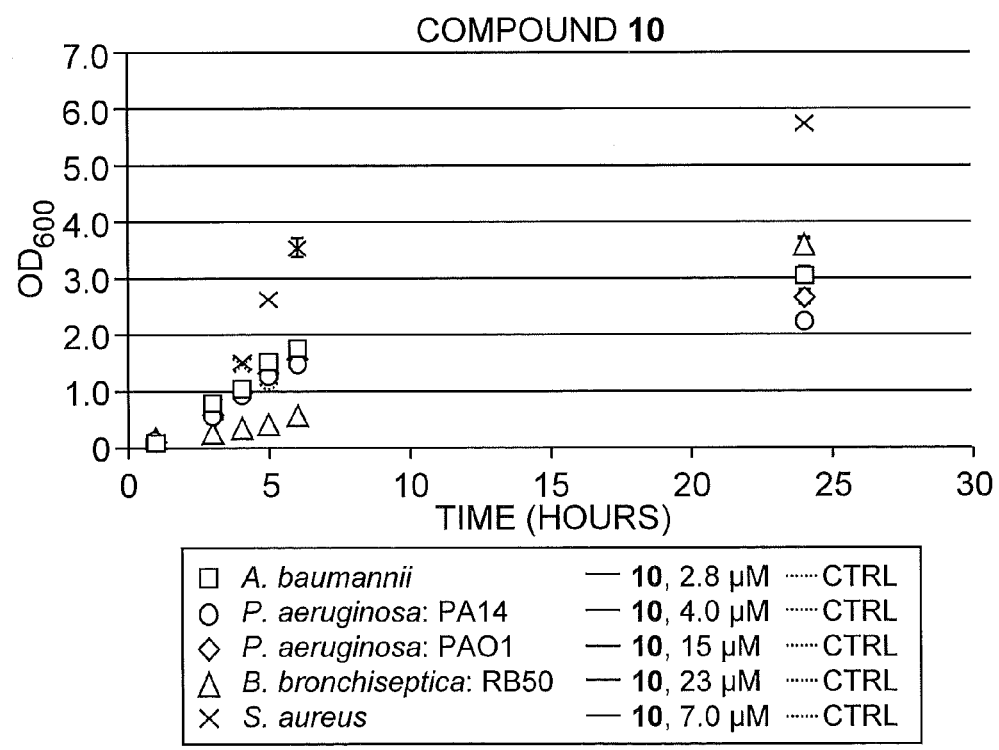
Figure 4B:
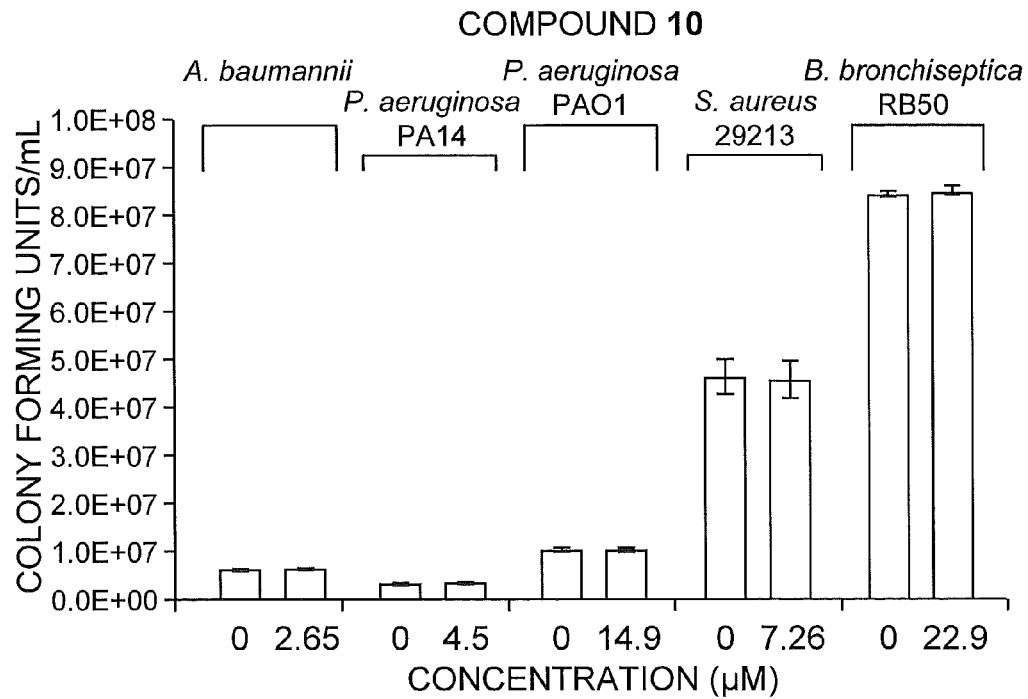

When 10 was assayed for the ability to inhibit *A. baumanni* biofilm formation, we noted an IC$_{50}$ value of 2.8 μM. Furthermore, 10 revealed IC$_{50}$ values of 15 μM, 4.0 μM, and 23 μM against PAO1, PA14, and Rb50 (FIG. 1B and Table 2). We also tested the ability of 10 to inhibit *Staphylococcus aureus* biofilm development. 10 revealed an IC$_{50}$ value of 7.0 μM against *S. aureus*. Colony counts and growth curves of each bacterial strain grown in the presence of 10 revealed that activity was not due to bactericidal activity (FIGS. 3B, 4B), which, to the best of our knowledge, is the first example of a non-bactericidal small molecule that will inhibit biofilm development across both order and phylum (D. J. Musk, P. J. Hergenrother, *Current Medicinal Chemistry* 2006, 18, 2163-2177).

TABLE 2

Effect of chain length on activity.[a]

| n | *A. baumannii* | PAO1 | PA14 | Rb50 | *S. aureus* |
|---|---|---|---|---|---|
| 4 (10) | 2.8 | 15 | 4.0 | 23 | 7.0 |
| 5 (11) | 0.98 | 5.6 | 0.53 | 9.5 | 0.81 |
| 6 (12) | 6.8 | 2.7 | 22 | 70 | 4.6 |

[a]IC$_{50}$ values are indicated in μM.

Figure 1C:
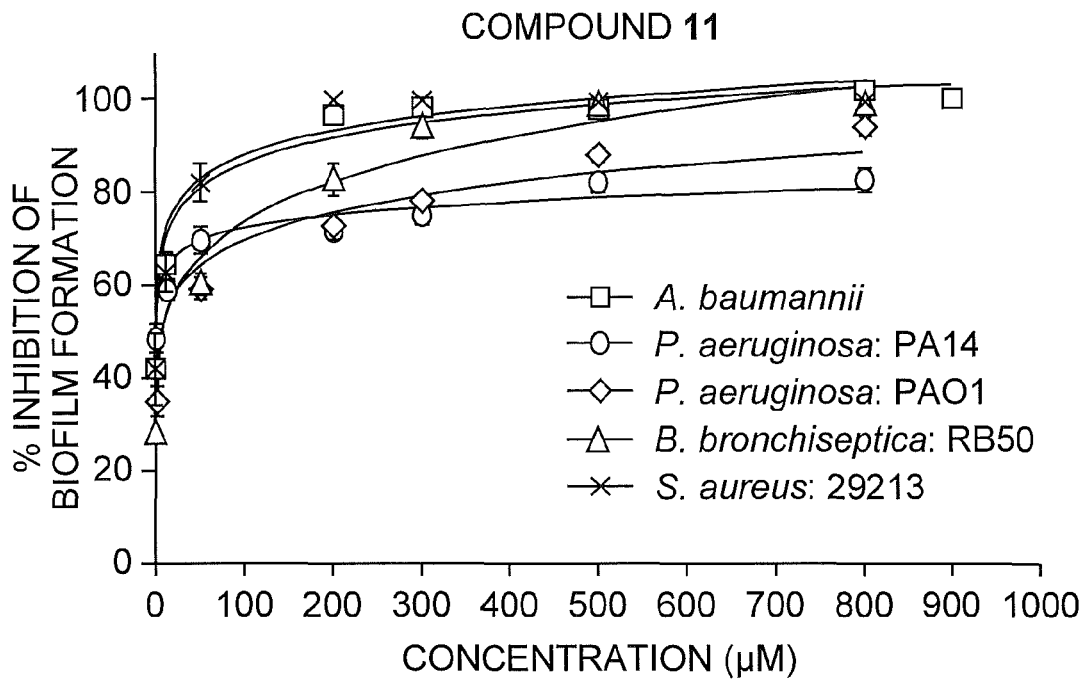

Increasing the methylene spacer to 5 carbons (11), again led to an increase in activity. 11 revealed IC$_{50}$ values of 980 nM, 5.6 μM, 530 nM, 9.5 μM, and 810 nM against *A. baumannii*, PAO1, PA14, Rb50, and *S. aureus* respectively (FIG. 1C).

Figure 1D:
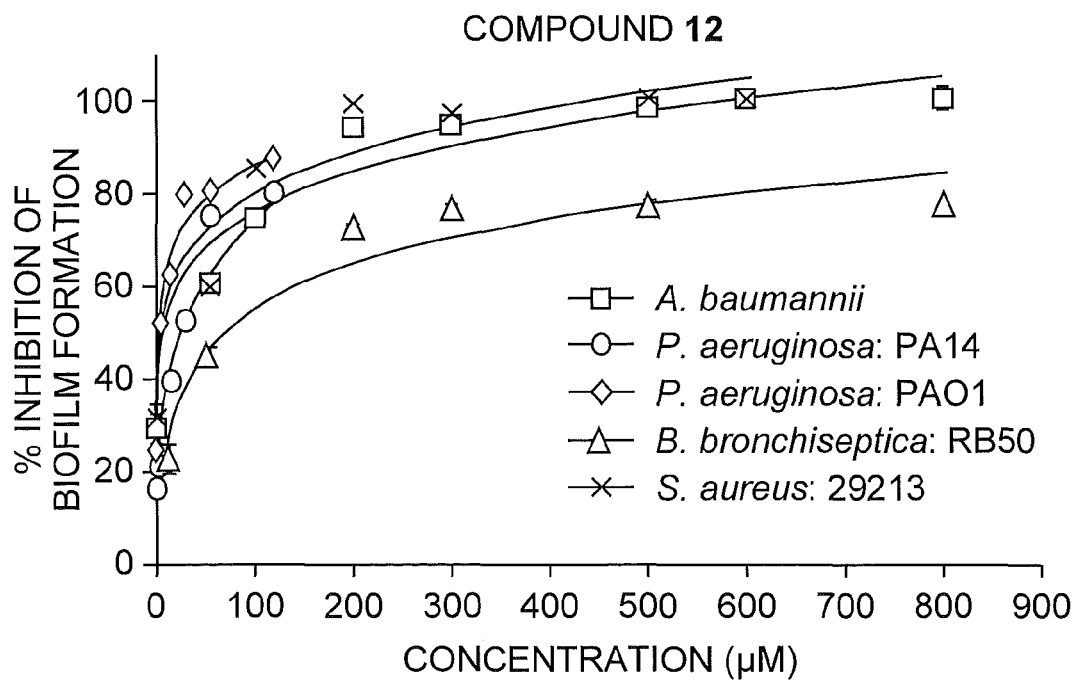
Figure 3C:
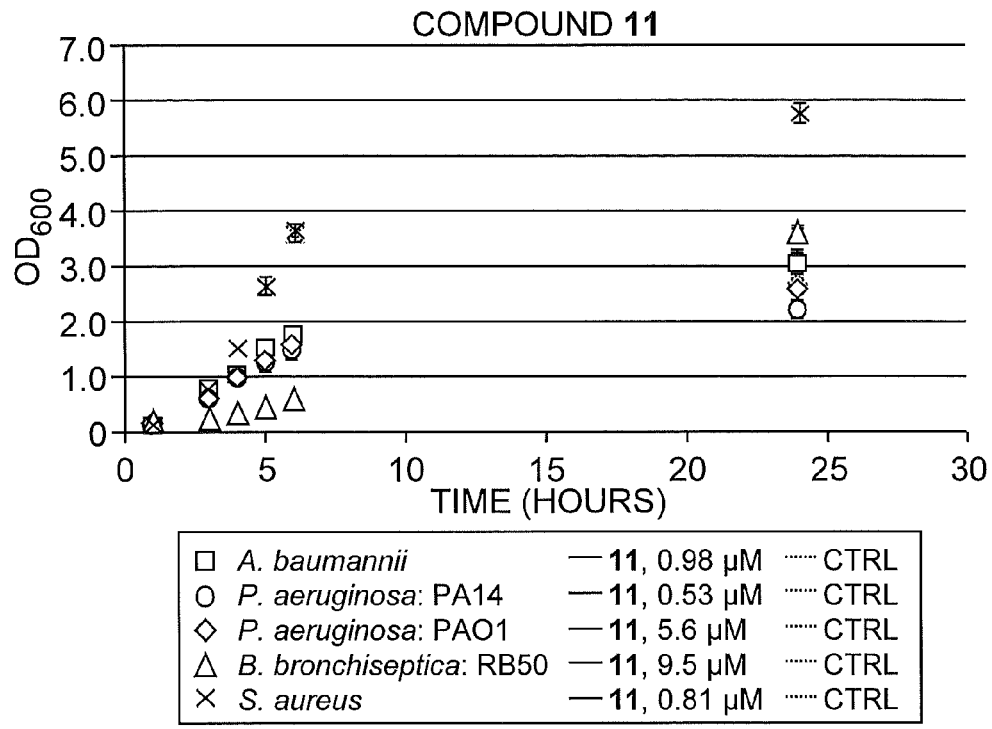
Figure 3D:
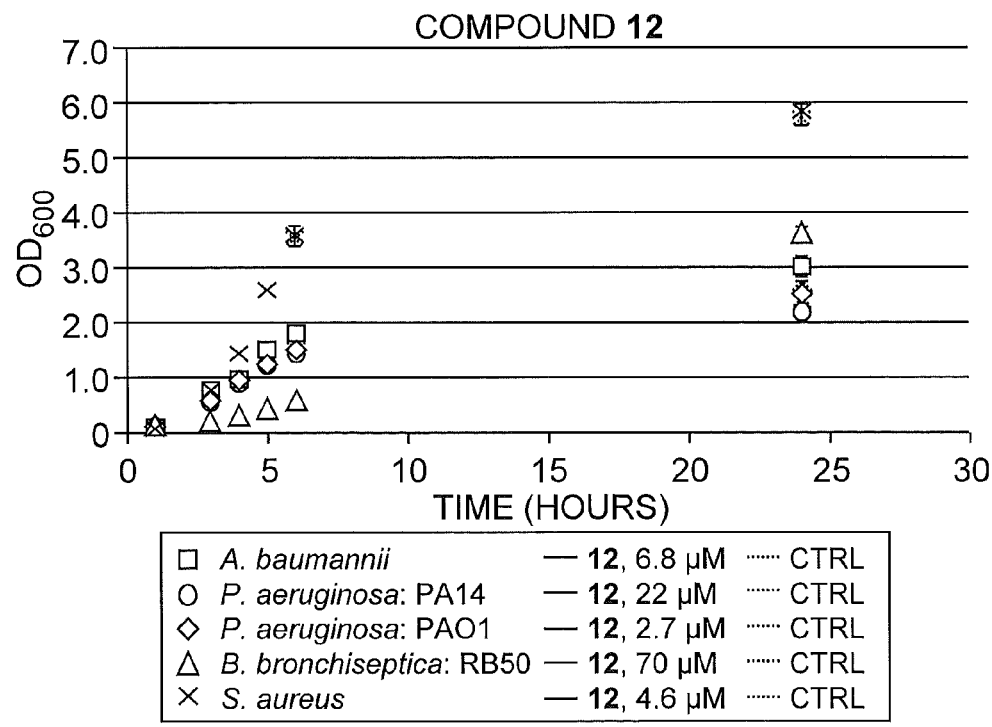
Figure 4C:
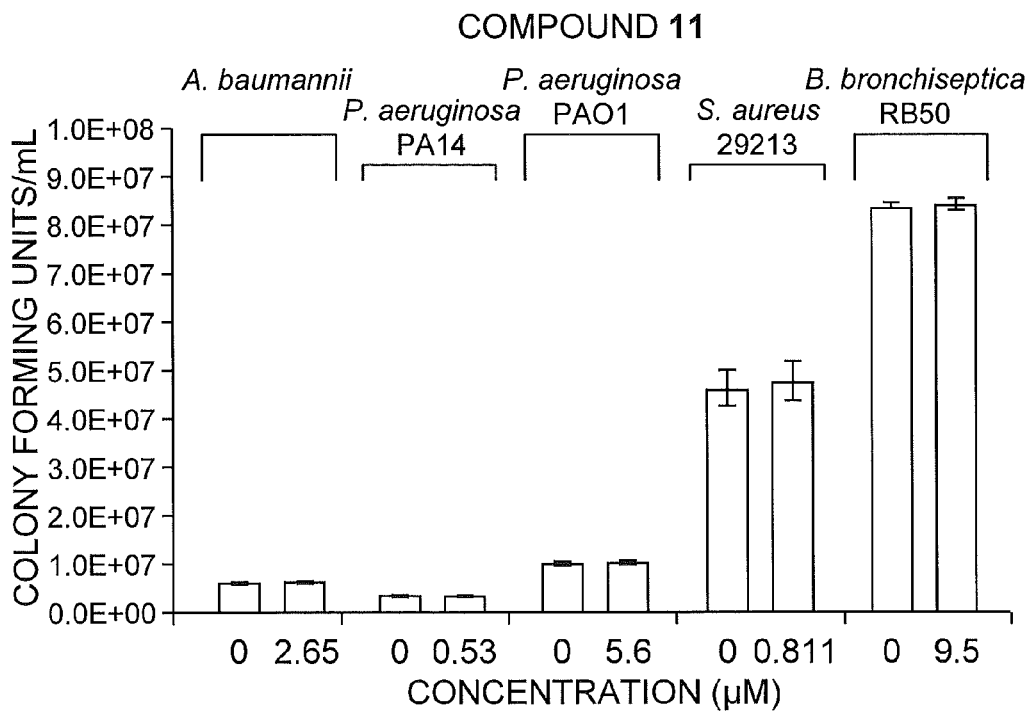
Figure 4D:
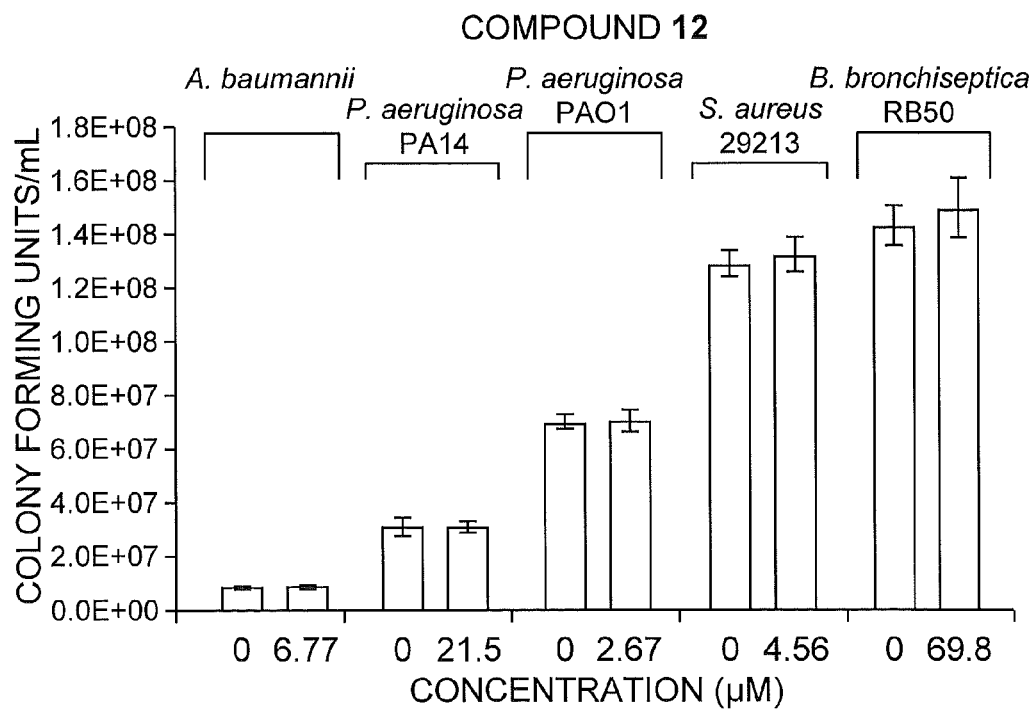
Figure 5A:
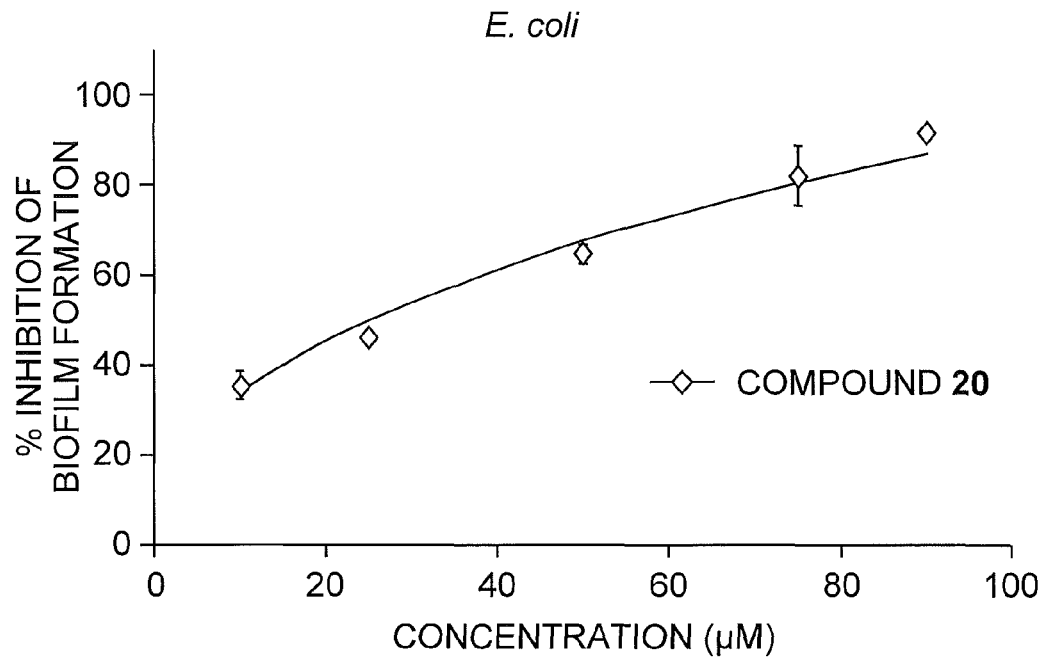
FIG. 5A-5H. Bacterial biofilm inhibition and dispersion dose response curves for compounds 20-25. 5A: Dose response curve for 20 inhibition of *E. coli*. 5B: Dose response curves for 23 inhibition of PA14, MRSA, MDRAB, *E. coli* and *E. faecium*. 5C: Dose response curves for 23 dispersion of PA14, MRSA, MDRAB, *E. coli* and *E. faecium*. 5D: Dose response curves for 24 inhibition of PA14, MRSA, MDRAB, *E. coli* and *E. faecium*. 5E: Dose response curves for 24 dispersion of PA14, MRSA, MDRAB, *E. coli* and *E. faecium*. 5F: Dose response curves for 21, 22 and 25 inhibition of *S. epidermidis*. 5G: Dose response curves for 25 inhibition of PA14, MRSA, MDRAB, *E. faecium* and *E. coli*. 5H: Does response curves for 25 dispersion of PA14, MRSA, MDRAB and *E. faecium*.
Figure 5B:
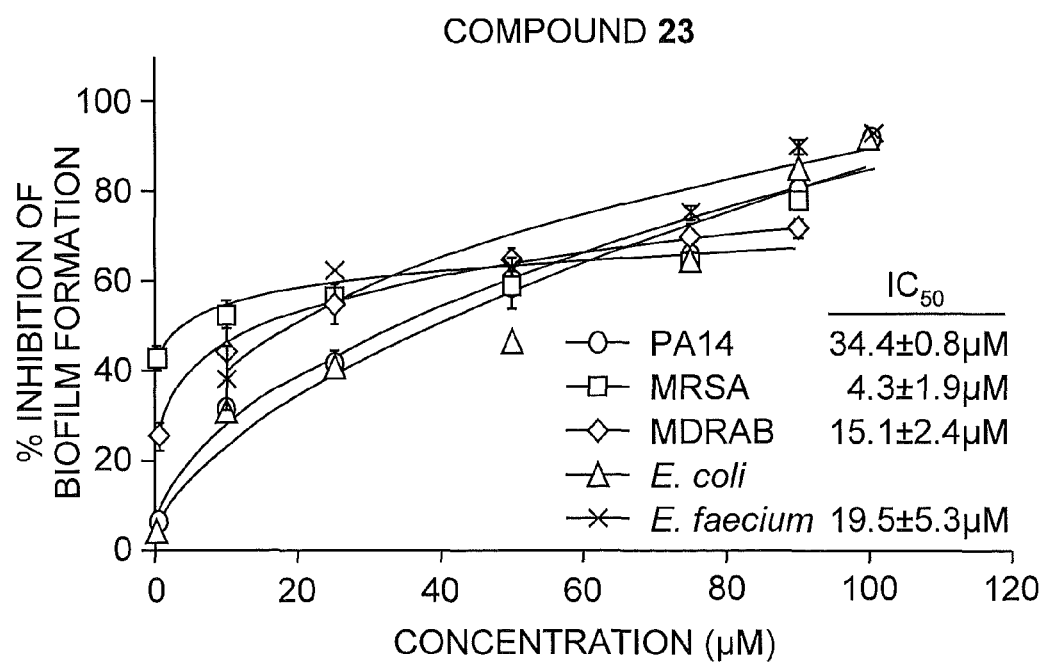
Figure 5C:
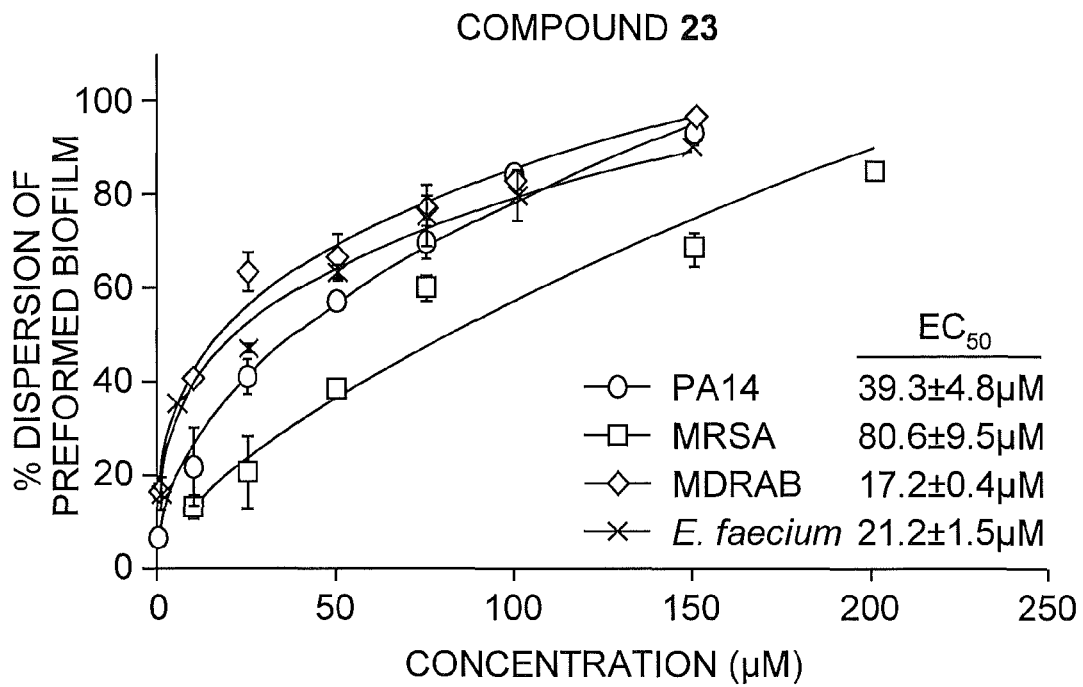
Figure 5D:
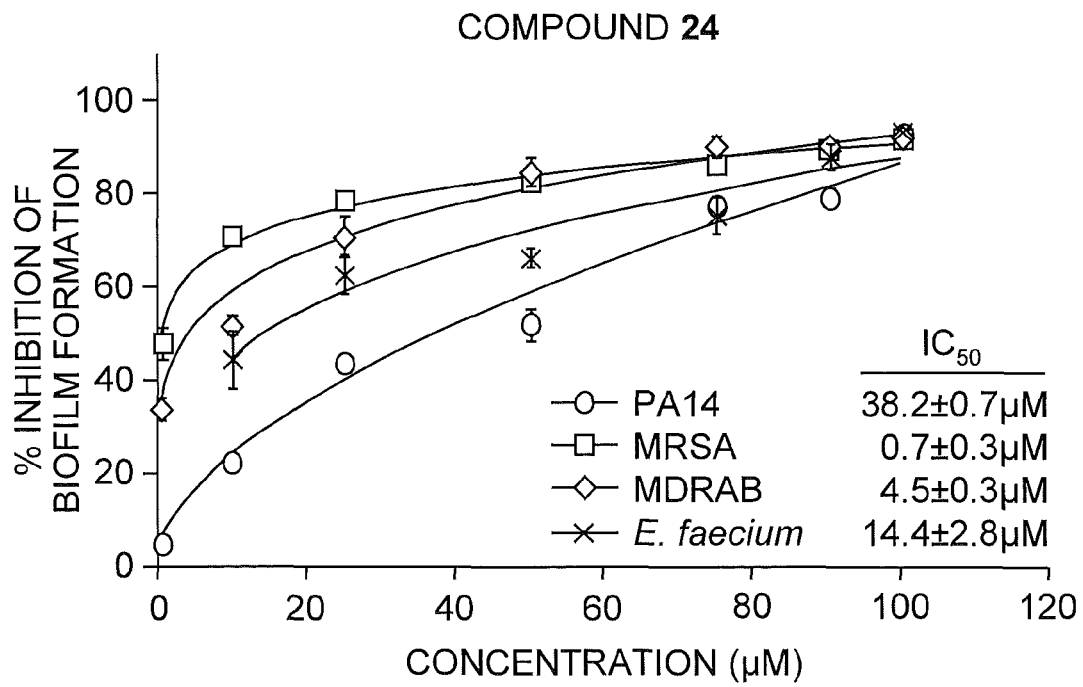
Figure 5E:
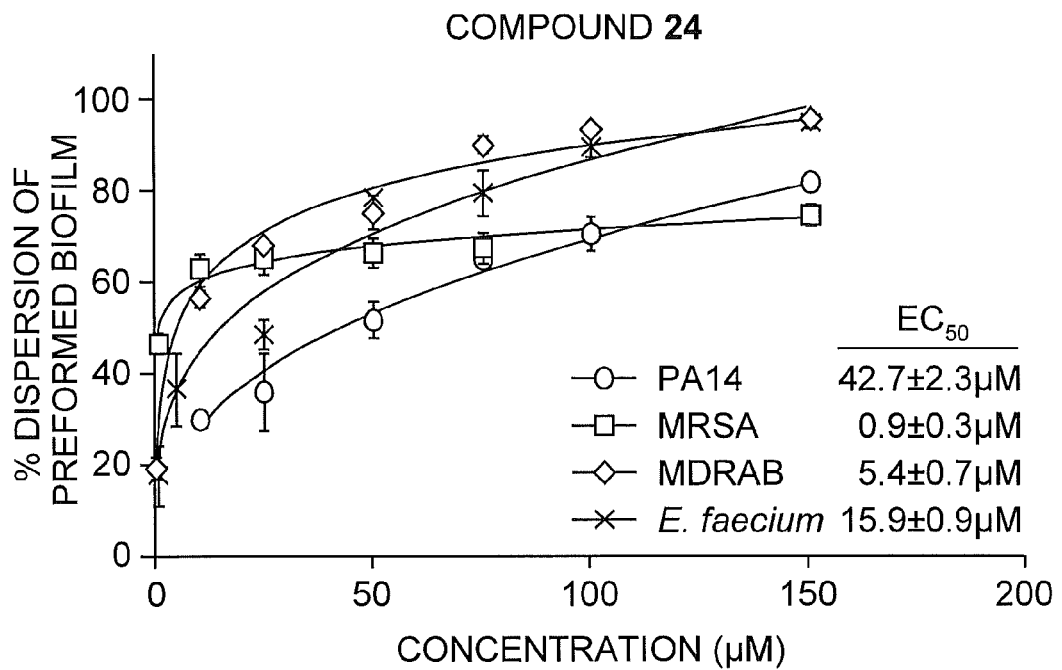
Figure 5F:
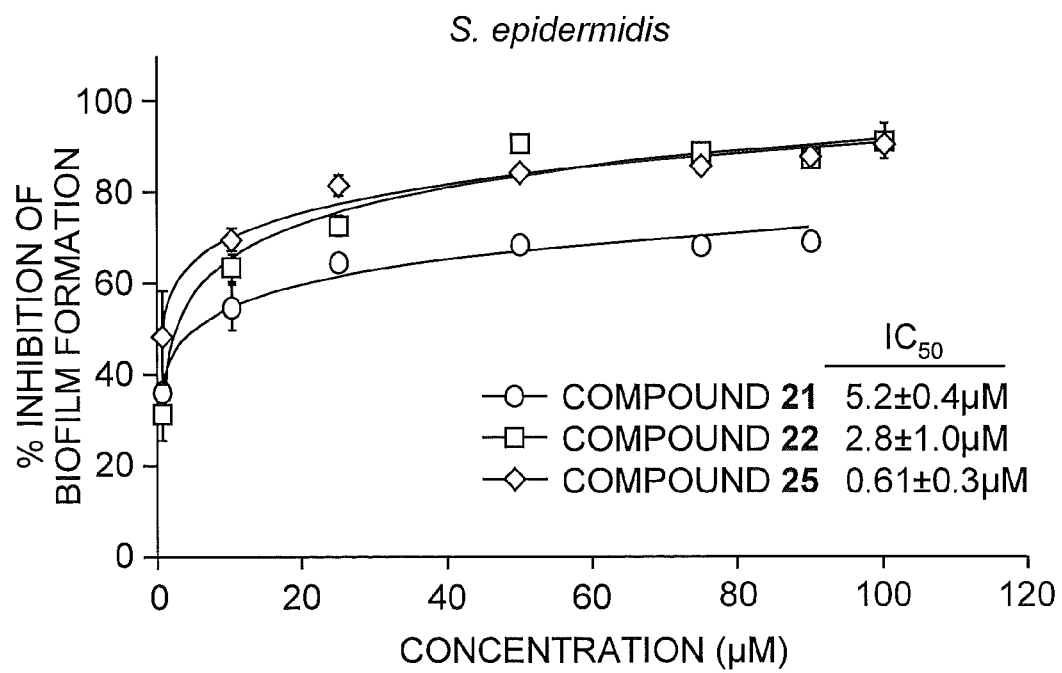
Figure 5G:
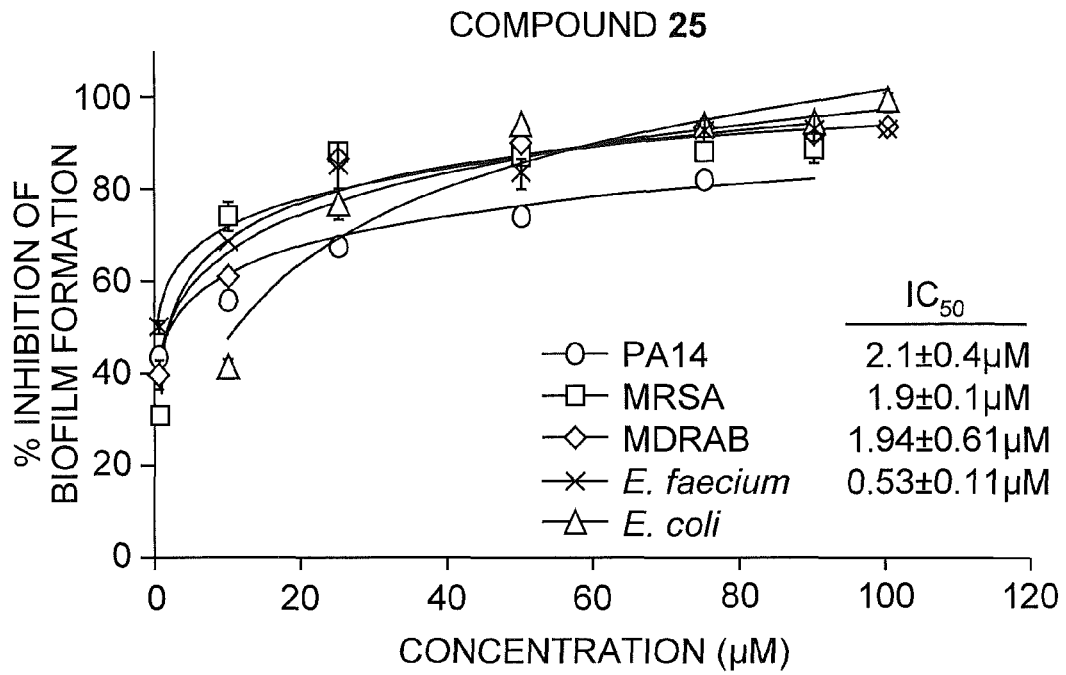
Figure 5H:
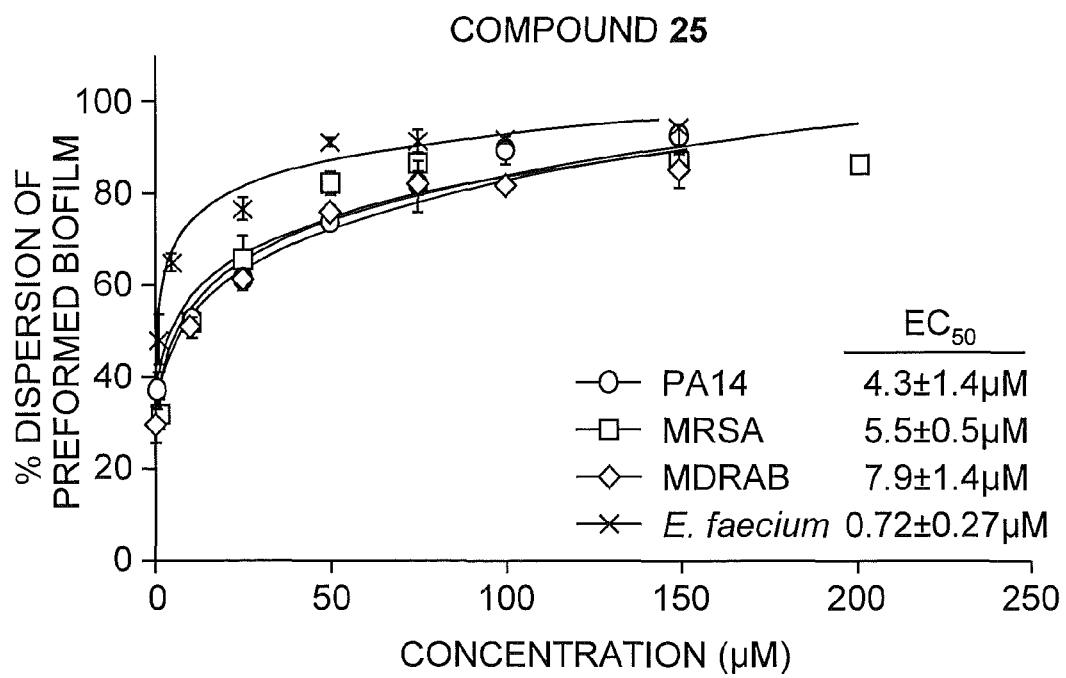
Figure 6A:
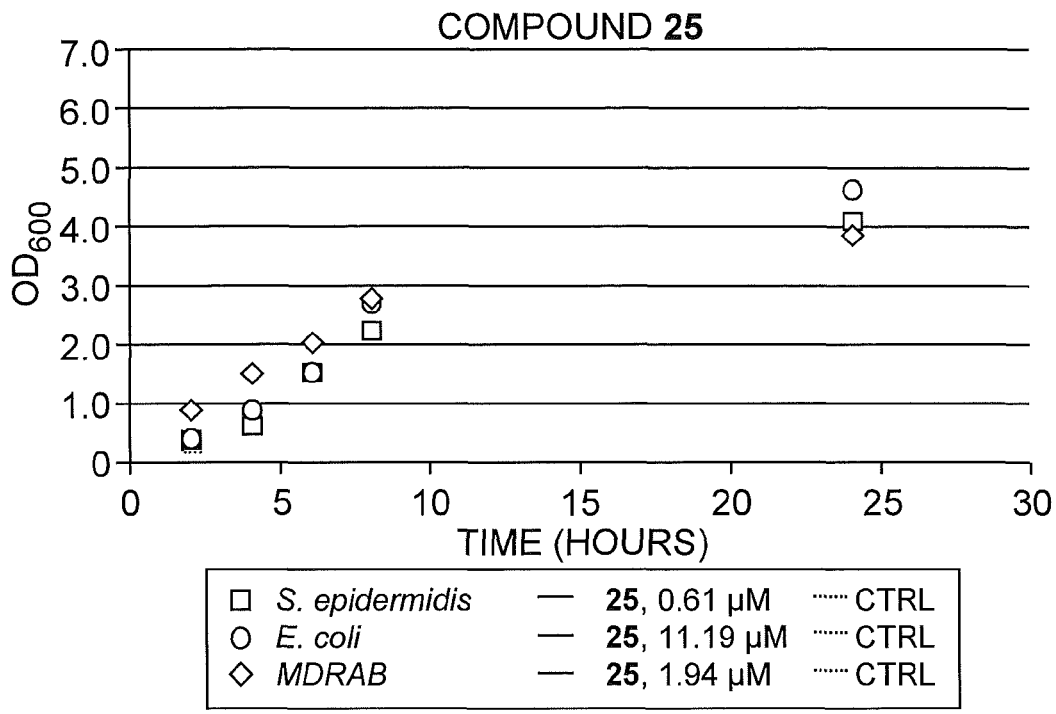
FIG. 6A-6F. Planktonic growth curves for bacteria grown in the presence or absence of compounds 20-25. 6A: In the presence or absence of 25, planktonic growth curves for *S. epidermidis* (0.61 µM), *E. coli* (11.19 µM) and MDRAB (1.94 µM). 6B: Planktonic growth curves for MRSA in the presence or absence of 23 (4.33 µM) and 25 (1.88 µM). 6C: Planktonic growth curves for PA14 in the presence or absence of 23 (34.38 µM) and 24 (38.14 µM). 6D: Planktonic growth curves for PAO1 in the presence or absence of 24 (1.09 µM) and 26 (64.4 µM). 6E: Planktonic growth curves for *S. epidermidis* in the presence or absence of 21 (5.19 µM) and 22 (2.75 µM). 6F: Planktonic growth curves for *E. coli* in the presence or absence of 20 (40.09 µM).
Figure 6B:
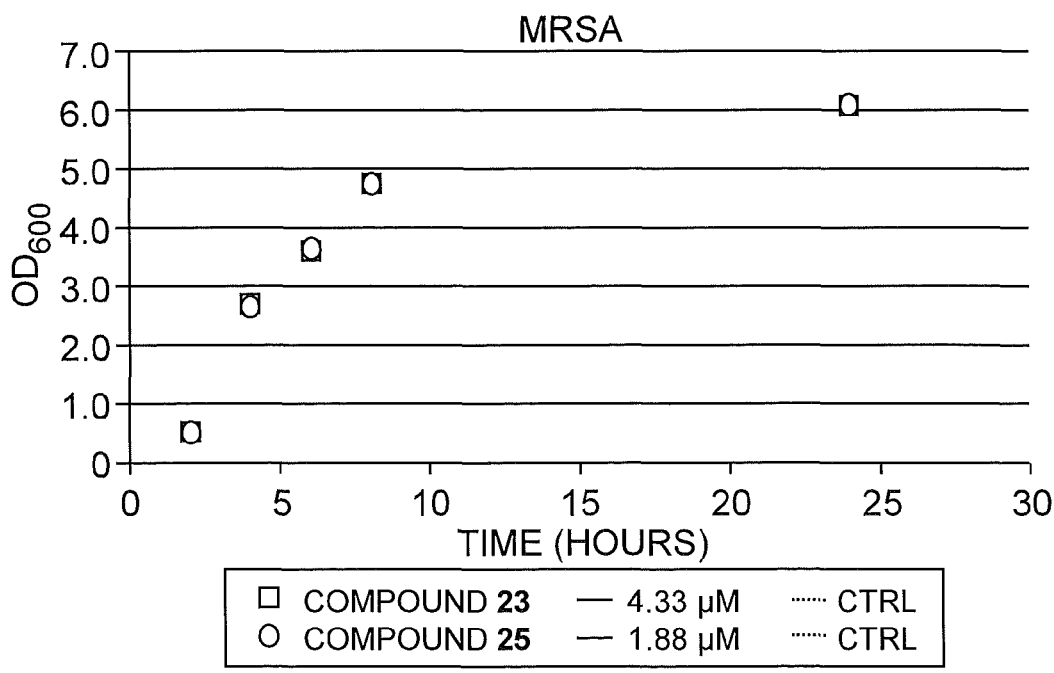
Figure 6C:
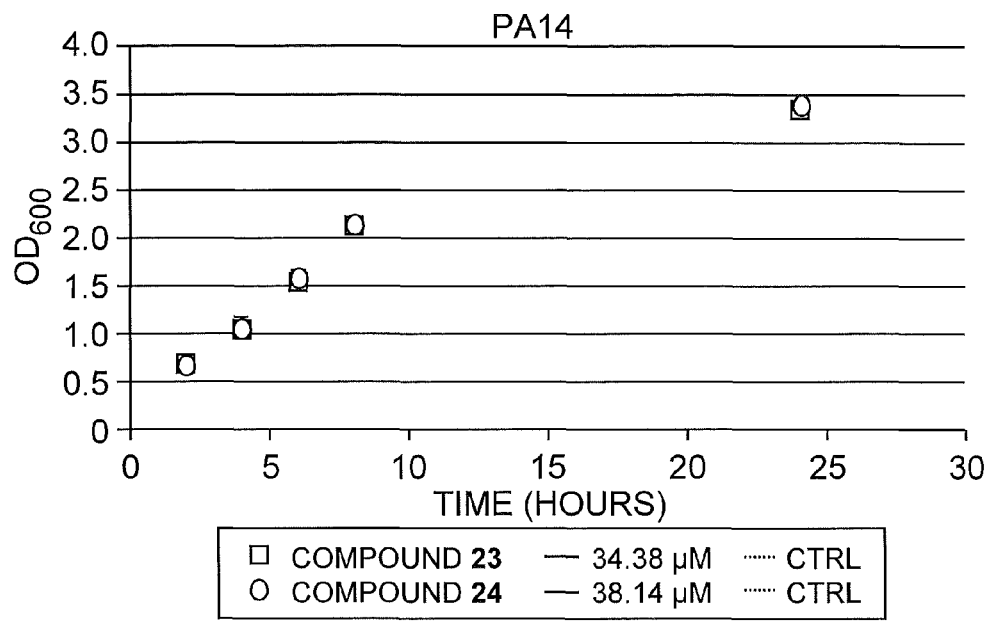
Figure 6D:
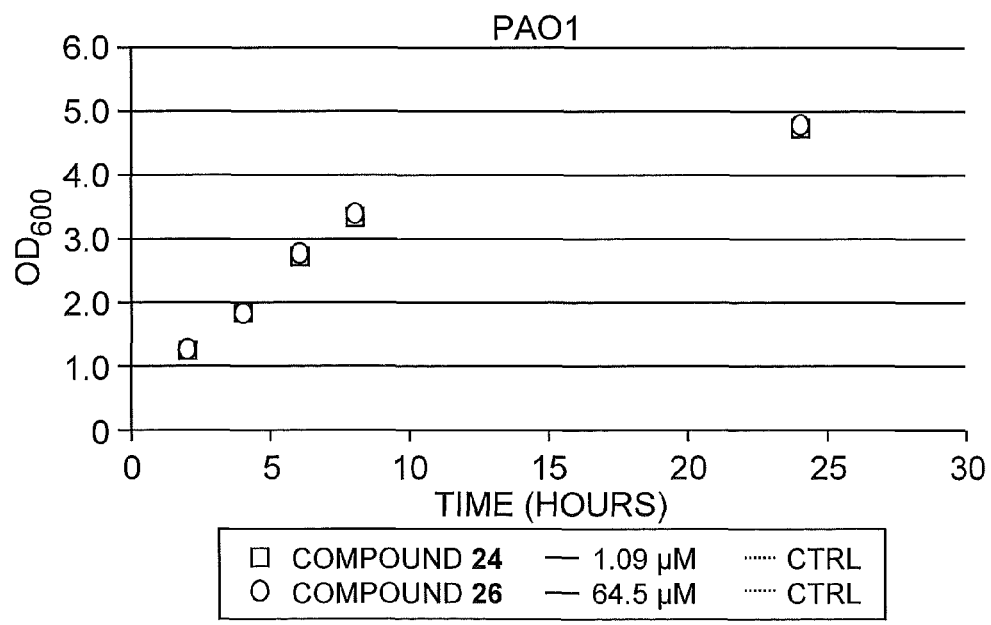
Figure 6E:
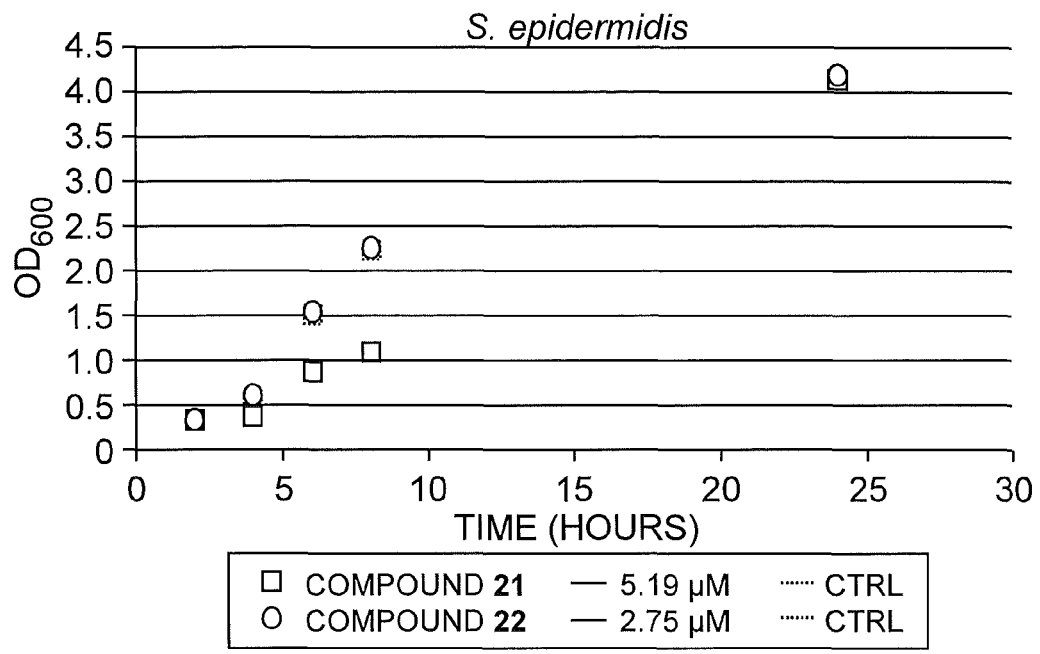
Figure 6F:
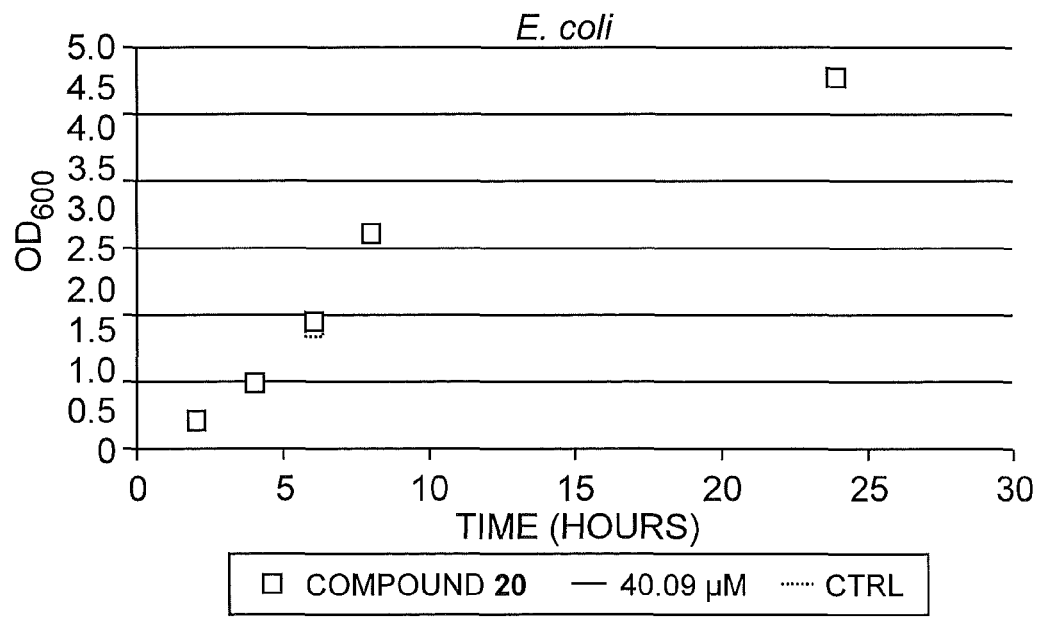

Addition of another methylene group (6 carbons, 12) did not lead to an increase in activity. We observed IC$_{50}$ values of 6.8 μM, 2.7 μM, 22 μM, 70 μM, and 4.6 μM against *A. baumannii*, PAO1, PA14, Rb50, and *S. aureus*, respectively (FIG. 1D). Follow up colony count and growth curve analysis revealed that inhibition of biofilm development for both 11 and 12 was not due to microbicidal activity (FIGS. 3C, 4C).

Figure 2B:
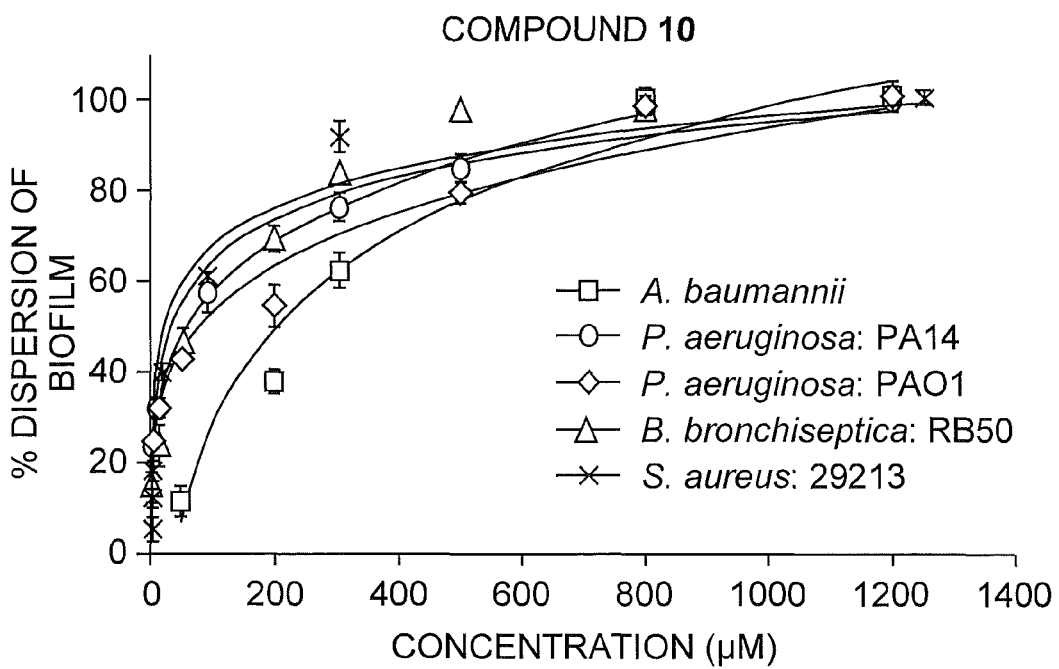
Figure 2C:
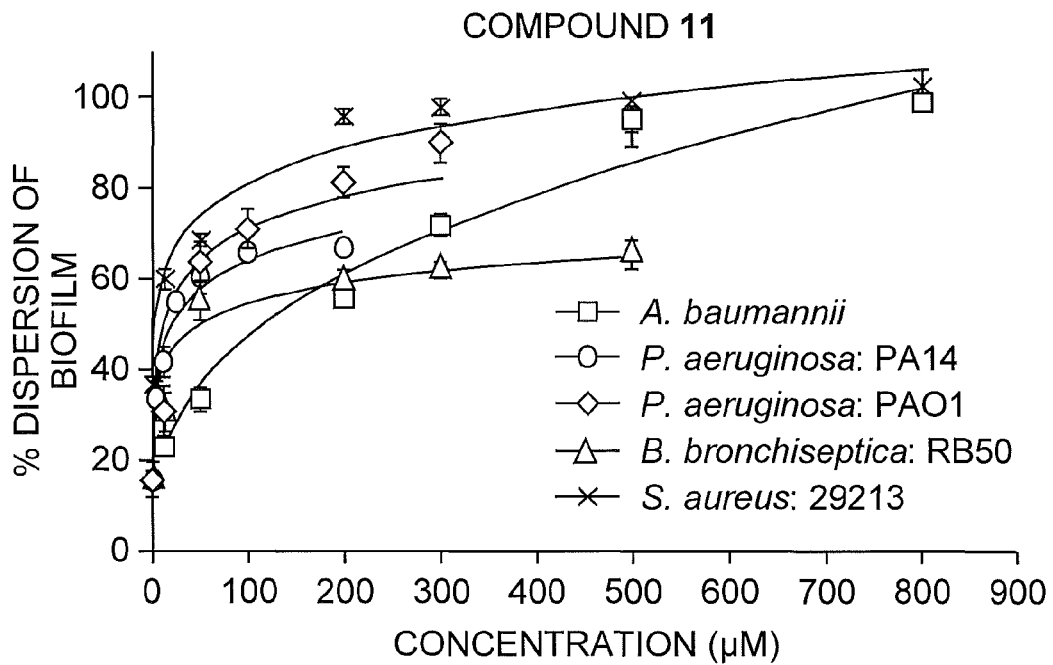
Figure 2D:
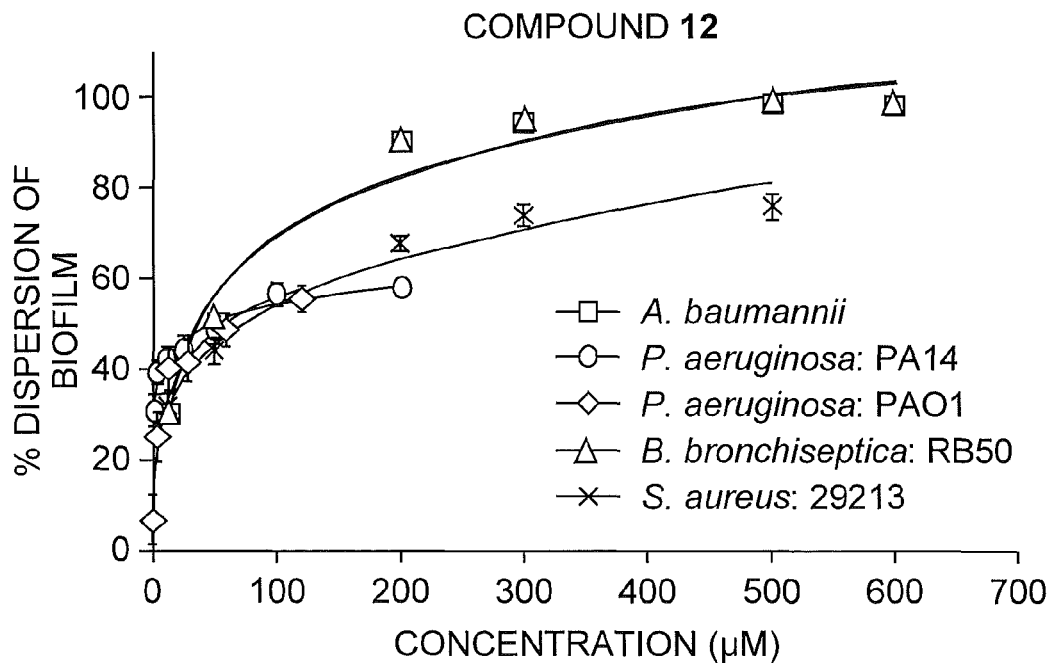

Finally, we have tested for the ability of a single administration of 2-AIT conjugates 10-12 to disperse pre-formed bacterial biofilms (FIGS. 2B, 2C, 2D). The summary of these experiments is outlined in Table 3. As can be seen, each compound was able to disperse the pre-formed biofilm, across bacterial order and phylum.

TABLE 3

Dispersion activity.

| n | *A. baumannii* | PAO1 | PA14 | Rb50 | *S. aureus* |
|---|---|---|---|---|---|
| 4 (10) | 210 | 81 | 35 | 59 | 16 |
| 5 (11) | 120 | 11 | 22 | 55 | 2.6 |
| 6 (12) | 36 | 51 | 48 | 75 | 37 |

[a]EC$_{50}$ values are indicated in μM.

In conclusion, we have developed a synthetic approach to access 2-aminoimidazole/triazole (2-AIT) conjugates that is underpinned by the Cu(I)-catalyzed [3+2] alkyne/azide cycloaddition. Using this chemistry, we have assembled a focused library of 2-AIT conjugates and, using an initial hit from this library as lead, derived compounds that are able to inhibit and disperse bacterial biofilms across both order and phylum. Mechanistic studies are currently underway to determine how 2-AIT conjugates 10-12 inhibit and disperse biofilms. Furthermore, given the promising anti-biofilm activity displayed by these and other 2-AI derivatives (Melander et al., U.S. Patent Application Publication No. 2008/0181923; J. J. Richards, R. W. Huigens, T. E. Ballard, A. Basso, J. Cavanagh, C. Melander, *Chemical Communications* 2008, 14, 1698-1700; J. J. Richards, T. E. Ballard, C. Melander, *Organic and Biomolecular Chemistry* 2008, 6, 1356-1363; J. J. Richards, T. E. Ballard, R. W. Huigens, C. Melander, *ChemBioChem* 2008, 9, 1267-1279; R. W. Huigens, L. Ma, C. Gambino, A. Basso, P. D. R. Moeller, J. Cavanagh, D. J. Wozniak, C. Melander, *Molecular Biosystems* 2008, 4, 614-21; R. W. Huigens, G. Parise, J. J. Richards, T. E. Ballard, W. Zeng, R. Deora, C. Melander, *Journal of the American Chemical Society* 2007, 22, 6966-6967), we are continuing to develop methodology to access further functionalized libraries based upon the 2-AI core motif.

Example 2

Protocols for 2-AIT Conjugate Synthesis and Activity Testing. All reagents used for chemical synthesis were purchased from commercially available sources and used without further purification. Chromatography was performed using 60 Å mesh standard grade silica gel from Sorbtech (Sorbent Technologies, Inc., Atlanta, Ga.). NMR solvents were obtained from Cambridge Isotope Laboratories, Inc. (Andover, Mass.) and used as received. $^1$H NMR (300 MHz or 400 MHz) and $^{13}$C NMR (75 MHz or 100 MHz) spectra were recorded at 25° C. on Varian Mercury spectrometers. Chemical shifts (δ) are given in ppm relative to tetramethylsilane or the respective NMR solvent; coupling constants (J)

are in hertz (Hz). Abbreviations used are s=singlet, bs=broad singlet, d=doublet, dd=doublet of doublets, t=triplet, dt=doublet of triplets, bt=broad triplet, qt=quartet, m=multiplet, bm=broad multiplet and br=broad. High and low resolution mass spectra were obtained at the North Carolina State Mass Spectrometry Laboratory for Biotechnology. FAB experiments were carried out with a JOEL HX110HF mass spectrometer while ESI experiments were carried out on an Agilent LC-TOF mass spectrometers.

*A. baumannii* (strain #19606) was obtained from ATCC. *P. aeruginosa* strains PA14 and PAO1 were provided by the Wozniak group at WFT School of Medicine while *B. bronchiseptica* strain Rb50 was donated by the Deora group at the WFT School of Medicine. *S. aureus* (strain #29213) was also obtained from the ATCC.

Chemical Library:

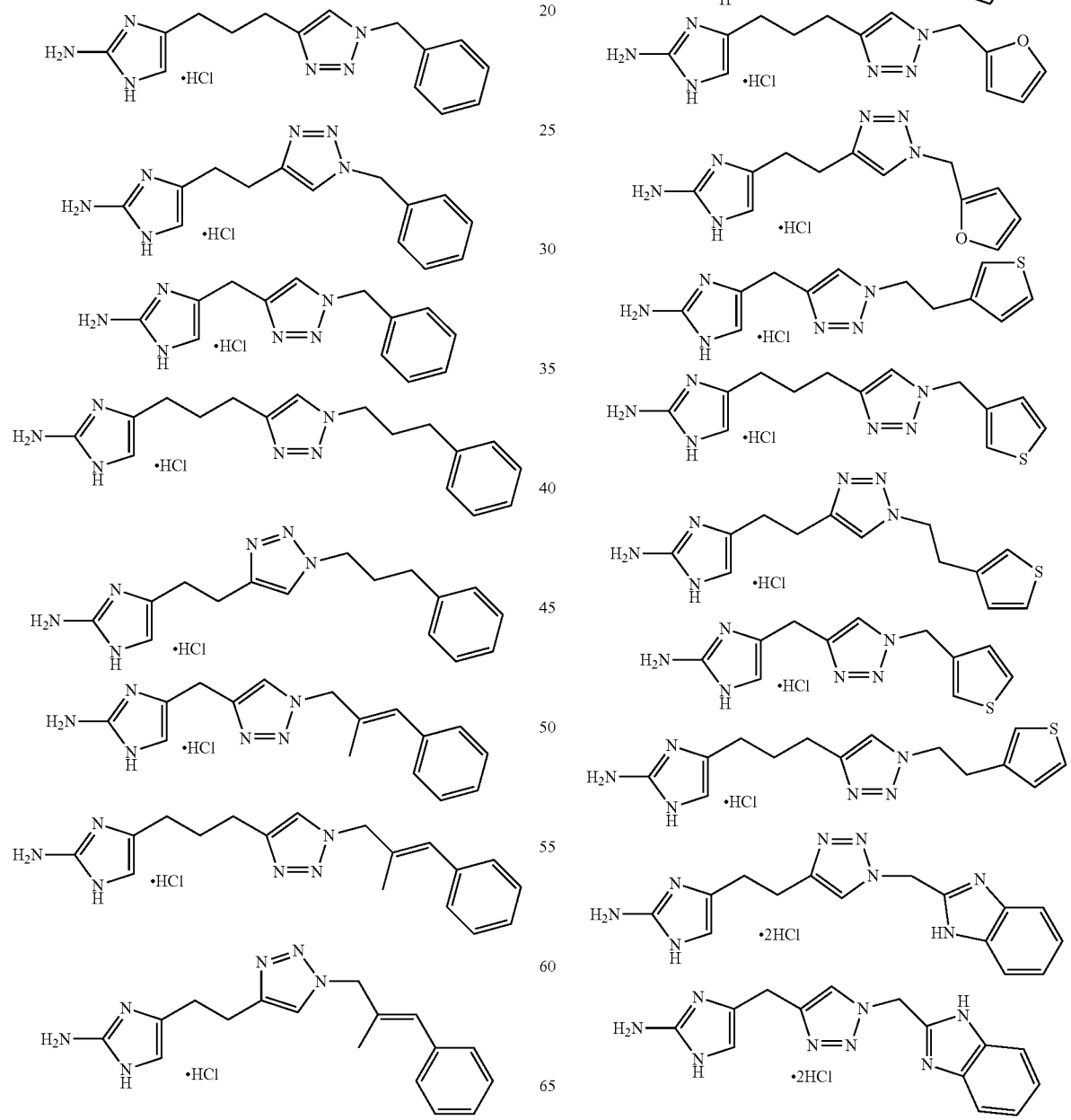

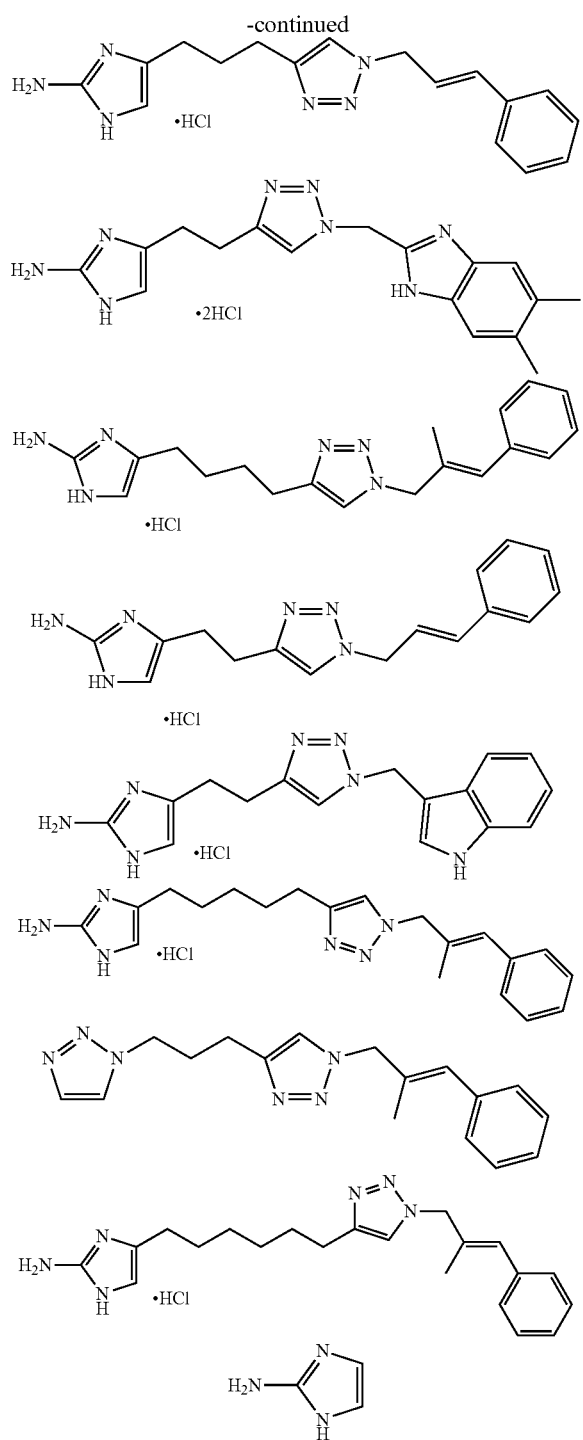

Synthesis:

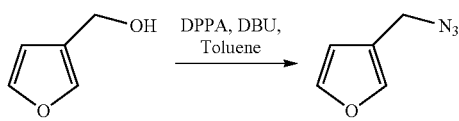

To a 50 mL round-bottomed flask equipped with a magnetic stirbar was added 3-furan methanol (1.00 g, 10.2 mmol) and a solution of diphenyl phosphoryl azide (3.37 g, 12.2 mmol) in toluene (30 mL). The stirring solution is allowed to cool to 0° C., in which 1, 8 Diazabycyclo [5.4.0.]undec-7-ene (1.86 g, 12.2 mmol) was added dropwise. The reaction is allowed to slowly warm to ambient temperature for an additional 16 hours of stirring. After this period, the reaction mixture is washed with water (2×20 mL) and then with 5% HCl (20 mL). Volatiles are evaporated under reduced pressure. The resulting residue is then purified by column chromatography (1:9 ethyl acetate/hexane) providing 3-azidomethyl furan (1.19 g, 95%) as a colorless oil. $^1$H NMR (400 MHz, CDCl$_3$) δ 7.46 (d, 1H), δ 7.44 (s, 1H), δ 6.42 (d, 1H), δ 4.20 (s, 2H). ppm; $^{13}$C NMR (75 MHz, CDCl$_3$) δ 144.1, 141.1, 110.4, 92.1, 45.8 ppm; LRMS (EI) Calcd for C$_5$H$_5$N$_3$O (M$_+$) 123, found 123.

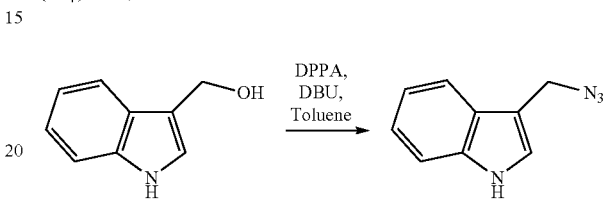

Following the same procedure used to synthesize 3-azidomethyl furan, indole-3-methanol (2.00 g, 13.6 mmol) was converted to 3-azidomethyl indole (1.31 g, 56%) as a yellow oil. $^1$H NMR (300 MHz, CDCl$_3$) δ 8.19 (bs, 1H), δ 7.71 (d, 1H), δ 7.39 (m, 2H), δ 7.19 (m, 2H), δ 4.54 (s, 2H) ppm; $^{13}$C NMR (75 MHz, CDCl$_3$) δ 130.3, 125.9, 125.3, 122.2, 120.3, 120.3, 119.7, 118.7, 111.9 ppm; LRMS (EI) calcd for C$_9$H$_8$N$_4$ (M$_+$) 172, found 172.

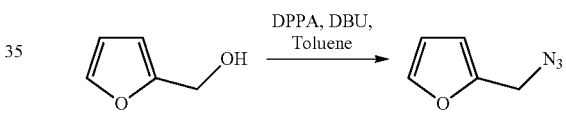

Following the same procedure used to synthesize 3-azidomethyl furan, furfuryl alcohol (2.50 g, 25.5 mmol) was converted to 2-azidomethyl furan (2.96 g, 95%) as a colorless oil. $^1$H NMR (300 MHz, CDCl$_3$) δ 7.43 (d, 1H), δ 6.36 (m, 2H), δ 4.29 (s, 2H) ppm; $_{13}$C NMR (75 MHz, CDCl$_3$) δ 148.2, 110.7, 109.6, 47.2 ppm; LRMS (EI) calcd for C$_5$H$_5$N$_3$O (M$_+$) 123, found 123.

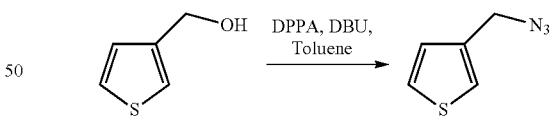

Following the same procedure used to synthesize 3-azidomethyl furan, thiophene-3-methanol (3.14 g, 27.6 mmol) was converted to 3-azidomethyl thiophene (3.72 g, 97%) as a colorless oil. $^1$H NMR (300 MHz, CDCl$_3$) δ 7.38 (d, 1H), δ 7.23 (s, 1H), δ 7.10 (d, 1H), δ 4.36 (s, 2H) ppm; $^{13}$C (75 MHz, CDCl$_3$) δ 136.4, 127.6, 127.1, 124.0, 49.9 ppm; LRMS (EI) calcd for C$_5$H$_5$N$_3$S (M$_+$) 139, found 139.

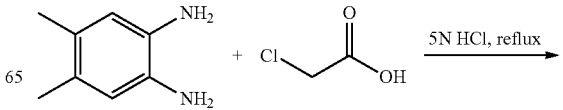

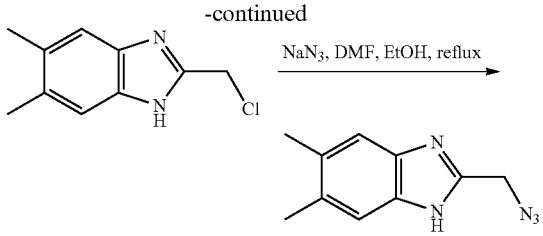

2-chloroethyl-5,6-dimethyl-1H-benzimidazole was synthesized through the treatment of 4,5-dimethyl-1,2-phenylenediamine to conditions outlined by Hortelano (Raban et al., Org. Chem. 1985, 50 (13), 2205-2210). The resulting product was transformed to 2-azidomethyl-5,6-dimethyl-1H-benzimidazole following conditions outlined by Hankovszky resulting in a yellow solid (Hiales et al., *Synthesis* 1978, 4, 313-315). $_1$H NMR (300 MHz, CDCl$_3$) δ 7.26 (s, 2H), δ 4.72 (s, 2H), δ 2.37 (s, 6H) ppm; $^{13}$C NMR (75 MHz, DMSO) δ 153.7, 134.3, 130.1, 125.1, 124.6, 117.2, 113.6, 48.0, 20.6, 19.6 ppm; HRMS (FAB) calcd for C$_{10}$H$_{11}$N$_5$(M$_+$) 201.1014, found 201.1010.

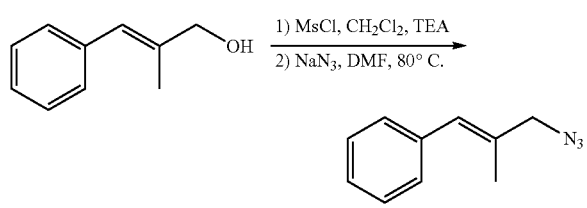

To a 100 mL round-bottomed flask equipped with a magnetic stir was added trans-2-methyl-3-phenyl-2-propen-1-ol (2.00 g, 13.5 mmol) and 75 mL of methylene chloride. The solution was then cooled to 0° C. while stirring. Then, triethylamine (2.75 g, 27.0 mmol) is added followed by a dropwise addition of methanesulfonyl chloride (2.34 g, 20.4 mmol) and a two hour stir period. The reaction mixture is washed with water (2×75 mL), dried with sodium sulfate and then concentrated de vacuo. The crude mixture is then dissolved in 75 mL of DMF and then stirred via magnetic stir bar. To this mixture, sodium azide (1.76 g, 27.0 mmol) is added. The reaction mixture is then heated to 80° C. and allowed to stir for two hours. At this time, volatiles are concentrated de vacuo and the resulting residue is purified via column chromatography (1:9 ethyl acetate/hexane) providing (3-Azido-2-methyl propenyl)-benzene (2.08 g, 89%) as a colorless oil. $_1$H NMR (300 MHz, CDCl$_3$) δ 7.36-7.25 (m, 5H), δ 6.53 (s, 1H), δ 3.87 (s, 2H) ppm; $_{13}$C NMR (75 MHz, CDCl$_3$) δ 129.4, 129.2, 128.9, 128.6, 128.4, 127.1, 59.9, 52.0, 22.3, 16.5 ppm; LRMS (EI) calcd for C$_{10}$H$_{11}$N$_3$(M$_+$) 173, found 173.

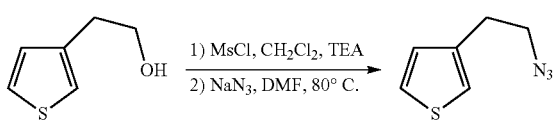

Following the same procedure used to synthesize (3-Azido-2-methyl-propenyl)benzene, thiophene-3-ethanol (2.00 g, 15.5 mmol) was converted to 3-azidoethyl-thiophene (2.06 g, 86%) as a colorless oil. $_1$H NMR (300 MHz, CDCl$_3$) δ 7.36 (s, 1H), δ 7.14 (d, 1H), δ 7.04 (d, 1H), δ 3.54 (t, 2H), δ 2.98 (t, 2H) ppm; $^{13}$C NMR (75 MHz, CDCl$_3$) δ 138.7, 128.4, 126.3, 122.2, 52.0, 30.1 ppm; LRMS (EI) calcd for C$_6$H$_7$N$_3$S (M$_+$) 153, found 153.

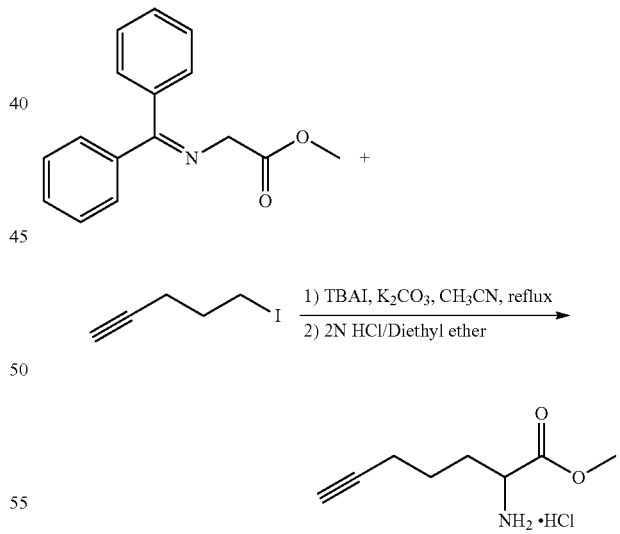

2-Amino-hex-5-ynoic acid methyl ester hydrochloride was synthesized using the same methods previously reported for the synthesis of 2-Amino-pent-4-ynoic acid methyl ester hydrochloride (Kotha et al., *Tetrahedron* 2002, 58, 9203-9208). $_1$H NMR (300 MHz, D$_2$O) δ 4.16 (t, 1H), δ 3.71 (s, 3H), δ 2.32 (t, 1H), δ 2.29 (m, 2H), δ 2.06 (m, 2H) ppm; $_{13}$C NMR (75 MHz, D$_2$O) δ 170.4, 82.4, 71.4, 53.9, 52.1, 28.7, 14.4 ppm; HRMS (ESI) calcd for C$_7$H$_{11}$NO$_2$ (M$_+$) 142.0859, found 142.862.

2-Amino-hept-6-ynoic acid methyl ester hydrochloride was synthesized using the same methods previously reported for the synthesis of 2-Amino-pent-4-ynoic acid methyl ester hydrochloride (Kotha et al., Tetrahedron 2002, 58, 9203-9208). $_1$H NMR (300 MHz, DMSO) δ 8.75 (s, 2H), δ 3.99 (m, 1H), δ 3.72 (s, 3H), δ 2.82 (t, 1H), δ 2.17 (m, 2H), δ 1.89 (m, 2H), δ 1.51 (m, 2H) ppm; $^{13}$C NMR (75 MHz, DMSO) δ 163.7, 83.1, 69.2, 60.9, 30.6, 29.5, 23.9, 17.6 ppm; HRMS (ESI) calcd for C$_8$H$_{13}$NO$_2$ (M$_+$) 156.1019, found 156.1017.

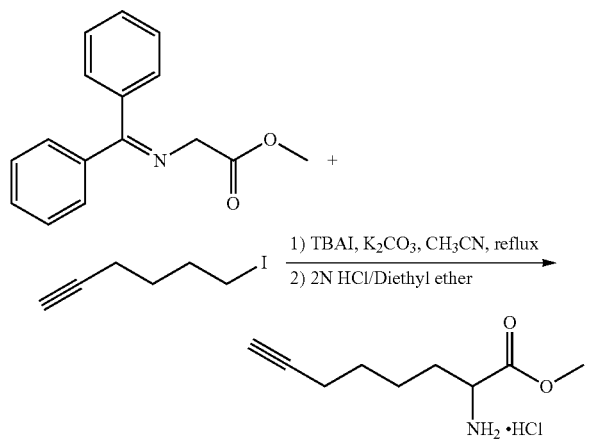

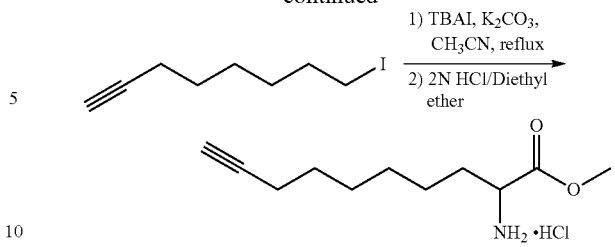

2-Amino-oct-7-ynoic acid methyl ester hydrochloride was synthesized using the same methods previously reported for the synthesis of 2-Amino-pent-4-ynoic acid methyl ester hydrochloride (Kotha et al., Tetrahedron 2002, 58, 9203-9208). $_1$H NMR (300 MHz, D$_2$O) δ 4.16 (t, 1H), δ 3.84 (s, 3H), δ 2.35 (t, 1H), δ 2.24 (m, 2H), δ 1.95 (m, 2H), δ 1.52 (m, 4H) ppm; $_{13}$C NMR (75 MHz, D$_2$O) δ 170.9, 85.6, 69.6, 53.6, 52.9, 29.3, 27.0, 23.4, 17.3 ppm; HRMS (ESI) calcd for C$_9$H$_{15}$NO$_2$(M$_+$) 170.1176, found 170.1171.

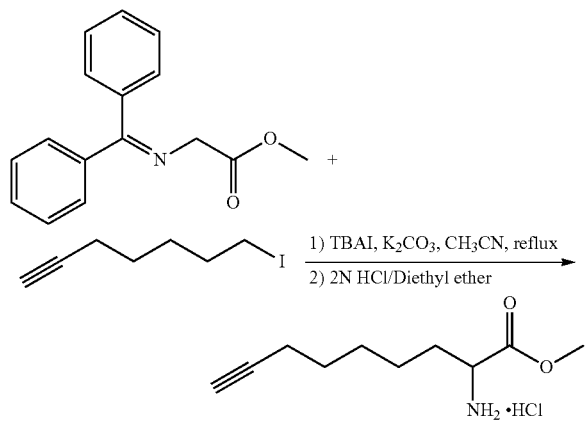

2-Amino-non-8-ynoic acid methyl ester hydrochloride was synthesized using the same methods previously reported for the synthesis of 2-Amino-pent-4-ynoic acid methyl ester hydrochloride (Kotha et al., Tetrahedron 2002, 58, 9203-9208). $_1$H NMR (300 MHz, D$_2$O) δ 4.21 (t, 1H), δ 3.90 (s, 3H), δ 2.41 (t, 1H), δ 2.28 (m, 2H), δ 2.01 (m, 2H), δ 1.51 (m, 6H) ppm; $_{13}$C NMR (75 MHz, D$_2$O) δ 171.1, 86.4, 69.4, 53.7, 53.1, 29.8, 27.5, 27.4, 23.8, 17.6 ppm; HRMS (ESI) calcd for C$_{10}$H$_{18}$NO$_2$(M$_+$) 184.1332, found 184.1329.

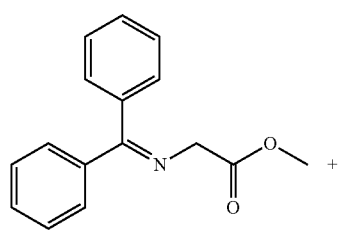

2-Amino-dec-9-ynoic acid methyl ester hydrochloride was synthesized using the same methods previously reported for the synthesis of 2-Amino-pent-4-ynoic acid methyl ester hydrochloride (Kotha et al., Tetrahedron 2002, 58, 9203-9208). $^1$H NMR (300 MHz, D$_2$O) δ 4.16 (t, 1H), δ 3.86 (s, 3H), δ 2.36 (t, 1H), δ 2.21 (m, 2H), δ 1.98 (m, 2H), δ 1.55-1.39 (m, 8H) ppm; $_{13}$C NMR (75 MHz, D$_2$O) δ 171.2, 86.7, 69.3, 53.7, 53.1, 29.8, 27.7, 27.7, 27.6, 24.1, 17.6 ppm; HRMS (ESI) calcd for C$_{11}$H$_{20}$NO$_2$(M$_+$) 198.1488, found 198.1488.

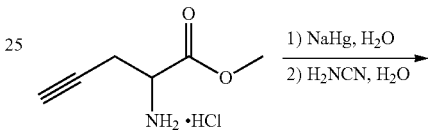

2-Amino-pent-4-ynoic acid methyl ester hydrochloride (2.91 g, 17.8 mmol) was treated to an Akabori reduction followed by a cyanamide condensation employing conditions previously reported to produce 4-Prop-2-ynyl-1H-imidazol-2-ylamine hydrochloride (1.65 g, 59%) as a yellow oil (Olofson et al., Journal of Organic Chemistry 1997, 62, (23), 7918-7919). $_1$H NMR (300 MHz, CD$_3$OD) δ 6.30 (s, 1H), δ 5.02 (d, 2H), δ 2.26 (t, 1H) ppm; $^{13}$C NMR (75 MHz, CD$_3$OD) δ 150.1, 127.2, 109.6, 83.6, 69.8, 15.9 ppm; HRMS (ESI) calcd for C$_6$H$_7$N$_3$ (M$_+$) 122.0712, found 122.0713.

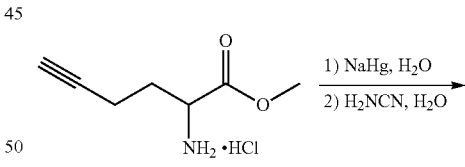

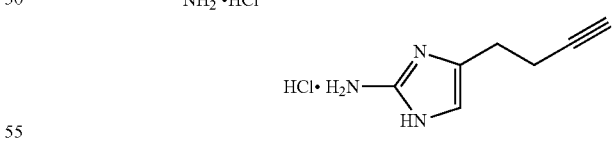

2-Amino-hex-5-ynoic acid methyl ester hydrochloride (2.53 g, 14.2 mmol) was treated to an Akabori reduction followed by a cyanamide condensation employing conditions previously reported to produce 4-But-3-ynyl-1H-imidazol-2-ylamine hydrochloride (1.17 g, 48%) as a pale yellow oil (Olofson et al., Journal of Organic Chemistry 1997, 62, (23), 7918-7919). $^1$H NMR (300 MHz, CD$_3$OD) δ 6.52 (s, 1H), δ 2.61 (t, 2H), δ 2.42 (m, 2H), δ 2.27 (t, 1H) ppm; $^{13}$C NMR (75 MHz, CD$_3$OD) δ 147.4, 126.2, 109.4, 81.9, 69.9, 23.8, 17.4 ppm; HRMS (ESI) calcd for C$_7$H$_{10}$N$_3$ (M$_+$) 136.0869, found 136.0865.

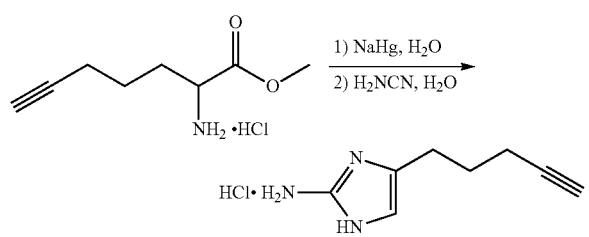

2-Amino-hept-6-ynoic acid methyl ester hydrochloride (2.00 g, 10.4 mmol) was treated to an Akabori reduction followed by a cyanamide condensation employing conditions previously reported to produce 4-Pent-4-ynyl-1H-imidazol-2-ylamine hydrochloride (1.75 g, 90%) as a pale oil (Olofson et al., Journal of Organic Chemistry 1997, 62, (23), 7918-7919). $_1$H NMR (300 MHz, CDCl$_3$) δ 6.68 (bs, 2H), δ 6.24 (s, 1H), δ 2.51 (t, 2H), δ 2.17 (t, 1H), δ 1.95 (s, 1H), δ 1.74 (m, 2H) ppm; $^{13}$C NMR (75 MHz, CDCl$_3$) δ 148.3, 132.7, 111.6, 84.4, 69.1, 28.0, 26.0, 18.2 ppm; HRMS (ESI) calcd for C$_{10}$H$_{16}$N$_3$(M$_+$) 150.1026, found 150.1029.

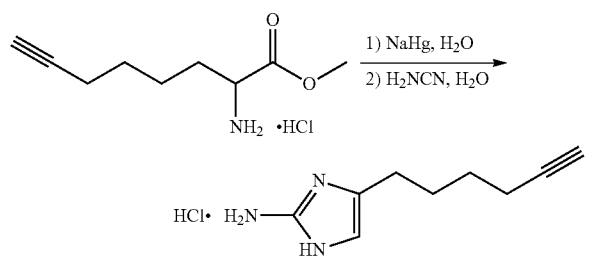

2-Amino-oct-7-ynoic acid methyl ester hydrochloride (2.90 g, 14.1 mmol) was treated to an Akabori reduction followed by a cyanamide condensation employing conditions previously reported to produce 4-Hex-5-ynyl-1H-imidazol-2-ylamine hydrochloride (2.45 g, 87%) as a pale yellow solid (Olofson et al., Journal of Organic Chemistry 1997, 62, (23), 7918-7919). $^1$H NMR (300 MHz, CD$_3$OD) δ 6.43 (s, 1H), δ 2.44 (t, 2H), 2.14 (t, 1H), δ 2.12 (m, 2H), δ 1.64 (m, 2H), δ 1.47 (m, 2H) ppm; $_{13}$C NMR (75 MHz, CD$_3$OD) δ 147.3, 127.6, 108.5, 83.4, 68.7, 27.7, 27.1, 23.8, 17.5 ppm; HRMS (ESI) calcd for C$_9$H$_{14}$N$_3$ (M$_+$) 164.1182, found 164.1182.

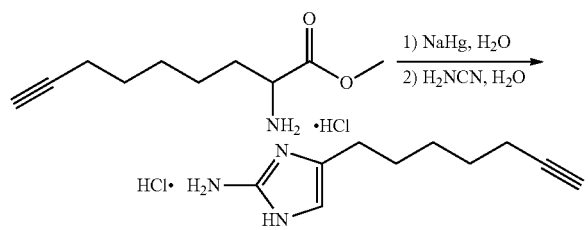

2-Amino-non-8-ynoic acid methyl ester hydrochloride (2.02 g, 9.20 mmol) was treated to an Akabori reduction followed by a cyanamide condensation employing conditions previously reported to produce 4-Hept-6-ynyl-1H-imidazol-2-ylamine hydrochloride (1.04 g, 53%) as a pale yellow solid (Olofson et al., Journal of Organic Chemistry 1997, 62, (23), 7918-7919). $^1$H NMR (300 MHz, CD$_3$OD) δ 6.17 (s, 1H), δ 2.19 (t, 2H), δ 1.90 (t, 1H), δ 1.86 (m, 2H), δ 1.24-1.13 (m, 6H) ppm; $^{13}$C NMR (75 MHz, CD$_3$OD) δ 147.5, 128.3, 108.8, 83.8, 65.5, 28.4, 28.3, 28.2, 24.5, 17.8 ppm; HRMS (ESI) calcd for C$_{10}$H$_{16}$N$_3$(M$_+$) 178.1338, found 178.1337.

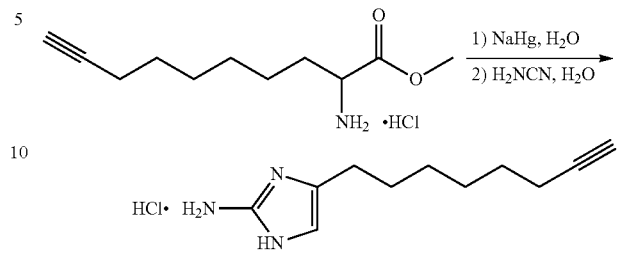

2-Amino-dec-9-ynoic acid methyl ester hydrochloride (1.50 g, 6.42 mmol) was treated to an Akabori reduction followed by a cyanamide condensation employing conditions previously reported to produce 4 Oct. 7-ynyl-1H-imidazol-2-ylamine hydrochloride (0.774 g, 53%) as a pale yellow solid (Olofson et al., Journal of Organic Chemistry 1997, 62, (23), 7918-7919). $^1$H NMR (400 MHz, CD$_3$OD) δ 6.09 (s, 1H), δ 2.19 (t, 2H), δ 1.95 (t, 1H), 1.93 (m, 2H), δ 1.39-1.11 (m, 8H) ppm; $_{13}$C NMR (75 MHz, CD$_3$OD) δ 148.5, 131.0, 110.1, 83.9, 68.3, 28.6, 28.5, 28.4, 28.3, 25.7, 17.8 ppm; HRMS (ESI) calcd for C$_{11}$H$_{18}$N$_3$ (M$_+$) 192.1495, found 192.1495.

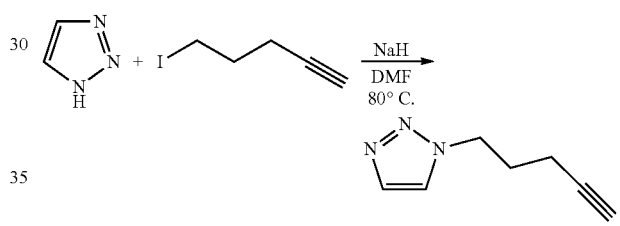

To a 50 mL round-bottomed flask equipped with a magnetic stirbar was added 1-H-1,2,3-triazole (0.192 g, 2.78 mmol) and DMF (10 mL) and then cooled to 0° C. while stirring. Then, sodium hydride (60% dispersion in mineral oil) (0.133 g, 3.33 mmol) is added to the reaction mixture and was slowly allowed to warm to ambient temperature. Then, 1-iodo-4 pentyne (0.647 g, 3.33 mmol) was added dropwise. The reaction mixture was then heated to 80° C. and allowed to stir for 2.5 hours. Water (20 mL) was then added to the reaction mixture and then extracted with ethyl acetate (2×20 mL). The organic phase was dried with sodium sulfate and concentrated de vacuo followed by a purification by column chromatography (ethyl acetate/hexane) to produce 1-Pent-4-ynyl-1H-[1,2,3]triazole (0.349 g, 93%) as a colorless oil. $_1$H NMR (300 MHz, CDCl$_3$) δ 7.67 (s, 1H), δ 7.59 (s, 1H), δ 4.53 (t, 2H), δ 2.20 (t, 2H), δ 2.17 (m, 2H), δ 2.04 (s, 1H) ppm; $^{13}$C NMR (75 MHz, CDCl$_3$) δ 133.9, 123.9, 82.2, 70.4, 48.7, 28.9, 15.7 ppm; HRMS (ESI) calcd for C$_7$H$_{10}$N$_3$ (M$_+$) 136.0869, found 136.0866.

General procedure for click reactions: The terminal alkyne (1.0 equiv.) was dissolved in a 1:1:1 mixture of tert-butyl alcohol, water and methylene chloride (ca. 10 mL per 0.300 g of terminal alkyne). To this solution, the appropriate azide (1.2 equiv.) was added while stirring vigorously at room temperature. Copper (II) sulfate pentahydrate (15 mol %) and sodium ascorbate (45 mol %) were then added sequentially to the solution. Reaction mixtures were allowed to stir until completion via TLC analysis (12-24 hrs). The solvents were then removed de vacuo in which the resulting residue was dissolved in methanol and purified by flash chromatography (10-20% ammonia saturated methanol:methylene chloride). The resulting fractions were evaporated under reduced pressure followed by a 24 hr high vacuum treatment to remove all ammonia traces. Methanol saturated with HCl is then added to the purified product in which all volatiles are then removed under reduced pressure.

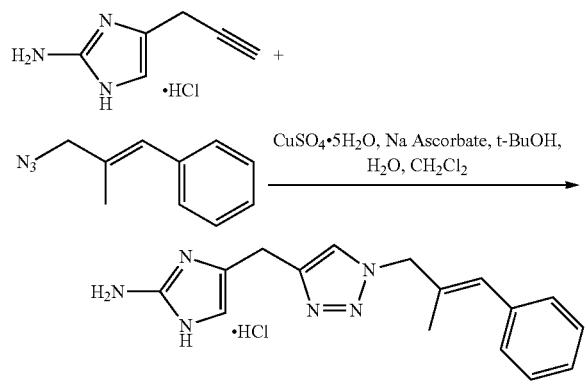

4-Prop-2-ynyl-1H-imidazol-2-ylamine hydrochloride (0.127 g, 0.809 mmol) was reacted with (3-Azido-2-methyl-propenyl)-benzene (0.168 g, 0.971 mmol) following the general procedure for click reactions outlined above to produce 4-[1-(2-Methyl-3-phenyl-allyl)-1H [1,2,3]triazol-4-ylmethyl]-1H-imidazol-2-ylamine hydrochloride (0.244 g, 91%) of a pale yellow solid. $_1$H NMR (300 MHz, D$_2$O) δ 7.94 (s, 1H), δ 7.40-7.35 (m, 5H), δ 6.56 (s, 1H), δ 5.10 (s, 2H), δ 3.99 (s, 2H), δ 1.76 (s, 3H) ppm; $_{13}$C δ 145.8, 138.1, 136.9, 136.5, 136.4, 132.8, 128.3, 128.0, 127.6, 125.3, 123.4, 49.3, 23.8, 23.4; HRMS (ESI) calcd for C$_{16}$H$_{18}$N$_6$(M$_+$) 295.1665, found 295.1665.

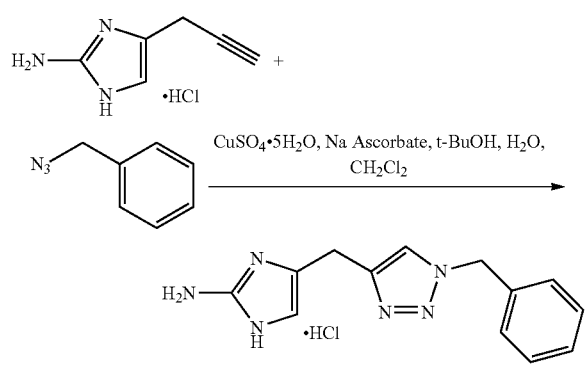

4-Prop-2-ynyl-1H-imidazol-2-ylamine hydrochloride (0.095 g, 0.603 mmol) was reacted with benzyl azide (0.096 g, 0.723 mmol) following the general procedure for click reactions outlined above to produce 4-(1-Benzyl-1H-[1,2,3]thiazol-4-ylmethyl)-1H-imidazol 2-ylamine hydrochloride (0.151 g, 86%) of a pale yellow solid. $_1$H NMR (300 MHz, D$_2$O) δ 7.79 (s, 1H), δ 7.42-7.35 (m, 5H), δ 6.43 (s, 1H), δ 5.58 (s, 2H), δ 3.86 (s, 2H) ppm; $_{13}$C δ 145.4, 136.6, 136.4, 128.8, 128.7, 126.9, 126.8, 126.3, 124.1, 121.8, 109.6, 53.3, 24.1 ppm; HRMS (ESI) calcd for C$_{13}$H$_{16}$N$_6$O (M$_+$) 254.1352, found 254.1352.

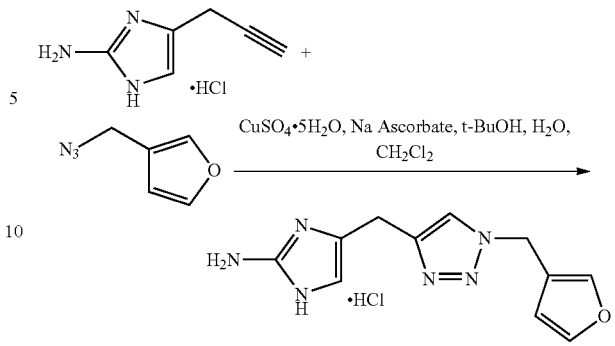

4-Prop-2-ynyl-1H-imidazol-2-ylamine hydrochloride (0.101 g, 0.639 mmol) was reacted with 3-azidomethyl-furan (0.094 g, 0.767 mmol) following the general procedure for click reactions outlined above to produce 4-(1-Furan-3-ylmethyl-1H-[1,2,3]triazol-4-ylmethyl)-1H-imidazol-2-ylamine hydrochloride (0.077 g, 43%) of a pale yellow solid. $^1$H NMR (300 MHz, CD$_3$OD) δ 8.12 (s, 1H), δ 7.60 (s, 1H), δ 7.38 (s, 1H), δ 6.53 (s, 1H), δ 6.37 (s, 1H), δ 5.46 (s, 2H), δ 3.95 (s, 2H) ppm; $^{13}$C NMR (75 MHz, CD$_3$OD) δ 146.1, 145.3, 144.1, 141.0, 123.3, 123.1, 110.3, 110.2, 109.9, 51.3, 19.9 ppm; HRMS (ESI) calcd for C$_{11}$H$_{12}$N$_6$O (M$_+$) 244.1145, found 244.1145.

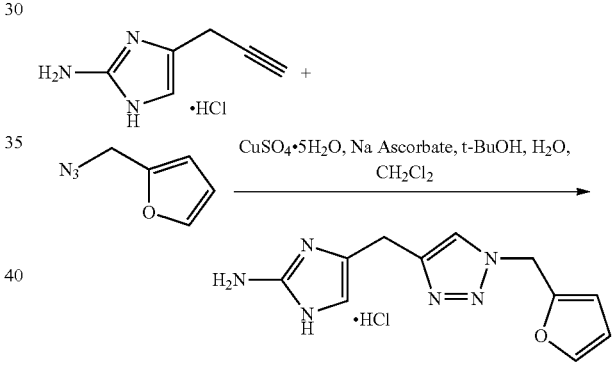

4-Prop-2-ynyl-1H-imidazol-2-ylamine hydrochloride (0.096 g, 0.061 mmol) was reacted with 2-azidomethyl-furan (0.089 g, 0.729 mmol) following the general procedure for click reactions outlined above to produce 4-(1-Furan-2-ylmethyl-1H-[1,2,3]triazol-4-ylmethyl)-1H-imidazol-2-ylamine hydrochloride (0.078 g, 46%) as a pale yellow solid. $_1$H NMR (300 MHz, CD$_3$OD) δ 7.93 (s, 1H), δ 7.41 (s, 1H), 6.49 (s, 2H), δ 6.32 (s, 1H), δ 5.56 (s, 2H), δ 3.89 (s, 2) ppm; $_{13}$C NMR (75 MHz, CD$_3$OD) δ 146.2, 146.1, 142.4, 141.5, 122.3, 122.2, 108.9, 109.2, 108.8, 51.6, 18.9 ppm; HRMS (ESI) calcd for C$_{11}$H$_{12}$N$_6$O (M$_+$) 245.1145, found 245.1147.

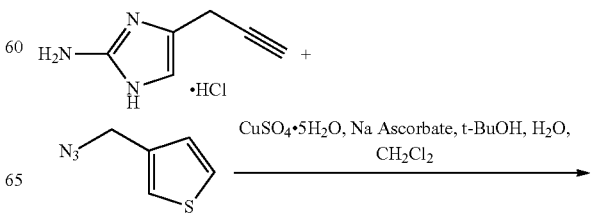

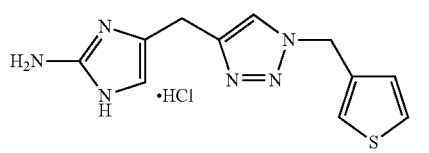

4-Prop-2-ynyl-1H-imidazol-2-ylamine hydrochloride (0.096 (0.061 mmol) was reacted with 3-azidomethyl thiophene (0.102 g, 0.732 mmol) following the general procedure for click reactions outlined above to produce 4-(1-Thiophen-3-ylmethyl-1H-[1,2,3]triazol-4-ylmethyl)-1Himidazol-2-ylamine hydrochloride (0.079 g, 44%) of a pale yellow solid. $_1$H NMR (300 MHz, CD$_3$OD) δ 8.18 (s, 1H), δ 7.44 (s, 1H), δ 7.30 (d, 1H), δ 6.98 (d, 1H), δ 6.53 (s, 1H), δ 5.57 (s, 2H), δ 3.95 (s, 2H) ppm; $_{13}$C (75 MHz, CD$_3$OD) δ 145.7, 145.1, 143.7, 139.7, 129.8, 121.8, 111.5, 109.8, 109.2, 52.7, 21.5 ppm; HRMS (ESI) calcd for C$_{11}$H$_{12}$N$_6$S (M$_+$) 260.0919, found 260.0919.

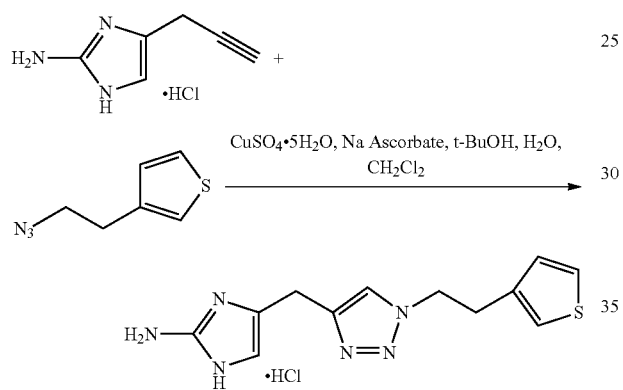

4-Prop-2-ynyl-1H-imidazol-2-ylamine hydrochloride (0.101 g, 0.641 mmol was reacted with 3-(2-Azido-ethyl)-thiophene (0.118 g, 0.769 mmol) following the general procedure for click reactions outlined above to produce 4-[1-(2-Thiophen-3-yl-ethyl)-1H [1,2,3]triazol-4-ylmethyl]-1H-imidazol-2-ylamine hydrochloride (0.119 g, 60%) of a pale yellow solid. $_1$H NMR (300 MHz, CD$_3$OD) δ 7.42 (s, 1H), δ 7.19 (t, 1H), δ 6.90 (s, 1H), □ 6.78 (d, 1H), δ 6.09 (s, 1H), δ 4.47 (t, 2H), δ 3.67 (s, 2H), δ 3.09 (t, 2H) ppm; $_{13}$C; (75 MHz, CD$_3$OD) δ 151.2, 145.7, 137.7, 130.5, 127.8, 125.8, 122.9, 121.9, 110.3, 50.798, 30.7, 23.3 ppm; HRMS (ESI) calcd for C$_{12}$H$_{14}$N$_6$S (M$_+$) 274.1001, found 274.1007.

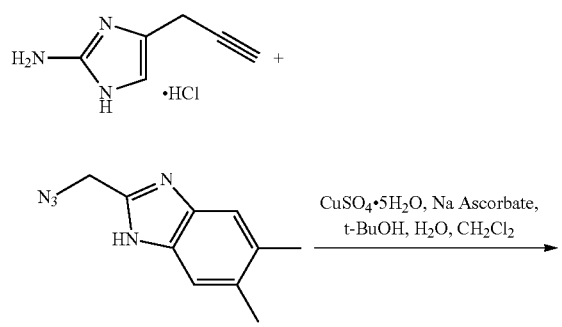

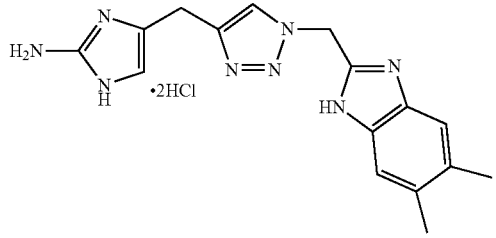

4-Prop-2-ynyl-1H-imidazol-2-ylamine hydrochloride (0.047 g, 0.295 mmol) was reacted with 2-azidomethyl-5,6-dimethyl-1H-benzimidazole (0.071 g, 0.354 mmol) following the general procedure for click reactions outlined above to produce 4-[1-(5,6 Dimethyl-1H-benzoimidazol-2-ylmethyl)-1H-[1,2,3]triazol-4-ylmethyl]-1H-imidazol-2-ylamine dihydrochloride (0.029 g, 25%) of a yellow solid. $^1$H NMR (300 MHz, CD$_3$OD) δ 8.09 (s, 1H), δ 7.45 (s, 2H), δ 6.52 (s, 1H), δ 6.08 (s, 2H), δ 3.93 (s, 2H), δ 2.35 (s, 6H) ppm; $_{13}$C (75 MHz, CD$_3$OD) δ 142.2, 136.9, 136.6, 124.5, 124.3, 113.8, 113.4, 110.0, 100.4, 85.8, 80.6, 75.3, 74.1, 45.0, 20.9, 19.28 ppm; HRMS (ESI) calcd for C$_{16}$H$_{18}$N$_8$ (M$_+$) 323.1727, found 323.1734.

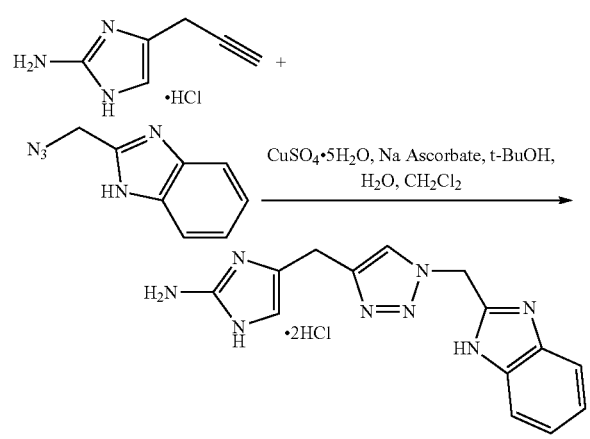

4-Prop-2-ynyl-1H-imidazol-2-ylamine hydrochloride (0.091 g, 0.576 mmol) was reacted with 2-azidomethyl-1H-benzimidazole, which was synthesized using previously reported methods (Hiales et al., Synthesis 1978, 4, 313-315), (0.120 g, 0.691 mmol) following the general procedure for click reactions outlined above to produce 4-[1-(1H-Benzoimidazol-2-ylmethyl)-1H-[1,2,3]triazol-4-ylmethyl] 1Himidazol-2-ylamine dihydrochloride (0.125 g, 59%) of a yellow solid. $_1$H NMR (300 MHz, CD$_3$OD) δ 8.01 (s, 1H), δ 7.58 (d, 2H), δ 7.31 (t, 2H), δ 6.44 (s, 1H), δ 5.98 (s, 2H) δ 3.84 (s, 2H) ppm; $_{13}$C (75 MHz, CD$_3$OD) δ 135.6, 124.7, 123.7, 123.5, 122.8, 112.8, 112.3, 108.4, 83.6, 78.9, 74.0, 73.2, 44.2, 19.3 ppm; HRMS (ESI) calcd for C$_{14}$H$_{14}$N$_8$(M$_+$) 295.1414, found 295.1420.

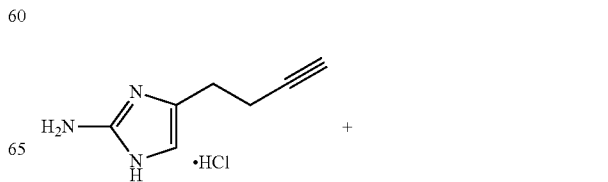

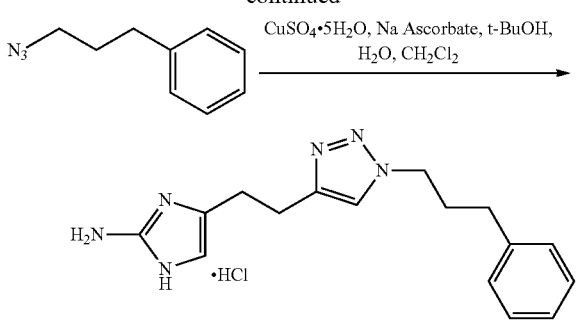
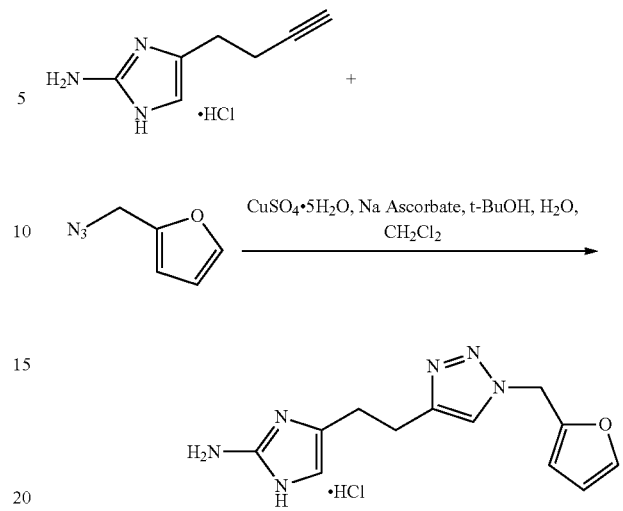

4-But-3-ynyl-1H-imidazol-2-ylamine hydrochloride (0.0735 g, 0.428 mmol) was reacted with (3-azido-propyl)benzene, which was synthesized using previously reported methods (Suenaga et al., Tetrahedron Letters 2003, 44, 5799-5801), (0.083 g, 0.514 mmol) following the general procedure for click reactions outlined above to produce 4-{2-[1-(3-Phenyl-propyl)-1H-[1,2,3]triazol-4-yl]-ethyl}-1H-imidazol-2-ylamine hydrochloride (0.051 g, 36%) of a pale yellow oil. $_1$H NMR (300 MHz, CD$_3$OD) δ 7.87 (s, 1H), δ 7.32-7.22 (m, 5H), δ 6.54 (s, 1H), δ 4.31 (t, 2H), δ 3.05 (t, 2H), δ 2.93 (t, 2H), δ 2.67 (t, 2H), δ 2.23 (m, 2H) ppm; $_{13}$C (75 MHz CD$_3$OD) δ 153.3, 146.6, 140.4, 134.3, 128.8, 128.7, 128.6, 126.6, 121.5, 67.5, 53.9, 32.8, 32.9, 29.5 ppm; HRMS (ESI) calcd for C$_{16}$H$_{20}$N$_6$ (M$_+$) 296.1822, found 296.1828.

4-But-3-ynyl-1H-imidazol-2-ylamine hydrochloride (0.068 g, 0.399 mmol) was reacted with 2-azidomethyl furan (0.059 g, 0.478 mmol) following the general procedure for click reactions outlined above to produce 4-[2-(1-Furan-2-ylmethyl-1H-[1,2,3]triazol-4-yl)-ethyl]-1H-imidazol-2-ylamine hydrochloride (0.085 g, 72%) of a pale yellow solid. $_1$H NMR (300 MHz, CD$_3$OD) δ 8.06 (s, 1H), δ 7.53 (s, 1H), δ 6.59 (t, 1H), δ 6.49 (s, 1H), δ 6.44 (dd, 1H), δ 3.05 (t, 2H), δ 2.89 (t, 2H) ppm; $_{13}$C (75 MHz, CD$_3$OD) δ 156.4, 154.9, 147.5, 144.1, 126.0, 125.1, 123.8, 110.7, 109.3, 69.8, 23.8, 17.4 ppm; HRMS (ESI) calcd for C$_{12}$H$_{14}$N$_6$O (M$_+$) 259.1301, found 259.1305.

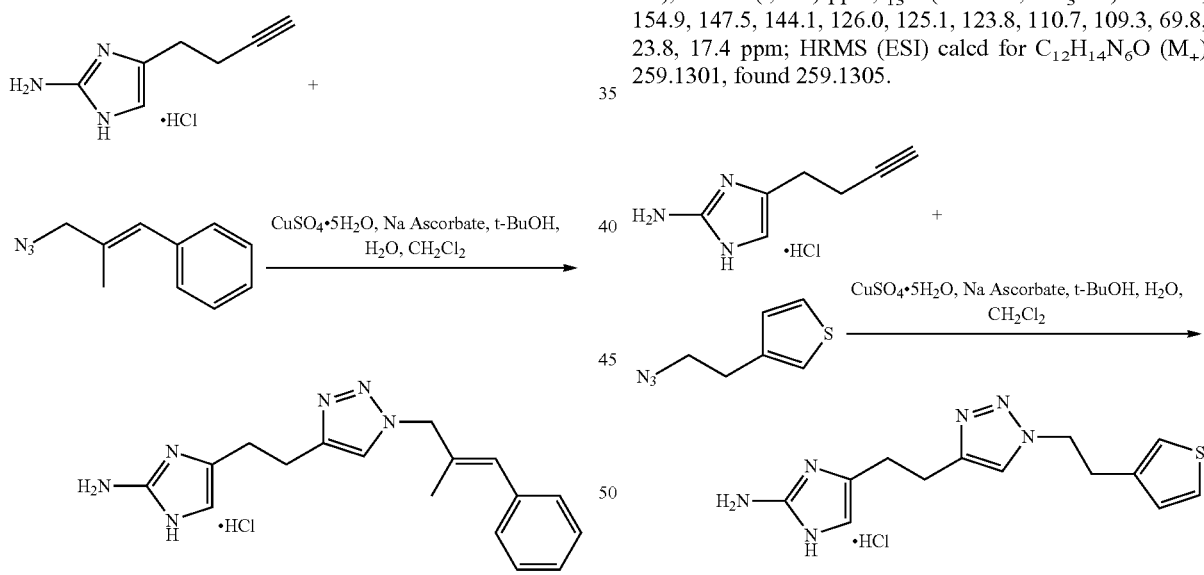

4-But-3-ynyl-1H-imidazol-2-ylamine hydrochloride (0.062 g, 0.362) was reacted with (3-Azido-2-methyl-propenyl)-benzene (0.075 g, 0.434 mmol) following the general procedure for click reactions outlined above to produce 4-{2-[1-(2-Methyl-3-phenyl-allyl)-1H-[1,2,3]triazol-4-yl]-ethyl}-1H-imidazol-2-ylamine hydrochloride (0.054 g, 43%) of a pale yellow oil. $_1$H NMR (300 MHz, CD$_3$OD) δ 8.39 (s, 1H), δ 7.12-7.07 (m, 5H), δ 6.54 (s, 1H), δ 6.36 (s, 1H), δ 5.09 (s, 2H), δ 3.01 (t, 2H), δ 2.76 (t, 2H), δ 1.60 (s, 311) ppm; $_{13}$C; 147.7, 143.1, 136.3, 132.7, 129.9, 128.9, 128.6, 128.5, 128.2, 127.4, 127.1, 124.9, 109.9, 61.2, 23.0, 22.3, 14.7 ppm; HRMS (ESI) calcd for C$_{16}$H$_{20}$N$_6$(M$_+$) 308.1749, found 308.1742.

4-But-3-ynyl-1H-imidazol-2-ylamine hydrochloride (0.078 g, 0.45 mmol) was reacted with 3-(2-Azido-ethyl)-thiophene (0.083 g, 0.543 mmol) following the general procedure for click reactions outlined above to produce 4-{2-[1-(2-Thiophen-3-yl-ethyl)-1H-[1,2,3]triazol-4-yl]-ethyl}-1H-imidazol-2-ylamine hydrochloride (0.069 g, 47%) of a pale yellow oil. $^1$H NMR (300 MHz, CD$_3$OD) δ 7.33 (s, 1H), δ 7.19 (dd, 1H), δ 6.85 (d, 1H), δ 6.72 (d, 1H), δ 6.06 (s, 1H), δ 4.45 (t, 2H), δ 3.08 (t, 2H), δ 2.79 (t, 2H), δ 2.59 (t, 2H), ppm $_{13}$C (75 MHz, CD$_3$OD) 149.3, 147.0, 137.7, 132.1, 127.7, 125.8, 122.4, 121.9, 110.6, 50.8, 30.7, 26.6, 24.8 ppm; HRMS (ESI) calcd for C$_{13}$H$_{17}$N$_6$S (M$_+$) 289.1229, found 289.1231.

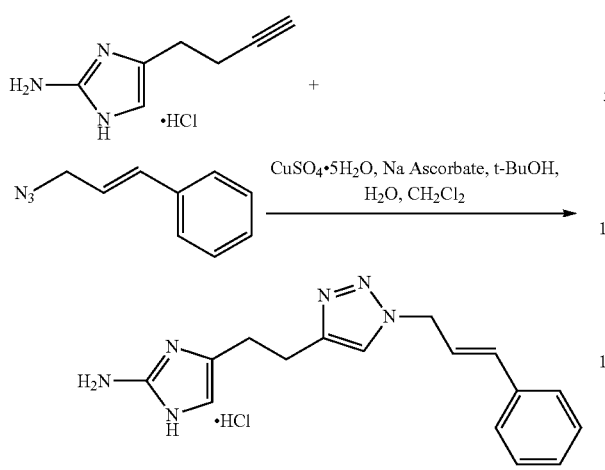

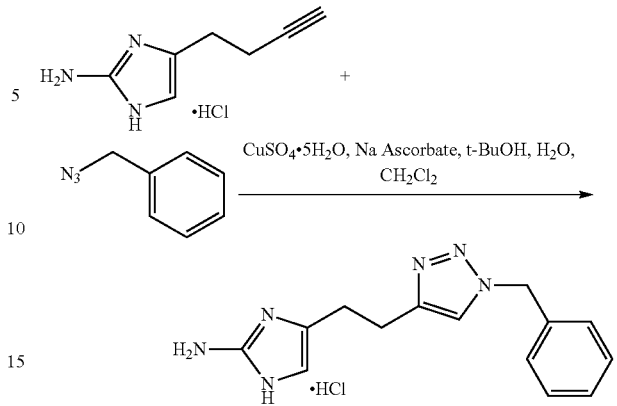

4-But-3-ynyl-1H-imidazol-2-ylamine hydrochloride (0.066 g, 0.383 mmol) was reacted with (3-azido-propenyl)-benzene, which was synthesized using previously reported methods (Rad et al., Tetrahedron Letters 2007, 48, 3445-3449), (0.079 g, 0.460 mmol) following the general procedure for click reactions outlined above to produce 4-{2-[1-(3-Phenyl-allyl)-1H-[1,2,3]triazol-4-yl]-ethyl}-1H-imidazol-2-ylamine hydrochloride (0.049 g, 39%) of a pale yellow oil. $_1$H NMR (300 MHz, CD$_3$OD) δ 8.19 (s, 1H), δ 7.44 (d, 2H), δ 7.29 (m, 3H), δ 6.73 (d, 1H), δ 6.53 (s, 1H), δ 6.42 (m, 2H), δ 5.24 (d, 2H), δ 3.07 (t, 2H), δ 2.88 (t, 2H) ppm; $_{13}$C 148.6, 145.3, 139.4, 139.2, 129.8, 129.7, 129.6, 128.5, 128.4, 127.6, 54.6, 47.3, 45.9, 26.3, 22.6 ppm; HRMS (ESI) calcd for C$_{16}$H$_{19}$N$_6$(M$_+$) 295.1665, found 295.1670.

4-But-3-ynyl-1H-imidazol-2-ylamine hydrochloride (0.073 g, 0.423 mmol) was reacted with benzyl azide (0.068 g, 0.509 mmol) following the general procedure for click reactions outlined above to produce 4-[2-(1-Benzyl-1H-[1,2,3]triazol-4-yl)-ethyl]-1H-imidazol-2-ylamine hydrochloride (0.059 g, 46%) as a pale yellow oil. $^1$H NMR (300 MHz, CD$_3$OD) δ 7.83 (d, 1H), δ 7.37-7.24 (m, 5H), δ 6.44 (d, 1H), δ 5.54 (d, 2H), δ 2.96 (m, 2H), δ 2.83 (m, 2H) ppm; $_{13}$C (75 MHz, CD$_3$OD) δ 163.7, 147.3, 146.4, 135.7, 128.8, 128.4, 127.9, 127.8, 126.5, 122.6, 109.1, 53.7, 24.1, 23.9 ppm; HRMS (ESI) calcd for C$_{14}$H$_{16}$N$_6$ (M$_+$) 269.1515, found 269.1513.

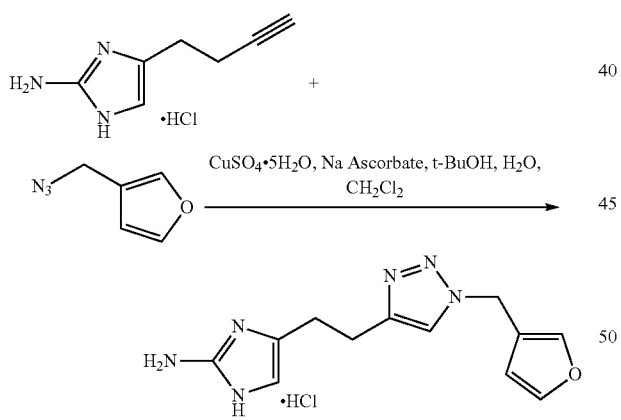

4-But-3-ynyl-1H-imidazol-2-ylamine hydrochloride (0.066 g, 0.384 mmol) was reacted with 3-azidomethyl-furan (0.057 g, 0.461 mmol) following the general procedure for click reactions outlined above to produce 4-[2-(1-Furan-3-ylmethyl-1H-[1,2,3]triazol-4-yl)-ethyl]-1H-imidazol-2-ylamine hydrochloride (0.061 g, 54%) as a pale yellow solid. $_1$H NMR (300 MHz, CD$_3$OD) δ 7.70 (s, 1H), δ 7.61 (s, 1H), δ 7.46 (s, 1H), δ 6.42 (s, 1H), δ 6.38 (s, 1H), δ 5.41 (s, 2H), δ 2.95 (t, 2H), δ 2.83 (t, 2H) ppm; $_{13}$C (75 MHz, CD$_3$OD) δ 146.3, 144.2, 141.6, 141.5, 126.5, 122.3, 120.2, 109.9, 109.1, 44.8, 24.2, 23.9 ppm; HRMS (ESI) calcd for C$_{12}$H$_{14}$N$_6$O (M$_+$) 259.1301, found 259.1306.

4-But-3-ynyl-1H-imidazol-2-ylamine hydrochloride (0.073 g, 0.429 mmol) was reacted with 3-azidomethyl-indole (0.089 g, 0.515 mmol) following the general procedure for click reactions outlined above to produce 4-{2-[1-(1H-Indol-3-ylmethyl)-1H-[1,2,3]triazol-4-yl]-ethyl}-1Himidazol-2-ylamine hydrochloride (0.086 g, 58%) as a yellow oil. $^1$H NMR (300 MHz, CD$_3$OD) δ 8.11 (s, 1H), δ 7.84 (m, 2H), δ 7.41 (m, 2H), δ 7.06 (d, 1H), δ 5.66 (s, 2H), δ 3.04 (t, 2H), δ 2.85 (t, 2H) ppm; $_{13}$C (75 MHz, CD$_3$OD) δ 147.5, 144.9, 144.8, 134.7, 131.9, 127.2, 127.1, 125.8, 125.3, 124.4, 109.5, 49.9, 23.6, 23.2 ppm; HRMS (ESI) calcd for C$_{17}$H$_{19}$N$_7$ (M$_+$) 321.1701, found 321.1704.

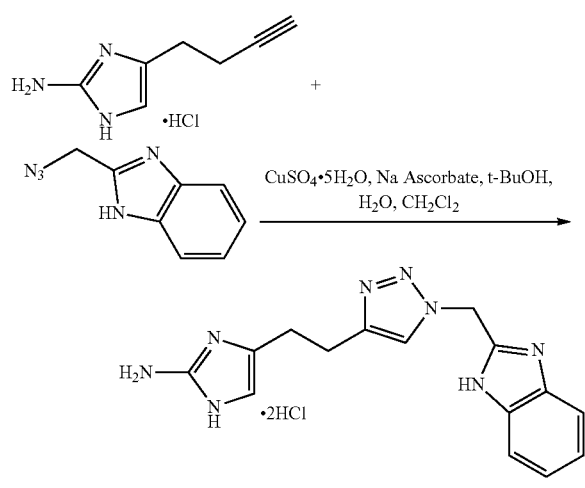

4-But-3-ynyl-1H-imidazol-2-ylamine hydrochloride (0.061 g, 0.361 mmol) was reacted with 2-azidomethyl-1-H-benzimidazole (0.075 g, 0.433 mmol) following the general procedure for click reactions outlined above to produce 4-{2-[1-(1H-Benzoimidazol-2-ylmethyl)-1H-[1,2,3]triazol-4-yl]-ethyl}-1H-imidazol-2-ylamine dihydrochloride (0.066 g, 48%) of a yellow solid. $_1$H NMR (300 MHz, CD$_3$OD) δ 8.05 (s, 1H), δ 7.68 (m. 2H), δ 7.48 (m, 2H), δ 6.38 (s, 1H), δ 6.15 (s, 2H'), δ 2.90 (t, 2H), δ 2.76 (t, 2H) ppm; $_{13}$C (75 MHz, CD$_3$OD) δ 147.4, 146.9, 146.8, 131.3, 127.0, 126.4, 124.1, 114.1, 109.2, 44.7, 24.0, 23.9 ppm; HRMS (ESI) calcd for C$_{15}$H$_{17}$N$_8$(M$_+$) 309.1570, found 309.1572.

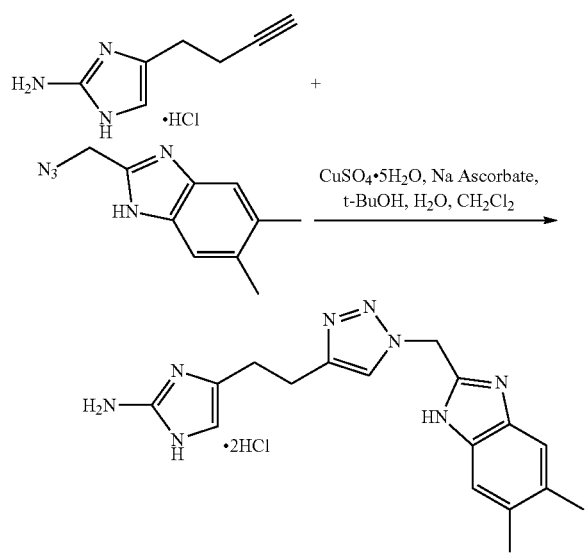

4-But-3-ynyl-1H-imidazol-2-ylamine hydrochloride (0.0734 g, 0.432 mmol) was reacted with 2-azidomethyl-5,6-dimethyl-1H-benzimidazole (0.104 g, 0.518 mmol) following the general procedure for click reactions outlined above to produce 4-{2-[1-(5,6-Dimethyl-1Hbenzoimidazol-2-ylmethyl)-1H-[1,2,3]triazol-4-yl]-ethyl}-1H-imidazol-2-ylamine dihydrochloride (0.104 g, 59%) of a pale yellow solid. $_1$H NMR (300 MHz, CD$_3$OD) δ 7.70 (s, 1H), δ 7.19 (s, 2H), δ 6.23 (s, 1H), δ 5.66 (s, 2H), δ 2.85 (t, 2H), δ 2.68 (t, 2H), □ 2.21 (s, 6H) ppm; $_{13}$C (75 MHz, CD$_3$OD) δ 148.2, 147.0, 146.9, 132.3, 128.9, 122.8, 120.0, 115.1, 109.7, 100.4, 25.1, 24.4, 19.2 ppm; HRMS (ESI) calcd for C$_{17}$H$_{20}$N$_8$(M$_+$) 337.1883, found 337.1886.

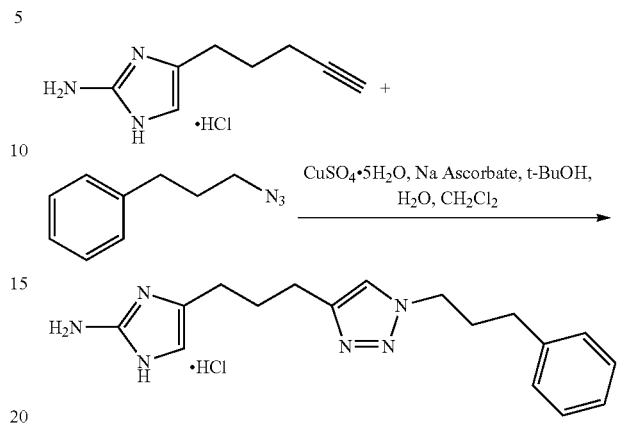

4-Pent-4-ynyl-1H-imidazol-2-ylamine hydrochloride (0.050 g, 0.269 mmol) was reacted with (3-azido-propyl)benzene (0.044 g, 0.273 mmol) following the general procedure for click reactions outlined above to produce 4-{3-[1-(3-Phenyl-propyl)-1H-[1,2,3]triazol-4-yl]-propyl}-1H-imidazol-2-ylamine hydrochloride (0.0318 g, 34%) as a pale yellow solid. $_1$H NMR (300 MHz, DMSO) δ 7.91 (s, 1H), δ 7.29-7.17 (m, 5H), δ 6.62 (s, 2H), δ 6.57 (s, 1H), δ 4.29 (t, 2H), δ 2.59 (t, 2H), δ 2.53 (t, 2H), δ 2.43 (t, 2H) δ 2.09 (m, 2H), δ 1.83 (m, 2H) ppm; $^{13}$C NMR (75 MHz, DMSO) δ 163.6, 156.2, 155.1, 147.4, 146.9, 141.4, 129.1, 127.1, 126.7, 122.6, 109.4, 49.4, 32.6, 32.0, 28.1, 24.9, 24.2 ppm; HRMS (ESI) calcd for C$_{17}$H$_{22}$N$_6$ (M$_+$) 310.1978, found 310.1977.

4-Pent-4-ynyl-1H-imidazol-2-ylamine hydrochloride (0.063 g, 0.340 mmol) was reacted with 3-azidomethyl-furan (0.050 g, 0.406 mmol) following the general procedure for click reactions outlined above to produce 4-[3-(1-Furan-3-ylmethyl-1H-[1,2,3]triazol-4-yl)-propyl]-1Himidazol-2-ylamine hydrochloride (0.061 g, 58%) as a pale yellow solid. $_1$H NMR (300 MHz, CD$_3$OD) δ 7.70 (s, 1H), δ 7.56 (s, 1H), δ 7.41 (s, 1H), δ 6.44 (s, 1H), δ 6.35 (s, 1H), δ 5.35 (s, 2H), δ 2.65 (t, 2H), δ 2.45 (t, 2H), δ 1.86 (m, 2H) ppm; $^{13}$C NMR (75 MHz, CD$_3$OD) δ 147.3, 147.3, 144.2, 141.6, 127.2, 122.1, 120.2, 109.9, 108.8, 44.7, 27.8, 24.2, 23.6 ppms; HRMS (ESI) calcd for C$_{13}$H$_{16}$N$_6$O (M$_+$) 272.1458, found 272.1462.

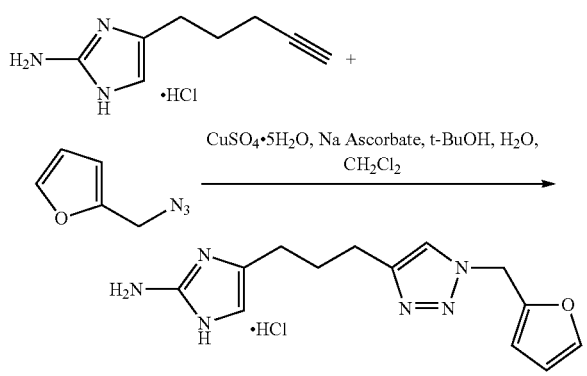

4-Pent-4-ynyl-1H-imidazol-2-ylamine hydrochloride (0.093 g, 0.500 mmol) was reacted with 2-azidomethyl-furan (0.074 g, 0.601 mmol) following the general procedure for click reactions outlined above to produce 4-[3-(1-Furan-2-ylmethyl-1H-[1,2,3]triazol-4-yl)-propyl]-1Himidazol-2-ylamine hydrochloride (0.075, 50%) as a pale yellow solid. $_1$H NMR (300 MHz, DMSO) δ 7.85 (s, 1H), δ 7.65 (s, 1H), δ 6.70 (s, 2H), δ 6.64 (s, 1H), δ 6.52 (t, 1H), δ 6.46 (s, 1H), δ 5.58 (s, 2H), δ 2.61 (t, 2H), δ 2.41 (t, 21-1), δ 1.82 (m, 2H) ppm; $^{13}$C NMR (75 MHz, DMSO) δ 163.6, 149.4, 147.9, 147.4, 144.3, 128.5, 122.6, 111.5, 110.3, 109.9, 46.3, 28.4, 24.9 ppm; HRMS (ESI) calcd for $C_{13}H_{16}N_6O$ (M$_+$) 272.1458, found 272.1460.

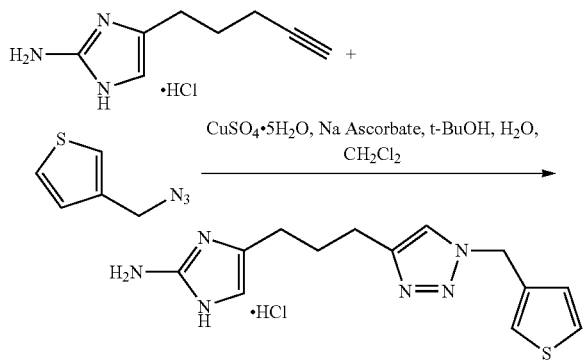

4-Pent-4-ynyl-1H-imidazol-2-ylamine hydrochloride (0.090 g, 0.486 mmol) was reacted with 3-Azidomethyl-thiophene (0.081 g, 0.582 mmol) following the general procedure for click reactions outlined above to produce 4-[3-(1-Thiophen-3-ylmethyl-1H-[1,2,3]triazol-4-yl)-propyl]-1H-imidazol-2-ylamine hydrochloride (0.0727 g, 46%) as a pale yellow solid. $_1$H HMR (300 MHz, CD$_3$OD) δ 7.61 (s, 1H), δ 7.24 (s, 1H), δ 7.23 (d, 1H), δ 6.87 (d, 1H), δ 6.29 (s, 1H), δ 2.54 (t, 2H), 2.33 (t, 2H), δ 1.75 (m, 2H) ppm; $^{13}$C NMR (75 MHz, CD$_3$OD) δ 147.6, 147.4, 147.3, 136.1, 127.9, 127.0, 126.9, 124.2, 122.2, 109.1, 53.1, 27.9, 24.3; HRMS (ESI) calcd for $C_{13}H_{16}N_6S$ (M$_+$) 289.1229, found 289.1234.

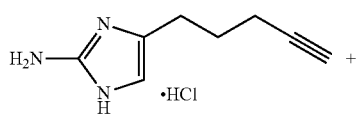

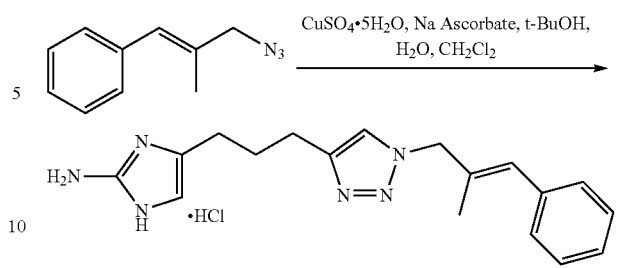

4-Pent-4-ynyl-1H-imidazol-2-ylamine hydrochloride (0.096 g, 0.517 mmol) was reacted with (3-Azido-2-methyl-propenyl)-benzene (0.110 g, 0.635 mmol) following the general procedure for click reactions outlined above to produce 5-{3-[1-(2-Methyl-3-phenyl-allyl)-1H-[1,2,3]triazol-4-yl]-propyl}-1H-imidazol-2-ylamine hydrochloride (0.076, 41%) as a pale yellow solid. $_1$H NMR (300 MHz, CD$_3$OD) δ 7.65 (s, 1H), δ 7.14-7.04 (m, 5H), δ 6.35 (s, 1H), δ 6.28 (s, 1H), δ 4.94 (s, 2H), δ 2.57 (t, 2H), δ 2.34 (t, 2H), δ 1.75 (m, 2H), δ 1.57 (s, 3H) ppm; $_{13}$C NMR (75 MHz, CD$_3$OD) δ 147.5, 136.9, 132.5, 129.7, 128.8, 128.6, 128.4, 128.3, 128.2, 126.9, 122.5, 109.2, 58.1, 61.9, 28.0, 24.3, 24.3, 24.1, 14.6 ppm; FIRMS (ESI) calcd for $C_{18}H_{22}N_6$ (M$_+$) 323.1978, found 323.1984.

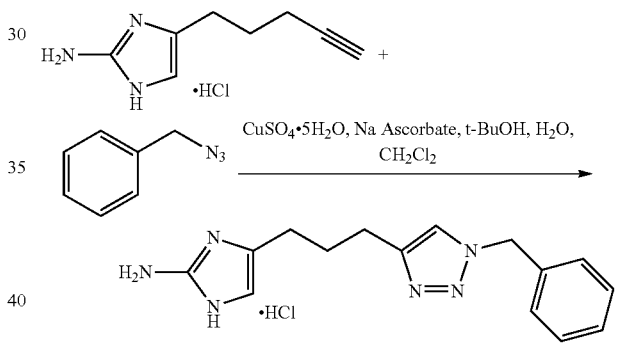

4-Pent-4-ynyl-1H-imidazol-2-ylamine hydrochloride (0.081 g, 0.437 mmol) was reacted with benzyl azide (0.071 g, 0.533 mmol) following the general procedure for click reactions outlined above to produce 4-[3-(1-Benzyl-1H-[1,2,3]triazol-4-yl)-propyl]-1H-imidazol-2-ylamine hydrochloride (0.073 g, 53%) as a pale yellow solid. 111 NMR (300 MHz, DMSO) δ 7.93 (s, 1H), δ 7.37-7.27 (m, 5H), δ 6.63 (s, 2H), δ 6.44 (s, 1H), δ 2.61 (t, 2H), δ 2.40 (t, 2H), δ 1.82 (m, 2H) ppm; $_{13}$C NMR (75 MHz, DMSO) δ 163.5, 148.1, 147.4, 135.9, 129.4, 128.7, 128.5, 128.4, 122.8, 122.8, 115.9, 109.9, 53.3, 28.5, 25.0; HRMS (ESI) calcd for $C_{15}H_{18}N_6$ (M$_+$) 282.1665, found 282.1674.

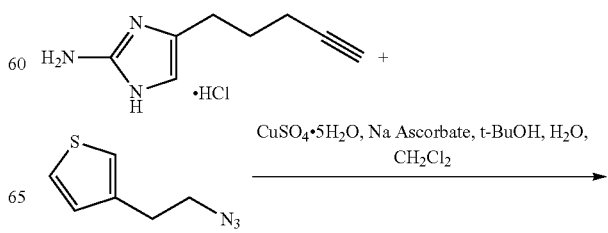

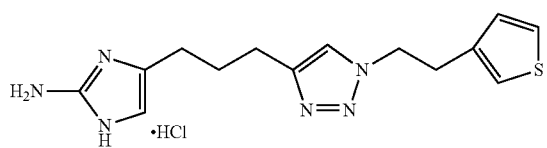

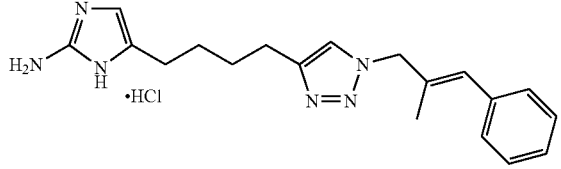

4-Pent-4-ynyl-1H-imidazol-2-ylamine hydrochloride (0.090 g, 0.485 mmol) was reacted with 3-(2-Azido-ethyl)-thiophene (0.089 g, 0.581 mmol) following the general procedure for click reactions outlined above to produce 4-{3-[1-(2-Thiophen-3-yl-ethyl)-1H-[1,2,3]triazol-4-yl]-propyl}-1H-imidazol-2-ylamine hydrochloride (0.067 g, 41%) as a pale yellow solid. $_1$H NMR (300 MHz, CD$_3$OD) δ 7.42 (s, 1H), δ 7.12 (d, 1H), δ 6.83 (s, 1H), δ 6.70 (d, 1H), δ 6.29 (s, 1H), δ 4.41 (t, 2H), δ 3.04 (t, 2H), δ 2.50 (t, 2H), δ 2.29 (t, 2H), δ 1.72 (m, 2H) ppm; $_{13}$C NMR (75 MHz, CD$_3$OD) δ 146.8, 146.8, 137.7, 127.8, 127.6, 125.7, 122.6, 121.9, 109.0, 50.7, 30.7, 27.9, 23.7 ppm; HRMS (ESI) calcd for C$_{14}$H$_{18}$N$_6$S (M$_+$) 302.1313, found 302.1317.

4-Hex-5-ynyl-1H-imidazol-2-ylamine hydrochloride (0.089 g, 0.4.47 mmol) was reacted with (3-Azido-2-methyl-propenyl)-benzene (0.085 g, 0.491 mmol) following the general procedure for click reactions outlined above to produce 4-{4-[1-(2-Methyl-3-phenyl-allyl)-1H-[1,2,3]triazol-4-yl]-butyl}-1H-imidazol-2-ylamine (0.132 g, 79%) as a pale yellow solid. $_1$H NMR (300 MHz, CD$_3$OD) δ 8.36 (s, 1H), 7.03 (m, 5H), 6.49 (s, 1H), 6.25 (s, 1H), 5.05 (s, 2H), 2.67 (t, 2H), δ 2.73 (t, 2H), δ 1.56 (s, 3H), δ 1.42 (m, 4H) ppm; $_{13}$C NMR (75 MHz, CD$_3$OD) δ 147.3, 144.7, 136.4, 132.7, 129.9, 128.9, 128.6, 128.5, 128.3, 127.5, 127.2, 126.9, 108.7, 61.2, 27.4, 27.3, 23.8, 22.8, 14.8 bpm; HRMS (ESI) calcd for C$_{19}$H$_{24}$N$_6$ (M$_+$) 336.2135, found 336.2134.

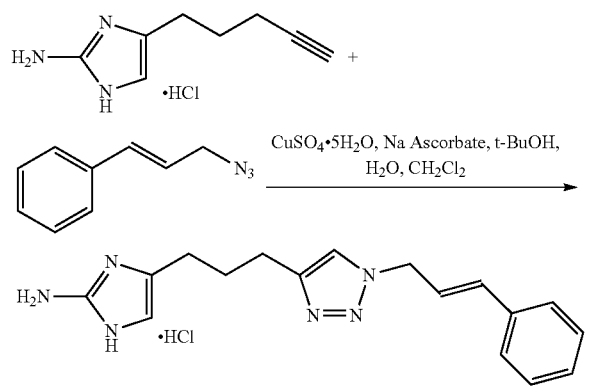

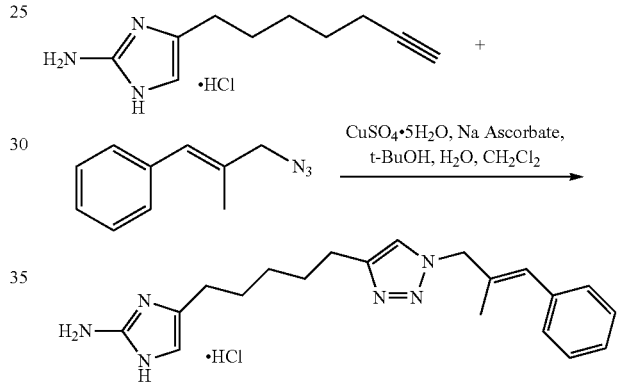

4-Pent-4-ynyl-1H-imidazol-2-ylamine hydrochloride (0.115 g, 0.620 mmol) was reacted with (3-azido-propenyl)-benzene (0.119 g, 0.748 mmol) following the general procedure for click reactions outlined above to produce 4-{3-[1-(3-Phenyl-allyl)-1H-[1,2,3]triazol-4-yl]-propyl}-1Himidazol-2-ylamine hydrochloride (0.082 g, 43%) as a pale yellow solid. 111 NMR (300 MHz, CDCl$_3$) δ 7.34-7.24 (m, 6H), δ 6.67 (d, 1H), δ 6.34 (q, 1H), δ 6.25 (s, 1H), δ 5.08 (d, 2H), δ 2.72 (t, 2H), δ 2.47 (t, 2H), δ 1.91 (m, 2H) ppm; $_{13}$C (75 MHz, CD$_3$OD) 149.1, 137.9, 133.5, 129.5, 128.9, 128.7, 128.3, 128.2, 127.7, 126.8, 54.8, 48.9, 31.3, 29.6, 27.5 ppm; FIRMS (ESI) calcd for C$_{17}$H$_{21}$N$_6$(M$_+$) 308.1822, found 308.1821.

4-Hept-6-ynyl-1H-imidazol-2-ylamine hydrochloride (0.060 g, 0.281 mmol) was reacted with (3-Azido-2-methyl-propenyl)-benzene (0.058 g, 0.336 mmol) following the general procedure for click reactions outlined above to produce 4-{5-[1-(2-Methyl-3-phenyl-allyl)-1H-[1,2,3]triazol-4-yl]-pentyl}-1H-imidazol-2-ylamine hydrochloride (0.064 g, 65%) as a pale yellow solid. $_1$H NMR (300 MHz, CD$_3$OD) δ 8.23 (s, 1H), δ 6.93-6.83 (m, 5H), δ 6.38 (s, 1H), δ 6.08 (s, 1H), δ 4.93 (s, 2H), δ 2.51 (t, 2H), δ 2.09 (t, 2H), δ 1.43 (s, 3H), δ 1.41 (m, 2H), δ 1.25 (m, 2H), δ 1.05 (m, 2H) ppm; $_{13}$C (75 MHz, CD$_3$OD) δ 147.7, 144.8, 136.3, 132.8, 129.8, 128.9, 128.6, 128.5, 128.2, 127.6, 127.5, 127.0, 108.5, 61.3, 28.0, 27.6, 27.5, 24.0, 22.9, 14.7 ppm; HRMS (ESI) calcd for C$_{20}$H$_{27}$N$_6$ (M$_+$) 351.2291, found 351.2291.

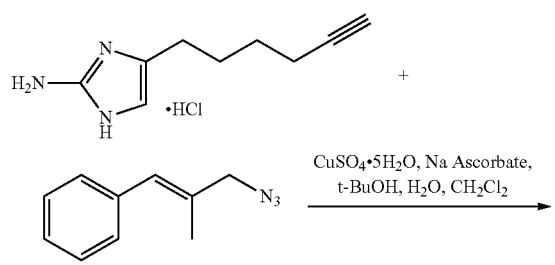

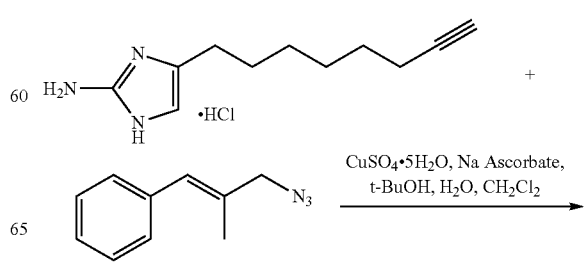

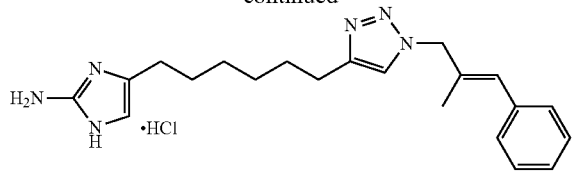

4-Oct-7-ynyl-1H-imidazol-2-ylamine hydrochloride (0.098 g, 0.568 mmol) was reacted with (3-Azido-2-methylpropenyl)-benzene (0.118 g, 0.681 mmol) following the general procedure for click reactions outlined above to produce 4-{6-[1-(2-Methyl-3-phenyl-allyl)-1H-[1,2,3]triazol-4-yl]-hexyl}-1H-imidazol-2-ylamine hydrochloride (0.147 g, 85%) as a pale yellow solid. $_1$H NMR (300 MHz, CD$_3$OD) δ 8.42 (s, 1H), δ 7.25-7.15 (m, 5H), δ 6.65 (s, 1H), δ 6.36 (s, 1H), δ 5.23 (s, 2H), δ 2.78 (t, 2H), δ 2.38 (t, 2H), δ 1.74 (s, 3H), δ 1.64 (m, 2H), δ 1.51 (m, 2H), δ 1.33 (m, 4H) ppm; $_{13}$C (75 MHz, CD$_3$OD) δ 147.5, 136.3, 132.9, 132.8, 129.9, 128.9, 128.6, 128.5, 128.3, 127.7; HRMS (ESI) calcd for $C_{21}H_{29}N_6(M_+)$ 365.2448, found 365.2448.

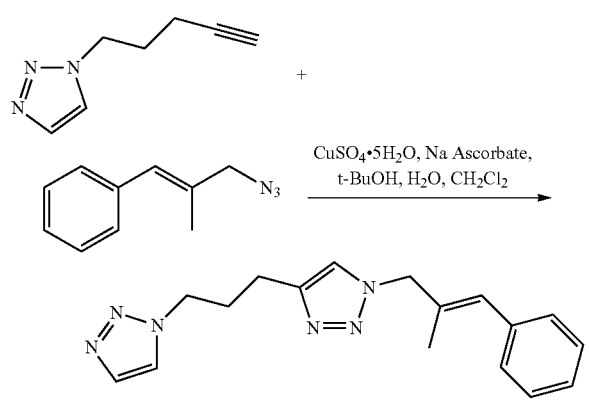

1-Pent-4-ynyl-1H-[1,2,3]triazole (0.100 g, 0.739 mmol) was reacted with (3-Azido-2-methylpropenyl)-benzene (0.154 g, 0.889 mmol) following the general procedure for click reactions outlined above to produce 1-(2-Methyl-3-phenyl-allyl)-4-(3-[1,2,3]triazol-1-yl-propyl)-1H-[1,2,3]triazole (0.227 g, Quantitative) as a white solid. $_1$H NMR (300 MHz, DMSO) δ 7.91 (s, 1H), δ 7.77 (s, 2H), δ 7.40-7.25 (m, 5H), δ 6.47 (s, 1H), δ 5.05 (s, 2H), δ 4.48 (t, 2H), δ 2.62 (t, 2H), δ 2.50 (t, 2H), δ 2.21 (m, 2H), δ 1.74 (s, 3H) ppm; $_{13}$C (75 MHz, DMSO) δ 146.4, 137.1, 134.8, 133.6, 132.8, 129.4, 129.3, 129.2, 128.9, 127.6, 123.0, 57.9, 54.0, 32.9, 29.6, 22.7, 16.2 ppm; HRMS (ESI) calcd for $C_{17}H_{21}N_6(M_+)$ 309.1822, found 309.1821.

Example 5

Bacterial Biofilm Regulation Studies

General Static Bacterial Biofilm Inhibition Assay Procedure for *A. baumannii, P. aeruginosa, B. bronchiseptica* and *S. aureus*: Biofilm inhibition assays were performed by taking an overnight culture of bacterial strain and subculturing it at an OD600 of 0.01 into the necessary growth liquid medium (LB for *A. baumannii*, LBNS for *P. aeruginosa*, Stainer Scholte medium that was supplemented with 104/mL of 100× nutrient complex for *B. bronchiseptica* and TSBG for *S. aureus*) for the strain. The compound being tested was then added at a predetermined concentration and then aliquoted (100 μL) into the wells of a 96-well PVC microtiter plate (Wells not used for samples are filled with 100 μL of deionized water). Plates were then wrapped in GLAD Press n' Seal® and incubated under stationary conditions at 37° C. After 24 hours, the media was discarded from the wells and the plates were washed thoroughly with tap water. Plates were then stained with 100 μL of 0.1% solution of crystal violet (CV) and then incubated at an ambient temperature for 30 minutes. Sample plates were then washed with tap water again and the remaining stain was solubilized with 200 μl, of 95% ethanol. Biofilm inhibition was quantitated by measuring the OD$_{540}$ for each well by transferring 125 μL of the solubilized CV stain into a polystyrene microtiter dish for analysis.

General Static Bacterial Biofilm Dispersion Assay Procedure for *A. baumannii, P. aeruginosa* and *S. aureus*: Dispersion assays were performed by taking an overnight culture of bacterial strain and subculturing it at an OD$_{600}$ of 0.01 into the necessary growth liquid medium. The resulting bacterial suspension was aliquoted (100 μL) into the wells of a 96-well PVC microtiter plate. Plates were then wrapped in GLAD Press n' Seal® followed by an incubation under stationary conditions at an ambient temperature. After 24 hours, the media was discarded from the wells and the plates were washed thoroughly with tap water. Predetermined concentrations of the compound were then made in the same medium used to initially grow the biofilms and then aliquoted (100 μL) into the wells of the 96-well PVC microtiter plate with the established biofilms. Plates were then wrapped in GLAD Press n' Seal® and incubated under stationary conditions at 37° C. After 24 hours, the media was discarded from the wells and the plates were washed thoroughly with tap water. Plates were then stained with 100 μL of 0.1% solution of crystal violet (CV) and then incubated at room temperature for 30 minutes. Plates were then washed with tap water again and the remaining stain was solubilized with 200 μL of 95% ethanol. Biofilm dispersion was quantitated by measuring the OD$_{540}$ for each well by transferring 125 μL of the solubilized CV stain into a polystyrene microtiter dish for analysis.

General Static Bacterial Biofilm Dispersion Assay Procedure for *B. bronchiseptica*: This procedure is identical to the general dispersion procedure described above except that initial biofilm formation in the absence of the test compound was carried out at 37° C.

General Planktonic Growth Curve Procedure: The bacterial strains are grown in the absence and in the presence of the test compound at the IC$_{50}$ value starting at an OD$_{600}$ of 0.01 in culture tubes in an incubator shaker at 37° C. at 200 rpm. The OD$_{600}$ was recorded at 1, 3, 4, 5, 6 and 24 hours.

General Colony Count Procedure for *A. baumannii, P. aeruginosa, B. bronchiseptica* and *S. aeureus*: Colony counts were performed by incubating either bacterial strain in the presence and absence of the test compound at 37° C. in culture tubes until the sample with the absence of the test compound reached an OD$_{600}$ of 0.40 from a starting OD$_{600}$ of 0.01. This typically took three to four hours. Once the OD$_{600}$ of approximately 0.40 was observed, 100 μL were taken from each culture tube from which serial dilutions were made. Then, 10 μL were removed from each serial dilution and plated out on a square gridded petri-dish followed by 16 hours of incubation at 37° C. period (48 hours for *B. bronchiseptica*) to grow countable colonies. Viable bacteria were quantified through employment of the track-dilution method (Jett et al., Bio Techniques. 1997, 23, 648-650).

Example 6

Synthesis of additional compounds. All reagents used for chemical synthesis were purchased from commercially available sources and used without further purification. Chromatography was performed using 60 Å mesh standard grade silica gel from Sorbtech. NMR solvents were obtained from Cambridge Isotope Labs and used as is. $^1$H NMR (300 MHz or 400 MHz) and $^{13}$C NMR (75 MHz or 100 MHz) spectra were recorded at 25° C. on Varian Mercury spectrometers. Chemical shifts (δ) are given in ppm relative to tetramethylsilane or the respective NMR solvent; coupling constants (J) are in hertz (Hz). Abbreviations used are s=singlet, bs=broad singlet, d=doublet, dd=doublet of doublets, t=triplet, dt=doublet of triplets, bt=broad triplet, qt=quartet, m=multiplet, bm=broad multiplet and br=broad. Mass spectra were obtained at the NCSU Department of Chemistry Mass Spectrometry Facility.

Listing of Compounds:

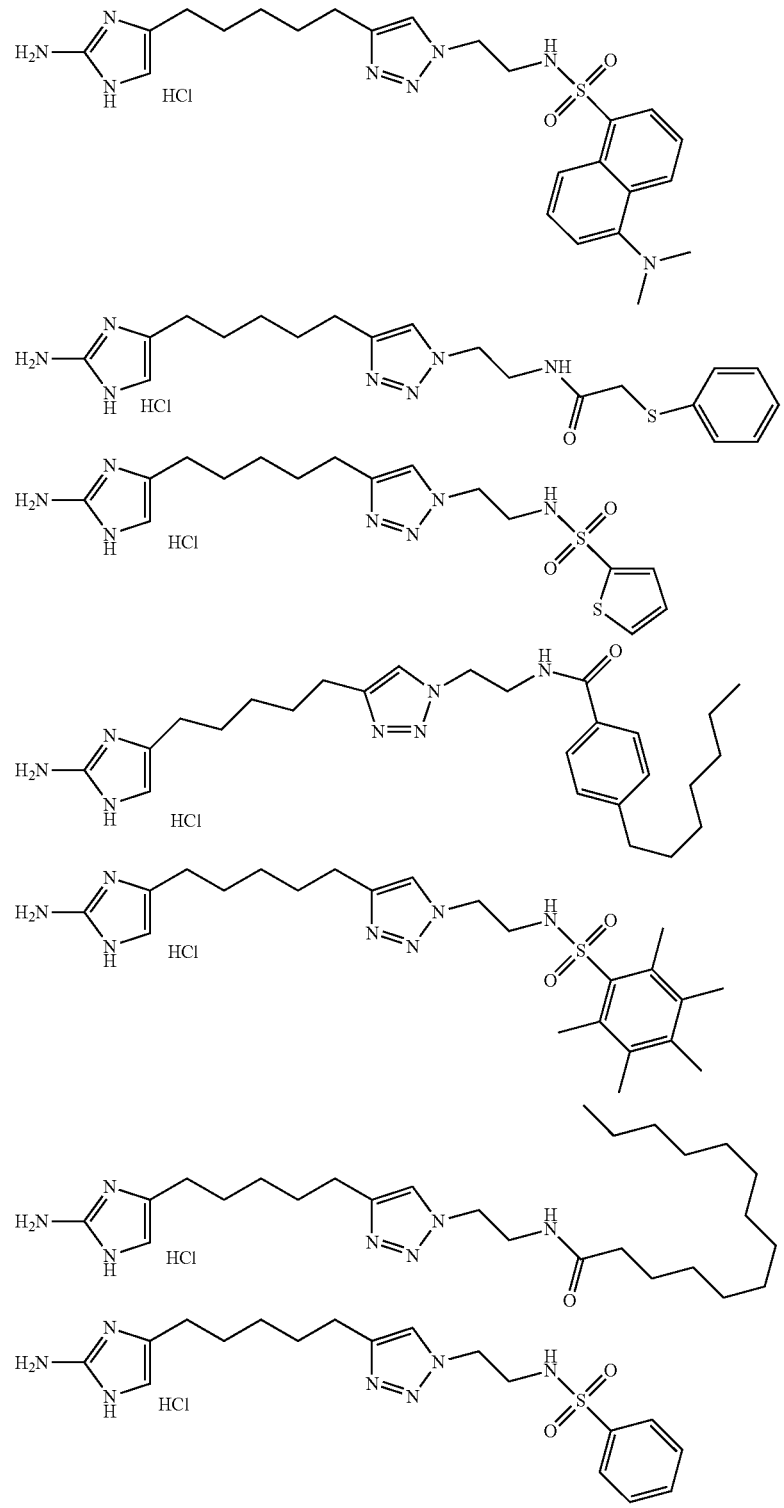

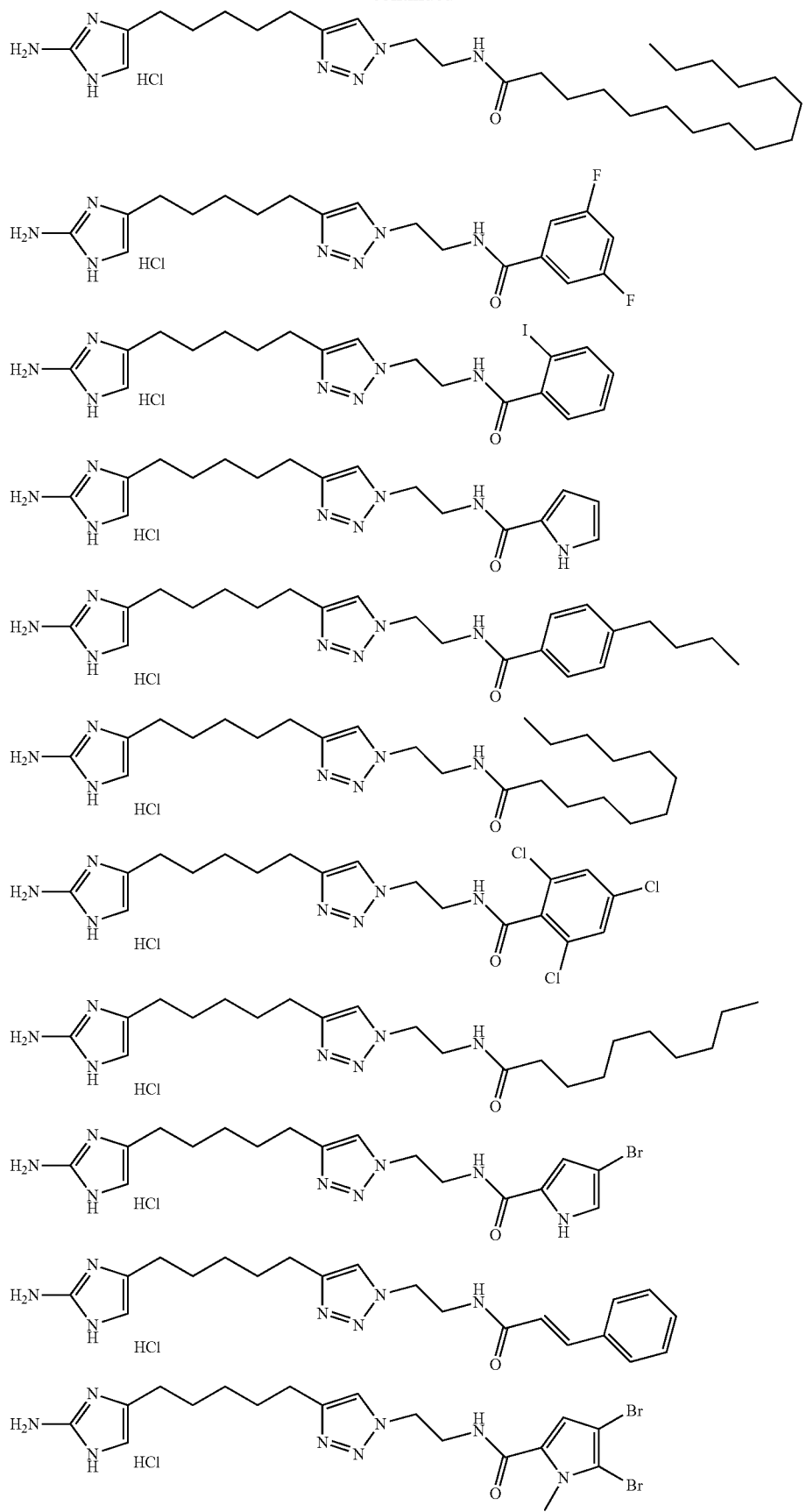

-continued

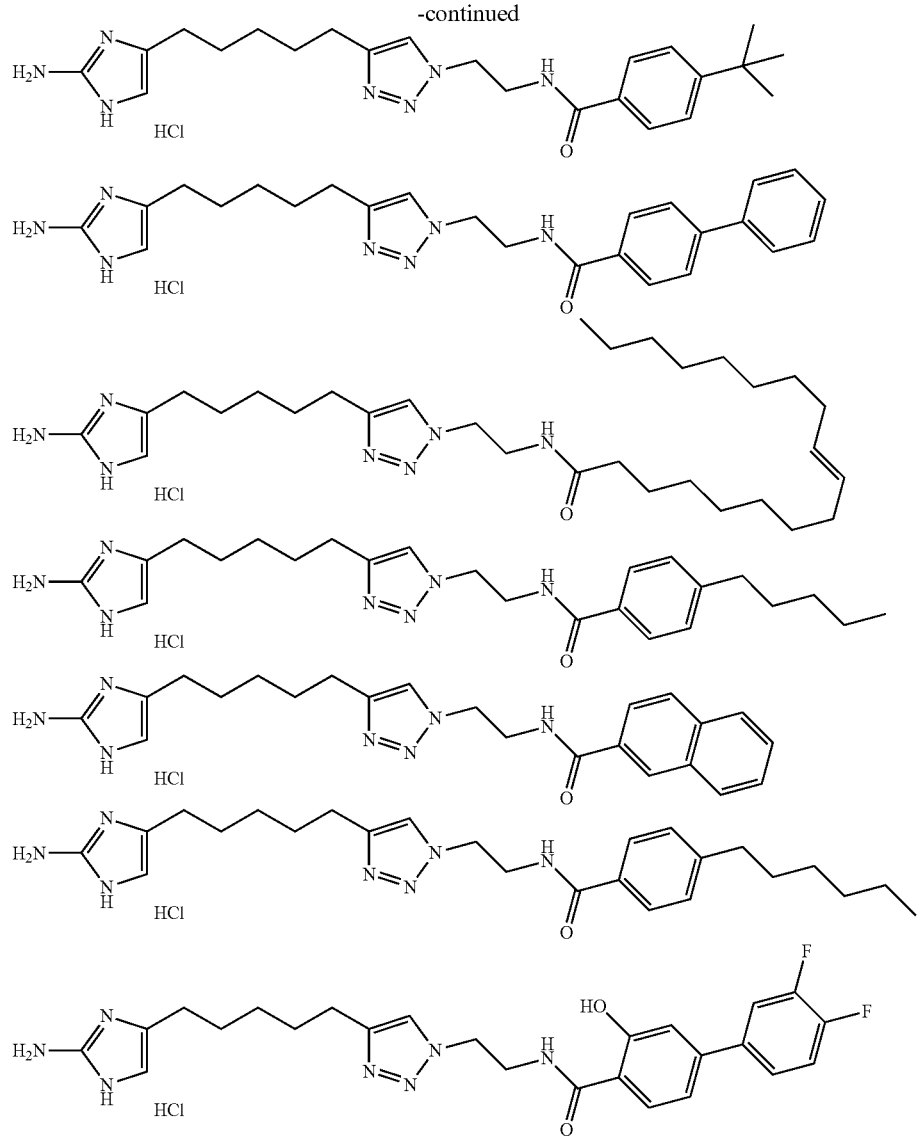

Detailed Synthesis:

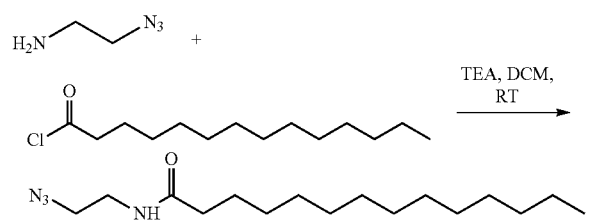

N-(2-azidoethyl)tetradecanamide: To a 25 mL round-bottomed flask equipped with a magnetic stir bar was added 2-azidoethanamine (0.102 g, 1.18 mmol), DCM (5 mL) and then triethylamine (0.239 g, 2.37 mmol). To this reaction mixture, tetradecanoyl chloride (0.292 g, 1.18 mmol) was added dropwise and allowed to stir at room temperature for 24 hr. Then, the reaction mixture was concentrated de vacuo and then purified via silica gel column chromatography (100% dichloromethane to 1:40 methanol:dichloromethane) to give N-(2-azidoethyl)tetradecanamide (0.245 g, 79% yield). $^1$H NMR (300 MHz, CDCl$_3$) δ 5.86 (s, 1H), S 3.42 (s, 4H), δ 2.18 (t, 2H), δ 1.62 (m, 2H), δ 1.24 (m, 20H), δ 0.87 (t, 3H) ppm; $^{13}$C NMR (75 MHz, CDCl$_3$) δ 173.7, 51.2, 39.1, 36.9, 32.1, 29.9, 29.8, 29.7, 29.6, 29.5, 25.9, 22.9, 14.4 ppm; HRMS (ESI) calcd for C$_{16}$H$_{32}$N$_4$O (M+) 296.2576, found 296.2566.

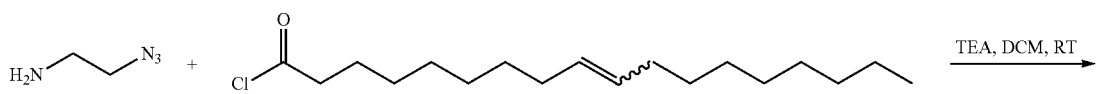

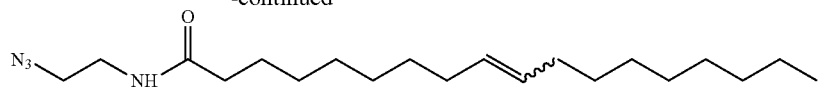

N-(2-azidoethyl)octadec-9-enamide: As in the synthesis of N-(2-azidoethyl)tetradecanamide, octadec-9-enoyl chloride (0.374 g, 1.24 mmol) was reacted with 2-azidoethanamine (0.107 g, 1.24 mmol) and triethylamine (0.252 g, 2.49 mmol) in dichloromethane (5 mL) to give N-(2-azidoethyl)octadec-9-enamide (0.309 g, 71%). $^1$H NMR (300 MHz, CDCl$_3$) δ 6.30 (s, 1H), δ 5.29 (m, 2H), δ 3.39 (d, 2H), δ 3.38 (d, 2H) δ2.19 (t, 2H), δ 1.97 (m, 4H), δ 1.59 (t, 2H), δ 1.26 (m, 20H), δ 0.84 (t, 3H) ppm; $^{13}$C NMR (75 MHz, CDCl$_3$) δ 173.9, 130.2, 129.9, 51.1, 39.1, 36.8, 32.1, 30.0, 29.9, 29.7, 29.5, 29.4, 29.3, 27.4, 27.3, 25.9, 22.9, 14.3 ppm; HRMS (ESI) calcd for C$_{20}$H$_{38}$N$_4$O (M+) 350.3046, found 350.3039.

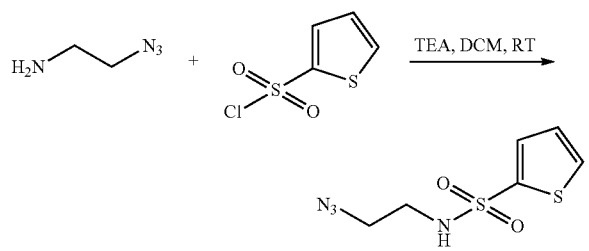

N-(2-azidoethyl)thiophene-2-sulfonamide: As in the synthesis of N-(2-azidoethyl)tetradecanamide, thiophene-2-sulfonyl chloride (0.218 g, 1.19 mmol) was reacted with 2-azidoethanamine (0.103 g, 1.19 mmol) and triethylamine (0.241 g, 2.39 mmol) in dichloromethane (5 mL) to give N-(2-azidoethyl)thiophene-2-sulfonamide (0.221 g, 80%). $^1$H NMR (300 MHz, CDCl$_3$) δ 7.62 (d, 1H), δ 7.59 (d, 1H), 7.08 (t, 1H), 5.52 (s, 1H), 3.41 (t, 2H), 3.17 (q, 2H) ppm; $^{13}$C NMR (75 MHz, CDCl$_3$) δ 140.6, 132.7, 132.6, 127.9, 50.9, 42.9 ppm; HRMS (ESI) calcd for C$_6$H$_8$N$_4$O$_2$S$_2$ (M+) 232.0089, found 232.0084.

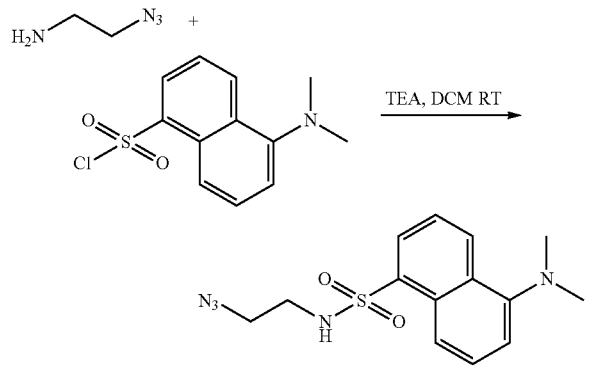

N-(2-azidoethyl)-5-(dimethylamino)naphthalene-1-sulfonamide: As in the synthesis of N-(2-azidoethyl)tetradecanamide, 5-(dimethylamino)naphthalene-1-sulfonyl chloride (0.321 g, 1.19 mmol) was reacted with 2-azidoethanamine (0.103 g, 1.19 mmol) and triethylamine (0.241 g, 2.38 mmol) in dichloromethane (5 mL) to give N-(2-azidoethyl)-5-(dimethylamino)naphthalene-1-sulfonamide (0.328 g, 86%). $^1$H NMR (300 MHz, CDCl$_3$) δ 8.52 (d, 1H), δ 8.28 (d, 1H), δ 8.22 (d, 1H), δ 7.53 (t, 1H), δ 7.50 (t, 1H-1), δ 7.17 (d, 1H), δ 5.58 (t, 1H), δ 3.28 (t, 2H), δ 3.03 (q, 2H), δ 2.85 (s, 6H) ppm; $^{13}$C NMR (75 MHz, CDCl$_3$) δ 152.3, 134.8, 130.9, 130.1, 129.7, 128.9, 123.4, 118.9, 115.6, 51.0, 45.6, 42.6 ppm; HRMS (ESI) calcd for C$_{14}$H$_{17}$N$_5$O$_2$S (M+) 319.1103, found 319.1104.

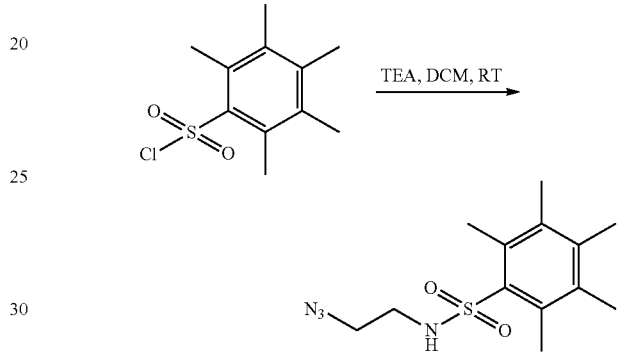

N-(2-azidoethyl)-2,3,4,5,6-pentamethylbenzenesulfonamide: As in the synthesis of N-(2-azidoethyl)tetradecanamide, 2,3,4,5,6-pentamethylbenzene-1-sulfonyl chloride (0.304 g, 1.23 mmol) was reacted with 2-azidoethanamine (0.106 g, 1.23 mmol) and triethylamine (0.249 g, 2.46 mmol) in dichloromethane (5 mL) to give N-(2-azidoethyl)-2,3,4,5,6-pentamethylbenzenesulfonamide (0.296 g, 81%). $^1$H NMR (300 MHz, CDCl$_3$) δ 5.12 (t, 1H) δ 3.35 (t, 2H), δ 3.05 (q, 2H), 2.59 (s, 6H), δ 2.28 (s, 3H), 2.24 (s, 6H) ppm; $^{13}$C NMR (75 MHz, CDCl$_3$) δ 139.9, 136.1, 135.2, 134.2, 51.1, 42.3, 19.2, 17.9, 17.3 ppm; HRMS (ESI) calcd for C$_{13}$H$_{20}$N$_4$O$_2$S (M+) 296.1307, found 296.1304.

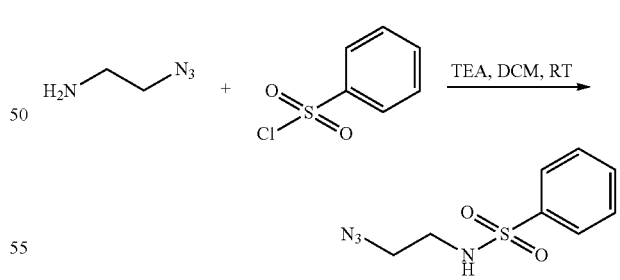

N-(2-azidoethyl)benzenesulfonamide: As in the synthesis of N-(2-azidoethyl)tetradecanamide, benzenesulfonyl chloride (0.201 g, 1.16 mmol) was reacted with 2-azidoethanamine (0.100 g, 1.16 mmol) and triethylamine (0.235 g, 2.32 mmol) in dichloromethane (5 mL) to give N-(2-azidoethyl)benzenesulfonamide (0.289 g, 84%). $^1$H NMR (300 MHz, CDCl$_3$) δ 7.90 (d, 2H), δ 7.55 (m, 3H), δ 5.47 (s, 1H), δ 3.39 (t, 2H), δ 3.12 (t, 2H) ppm; $^{13}$C NMR (75 MHz, CDCl$_3$) 139.8, 133.2, 129.5, 127.2, 50.9, 42.6 ppm; HRMS (ESI) calcd for C$_6$H$_8$N$_4$O$_2$S (M+) 226.0524, found 226.0523.

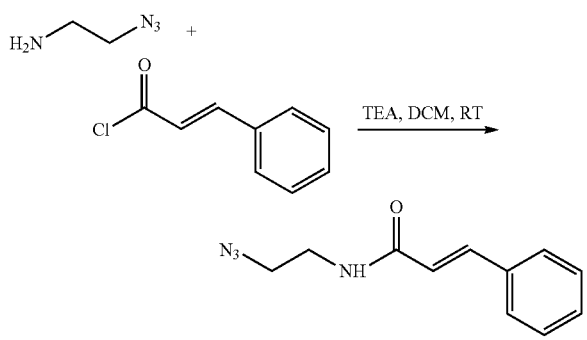

(E)-N-(2-azidoethyl)-4-phenylbut-3-enamide: As in the synthesis of N-(2-azidoethyl)tetradecanamide, (E)-4-phenyl-but-3-enoyl chloride (0.198 g, 1.19 mmol) was reacted with 2-azidoethanamine (0.114 g, 1.19 mmol) and triethylamine (0.239 g, 2.37 mmol) in dichloromethane (5 mL) to give (E)-N-(2-azidoethyl)-4-phenylbut-3-enamide (0.168 g, 55%). $^1$H NMR (300 MHz, CDCl$_3$) δ 7.68 (d, 1H), δ 7.45 (d, 2H), δ 7.29 (m, 3H), δ 7.04 (t, 1H), δ 6.59 (d, 1H), δ 3.55 (q, 2H), δ 3.47 (t, 2H) ppm; $^{13}$C NMR (75 MHz, CDCl$_3$) δ 166.9, 141.6, 134.9, 130.1, 129.1, 128.1, 120.8, 51.1, 39.4 ppm; HRMS (ESI) calcd for C$_{11}$H$_{12}$N$_4$O (M+) 216.1011, found 216.1005.

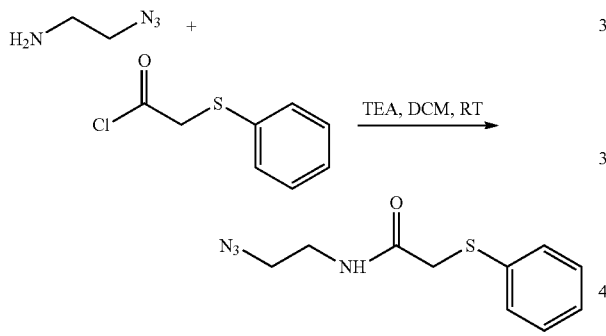

N-(2-azidoethyl)-2-(phenylthio)acetamide: As in the synthesis of N-(2-azidoethyl)tetradecanamide, 2-(phenylthio)acetyl chloride (0.222 g, 1.19 mmol) was reacted with 2-azidoethanamine (0.102 g, 1.19 mmol) and triethylamine (0.240 g, 2.37 mmol) in dichloromethane (5 mL) to give N-(2-azidoethyl)-2-(phenylthio)acetamide (0.179 g, 64%). $^1$H NMR (300 MHz, CDCl$_3$) δ 7.29 (m, 4H), δ 7.18 (m, 2H), δ 3.60 (s, 2H), 3.34 (m, 4H) ppm; $^{13}$C NMR (75 MHz, CDCl$_3$) δ 168.6, 134.8, 129.5, 128.6, 127.1, 50.8, 39.3, 37.7 ppm; HRMS (ESI) calcd for C$_{10}$H$_{12}$N$_4$OS (M+) 236.0732, found 236.0729.

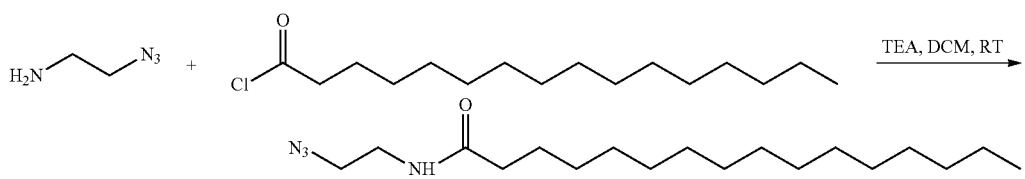

N-(2-azidoethyl)palmitamide: As in the synthesis of N-(2-azidoethyl)tetradecanamide, (0.338 g, 1.23 mmol) was reacted with 2-azidoethanamine (0.106 g, 1.23 mmol) and triethylamine (0.249 g, 2.46 mmol) in dichloromethane (5 mL) to give N-(2-azidoethyl)palmitamide (0.336 g, 84%). $^1$H NMR (300 MHz, CDCl$_3$) δ 6.11 (s, 1H), δ 3.41 (s, 4H), δ 2.17 (t, 2H), δ 1.60 (m, 2H), δ 1.23 (m, 24H), δ 0.85 (t, 3H) ppm; $^{13}$C NMR (75 MHz, CDCl$_3$) δ 173.9, 51.1, 39.1, 36.9, 32.1, 29.9, 29.8, 29.8, 29.7, 29.6, 29.5, 25.9, 22.9, 14.3 ppm; HRMS (ESI) calcd for C$_{18}$H$_{36}$N$_4$O (M+) 324.2889, found 324.2879.

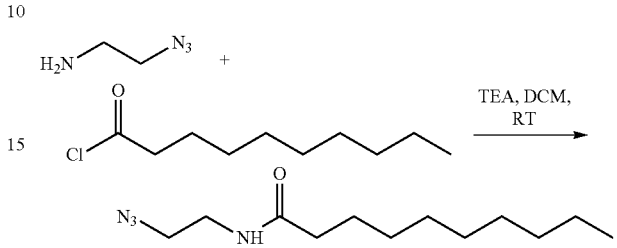

N-(2-azidoethyl)decanamide: As in the synthesis of N-(2-azidoethyl)tetradecanamide, decanoyl chloride (0.251 g, 1.32 mmol) was reacted with 2-azidoethanamine (0.114 g, 1.32 mmol) and triethylamine (0.267 g, 2.64 mmol) in dichloromethane (5 mL) to give N-(2-azidoethyl)decanamide (0.262 g, 83%). $^1$H NMR (300 MHz, CDCl$_3$) δ 6.49 (s, 1H), δ 3.36 (s, 2H), δ 3.35 (s, 2H), δ 2.14 (t, 2H), δ 1.46 (m, 2H), δ 1.21 (m, 12H), δ 0.81 (t, 3H) ppm; $^{13}$C NMR (75 MHz, CDCl$_3$) δ 174.1, 50.9, 39.1, 36.8, 32.0, 29.7, 29.6, 29.5, 29.4, 25.9, 22.8, 14.3 ppm; HRMS (ESI) calcd for C$_{12}$H$_{24}$N$_4$O (M+) 240.1950, found 240.1947.

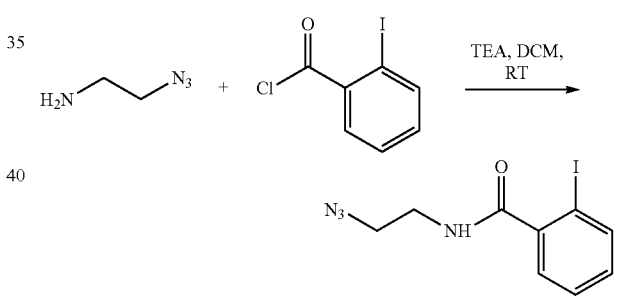

N-(2-azidoethyl)-2-iodobenzamide: As in the synthesis of N-(2-azidoethyl)tetradecanamide, 2-iodobenzoyl chloride (0.312 g, 1.17 mmol) was reacted with 2-azidoethanamine (0.101 g, 1.17 mmol) and triethylamine (0.237 g, 2.34 mmol) in dichloromethane (5 mL) to give N-(2-azidoethyl)-2-iodobenzamide (0.272 g, 74%). $^1$H NMR (300 MHz, CDCl$_3$) δ 7.84 (d, 1H), δ 7.33 (m, 2H), δ 7.08 (t, 1H), δ 6.51 (s, 1H), δ 3.54 (s, 2H), δ 3.53 (s, 2H) ppm; $^{13}$C NMR (75 MHz, CDCl$_3$) δ 169.9, 141.9, 140.0, 131.5, 128.4, 128.4, 92.7, 50.8, 39.6 ppm; HRMS (ESI) calcd for C$_9$H$_{91}$N$_4$O (M+) 315.9821, found 315.9820.

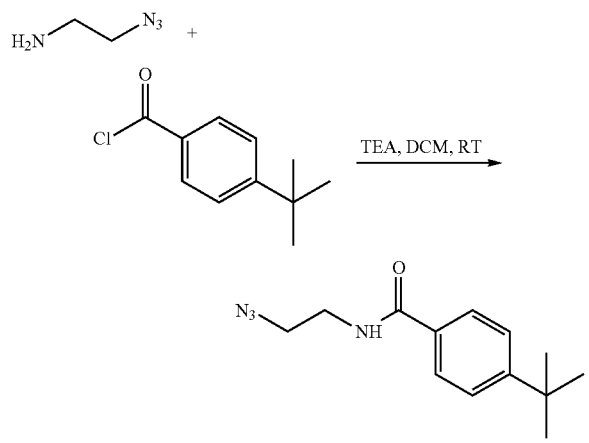

N-(2-azidoethyl)-4-tert-butylbenzamide: As in the synthesis of N-(2-azidoethyl)tetradecanamide, 4-tert-butylbenzoyl chloride (0.244 g, 1.23 mmol) was reacted with 2-azidoethanamine (0.106 g, 1.23 mmol) and triethylamine (0.249 g, 2.47 mmol) in dichloromethane (5 mL) to give N-(2-azidoethyl)-4-tert-butylbenzamide (0.221 g, 73%). $^1$H NMR (300 MHz, CDCl$_3$) δ 7.73 (d, 2H), δ 7.43 (d, 2H), δ 6.95 (t, 1H), δ 3.59 (q, 2H), δ 3.50 (t, 2H), δ 1.31 (s, 9H) ppm; $^{13}$C NMR (75 MHz, CDCl$_3$) δ 168.2, 155.4, 131.4, 127.2, 125.8, 51.1, 39.7, 35.2, 31.4 ppm; HRMS (ESI) calcd for C$_{13}$H$_{18}$N$_4$O (M+) 246.1480, found 246.1479.

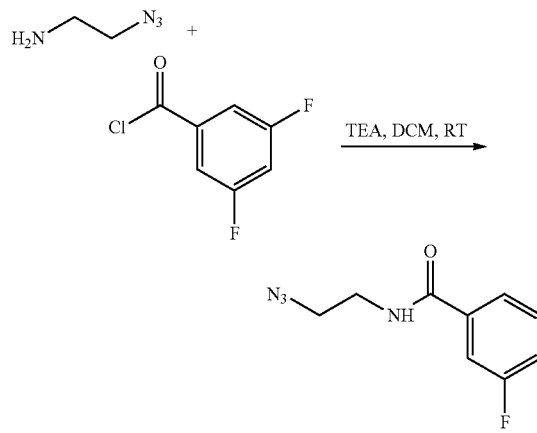

N-(2-azidoethyl)-3,5-difluorobenzamide: As in the synthesis of N-(2-azidoethyl)tetradecanamide, 3,5-difluorobenzoyl chloride (0.219 g, 1.24 mmol) was reacted with 2-azidoethanamine (0.107 g, 1.24 mmol) and triethylamine (0.251 g, 2.48 mmol) in dichloromethane (5 mL) to give N-(2-azidoethyl)-3,5-difluorobenzamide (0.280 g, 59%). $^1$H NMR (300 MHz, CDCl$_3$) δ 7.32 (s, 2H), 7.29 (s, 1H), 6.91 (t, 1H), 3.58 (q, 2H), 3.51 (t, 2H) ppm; $^{13}$C NMR (75 MHz, CDCl$_3$) δ 165.9, 164.7, 161.5, 161.4, 137.6, 110.7, 106.9, 50.7, 39.9 ppm; HRMS (ESI) calcd for C$_9$H$_8$F$_2$N$_4$O$_2$S (M+) 226.0666, found 226.0662.

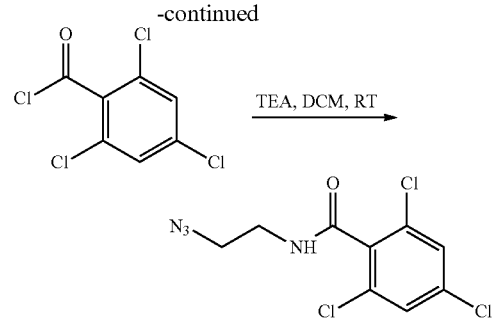

N-(2-azidoethyl)-2,4,6-trichlorobenzamide: As in the synthesis of N-(2-azidoethyl) tetradecanamide, (0.301 g, 1.23 mmol) was reacted with 2-azidoethanamine (0.106 g, 1.23 mmol) and triethylamine (0.249 g, 2.47 mmol) in dichloromethane (5 mL) to give N-(2-azidoethyl)-2,4,6-trichlorobenzamide (0.317 g, 88%). $^1$H NMR (300 MHz, CDCl$_3$) δ 7.27 (2H, s), δ 6.88 (s, 1H), δ 3.54 (s, 2H), δ 3.53 (s, 2H) ppm; $^{13}$C NMR (75 MHz, CDCl$_3$) δ 164.4, 135.9, 134.3, 132.9, 128.2, 50.7, 39.4 ppm; HRMS (ESI) calcd for C$_9$H$_7$N$_4$O (M+) 291.9685, found 291.9681.

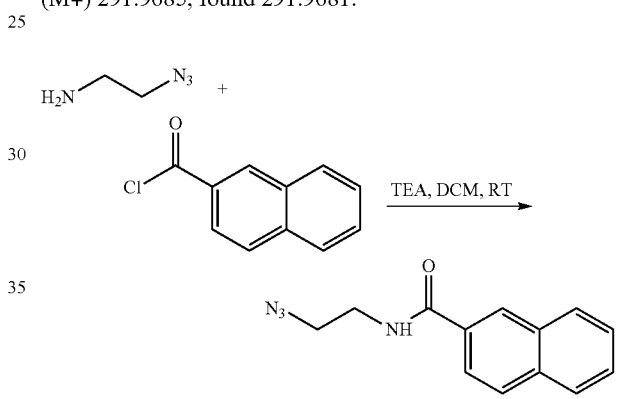

N-(2-azidoethyl)-2-naphthamide: As in the synthesis of N-(2-azidoethyl)tetradecanamide, 2-naphthoyl chloride (0.237 g, 1.24 mmol) was reacted with 2-azidoethanamine (0.107 g, 1.24 mmol) and triethylamine (0.252 g, 2.49 mmol) in dichloromethane (5 mL) to give N-(2-azidoethyl)-2-naphthamide (0.234 g, 77%). $^1$H NMR (300 MHz, CDCl$_3$) δ 8.69 (s, 1H), δ 7.84 (m, 4H), δ 7.50 (m, 2H), 6.97 (t, 1H), δ 3.68 (q, 2H), 3.56 (t, 2H) ppm; $^{13}$C NMR (75 MHz, CDCl$_3$) δ 168.3, 135.1, 132.8, 131.5, 129.2, 128.8, 128.0, 127.9, 127.1, 123.8, 51.2, 39.8 ppm; HRMS (ESI) calcd for C$_{13}$H$_{12}$N$_4$O (M+) 240.1011, found 240.1007.

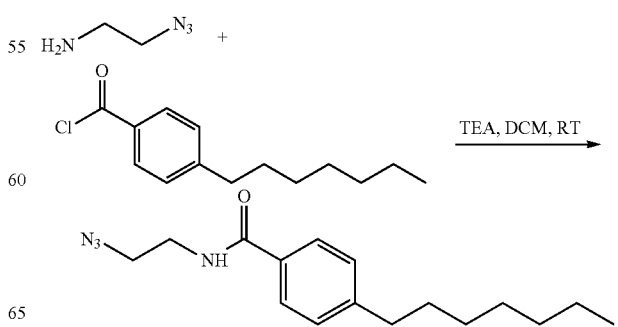

N-(2-azidoethyl)-4-heptylbenzamide: As in the synthesis of N-(2-azidoethyl)tetradecanamide, 4-heptylbenzoyl chloride (0.289 g, 1.21 mmol) was reacted with 2-azidoethanamine (0.104 g, 1.21 mmol) and triethylamine (0.245 g, 2.42 mmol) in dichloromethane (5 mL) to give N-(2-azidoethyl)-4-heptylbenzamide (0.260 g, 75%). $^1$H NMR (300 MHz, CDCl$_3$) δ 7.73 (d, 2H), δ 7.19 (d, 3H), δ 3.57 (q, 2H), δ 3.47 (t, 2H), δ 2.61 (t, 2H), δ 1.61 (m, 2H), δ 1.26 (m, 8H), δ 0.87 (t, 3H) ppm; $^{13}$C NMR (75 MHz, CDCl$_3$) δ 168.3, 147.3, 131.7, 128.8, 127.4, 50.9, 39.7, 36.1, 32.0, 31.4, 29.4, 29.3, 22.9, 14.3 ppm; HRMS (ESI) calcd for C$_{16}$H$_{24}$N$_4$O (M+) 288.1950, found 288.1943.

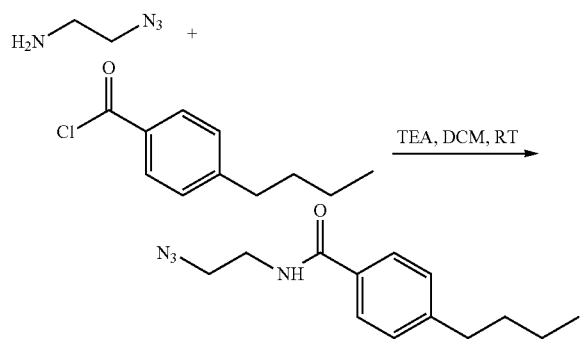

N-(2-azidoethyl)-4-butylbenzamide: As in the synthesis of N-(2-azidoethyl)tetradecanamide, (0.242 g, 1.22 mmol) was reacted with 2-azidoethanamine (0.105 g, 1.22 mmol) and triethylamine (0.246 g, 2.43 mmol) in dichloromethane (5 mL) to give N-(2-azidoethyl)-4-butylbenzamide (0.224 g, 75%). $^1$H NMR (300 MHz, CDCl$_3$) δ 7.73 (d, 2H), δ 7.39 (t, 1H), δ 7.17 (d, 2H), δ 3.55 (q, 2H), δ 3.45 (t, 2H), δ 2.60 (t, 2H), δ 1.56 (m, 2H), δ 1.30 (m, 2H), δ 0.90 (t, 3H) ppm; $^{13}$C NMR (75 MHz, CDCl$_3$) δ 168.5, 147.2, 131.7, 128.8, 127.4, 50.9, 39.7, 35.7, 33.5, 22.5, 14.1 ppm; HRMS (ESI) calcd for C$_{13}$H$_{18}$N$_4$O (M+) 246.1481, found 246.1476.

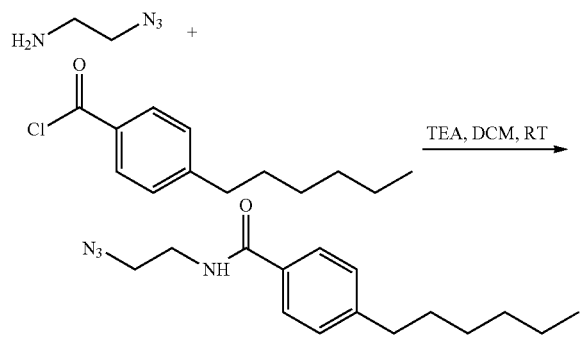

N-(2-azidoethyl)-4-hexylbenzamide: As in the synthesis of N-(2-azidoethyl)tetradecanamide, 4-hexylbenzoyl chloride (0.293 g, 1.30 mmol) was reacted with 2-azidoethanamine (0.112 g, 1.30 mmol) and triethylamine (0.264 g, 2.61 mmol) in dichloromethane (5 mL) to give N-(2-azidoethyl)-4-hexylbenzamide (0.299 g, 84%). $^1$H NMR (300 MHz, CDCl$_3$) δ 7.75 (d, 2H), δ 7.43 (t, 1H), δ 7.17 (d, 2H), δ 3.55 (q, 2H), δ 3.46 (t, 2H), δ 2.59 (t, 2H), δ 1.58 (m, 2H), δ 1.29 (m, 4H), δ 0.87 (t, 3H) ppm; $^{13}$C NMR (75 MHz, CDCl$_3$) δ 168.6, 147.3, 131.7, 130.3, 128.8, 127.5, 50.9, 39.7, 35.9, 31.6, 31.1, 22.7, 14.2 ppm; HRMS (ESI) calcd for C$_{15}$H$_{22}$N$_4$O (M+) 274.1794, found 274.1789.

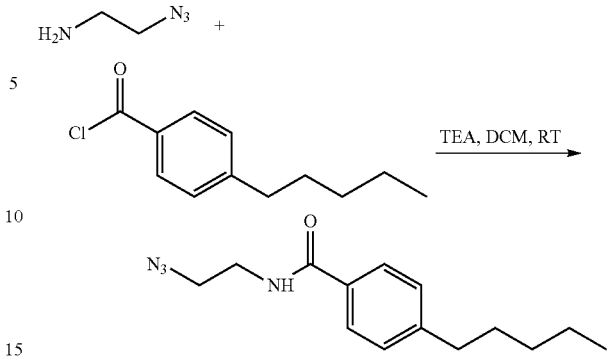

N-(2-azidoethyl)-4-pentylbenzamide: As in the synthesis of N-(2-azidoethyl)tetradecanamide, 4-pentylbenzoyl chloride (0.283 g, 1.35 mmol) was reacted with 2-azidoethanamine (0.116 g, 1.35 mmol) and triethylamine (0.273 g, 2.69 mmol) in dichloromethane (5 mL) to give N-(2-azidoethyl)-4-pentylbenzamide (0.267 g, 76%). $^1$H NMR (300 MHz, CDCl$_3$) δ 7.74 (d, 2H), δ 7.61 (t, 1H), δ 7.15 (d, 2H), δ 3.54 (q, 2H), δ 3.44 (t, 2H), δ 2.58 (t, 2H), δ 1.57 (m, 2H), δ 1.26 (m, 4H), δ 0.86 (t, 3H) ppm; $^{13}$C NMR (75 MHz, CDCl$_3$) δ 168.6, 147.2, 131.7, 128.7, 127.5, 50.8, 39.7, 35.9, 31.6, 31.1, 22.7, 14.2 ppm; HRMS (ESI) calcd for C$_{14}$H$_{20}$N$_4$O (M+) 260.1637, found 260.1632.

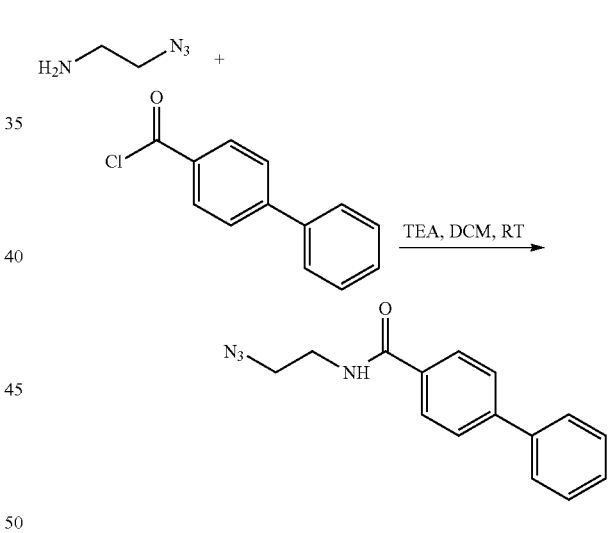

N-(2-azidoethyl)biphenyl-4-carboxamide: As in the synthesis of N-(2-azidoethyl)tetradecanamide, (0.283 g, 1.31 mmol) was reacted with 2-azidoethanamine (0.113 g, 1.31 mmol) and triethylamine (0.264 g, 2.61 mmol) in dichloromethane (5 mL) to give N-(2-azidoethyl)biphenyl-4-carboxamide (0.297 g, 85%). $^1$H NMR (300 MHz, CDCl$_3$) δ 7.88 (d, 2H), δ 7.67 (m, 4H), δ 7.44 (m, 3H), δ 6.63 (s, 1H), δ 3.67 (q, 2H), 8 (3.58 (t, 2H) ppm; $^{13}$C NMR (75 MHz, CDCl$_3$) δ 167.8, 144.8, 140.1, 132.9, 129.2, 128.3, 127.8, 127.5, 127.4, 51.2, 39.7 ppm; HRMS (ESI) calcd for C$_{15}$H$_{14}$N$_4$O (M+) 266.1168, found 266.1162.

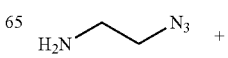

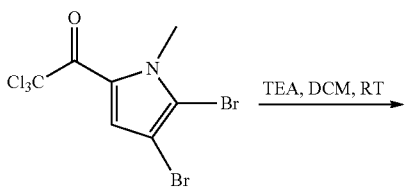

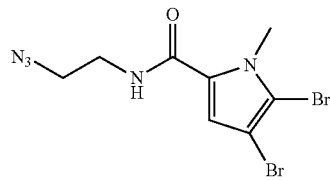

N-(2-azidoethyl)-4,5-dibromo-1-methyl-1H-pyrrole-2-carboxamide: As in the synthesis of N-(2-azidoethyl)tetradecanamide, (0.529 g, 1.38 mmol) was reacted with 2-azidoethanamine (0.119 g, 1.38 mmol) and triethylamine (0.279 g, 2.75 mmol) in dichloromethane (5 mL) to give N-(2-azidoethyl)-4,5-dibromo-1-methyl-1H-pyrrole-2-carboxamide (0.331 g, 69%). $^1$H NMR (300 MHz, CD$_3$OD) δ 6.84 (s, 1H), δ 3.91 (s, 3H), δ 3.50 (d, 2H), δ 3.25 (d, 2H) ppm; $^{13}$C NMR (75 MHz, CD$_3$OD) δ 161.7, 127.7, 114.7, 111.4, 97.8, 50.4, 38.9, 35.1 ppm; HRMS (ESI) calcd for C$_8$H$_9$N$_5$O (M+) 348.9174, found 348.9183.

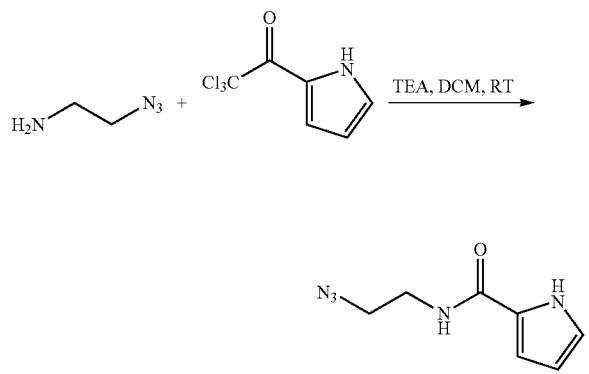

N-(2-azidoethyl)-1H-pyrrole-2-carboxamide: As in the synthesis of N-(2-azidoethyl)tetradecanamide, (0.249 g, 1.17 mmol) was reacted with 2-azidoethanamine (0.101 g, 1.17 mmol) and triethylamine (0.237 g, 2.34 mmol) in dichloromethane (5 mL) to give N-(2-azidoethyl)-1H-pyrrole-2-carboxamide (0.137 g, 66%). $^1$H NMR (300 MHz, CD$_3$OD) δ 6.88 (d, 1H), δ 6.77 (d, 1H), δ 6.14 (t, 1H), δ 3.46 (t, 2H), δ 3.37 (q, 2H) ppm; $^{13}$C NMR (75 MHz, CD$_3$OD) δ 162.9, 125.6, 122.2, 121.9, 110.9, 109.2, 50.6, 38.9 ppm; HRMS (ESI) calcd for C$_7$H$_9$N$_5$O (M+) 179.0807, found 179.0803.

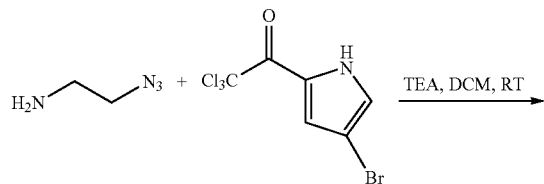

N-(2-azidoethyl)-4-bromo-1H-pyrrole-2-carboxamide:
As in the synthesis of N-(2-azidoethyl)tetradecanamide, (0.408 g, 1.34 mmol) was reacted with 2-azidoethanamine (0.115 g, 1.34 mmol) and triethylamine (0.270 g, 2.67 mmol) in dichloromethane (5 mL) to give N-(2-azidoethyl)-4-bromo-1H-pyrrole-2-carboxamide (0.299 g, 82%). $^1$H NMR (300 MHz, CD$_3$OD) δ 6.93 (s, 1H), δ 6.80 (s, 1H), δ 3.49 (t, 2H), δ 3.41 (t, 2H) ppm; $^{13}$C NMR (75 MHz, CD$_3$OD) 161.7, 126.1, 122.0, 112.4, 96.4, 50.5, 38.9 ppm; HRMS (ESI) calcd for C$_7$H$_8$BrN$_5$O (M+) 256.9912, found 256.9908.

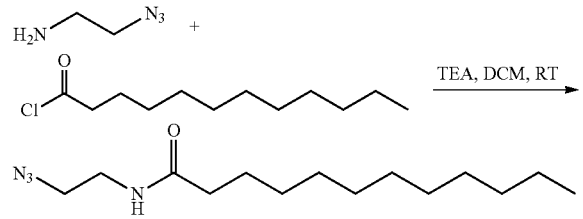

N-(2-azidoethyl)dodecanamide: As in the synthesis of N-(2-azidoethyl)tetradecanamide, (0.262 g, 1.19 mmol) was reacted with 2-azidoethanamine (0.103 g, 1.19 mmol) and triethylamine (0.242 g, 2.39 mmol) in dichloromethane (5 mL) to give N-(2-azidoethyl)dodecanamide (0.220 g, 69%). $^1$H NMR (300 MHz, CDCl$_3$) δ 6.11 (s, 1H), δ 3.40 (d, 2H), δ 3.37 (d, 2H), δ 2.17 (t, 2H), δ 1.59 (q, 2H), δ 1.22 (s, 14H), δ 0.84 (t, 3H) ppm; $^{13}$C NMR (75 MHz, CDCl$_3$) δ 173.8, 51.1, 39.1, 36.8, 32.1, 29.8, 29.7, 29.6, 29.5, 29.2, 25.9, 22.9, 14.3 ppm; HRMS (ESI) calcd for C$_{14}$H$_{28}$N$_4$O (M+) 268.2263, found 268.2259.

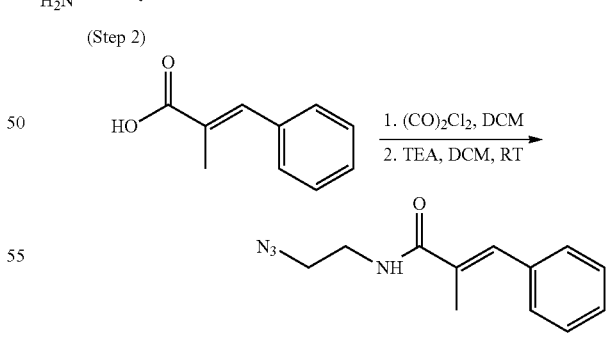

(E)-N-(2-azidoethyl)-2-methyl-3-phenylacrylamide: To a 25 mL round-bottomed flask equipped with a magnetic stir bar was added (E)-2-methyl-3-phenylacrylic acid (0.0.512 g, 3.15 mmol) and dichloromethane (10 mL). Oxalyl chloride (0.400 g, 3.15 mmol) was added dropwise to the reaction mixture and allowed to stir for one hour. Then, the reaction mixture was concentrated de vacuo. To the crude mixture was then added dichloromethane (10 mL), 2-azidoethanamine (0.299 g, 3.47 mmol) and then triethylamine (0.351 g, 3.47 mmol) and allowed to stir for two hours. The reaction mixture was then concentrated de vacuo and then purified via silica gel column chromatography (100% dichloromethane to 1:40 methanol:dichloromethane) to give (E)-N-(2-azidoethyl)-2-methyl-3-phenylacrylamide (0.698 g, 96% yield). $^1$H NMR (300 MHz, CDCl$_3$) δ 7.39 (m, 6H), δ 7.01 (s, 1H), δ 3.51 (t, 2H), δ 3.45 (t, 2H), δ 2.13 (s, 3H) ppm; $^{13}$C NMR (75 MHz, CDCl$_3$) δ 170.5, 136.2, 134.5, 132.0, 130.3, 129.6, 128.9, 128.6, 128.3, 50.9, 39.8, 14.5 ppm; HRMS (ESI) calcd for C$_{12}$H$_{14}$N$_4$O (M+) 230.1168, found 230.1165.

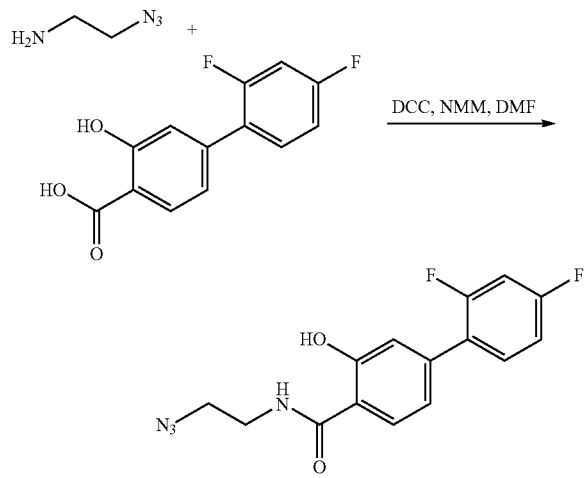

N-(2-azidoethyl)-2',4'-difluoro-3-hydroxybiphenyl-4-carboxamide: To a 25 mL round-bottomed flask equipped with a magnetic stir bar was added 2',4'-difluoro-3-hydroxybiphenyl-4-carboxylic acid (0.301, 1.20 mmol), N,N-Dimethylformamide (5 mL), N,N'-Dicyclohexylcarbodiimide (0.248 g, 1.20 mmol) and n-methylmorpholine (0.25 mL). The reaction mixture was cooled to 0° C. and allowed to stir. Then, 2-azidoethanamine (0.1037 g, 1.20 mmol) was added dropwise and allowed to slowly warm to room temperature while stirring for 24 hr. The reaction mixture was diluted with water, extracted with dichloromethane, washed with 1N HCl, washed with saturated sodium bicarbonate, washed with brine and then concentrated de vacuo. The resulting residue was then purified via silica gel column chromatography (1:40 methanol:dichloromethane to 1:10 methanol:dichloromethane) to give N-(2-azidoethyl)-2',4'-difluoro-3-hydroxybiphenyl-4-carboxamide (0.232 g, 61% yield). $^1$H NMR (300 MHz, CDCl$_3$) δ 7.60 (s, 1H), δ 7.47 (d, 1H), δ 7.29 (m, 2H), δ 7.02 (d, 1H), δ 6.88 (m, 2H) ppm; $^{13}$C NMR (75 MHz, CDCl$_3$) δ 170.3, 160.8, 135.1, 131.3, 131.2, 131.3, 131.2, 126.8, 118.8, 114.6, 112.0, 111.8, 104.8, 104.6, 104.3, 50.7, 39.3 ppm; HRMS (ESI) calcd for C$_{1-15}$H$_{12}$F$_2$N$_4$O$_3$ (M+) 318.0928, found 318.0933.

General procedure for click reactions and subsequent Boc deprotection: The terminal alkyne (1.0 equiv.) was dissolved in a 1:1:1 mixture of ethanol, water and methylene chloride (ca. 9 mL per 0.300 g of terminal alkyne). To this solution, the appropriate azide (1.0 equiv.) was added while stirring vigorously at room temperature. Copper (II) sulfate (15 mol %) and sodium ascorbate (45 mol %) were then added sequentially to the solution. Reaction mixtures were allowed to stir until completion via TLC analysis (12-24 hrs). The solvents were then removed de vacuo in which the resulting residue was dissolved in dichloromethane and purified via silica gel column chromatography (1:40 methanol:dichloromethane to 1:10 methanol: dichloromethane). To remove the Boc protecting group, the resulting product was then dissolved in a 1:4 trifluoroacetic acid: dichloromethane mixture and allowed to stir for 5 hr. Upon completion, the reaction mixture was concentrated de vacuo and then left on a high vacuum overnight. Then, methanol supplemented with HCl was added to the product forming the HCl salt of the deprotected product and then was concentrated de vacuo. The resulting residue was washed with diethyl ether and then placed on a high vacuum overnight.

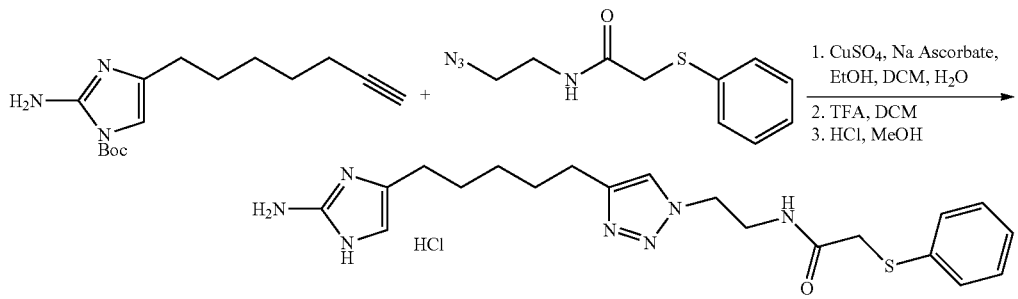

N-(2-(4-(5-(2-amino-1H-imidazol-4-yl)pentyl)-1H-1,2,3-triazol-1-yl)ethyl)-2-(phenylthio)acetamide hydrochloride: tert-butyl 2-amino-4-(hept-6-ynyl)-1H-imidazole-1-carboxylate (0.112 g, 0.405 mmol) was reacted with N-(2-azidoethyl)-2-(phenylthio)acetamide (0.096 g, 0.405 mmol) following the general click procedure to give tert-butyl 2-amino-4-(5-(1-(2-(2-(phenylthio)acetamido)ethyl)-1H-1,2,3-triazol-4-yl)pentyl)-1H-imidazole-1-carboxylate $^1$H NMR (300 MHz, CDCl$_3$) δ 7.45 (s, 1H0, δ 7.19 (m, 5H), δ 7.13 (s, 1H), δ 6.43 (s, 1H), δ 6.13 (bs, 2H0, δ 4.29 (s, 2H), δ 3.68 (s, 2H), δ 3.57 (s, 2H), δ 2.56 (s, 2H), δ 2.35 (s, 2H), δ 1.52 (m, 15H) ppm; $^{13}$C NMR (75 MHz, CDCl$_3$) δ 187.8, 172.0, 169.1, 162.4, 156.9, 135.0, 129.5, 128.3, 126.8, 121.8, 85.00, 49.4, 39.9, 37.4, 29.4, 28.9, 28.4, 28.2, 27.6, 25.6 ppm; HRMS (ESI) calcd for C$_{25}$H$_{35}$N$_7$O$_3$S (M+) 513.2522, found 513.2522, which was subsequently deprotected to give N-(2-(4-(5-(2-amino-1H-imidazol-4-yl)pentyl)-1H-1,2,3-triazol-1-yl)ethyl)-2-(phenylthio)acetamide hydrochloride (0.133 g, 73% yield). $^1$H NMR (300 MHz, CD$_3$OD) δ 8.47 (s, 1H), δ

7.30 s, 4H), δ 7.19 (s, 1H), δ 6.58 (s, 1H), δ 4.66 (s, 2H), δ 3.76 (s, 2H), δ 3.64 (s, 2H), δ 2.84 (s, 2H), δ 2.34 (s, 2H), δ 1.73 (s, 2H), δ 1.64 (s, 2H), δ 1.26 (s, 2H) ppm; $^{13}$C NMR (75 MHz, CD$_3$OD) δ 170.9, 159.3, 158.9, 147.2, 135.6, 128.1, 128.9, 127.6, 126.6, 108.7, 108.6, 52.-, 39.1, 37.5, 37.2, 36.6, 36.1, 30.8, 28.1, 27.9, 27.7, 24.2, 23.7, 23.6 ppm; HRMS (ESI) calcd for C$_{20}$H$_{27}$N$_7$OS (M+) 413.1998, found 413.1991.

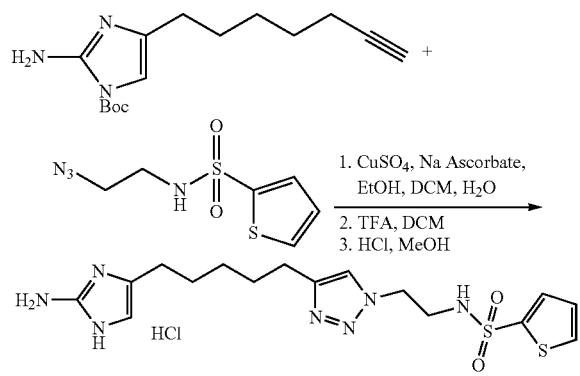

N-(2-(4-(5-(2-amino-1H-imidazol-4-yl)pentyl)-1H-1,2,3-triazol-1-yl)ethyl)thiophene-2-sulfonamide hydrochloride: tert-butyl 2-amino-4-(hept-6-ynyl)-1H-imidazole-1-carboxylate (0.105 g, 0.379 mmol) was reacted with N-(2-azidoethyl)thiophene-2-sulfonamide (0.099 g, 0.379 mmol) following the general click procedure to give tert-butyl 2-amino-4-(5-(1-(2-(thiophene-2-sulfonamido)ethyl)-1H-1,2,3-triazol-4-yl)pentyl)-1H-imidazole-1-carboxylate $^1$H NMR (300 MHz, CDCl$_3$) δ 7.49 (s, 3H), δ 7.39 (S, 1H), δ 6.99 (s, 1H), δ 6.41 (bm, 3H), δ 4.43 (s, 2H), δ 3.42 (s, 2H), δ 2.54 (s, 2H), δ 2.09 (s, 2H), δ 1.51 (m, 13H), δ 1.19 (s, 2H) ppm; $^{13}$C NMR (75 MHz, CDCl$_3$) δ 150.8, 149.4, 148.1, 141.1, 138.3, 132.2, 132.1, 127.7, 122.6, 85.2, 53.8, 50.2, 43.2, 31.2, 29.9, 29.2, 28.8, 28.1, 25.5 ppm; HRMS (ESI) calcd for C$_{21}$H$^{31}$N$_7$O$_4$S$_2$ (M+) 509.1879, found 509.1879, which was subsequently deprotected to give N-(2-(4-(5-(2-amino-1H-imidazol-4-yl)pentyl)-1H-1,2,3-triazol-1-yl)ethyl)thiophene-2-sulfonamide hydrochloride (0.098 g, 58% yield). $^1$H NMR (400 MHz, CD$_3$OD) δ 8.37 (s, 1H), δ 7.76 (s, 1H), δ 7.57 (s, 1H), δ 7.11 (s, 1H), δ 6.46 (s, 1H), δ 4.79 (s, 2H), δ 3.55 (s, 2H), δ 2.50 (s, 2H), δ 1.66-1.18 (bm, 8H) ppm; $^{13}$C NMR (100 MHz, CD$_3$OD) δ 175.6, 155.6, 147.2, 140.9, 132.7, 132.3, 127.8, 127.7, 108.8, 53.1, 42.2, 36.8, 28.1, 27.8, 27.5, 24.9, 24.3, 23.8 ppm; HRMS (ESI) calcd for C$_{16}$H$_{23}$N$_7$O$_2$S$_2$(M+) 409.1355, found 409.1354.

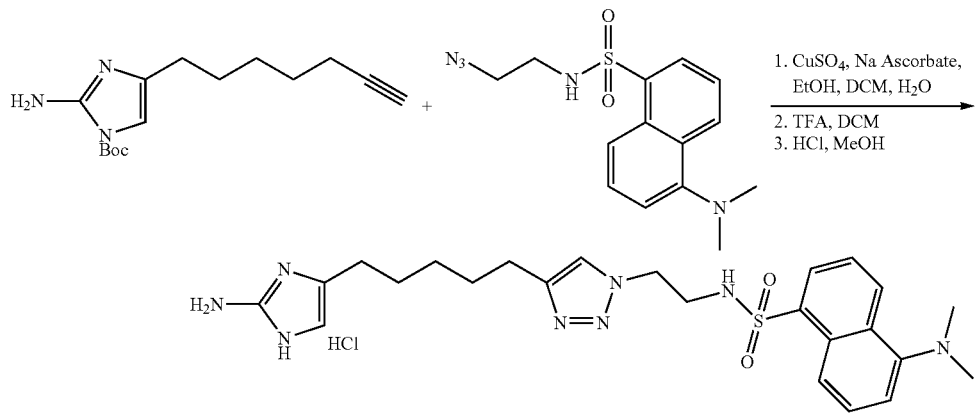

N-(2-(4-(5-(2-amino-1H-imidazol-4-yl)pentyl)-1H-1,2,3-triazol-1-yl)ethyl)-5-(dimethylamino)naphthalene-1-sulfonamide hydrochloride: tert-butyl 2-amino-4-(hept-6-ynyl)-1H-imidazole-1-carboxylate (0.112 g, 0.403 mmol) was reacted with N-(2-azidoethyl)-5-(dimethylamino)naphthalene-1-sulfonamide (0.140 g, 0.403 mmol) following the general click procedure to give tert-butyl 2-amino-4-(5-(1-(2-(5-(dimethylamino)naphthalene-1-sulfonamido)ethyl)-1H-1,2,3-triazol-4-yl)pentyl)-1H-imidazole-1-carboxylate $^1$H NMR (300 MHz, CDCl$_3$) δ 8.48 (d, 1H), δ 8.24 (d, 1H), δ 8.17 (d, 1H), δ 7.44 (m, 3H), δ 7.09 (s, 1H), δ 7.07 (d, 1H), δ 6.44 (s, 1H), δ 6.09 (bs, 2H), δ 4.32 (s, 2H), δ 3.36 (s, 2H), δ 2.52 (s, 2H), δ 2.22 (s, 2H), δ 1.43 (m, 13H), δ 1.22 (s, 2H) ppm; $^{13}$C NMR (75 MHz, CDCl$_3$) δ 176.9, 152.1, 149.6, 148.0, 138.6, 135.1, 130.7, 130.1, 129.7, 129.4, 128.5, 123.3, 122.4, 119.1, 115.5, 84.9, 67.5, 50.3, 50.2, 45.6, 42.9, 37.9, 29.1, 28.9, 28.2, 28.0, 25.5 ppm; HRMS (ESI) calcd for C$_{29}$H$_{40}$N$_8$O$_4$S (M+) 596.2893, found 596.2881, which was subsequently deprotected to give N-(2-(4-(5-(2-amino-1H-imidazol-4-yl)pentyl)-1H-1,2,3-triazol-1-yl)ethyl)-5-(dimethylamino)naphthalene-1-sulfonamide hydrochloride (0.139 g, 65% yield). $^1$H NMR (400 MHz, CD$_3$OD) δ 8.70 (t, 2H), δ 8.31 (s, 1H), δ 8.08 (s, 2H), δ 7.82 (s, 2H), δ 6.43 (s, 1H), δ 4.55 (s, 2H), δ 3.32 (s, 8H), 2.63 (s, 2H), δ 2.48 (s, 2H), δ 1.66 (s, 4H), δ 1.40 (s, 2H) ppm; $^{13}$C NMR (100 MHz, CD$_3$OD) δ 159.9, 147.3, 140.7, 136.8, 129.9, 129.3, 127.8, 127.7, 126.5, 119.3, 108.6, 108.4, 76.7, 67.3, 51.5, 42.3, 37.4, 36.5, 28.3, 27.9, 27.6, 24.1, 24.0, 23.7 ppm; HRMS (ESI) calcd for C$_{24}$H$_{32}$N$_8$O$_2$S (M+) 496.2369, found 496.2359.

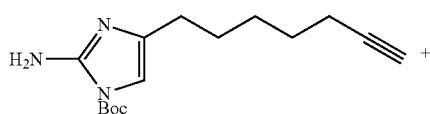

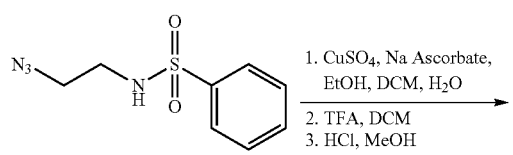

-continued

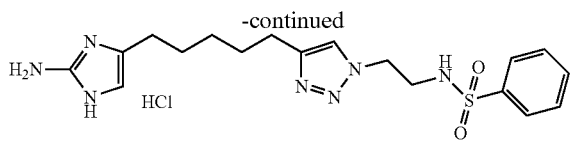

tert-butyl 2-amino-4-(5-(1-(2-(phenylsulfonamido)ethyl)-1H-1,2,3-triazol-4-yl)pentyl)-1H-imidazole-1-carboxylate hydrochloride: tert-butyl 2-amino-4-(hept-6-ynyl)-1H-imidazole-1-carboxylate (0.114 g, 0.410 mmol) was reacted with N-(2-azidoethyl)benzenesulfonamide (0.104 g, 0.410 mmol) following the general click procedure to give tert-butyl 2-amino-4-(5-(1-(2-(phenylsulfonamido)ethyl)-1H-1,2,3-triazol-4-yl)pentyl)-1H-imidazole-1-carboxylate $^1$H NMR (300 MHz, CDCl$_3$) δ 7.81 (d, 2H), δ 7.44 (m, 5H), δ 6.44 (s, 1H), δ 6.07 (s, 2H), δ 4.42 (t, 2H), δ 3.36 (t, 2H), δ 2.47 (t, 2H), δ 2.20 (s, 2H), δ 1.47 (m, 13H0, δ 1.29 (s, 2H) ppm; $^{13}$C NMR (75 MHz, CDCl$_3$) δ 202.9, 149.5, 148.2, 140.2, 132.8, 129.4, 127.1, 122.5, 106.5, 85.0, 53.7, 50.3, 42.9, 32.7, 31.2, 29.9, 29.2, 28.9, 28.2, 26.3, 25.5 ppm; HRMS (ESI) calcd for C$_{23}$H$_{33}$N$_7$O$_4$S (M+) 503.2315, found 503.2310, which was subsequently deprotected to give tert-butyl 2-amino-4-(5-(1-(2-(phenylsulfonamido)ethyl)-1H-1,2,3-triazol-4-yl)pentyl)-1H-imidazole-1-carboxylate hydrochloride (0.142 g, 64% yield). $^1$H NMR (300 MHz, CD$_3$OD) δ 7.81 (d, 2H), δ 7.56 (m, 4H), δ 6.47 (s, 1H), δ 4.62 (s, 2H), δ 3.41 (s, 2H), δ 2.78 (s, 2H), δ 2.48 (s, 2H), δ 1.72 (s, 2H), δ 1.63 (s, 2H), δ 1.42 (s, 2H) ppm; $^{13}$C NMR (75 MHz, CD$_3$OD) δ 176.2, 165.6, 159.9, 147.3, 140.2, 132.8, 129.3, 127.7, 126.8, 108.5, 108.4, 515.8, 42.3, 28.1, 27.9, 27.6, 24.1 ppm; HRMS (ESI) calcd for C$_{18}$H$_{25}$N$_7$O$_2$S (M+) 403.1790, found 403.1781.

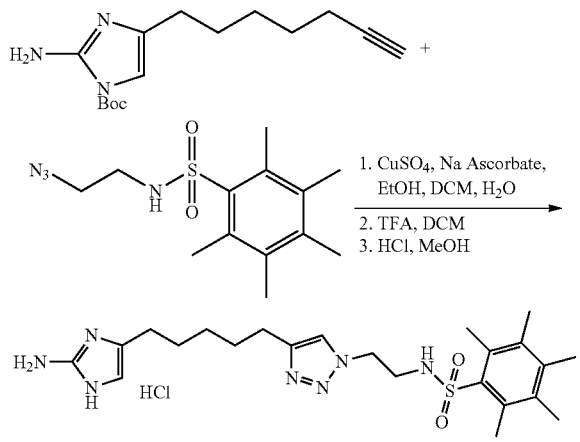

N-(2-(4-(5-(2-amino-1H-imidazol-4-yl)pentyl)-1H-1,2,3-triazol-1-yl)ethyl)-2,3,4,5,6-pentamethylbenzenesulfonamide hydrochloride: tert-butyl 2-amino-4-(hept-6-ynyl)-1H-imidazole-1-carboxylate (0.120 g, 0.434 mmol) was reacted with N-(2-azidoethyl)-2,3,4,5,6-pentamethylbenzenesulfonamide (0.141 g, 0.434 mmol) following the general click procedure to give tert-butyl 2-amino-4-(5-(1-(2-(2,3,4,5,6-pentamethylphenylsulfonamido)ethyl)-1H-1,2,3-triazol-4-yl)pentyl)-1H-imidazole-1-carboxylate $^1$H NMR (300 MHz, CDCl$_3$) δ 7.30 (s, 1H), δ 7.01 (s, 1H), δ 6.44 (s, 1H), δ 6.17 (s, 2H), δ 4.35 (s, 2H), δ 3.34 (s, 2H0, δ 2.47 (s, 2H), δ 2.48 (s, 6H), δ 2.20 (m, 1H), δ 1.43 (m, 15H) ppm; $^{13}$C NMR (75 MHz, CDCl$_3$) δ 149.6, 148.1, 139.7, 136.2, 134.9, 134.3, 122.4, 84.9, 53.7, 50.2, 42.5, 31.1, 29.3, 28.9, 28.4, 28.2, 25.6, 19.1, 17.9, 17.2 ppm; HRMS (ESI) calcd for C$_{28}$H$_{43}$N$_7$O$_4$S (M+) 573.3097, found 573.3086, which was subsequently deprotected to give N-(2-(4-(5-(2-amino-1H-imidazol-4-yl)pentyl)-1H-1,2,3-triazol-1-yl)ethyl)-2,3,4,5,6-pentamethylbenzenesulfonamide hydrochloride (0.143 g, 76% yield). $^1$H NMR (400 MHz, CD$_3$OD) δ 8.11 (s, 1H), δ 6.42 (s, 1H), δ 4.48 (s, 2H), δ 3.34 (s, 2H), δ 2.65 (s, 2H), δ 2.40 (s, 8H), δ 2.12 (s, 9H), δ 1.58 (s, 4H), δ 1.19 (s, 2H) ppm; $^{13}$C NMR (100 MHz, CD$_3$OD) δ 159.9, 147.3, 139.6, 136.1, 134.8, 134.0, 127.8, 127.6, 108.6, 108.4, 54.1, 51.5, 41.8, 36.5, 28.2, 28.1, 27.7, 24.1, 23.7, 18.2, 16.8, 16.1 ppm; HRMS (ESI) calcd for C$_{23}$H$_{35}$N$_7$O$_2$S (M+) 473.2573, found 473.2565.

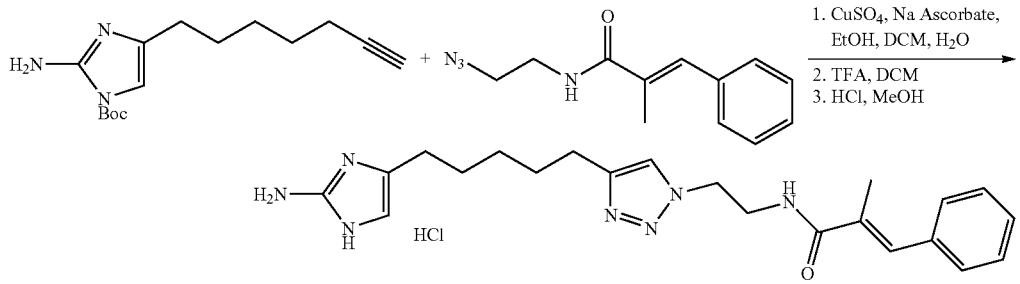

(E)-N-(2-(4-(5-(2-amino-1H-imidazol-4-yl)pentyl)-1H-1,2,3-triazol-1-yl)ethyl)-2-methyl-3-phenylacrylamide hydrochloride: tert-butyl 2-amino-4-(hept-6-ynyl)-1H-imidazole-1-carboxylate (0.1103 g, 0.397 mmol) was reacted with (E)-N-(2-azidoethyl)-2-methyl-3-phenylacrylamide (0.092 g, 0.397 mmol) following the general click procedure to give (E)-tert-butyl 2-amino-4-(5-(1-(2-(2-methyl-3-phenylacrylamido)ethyl)-1H-1,2,3-triazol-4-yl)pentyl)-1H-imidazole-1-carboxylate $^1$H NMR (300 MHz, CDCl$_3$) δ 7.28 (m, 7H), δ 6.94 (s, 2H), 6.06 (s, 2H), δ 4.46 (s, 2H), δ 3.79 (s, 2H), δ 2.61 (s, 2H), δ 2.27 (s, 2H0, δ 1.99 (s, 3H), δ 1.49 (bs, 11H), δ 1.18 (s, 4H) ppm; $^{13}$C NMR (75 MHz, CDCl$_3$) δ 192.4, 191.3, 170.4, 150.9, 140.2, 136.2, 134.8, 131.6, 129.6, 128.6, 128.1, 122.1, 95.8, 85.2, 74.3, 53.7, 52.6, 50.7, 49.4, 40.1, 29.9, 29.3, 28.9, 28.2, 25.6, 14.4 ppm; HRMS (ESI) calcd for C$_{27}$H$_{37}$N$_7$O$_3$ (M+) 507.2958, found 507.2942, which was subsequently deprotected to give (E)-N-(2-(4-(5-(2-amino-1H-imidazol-4-yl)pentyl)-1H-1,2,3-triazol-1-yl)ethyl)-2-methyl-3-phenylacrylamide hydrochloride (0.148 g, 84% yield). $^1$H NMR (400 MHz, CD$_3$OD) δ 8.78 (s, 1H), δ 7.33 (s, 4H), δ 7.26 (s, 1H), δ 7.19 (s, 1H), δ 6.42 (s, 1H), δ 4.78 (s, 2H), δ 3.84 (s, 2H), δ 2.87 (s, 2H), δ 2.44 (s, 2H), δ 1.99 (s, 3H), δ 1.76 (s, 2H), δ 1.59 (s, 2H), δ 1.42 (s, 2H) ppm; $^{13}$C NMR (100 MHz, CD$_3$OD) δ 174.7, 136.0, 134.4, 131.5, 129.3, 128.7, 128.3, 128.0, 127.6, 108.6, 94.6, 53.1, 39.2, 27.6, 27.9, 27.7, 27.6, 24.1, 23.8, 23.1, 14.3, 13.4 ppm; HRMS (ESI) calcd for $C_{22}H_{29}N_7O$ (M+) 407.2434, found 407.2429.

N-(2-(4-(5-(2-amino-1H-imidazol-4-yl)pentyl)-1H-1,2,3-triazol-1-yl)ethyl)heptadec-8-enamide hydrochloride: tert-butyl 2-amino-4-(hept-6-ynyl)-1H-imidazole-1-carboxylate

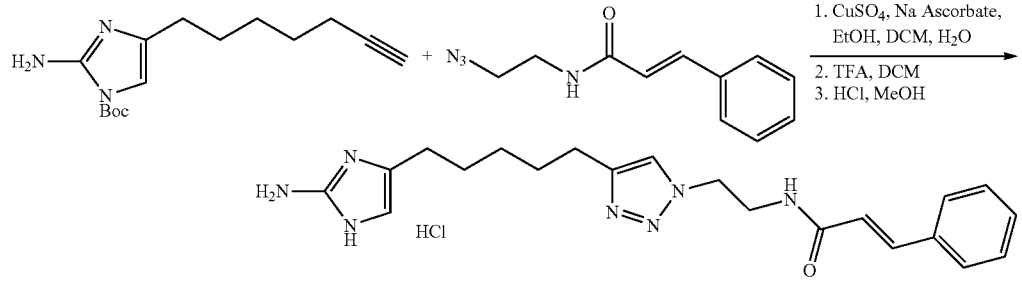

N-(2-(4-(5-(2-amino-1H-imidazol-4-yl)pentyl)-1H-1,2,3-triazol-1-yl)ethyl)cinnamamide hydrochloride: tert-butyl 2-amino-4-(hept-6-ynyl)-1H-imidazole-1-carboxylate (0.106 g, 0.384 mmol) was reacted with N-(2-azidoethyl)cinnamamide (0.083 g, 0.384 mmol) following the general click procedure to give (E)-tert-butyl 2-amino-4-(5-(1-(2-cinnamamidoethyl)-1H-1,2,3-triazol-4-yl)pentyl)-1H-imidazole-1-carboxylate $^1$H NMR (300 MHz, CDCl$_3$) δ 7.67 (s, 1H), δ 7.51 (d, 1H), δ 7.28 (m, 6H), δ 6.45 (t, 2H), δ 6.08 (s, 2H), δ 4.47 (s, 2H), δ 3.79 (s, 2H), δ 2.57 (s, 2H), δ 2.23 (s, 2H), δ 1.50 (bs, 13H), δ 1.28 (s, 2H) ppm; $^{13}$C NMR (75 MHz, CDCl$_3$) δ 166.9, 150.4, 149.5, 148.3, 141.2, 138.9, 134.9, 129.9, 128.9, 128.0, 122.1, 120.8, 106.5, 84.8, 53.7, 49.5, 39.9, 31.1, 29.3, 28.9, 28.3, 28.2, 25.6 ppm; HRMS (ESI) calcd for $C_{26}H_{35}N_7O_3$(M+) 493.2801, found 493.2800, which was subsequently deprotected to give N-(2-(4-(5-(2-amino-1H-imidazol-4-yl)pentyl)-1H-1,2,3-triazol-1-yl)ethyl)cinnamamide hydrochloride (0.097 g, 59% yield). $^1$H NMR (400 MHz, CD$_3$OD) δ 8.10 (s, 1H), δ 7.49 (s, 3H), δ 7.32 (s, 3H), δ 6.30 d, 1H), δ 6.39 (s, 1H), δ 4.66 (s, 2H), δ 3.83 (s, 2H), δ 2.73 (s, 2H), δ 2.40 (s, 2H), δ 1.57 (s, 2H), δ 1.55 (s, 2H), δ 1.36 (s, 2H) ppm; $^{13}$C NMR (100 MHz, CD$_3$OD) δ 167.8, 160.5, 150.2, 147.3, 141.1, 134.8, 130.7, 129.9, 128.8, 127.8, 127.6, 124.9, 23 9, 120.2, 108.5, 108.3, 53.1, 39.3, 36.5, 30.6, 28.4, 28.1, 27.6, 26.5, 24.2, 24.1, 23.7 ppm; HRMS (ESI) calcd for $C_{21}H_{27}N_7O$ (M+) 393.2277, found 393.2273.

(g, mmol) was reacted with N-(2-azidoethyl)octadec-9-enamide (g, mmol) following the general click procedure to give tert-butyl 2-amino-4-(5-(1-(2-heptadec-8-enamidoethyl)-1H-1,2,3-triazol-4-yl)pentyl)-1H-imidazole-1-carboxylate $^1$H NMR (300 MHz, CDCl$_3$) δ 7.26 (s, 1H), δ 6.81 (s, 1H), δ 6.42 (s, 2H), δ 5.88 (s, 1H), δ 5.27 (s, 2H), δ 4.38 (s, 2H), δ 3.65 (s, 2H), δ 2.60 (s, 2H), δ 2.09 (s, 2H), δ 1.53-1.01 (m, 35H), 0.79 (t, 3H) ppm; $^{13}$C NMR (75 MHz, CDCl$_3$) δ 174.2, 173.8, 148.3, 130.3, 130.1, 129.9, 129.8, 121.9, 85.1, 67.1, 49.5, 39.5, 39.1, 38.0, 37.7, 36.7, 36.6, 32.8, 32.3, 32.1, 31.7, 29.9, 29.8, 29.7, 29.5, 29.3, 29.2, 28.9, 28.7, 28.1, 28.0, 27.9, 27.4, 27.3, 27.3, 26.9, 25.9, 25.6, 25.3, 22.9, 22.8, 22.6, 14.3, 14.2 ppm; HRMS (ESI) calcd for $C_{35}H_{61}N_7O_3$ (M+) 627.4836, found 627.4823, which was subsequently deprotected to give N-(2-(4-(5-(2-amino-1H-imidazol-4-yl)pentyl)-1H-1,2,3-triazol-1-yl)ethyl)heptadec-8-enamide hydrochloride (0.128 g, 66% yield). $^1$H NMR (400 MHz, CD$_3$OD) δ 8.36 (s, 1H), δ 6.96 (s, 1H), δ 6.45 (s, 1H), δ 6.09 (s, 1H), δ 4.58 (s, 2H), δ 3.58 (s, 2H), δ 2.75 (s, 2H), δ 2.10 (s, 2H), δ 1.96 (s, 4H), δ 1.69 (s, 2H), δ 1.41 (m, 4H), 1.23 (s, 24H), δ 0.84 (s, 3H) ppm; $^{13}$C NMR (100 MHz, CD$_3$OD) δ 175.5, 158.8, 155.7, 147.3, 129.7, 129.6, 127.6, 108.5, 94.6, 76.7, 51.3, 50.4, 48.6, 48.4, 48.2, 47.9, 47.8, 47.5, 47.3, 38.9, 37.5, 36.6, 45.9, 45.8, 33.9, 32.6, 31.9, 31.5, 29.8, 29.5, 29.4, 29.3, 29.2, 29.1, 28.2, 27.8, 27.0, 25.8, 24.9, 24.2, 23.8, 22.5, 13.5, 13.3 ppm; HRMS (ESI) calcd for $C_{30}H_{53}N_7O$ (M+) 527.4312, found 527.4298.

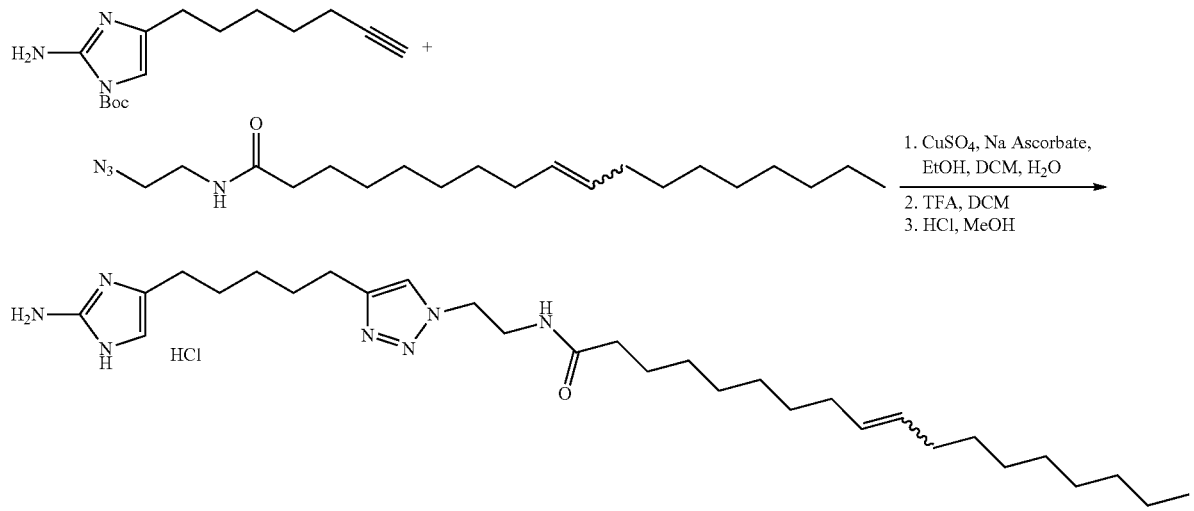

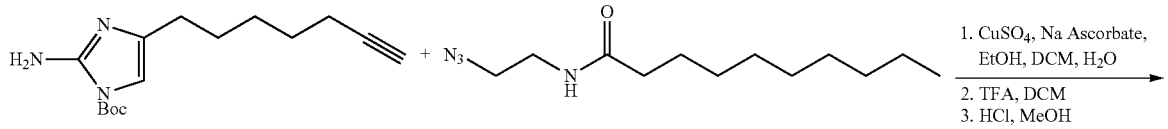

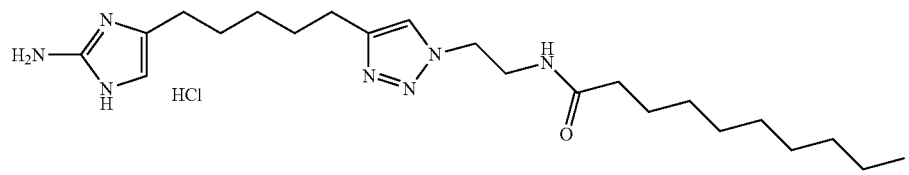

N-(2-(4-(5-(2-amino-1H-imidazol-4-yl)pentyl)-1H-1,2,3-triazol-1-yl)ethyl)decanamide hydrochloride: tert-butyl 2-amino-4-(hept-6-ynyl)-1H-imidazole-1-carboxylate (0.114 g, 0.412 mmol) was reacted with N-(2-azidoethyl)decanamide (0.099 g, 0.412 mmol) following the general click procedure to give tert-butyl 2-amino-4-(5-(1-(2-decanamidoethyl)-1H-1,2,3-triazol-4-yl)pentyl)-1H-imidazole-1-carboxylate $^1$H NMR (400 MHz, CDCl$_3$) δ 7.23 (s, 1H), δ 6.57 (s, 1H), δ 6.43 (s, 1H), δ 6.09 (s, 2H), δ 4.38 (s, 2H), δ 3.67 (s, 2H), δ 2.61 (t, 2H), δ 2.08 (s, 2H), 2.08 (t, 2H), δ 1.42 (m, 15H), δ 1.17 (m, 14H), δ 0.79 (t, 3H) ppm; $^{13}$C NMR (100 MHz, CDCl$_3$) δ 174.2, 149.7, 148.4, 138.8, 121.9, 106.6, 84.9, 49.5, 39.5, 36.7, 32.1, 31.3, 30.6, 29.9, 29.7, 29.6, 29.5, 29.5, 29.3, 29.0, 28.3, 28.2, 25.9, 25.6, 25.5, 22.9, 14.3 ppm; HRMS (ESI) calcd for C$_{27}$H$_{47}$N$_7$O$_3$(M+) 517.3740, found 517.3736, which was subsequently deprotected to give N-(2-(4-(5-(2-amino-1H-imidazol-4-yl)pentyl)-1H-1,2,3-triazol-1-yl)ethyl)decanamide hydrochloride (0.137 g, 73% yield). $^1$H NMR (300 MHz, CD$_3$OD) δ 8.55 (s, 1H), δ 6.53 (s, 1H), 4.72 (s, 2H), δ 3.75 (s, 2H), 2.89 (s, 2H), δ 2.54 (t, 2H), δ 2.16 (t, 2H), δ 1.81 (s, 2H), δ 1.69 (s, 2H), δ 1.49 (m, 4H), δ 1.28 (s, 12H), δ 0.89 (t, 3H) ppm; $^{13}$C NMR (75 MHz, CD$_3$OD) δ 175.7, 147.3, 128.5, 127.6, 125.1, 120.8, 108.6, 108.4, 105.6, 63.1, 59.3, 52.5, 48.6, 48.3, 48.1, 47.9, 47.7, 47.5, 57.3, 38.7, 336.6, 35.8, 36.6, 35.8, 31.8, 30.6, 29.4, 29.3, 29.3, 29.2, 28.0, 27.8, 27.7, 25.8, 24.1, 23.9, 23.3, 22.6 ppm; HRMS (ESI) calcd for C$_{22}$H$_{39}$N$_7$O (M+) 417.3216, found 417.3209.

N-(2-(4-(5-(2-amino-1H-imidazol-4-yl)pentyl)-1H-1,2,3-triazol-1-yl)ethyl)dodecanamide hydrochloride: tert-butyl 2-amino-4-(hept-6-ynyl)-1H-imidazole-1-carboxylate (0.107 g, 0.387 mmol) was reacted with N-(2-azidoethyl)dodecanamide (0.104 g, 0.387 mmol) following the general click procedure to give tert-butyl 2-amino-4-(5-(1-(2-dodecanamidoethyl)-1H-1,2,3-triazol-4-yl)pentyl)-1H-imidazole-1-carboxylate $^1$H NMR (300 MHz, CDCl$_3$) δ 7.36 (s, 1H), δ 6.94 (s, 1H), δ 6.49 (s, 1H), δ 6.23 (s, 2H), δ 4.46 (t, 2H), δ 3.74 (q, 2H), δ 2.68 (t, 2H0, δ 2.34 (t, 2H), δ 2.16 (t, 2H), δ 1.54 (m, 13H), δ 1.47 (m, 2H), δ 1.24 (m, 18H), δ 0.87 (t, 3H) ppm; $^{13}$C NMR (75 MHz, CDCl$_3$) δ 174.3, 150.4, 149.5, 148.3, 138.5, 121.9, 106.5, 84.9, 49.5, 39.5, 36.6, 34.1, 32.1, 29.8, 29.8, 29.7, 29.6, 29.5, 29.3, 28.9, 28.2, 28.1, 29.0, 26.9. 25.6, 22.9, 14.3 ppm; HRMS (ESI) calcd for C$_{29}$H$_{51}$N$_7$O$_3$ (M+) 545.4053, found 545.4053, which was subsequently deprotected to give N-(2-(4-(5-(2-amino-1H-imidazol-4-yl)pentyl)-1H-1,2,3-triazol-1-yl)ethyl)dodecanamide hydrochloride (0.155 g, 83% yield). $^1$H NMR (400 MHz, CD$_3$OD) δ 8.31 (s, 1H), δ 6.49 (s, 1H), δ 4.63 (s, 2H), δ 3.97 (s, 2H), δ 2.81 (s, 2H), δ 2.51 (t, 2H), δ 2.14 (t, 2H), δ 1.76 (s, 2H), δ 1.67 (s, 2H), δ 1.51 (s, 2H), δ 1.44 (s, 2H), δ 1.26 (bs, 16H), δ 0.71 (s, 3H) ppm; $^{13}$C NMR (100 MHz, CD$_3$OD) δ 175.6, 159.4, 147.3, 127.6, 108.5, 51.3, 48.6, 38.8, 35.8, 31.9, 29.6, 29.5, 29.4, 29.3, 29.2, 28.2, 28.1, 27.7, 24.8, 24.2, 23.9, 22.6, 22.5, 13.4, 13.3 ppm; HRMS (ESI) calcd for C$_{24}$H$_{43}$N$_7$O (M+) 445.3429, found 445.3524.

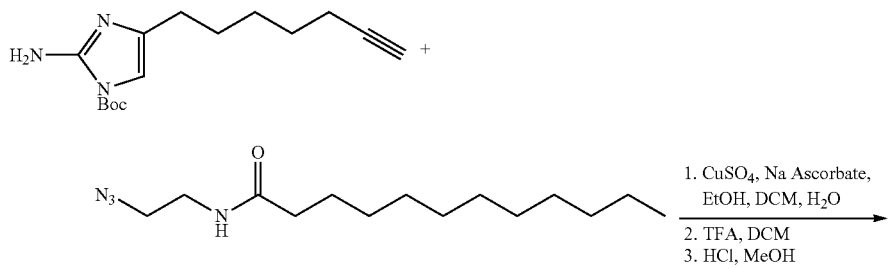

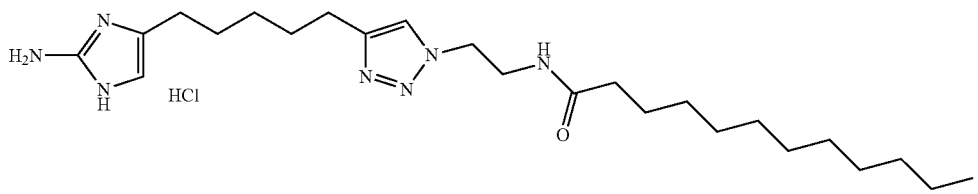

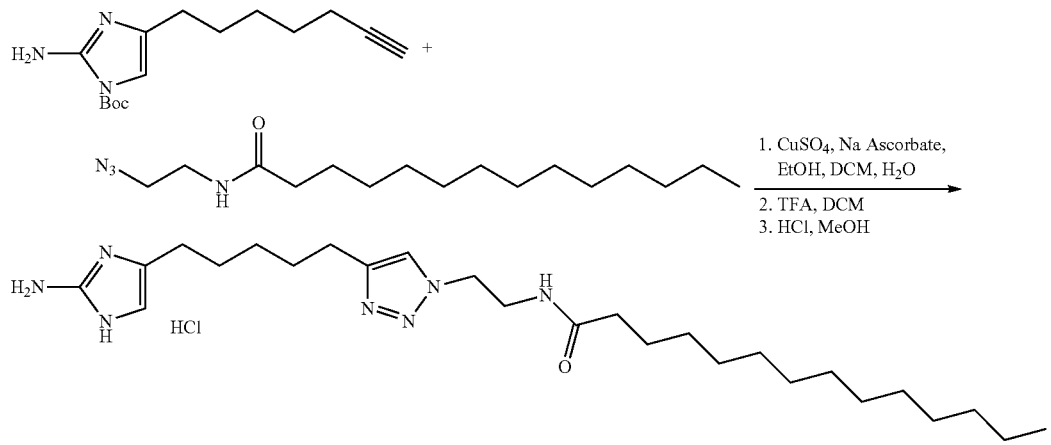

N-(2-(4-(5-(2-amino-1H-imidazol-4-yl)pentyl)-1H-1,2,3-triazol-1-yl)ethyl)tetradecanamide hydrochloride: tert-butyl 2-amino-4-(hept-6-ynyl)-1H-imidazole-1-carboxylate (0.111 g, 0.401 mmol) was reacted with N-(2-azidoethyl)tetradecanamide (0.130 g, 0.401 mmol) following the general click procedure to give tert-butyl 2-amino-4-(5-(1-(2-tetradecanamidoethyl)-1H-1,2,3-triazol-4-yl)pentyl)-1H-imidazole-1-carboxylate $^1$H NMR (300 MHz, CDCl$_3$) δ 7.26 (s, 1H), δ 6.85 (s, 1H), δ 6.42 (s, 1H), δ 6.05 (s, 1H), δ 4.38 (s, 2H), δ 3.66 (s, 2H), δ 2.60 (s, 2H), δ 2.11 (s, 2H), δ 2.08 (t, 2H), δ 1.41 (m, 13H), δ 1.32 (s, 2H), δ 1.17 (s, 18H), δ 0.77 (t, 3H) ppm; $^{13}$C NMR (75 MHz, CDCl$_3$) δ 202.9, 174.3, 149.6, 148.3, 121.9, 100.1, 84.8, 49.5, 42.3, 39.5, 36.7, 32.1, 29.9, 29.8, 29.7, 29.6, 29.5, 29.5, 29.3, 28.9, 28.1, 25.9, 25.6, 22.9, 14.3 ppm; HRMS (ESI) calcd for C$_{31}$H$_{55}$N$_7$O$_3$ (M+) 573.4366, found 573.4365, which was subsequently deprotected to give N-(2-(4-(5-(2-amino-1H-imidazol-4-yl)pentyl)-1H-1,2,3-triazol-1-yl)ethyl)tetradecanamide hydrochloride (0.118 g, 87% yield). $^1$H NMR (400 MHz, CD$_3$OD) δ 8.51 (s, 1H), δ 6.53 (s, 1H), δ 4.71 (s, 2H), δ 3.75 (s, 2H), δ 2.89 (s, 2H), δ 2.54 (t, 2H), δ 2.17 (t, 2H), δ 1.80 (s, 2H), δ 1.69 (s, 2H), δ 1.54 (s, 2H), δ 1.48 (s, 2H), δ 1.28 (s, 20H), 0.88 (t, 3H) ppm; $^{13}$C NMR (100 MHz, CD$_3$OD) δ 175.6, 161.8, 147.2, 127.6, 127.4, 108.5, 52.3, 38.8, 36.6, 35.8, 31.9, 30.6, 29.7, 29.6, 29.5, 29.4, 29.2, 28.0, 27.9, 27.7, 25.8, 24.1, 23.6, 23.4, 22.6, 13.4 ppm; HRMS (ESI) calcd for C$_{26}$H$_{47}$N$_7$O (M+) 473.3842, found 473.3834.

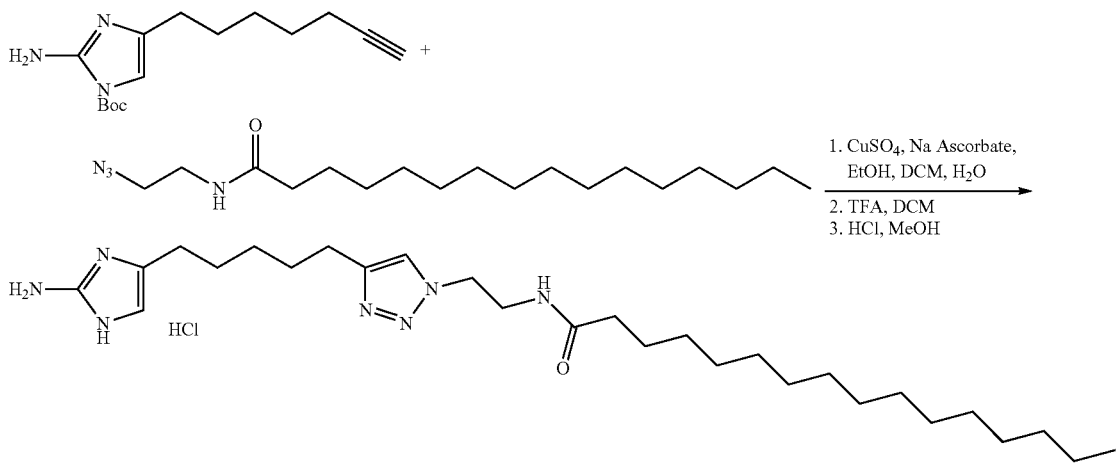

N-(2-(4-(5-(2-amino-1H-imidazol-4-yl)pentyl)-1H-1,2,3-triazol-1-yl)ethyl)palmitamide hydrochloride: tert-butyl 2-amino-4-(hept-6-ynyl)-1H-imidazole-1-carboxylate (0.087 g, 0.313 mmol) was reacted with N-(2-azidoethyl)palmitamide (0.102 g, 0.313 mmol) following the general click procedure to give tert-butyl 2-amino-4-(5-(1-(2-palmitamidoethyl)-1H-1,2,3-triazol-4-yl)pentyl)-1H-imidazole-1-carboxylate $^1$H NMR (300 MHz, CDCl$_3$) δ 7.29 (s, 1H), δ 6.78 (t, 1H), δ 6.41 (s, 1H), δ 6.19 (s, 2H), δ 4.39 (t, 2H), δ 3.67 (q, 2H), δ 2.61 (t, 2H), δ 2.12 (t, 2H), δ 2.07 (t, 2H), δ 1.42 (m, 13H), δ 1.42 (m, 2H), δ 1.32 (m, 22H), 0.81 (t, 3H) ppm; $^{13}$C NMR (75 MHz, CDCl$_3$) δ 176.8, 174.3, 173.9, 149.5, 148.3, 121.9, 106.4, 85.0, 67.2, 51.1, 49.5, 39.5, 39.1, 38.1, 36.8, 36.7, 32.1, 29.9, 29.8, 29.7, 29.6, 29.5, 29.3, 28.9, 28.3, 28.2, 27.9, 25.9, 25.6, 22.9, 14.3 ppm; HRMS (ESI) calcd for C$_{33}$H$_{59}$N$_7$O$_3$(M+) 601.4679, found 601.4671, which was subsequently deprotected to give N-(2-(4-(5-(2-amino-1H-imidazol-4-yl)pentyl)-1H-1,2,3-triazol-1-yl)ethyl)palmitamide hydrochloride (0.155 g, 92% yield). $^1$H NMR (300 MHz, CD$_3$OD) δ 8.59 (s, 1H), δ 6.53 (s, 1H), δ 4.72 (s, 2H), δ 3.75 (S, 2H), δ 2.90 (s, 2H), δ 2.54 (s, 2H), δ 2.16 (t, 2H), δ 1.80 (s, 2H), δ 1.69 (s, 2H), δ 1.51 (s, 4H), δ 1.28 (bs, 24H), δ 0.71 (t, 3H) ppm; $^{13}$C NMR (75 MHz, CD$_3$OD) δ 175.7, 147.2, 145.6, 128.4, 127.6, 108.6, 67.2, 52.7, 37.4, 36.5, 35.8, 31.9, 29.7, 29.5, 29.4, 29.2, 28.0, 27.9, 27.8, 27.7, 25.8, 24.1, 23.6, 23.2, 22.6 ppm; HRMS (ESI) calcd for C$_{28}$H$_{51}$N$_7$O (M+) 501.4155, found 501.4143.

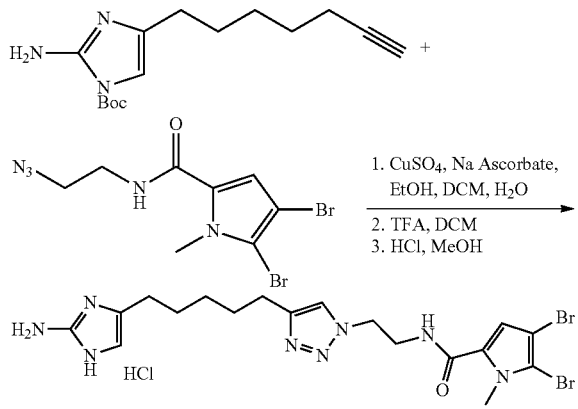

N-(2-(4-(5-(2-amino-1H-imidazol-4-yl)pentyl)-1H-1,2,3-triazol-1-yl)ethyl)-4,5-dibromo-1-methyl-1H-pyrrole-2-carboxamide hydrochloride: tert-butyl 2-amino-4-(hept-6-ynyl)-1H-imidazole-1-carboxylate (0.116 g, 0.417 mmol) was reacted with N-(2-azidoethyl)-4,5-dibromo-1-methyl-1H-pyrrole-2-carboxamide (0.145 g, 0.417 mmol) following the general click procedure to give tert-butyl 2-amino-4-(5-(1-(2-(4,5-dibromo-1-methyl-1H-pyrrole-2-carboxamido)ethyl)-1H-1,2,3-triazol-4-yl)pentyl)-1H-imidazole-1-carboxylate $^1$H NMR (300 MHz, CDCl$_3$) δ 7.76 (s, 1H), δ 7.32 (s, 1H), δ 6.81 (s, 1H), δ 6.49 (s, 1H), δ 6.17 (s, 2H), δ 4.52 (s, 2H), δ 3.94 (s, 3H), δ 3.84 (s, 2H), δ 2.65 (t, 2H), δ 2.30 (m, 2H), δ 1.58 (m, 13H), δ 1.35 (m, 2H); $^{13}$C NMR (75 MHz, CDCl$_3$) δ 161.2, 149.6, 148.2, 138.8, 127.4, 122.2, 114.3, 111.9, 106.5, 98.2, 84.5, 49.5, 39.7, 35.9, 29.3, 28.9, 28.2, 28.0, 27.7, 25.6 ppm; HRMS (ESI) calcd for C$_{23}$H$_{32}$N$_8$O$_3$ (M+) 626.0964, found 626.0960, which was subsequently deprotected to give N-(2-(4-(5-(2-amino-1H-imidazol-4-yl)pentyl)-1H-1,2,3-triazol-1-yl)ethyl)-4,5-dibromo-1-methyl-1H-pyrrole-2-carboxamide hydrochloride (0.151 g, 64% yield). $^1$H NMR (400 MHz, CD$_3$OD) δ 8.24 (s, 1H), δ 6.86 (s, 1H), δ 6.56 (s, 1H), δ 4.71 (s, 2H), δ 3.81 (s, 5H), 2.78 (s, 2H), δ 2.44 (t, 2H), δ 1.69 (s, 2H), δ 1.59 (s, 2H), δ 1.37 (s, 2H) ppm; $^{13}$C NMR (100 MHz, CD$_3$OD) δ 161.4, 150.2, 159.8, 159.4, 147.3, 127.6, 127.3, 114.9, 111.6, 108.4, 97.9, 51.3, 39.0, 35.2, 28.3, 28.0, 27.6, 24.2, 23.8 ppm; HRMS (ESI) calcd for C$_{18}$H$_{24}$Br$_2$N$_8$O (M+) 526.0439, found 526.0425.

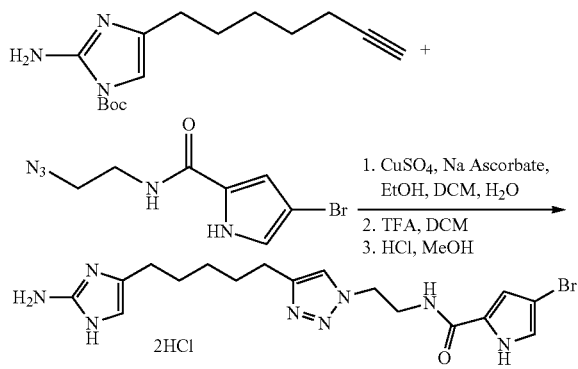

N-(2-(4-(5-(2-amino-1H-imidazol-4-yl)pentyl)-1H-1,2,3-triazol-1-yl)ethyl)-4-bromo-1H-pyrrole-2-carboxamide hydrochloride: tert-butyl 2-amino-4-(hept-6-ynyl)-1H-imidazole-1-carboxylate (0.104 g, 0.375 mmol) was reacted with N-(2-azidoethyl)-4-bromo-1H-pyrrole-2-carboxamide (0.131 g, 0.375 mmol) following the general click procedure to give tert-butyl 2-amino-4-(5-(1-(2-(4-bromo-1H-pyrrole-2-carboxamido)ethyl)-1H-1,2,3-triazol-4-yl)pentyl)-1H-imidazole-1-carboxylate $^1$H NMR (300 MHz, CDCl$_3$) δ 11.44 (s, 1H), δ 7.84 (s, 1H), δ 7.28 (s, 1H), δ 6.84 (s, 1H), δ 6.74 (s, 1H), δ 6.46 (s, 1H), δ 4.89 (s, 2H), δ 3.82 (s, 2H), δ 2.57 (s, 2H), δ 2.28 (s, 2H), δ 1.55 (m, 13H), δ 1.29 (m, 2H) ppm; $^{13}$C NMR (75 MHz, CDCl$_3$) δ 186.8, 161.4, 150.7, 149.3, 148.2, 137.6, 126.3, 122.5, 122.1, 113.1, 100.4, 96.9, 85.4, 49.6, 29.1, 28.7, 28.2, 27.7, 25.5 ppm; HRMS (ESI) calcd for C$_{22}$H$_{31}$BrN$_8$O$_3$ (M+) 534.1703, found 534.1705, which was subsequently deprotected to give N-(2-(4-(5-(2-amino-1H-imidazol-4-yl)pentyl)-1H-1,2,3-triazol-1-yl)ethyl)-4-bromo-1H-pyrrole-2-carboxamide hydrochloride (0.129 g, 73% yield). $^1$H NMR (400 MHz, CD$_3$OD) δ 8.42 (s, 1H), δ 6.93 (s, 1H), δ 6.82 (s, 1H), δ 6.47 (s, 1H), δ 4.76 (s, 2H), δ 3.87 (s, 2H), δ 2.79 (s, 2H), δ 2.45 (s, 2H), δ 1.69 (s, 2H), δ 1.60 (s, 2H), δ 1.37 (s, 2H) ppm; $^{13}$C NMR (100 MHz, CD$_3$OD) δ 161.4, 159.5, 159.1, 147.3, 147.2, 127.6, 125.8, 122.3, 122.1, 112.8, 108.6, 108.5, 96.4, 51.9, 38.9, 28.0, 27.9, 27.6, 24.1, 23.6 ppm; HRMS (ESI) calcd for C$_{17}$H$_{23}$BrN$_8$O (M+) 434.1178, found 434.1171.

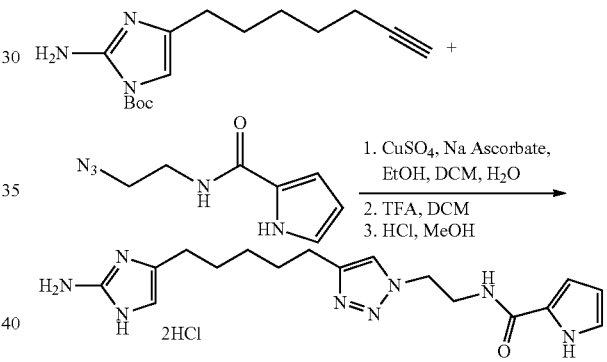

N-(2-(4-(5-(2-amino-1H-imidazol-4-yl)pentyl)-1H-1,2,3-triazol-1-yl)ethyl)-1H-pyrrole-2-carboxamide hydrochloride: tert-butyl 2-amino-4-(hept-6-ynyl)-1H-imidazole-1-carboxylate (0.097 g, 0.349 mmol) was reacted with N-(2-azidoethyl)-1H-pyrrole-2-carboxamide (0.063 g, 0.349 mmol) following the general click procedure to give tert-butyl 4-(5-(1-(2-(1H-pyrrole-2-carboxamido)ethyl)-1H-1,2,3-triazol-4-yl)pentyl)-2-amino-1H-imidazole-1-carboxylate $^1$H NMR (300 MHz, CDCl$_3$) δ 8.18 (s, 1H), δ 7.36 (d, 2H), δ 7.24 (s, 1H), δ 6.84 (t, 1H), δ 6.43 (s, 1H), 6.04 (s, 2H), 4.49 (s, 2H), δ 3.89 (s, 2H), δ 2.53 (s, 2H), δ 2.09 (s, 2H), δ 1.44 (m, 13H), δ 1.24 (s, 2H) ppm; $^{13}$C NMR (75 MHz, CDCl$_3$) δ 165.9, 164.8, 164.6, 161.5, 137.5, 122.3, 111.0, 110.7, 107.5, 107.1, 106.8, 85.1, 49.4, 40.5, 29.3, 28.9, 28.2, 25.5 ppm; HRMS (ESI) calcd for C$_{22}$H$_{32}$N$_8$O$_3$ (M+) 456.2597, found 456.2590, which was subsequently deprotected to give N-(2-(4-(5-(2-amino-1H-imidazol-4-yl)pentyl)-1H-1,2,3-triazol-1-yl)ethyl)-1H-pyrrole-2-carboxamide hydrochloride (0.129 g, 94% yield). $^1$H NMR (400 MHz, CD$_3$OD) δ 8.65 (s, 1H), δ 7.41 (s, 2H), δ 7.17 (s, 1H), δ 6.50 (s, 1H), δ 4.74 (s, 2H), δ 3.98 (s, 2H), δ 2.88 (s, 2H), δ 2.49 (s, 2H), δ 1.78 (m, 4H), δ 1.44 (s, 2H) ppm; $^{13}$C NMR (100 MHz, CD$_3$OD) δ 166.3, 164.5, 162.0, 161.9, 137.4, 110.6, 110.3, 110.2, 108.5, 17.1, 106.8, 59.3, 52.4, 39.5, 36.5, 27.9, 27.8, 27.6, 24.1, 23.5, 23.3 ppm; HRMS (ESI) calcd for C$_{17}$H$_{24}$N$_8$O (M+) 356.2073, found 356.2080.

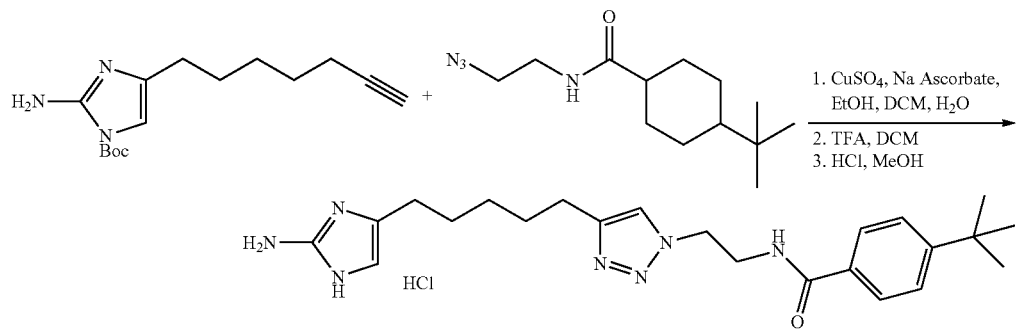

N-(2-(4-(5-(2-amino-1H-imidazol-4-yl)pentyl)-1H-1,2,3-triazol-1-yl)ethyl)-4-tert-butylbenzamide hydrochloride: tert-butyl 2-amino-4-(hept-6-ynyl)-1H-imidazole-1-carboxylate (0.070 g, 0.253 mmol) was reacted with N-(2-azidoethyl)-4-tert-butylbenzamide (0.062 g, 0.253 mmol) following the general click procedure to give tert-butyl 2-amino-4-(5-(1-(2-(4-tert-butylbenzamido)ethyl)-1H-1,2,3-triazol-4-yl)pentyl)-1H-imidazole-1-carboxylate $^1$H NMR (300 MHz, CDCl$_3$) δ 7.71 (d, 2H), δ 7.64 (t, 1H), δ 7.36 (d, 2H), δ 7.27 (s, 1H), δ 6.42 (s, 1H), δ 5.99 (s, 2H), δ 4.51 (t, 2H), δ 3.88 (q, 2H), δ 2.58 (t, 2H), δ 2.22 (t, 2H), δ 1.52 (m, 13H), δ 1.21 (m, 11H) ppm; $^{13}$C NMR (75 MHz, CDCl$_3$) δ 168.2, 155.3, 150.4, 149.6, 148.3, 138.9, 131.2, 127.3, 125.6, 122.2, 106.5, 84.8, 49.4, 40.2, 35.1, 31.3, 31.1, 29.3, 28.9, 28.3, 28.2, 28.1, 25.6 ppm; HRMS (ESI) calcd for C$_{28}$H$_{41}$N$_7$O$_3$ (M+) 523.3271, found 523.3270, which was subsequently deprotected to give N-(2-(4-(5-(2-amino-1H-imidazol-4-yl)pentyl)-1H-1,2,3-triazol-1-yl)ethyl)-4-tert-butylbenzamide hydrochloride (0.105 g, 90% yield). $^1$H NMR (400 MHz, CD$_3$OD) δ 8.48 (s, 1H), δ 7.76 (d, 2H), δ 7.48 (d, 2H), δ 6.50 (s, 1H), δ 4.84 (s, 2H), δ 3.95 (s, 2H), δ 2.85 (s, 2H), δ 2.46 (t, 2H), δ 1.73 (s, 2H), δ 1.57 (m, 2H), δ 1.39 (s, 2H), δ 1.31 (s, 9H) ppm; $^{13}$C NMR (100 MHz, CD$_3$OD) δ 169.2, 155.6, 147.3, 130.8, 129.9, 127.6, 127.2, 127.1, 126.7, 125.4, 125.3, 119.5, 108.6, 108.5, 52.3, 39.4, 34.6, 30.4, 27.9, 27.8, 27.6, 24.1, 23.2, 22.2 ppm; HRMS (ESI) calcd for C$_{23}$H$_{33}$N$_7$O (M+) 423.2747, found 423.2741.

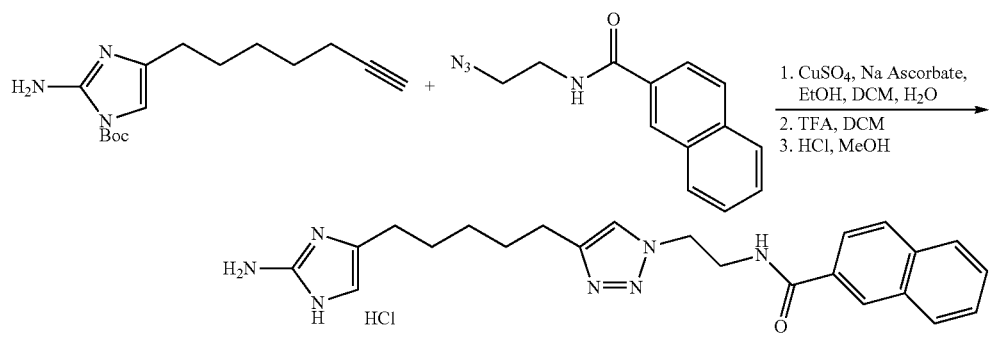

N-(2-(4-(5-(2-amino-1H-imidazol-4-yl)pentyl)-1H-1,2,3-triazol-1-yl)ethyl)-2-naphthamide hydrochloride: tert-butyl 2-amino-4-(hept-6-ynyl)-1H-imidazole-1-carboxylate (0.095 g, 0.344 mmol) was reacted with N-(2-azidoethyl)-2-naphthamide (0.083 g, 0.344 mmol) following the general click procedure to give tert-butyl 4-(5-(1-(2-(2-naphthamido)ethyl)-1H-1,2,3-triazol-4-yl)pentyl)-2-amino-1H-imidazole-1-carboxylate $^1$H NMR (300 MHz, CDCl$_3$) δ 8.24 (s, 1H), δ 8.01 (s, 1H), δ 7.72 (m, 4H), δ 7.39 (m, 2H), δ 7.26 (s, 1H), δ 6.33 (s, 1H), δ 6.04 (s, 2H), δ 4.51 (s, 2H), δ 3.88 (s, 2H0, δ 2.48 (t, 2H), δ 2.12 (s, 2H), δ 1.47 (m, 13H), δ 1.17 (s, 2H) ppm; $^{13}$C NMR (75 MHz, CDCl$_3$) δ 168.5, 150.4, 149.5, 148.3, 138.6, 134.9, 132.7, 131.4, 129.2, 128.5, 128.1, 127.9, 126.8, 124.0, 122.3, 106.5, 84.9, 49.4, 40.4, 29.9, 29.2, 28.9, 28.6, 28.2, 27.9, 28.6, 27.9, 27.8, 25.6 ppm; HRMS (ESI) calcd for C$_{28}$H$_{35}$N$_7$O$_3$ (M+) 517.2801, found 517.2792, which was subsequently deprotected to give N-(2-(4-(5-(2-amino-1H-imidazol-4-yl)pentyl)-1H-1,2,3-triazol-1-yl)ethyl)-2-naphthamide hydrochloride (0.140 g, 90% yield). $^1$H NMR (300 MHz, CD$_3$OD) δ ppm; $^{13}$C NMR (75 MHz, CD$_3$OD) δ ppm; HRMS (ESI) calcd for C$_{23}$H$_{27}$N$_7$O (M+) 417.2277, found 417.2274.

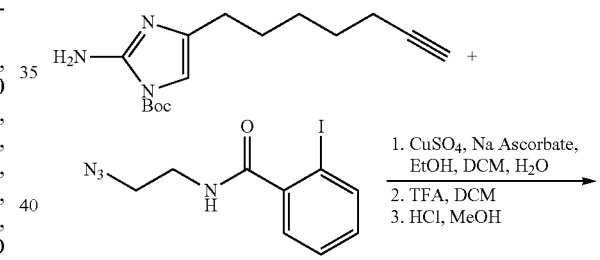

-continued

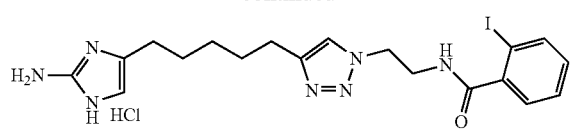

N-(2-(4-(5-(2-amino-4H-imidazol-4-yl)pentyl)-1H-1,2,3-triazol-1-yl)ethyl)-2-iodobenzamide hydrochloride: tert-butyl 2-amino-4-(hept-6-ynyl)-1H-imidazole-1-carboxylate (0.083 g, 0.299 mmol) was reacted with N-(2-azidoethyl)-2-iodobenzamide (0.095 g, 0.299 mmol) following the general click procedure to give tert-butyl 2-amino-4-(5-(1-(2-(2-iodobenzamido)ethyl)-1H-1,2,3-triazol-4-yl)pentyl)-1H-imidazole-1-carboxylate $^1$H NMR (300 MHz, CDCl$_3$) δ 7.74 (d, 2H), δ 7.57 (t, 1H), δ 7.36 (s, 1H), δ 7.22 (s, 2H0, δ 6.97 (m, 1H0, δ 6.39 (s, 1H), δ 5.97 (s, 2H), δ 4.48 (t, 2H0, δ 3.85 (m, 2H0, δ 2.44 (t, 2H), δ 2.18 (t, 2H), δ 1.45 (m, 13H, δ 1.18 (m, 2H) ppm; $^{13}$C NMR (75 MHz, CDCl$_3$) δ 170.3, 150.4, 149.5, 148.2, 141.8, 139.9, 138.7, 131.3, 128.4, 128.3, 122.3, 106.5, 92.8, 84.9, 49.2, 40.5, 29.2, 28.9, 28.3, 28.2, 28.0, 25.5 ppm; HRMS (ESI) calcd for C$_{24}$H$_{32}$N$_7$O$_3$(M+) 593.1611, found 593.1603, which was subsequently deprotected to give N-(2-(4-(5-(2-amino-1H-imidazol-4-yl)pentyl)-1H-1,2,3-triazol-1-yl)ethyl)-2-iodobenzamide hydrochloride (0.125 g, 79% yield). $^1$H NMR (400 MHz, CD$_3$OD) δ 8.35 (s, 1H), δ 7.88*d, 1H), δ 7.45 (t, 1H), δ 7.34 (d, 1H), δ 7.15 (t, 1H), δ 6.47 (s, 1H), δ 4.78 (s, 2H), δ 3.99 (s, 2H), δ 2.83 (s, 2H), δ 2.44 (t, 2H), δ 1.76 (s, 2H), δ 1.64 (s, 2H), δ 1.29 (s, 2H) ppm; $^{13}$C NMR (75 MHz, CD$_3$OD) δ 171.6, 159.2, 147.3, 142.1, 139.8, 131.2, 128.2, 127.7, 124.4, 92.1, 52.2, 40.8, 39.4, 31.2, 28.3, 28.1, 27.7, 24.1, 20.9, 15.9, 10.7 ppm; HRMS (ESI) calcd for C$_{19}$H$_{24}$IN$_7$O (M+) 493.1087, found 493.1085.

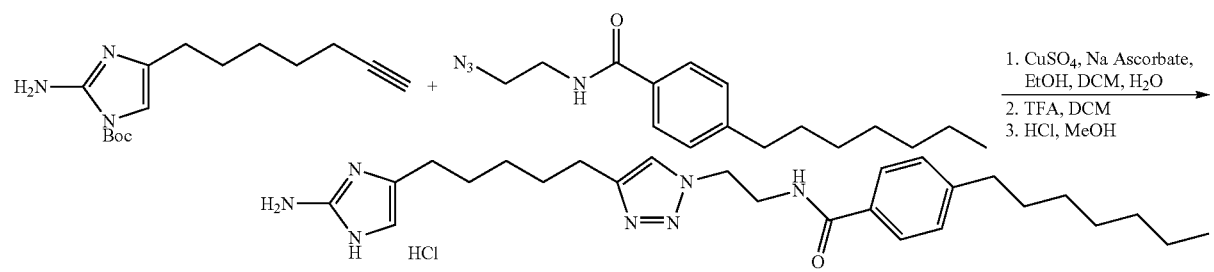

N-(2-(4-(5-(2-amino-1H-imidazol-4-yl)pentyl)-1H-1,2,3-triazol-1-yl)ethyl)-4-heptylbenzamide hydrochloride: tert-butyl 2-amino-4-(hept-6-ynyl)-1H-imidazole-1-carboxylate (0.125 g, 0.449 mmol) was reacted with N-(2-azidoethyl)-4-heptylbenzamide (0.129 g, 0.449 mmol) following the general click procedure to give tert-butyl 2-amino-4-(5-(1-(2-(4-heptylbenzamido)ethyl)-1H-1,2,3-triazol-4-yl)pentyl)-1H-imidazole-1-carboxylate $^1$H NMR (400 MHz, CDCl$_3$) δ 7.78 (s, 1H), δ 7.65 (d, 2H), δ 7.27 (s, 1H), δ 7.09 (d, 2H), δ 6.39 (s, 1H), δ 6.22 (s, 2H), δ 4.47 (s, 2H), δ 3.81 (s, 2H), δ 3.96 (s, 4H), δ 2.20 (s, 2H), δ 2.05 (s, 2H), 1.48 (m, 12H), δ 1.17 (m, 8H), δ 0.77 (t, 3H); $^{13}$C NMR (100 MHz, CDCl$_3$) δ 168.3, 149.6, 148.2, 147.1, 138.6, 131.5, 128.6, 127.4, 122.1, 106.4, 84.8, 67.1, 49.4, 40.2, 37.9, 36.9, 31.9, 31.3, 31.1, 29.8, 28.4, 29.3, 28.9, 28.3, 28.1, 28.0, 25.5, 22.8, 14.3 ppm; HRMS (PSI) calcd for C$_{31}$H$_{47}$N$_7$O$_3$(M+) 565.3704, found 656.3737, which was subsequently deprotected to give N-(2-(4-(5-(2-amino-1H-imidazol-4-yl)pentyl)-1H-1,2,3-triazol-1-yl)ethyl)-4-heptylbenzamide hydrochloride (0.194 g, 86% yield). $^1$H NMR (300 MHz, CD$_3$OD) δ 8.25 (s, 1H), δ 7.71 (d, 2H), δ 7.24 (d, 2H), 6.45 (s, 1H), δ 4.74 (s, 2H), 3.90 (s, 2H), δ 2.63 (s, 2H), δ 2.61 (t, 2H), δ 2.41 (S, 2H), δ 1.58 (m, 6H), δ 1.26 (m, 10H), δ 0.85 (t, 3H) ppm; $^{13}$C NMR (100 MHz, CD$_3$OD) δ 169.2, 150.2, 147.4, 131.2, 128.5, 127.6, 127.3, 108.4, 51.4, 39.6, 36.5, 35.6, 31.8, 331.3, 29.1, 29.1, 28.3, 28.0, 27.7, 24.1, 22.6, 13.4, 13.3 ppm; HRMS (ESI) calcd for C$_{26}$H$_{39}$N$_7$O (M+) 465.3216, found 465.3207.

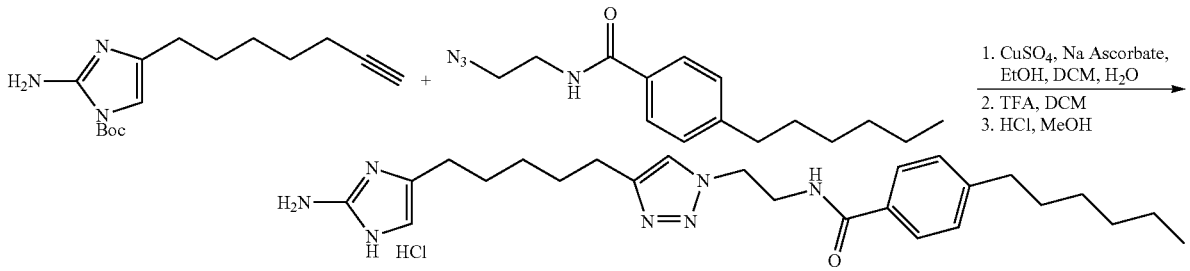

N-(2-(4-(5-(2-amino-1H-imidazol-4-yl)pentyl)-1H-1,2,3-triazol-1-yl)ethyl)-4-hexylbenzamide hydrochloride: tert-butyl 2-amino-4-(hept-6-ynyl)-1H-imidazole-1-carboxylate (0.097 g, 0.349 mmol) was reacted with N-(2-azidoethyl)-4-hexylbenzamide (0.096 g, 0.349 mmol) following the general click procedure to give tert-butyl 2-amino-4-(5-(1-(2-(4-hexylbenzamido)ethyl)-1H-1,2,3-triazol-4-yl)pentyl)-1H-imidazole-1-carboxylate $^1$H NMR (300 MHz, CDCl$_3$) δ 7.65 (d, 2H), δ 7.55 (t, 1H), δ 7.26 (s, 1H), δ 7.09 (d, 2H), δ 6.39 (s, 1H), δ 6.04 (s, 2H), δ 4.48 (t, 2H), δ 3.83 (q, 2H), δ 2.56 (q, 4H), δ 2.24 (t, 2H), δ 1.50 (m, 13H), δ 1.21 (m, 1H), δ 0.77 (t, 3H) ppm; $^{13}$C NMR (75 MHz, CDCl$_3$) δ 168.3, 148.3, 147.3, 138.7, 131.4, 128.7, 127.4, 122.2, 106.4, 84.9, 73.9, 49.5, 40.2, 36.0, 31.8, 31.3, 29.9, 29.3, 29.1, 28.9, 28.2, 28.1, 28.0, 25.6, 22.8, 14.3 ppm; HRMS (ESI) calcd for C$_{30}$H$_{45}$N$_7$O$_3$ (M+) 551.3584, found 551.3581, which was subsequently deprotected to give N-(2-(4-(5-(2-amino-1H-imidazol-4-yl)pentyl)-1H-1,2,3-triazol-1-yl)ethyl)-4-hexylbenzamide hydrochloride (0.164 g, 96% yield). $^1$H NMR (400 MHz, CD$_3$OD) δ 8.28 (s, 1H), δ 7.67 (d, 2H), δ 7.21 (d, 21-1), δ 6.43 (s, 1H), δ 4.72 (s, 2H), δ 3.87 (s, 2H), δ 2.74 (s, 2H), δ 2.58 (t, 2H), δ 2.31 (t, 21-1), δ 1.66 (s, 2H), δ 1.55 (s, 4H), δ 1.35 (s, 2H), δ 1.25 (s, 6H), δ 0.66 (t, 3H) ppm; $^{13}$C NMR (100 MHz, CD$_3$OD) δ 169.2, 159.5, 147.4, 147.3, 131.2, 108.4, 51.2, 48.5, 48.3, 48.1, 47.9, 47.7, 47.5, 47.3, 39.5, 36.5, 35.6, 31.6, 31.7, 31.2, 28.8, 28.2, 27.9, 27.7, 24.1, 23.9, 22.6, 13.3, 9.9 ppm; HRMS (ESI) calcd for C$_{25}$H$_{37}$N$_7$O (M+) 451.3059, found 451.3058.

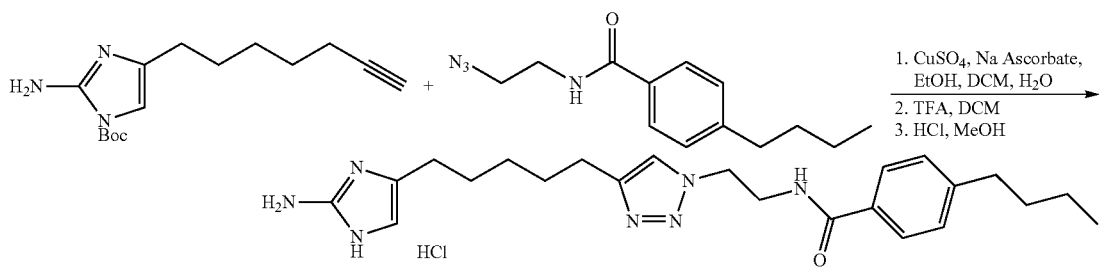

N-(2-(4-(5-(2-amino-1H-imidazol-4-yl)pentyl)-1H-1,2,3-triazol-1-yl)ethyl)-4-butylbenzamide hydrochloride: tert-butyl 2-amino-4-(hept-6-ynyl)-1H-imidazole-1-carboxylate (0.123 g, 0.443 mmol) was reacted with N-(2-azidoethyl)-4-butylbenzamide (0.109 g, 0.443 mmol) following the general click procedure to give tert-butyl 2-amino-4-(5-(1-(2-(4-butylbenzamido)ethyl)-1H-1,2,3-triazol-4-yl)pentyl)-1H-imidazole-1-carboxylate $^1$H NMR (300 MHz, CDCl$_3$) δ 7.67 (s, 1H0, δ 7.67 (d, 2H), δ 7.29 (s, 1H), δ 7.11 (d, 2H), δ 6.42 (s, 1H), δ 6.25 (s, 2H), δ 4.48 (s, 2H), δ 3.83 (s, 2H), δ 2.56 (t, 4H), δ 2.21 (s, 2H), 1.47 (m, 13H), δ 1.21 (m, 4H), δ 0.83 (t, 3H) ppm; $^{13}$C NMR (75 MHz, CDCl$_3$) δ168.3, 140.6, 149.5, 148.2, 147.1, 138.4, 131.5, 128.7, 127.4, 122.2, 106.4, 84.9, 49.4, 40.2, 35.7, 33.5, 29.2, 28.9, 28.3, 28.1, 27.9, 25.5, 22.4, 14.1 ppm; HRMS (ESI) calcd for C$_{28}$H$_{41}$N$_7$O$_3$(M+) 523.3271, found 523.3261, which was subsequently deprotected to give N-(2-(4-(5-(2-amino-1H-imidazol-4-yl)pentyl)-1H-1,2,3-triazol-1-yl)ethyl)-4-butylbenzamide hydrochloride (0.191 g, 94% yield). $^1$H NMR (300 MHz, CD$_3$OD) δ 8.43 (s, 1H), δ 7.69 (s, 2H), δ 7.22 (s, 2H), δ 6.44 (s, 1H), δ 4.73 (s, 2H), δ 3.89 (s, 2H), δ 3.34 (s, 2H), δ 2.59 (s, 4H), δ 2.41 (s, 2H), δ 1.54 (s, 4H), δ 1.29 (s, 4H), δ 0.88 (t, 3H) ppm; $^{13}$C NMR (75 MHz, CD$_3$OD) δ 169.2, 165.1, 160.3, 158.1, 147.4, 141.4, 131.2, 128.5, 127.7, 127.3, 126.9, 92.9, 39.6, 36.3, 33.4, 30.9, 28.0, 27.7, 24.1, 22.2, 13.2, 12.1, 10.9, 8.9, 6.2, 2.5 ppm; HRMS (ESI) calcd for C$_{23}$H$_{33}$N$_7$O (M+) 423.2747, found 423.2738.

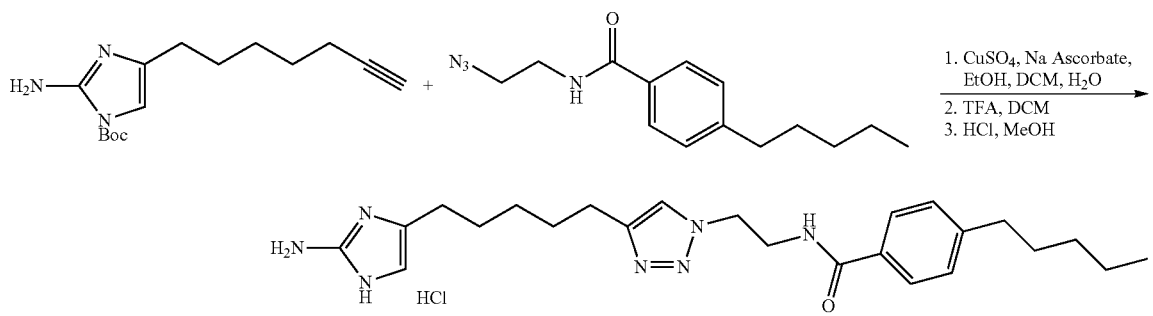

N-(2-(4-(5-(2-amino-1H-imidazol-4-yl)pentyl)-1H-1,2,3-triazol-1-yl)ethyl)-4-pentylbenzamide hydrochloride: tert-butyl 2-amino-4-(hept-6-ynyl)-1H-imidazole-1-carboxylate (0.113 g, 0.408 mmol) was reacted with N-(2-(4-(5-(2-amino-1H-imidazol-4-yl)pentyl)-1H-1,2,3-triazol-1-yl)ethyl)biphenyl-4-carboxamide hydrochloride (0.106 g, 0.408 mmol) following the general click procedure to give tert-butyl 2-amino-4-(5-(1-(2-(4-pentylbenzamido)ethyl)-1H-1,2,3-triazol-4-yl)pentyl)-1H-imidazole-1-carboxylate $^1$H NMR (300 MHz, CDCl$_3$) δ 7.75 (s, 1H), δ 7.57 (d, 2H), δ 7.27 (s, 1H), δ 7.12 (d, 2H), δ 4.48 (s, 2H), δ 3.84 (s, 2H), δ 2.55 (m, 4H), δ 2.22 (s, 2H0, δ 1.50 (s, 13H), δ 1.23 (s, 8H), δ 0.80 (t, 3H); $^{13}$C NMR (75 MHz, CDCl$_3$) δ ppm 168.3, 150.5, 149.5, 148.2, 147.2, 138.6, 131.5, 128.7, 127.4, 106.4, 84.8, 49.4, 40.2, 35.9, 31.6, 31.0, 29.3, 28.9, 28.1, 27.9, 25.6, 22.6, 14.2; HRMS (ESI) calcd for C$_{29}$H$_{43}$N$_7$O$_3$ (M+) 537.3427, found 537.3420, which was subsequently deprotected to give N-(2-(4-(5-(2-amino-1H-imidazol-4-yl)pentyl)-1H-1,2,3-triazol-1-yl)ethyl)-4-pentylbenzamide hydrochloride (0.178 g, 92% yield). $^1$H NMR (300 MHz, CD$_3$OD) δ 8.41 (s, 1H), δ 7.69 (d, 2H), δ 7.21 (d, 2H), δ 6.46 (s, 1H), δ 4.84 (s, 2H), δ 3.90 (s, 2H), δ 2.79 (s, 2H), δ 2.58 (t, 2H), δ 2.39 (t, 2H), δ 1.68 (s, 2H), δ 1.55 (s, 4H), δ 1.26 (s, 6H), δ 0.84 (t, 3H) ppm; $^{13}$C NMR (75 MHz, CD$_3$OD) δ 169.2, 159.5, 158.9, 147.5, 147.3, 131.1, 128.5, 127.6, 127.4, 108.5, 54.2, 51.9, 39.5, 35.6, 31.4, 30.9, 30.6, 28.4, 27.9, 27.6, 26.9, 24.1, 23.5, 22.9, 22.4, 13.3 ppm; HRMS (ESI) calcd for C$_{24}$H$_{35}$N$_7$O (M+) 437.2903, found 437.2892.

N-(2-(4-(5-(2-amino-1H-imidazol-4-yl)pentyl)-1H-1,2,3-triazol-1-yl)ethyl)-2,4,6-trichlorobenzamide hydrochloride: tert-butyl 2-amino-4-(hept-6-ynyl)-1H-imidazole-1-carboxylate (0.088 g, 0.318 mmol) was reacted with N-(2-azidoethyl)-2,4,6-trichlorobenzamide (0.093 g, 0.318 mmol) following the general click procedure to give tert-butyl 2-amino-4-(5-(1-(2-(2,4,6-trichlorobenzamido)ethyl)-1H-1,2,3-triazol-4-yl)pentyl)-1H-imidazole-1-carboxylate $^1$H NMR (300 MHz, CDCl$_3$) δ 8.22 (s, 1H), δ 7.34 (s, 1H), δ 7.26 (s, 2H), δ 6.42 (s, 1H), δ 5.97 (s, 1H), δ 4.51 (s, 2H), δ 3.94 (s, 2H), δ 2.45 (t, 2H), δ 2.20 (s, 2H), δ 1.47 (m 13H), δ 1.21 (m, 2H) ppm; $^{13}$C NMR (75 MHz, CDCl$_3$) δ 164.7, 148.0, 135.7, 134.6, 132.9, 128.7, 128.1, 127.3, 122.3, 84.9, 53.7, 49.3, 39.9, 31.8, 29.2, 28.9, 28.2, 25.5, 22.8, 14.3 ppm; HRMS (ESI) calcd for C$_{24}$H$_{30}$Cl$_3$N$_7$O$_3$ (M+) 569.1476, found 569.1477, which was subsequently deprotected to give N-(2-(4-(5-(2-amino-1H-imidazol-4-yl)pentyl)-1H-1,2,3-triazol-1-yl)ethyl)-2,4,6-trichlorobenzamide hydrochloride (0.116 g, 72% yield). $^1$H NMR (300 MHz, CD$_3$OD) δ 8.36 (s, 1H), δ 7.45 (s, 2H), δ 6.46 (s, 1H), δ 4.77 (s, 2H), δ 3.97 (s, 2H), δ 2.80 (s, 2H), δ 2.48 (t, 2H), δ 1.73 (s, 2H), δ 1.62 (s, 2H), δ 1.41 (s, 2H) ppm; $^{13}$C NMR (75 MHz, CD$_3$OD) δ 165.5, 147.3, 136.9, 134.5, 132.7, 128.2, 128.0, 127.6, 108.6, 51.2, 39.0, 28.1, 27.7, 24.1, 23.8 ppm; HRMS (ESI) calcd for C$_{19}$H$_{22}$Cl$_3$N$_7$O (M+) 469.0951, found 469.0941.

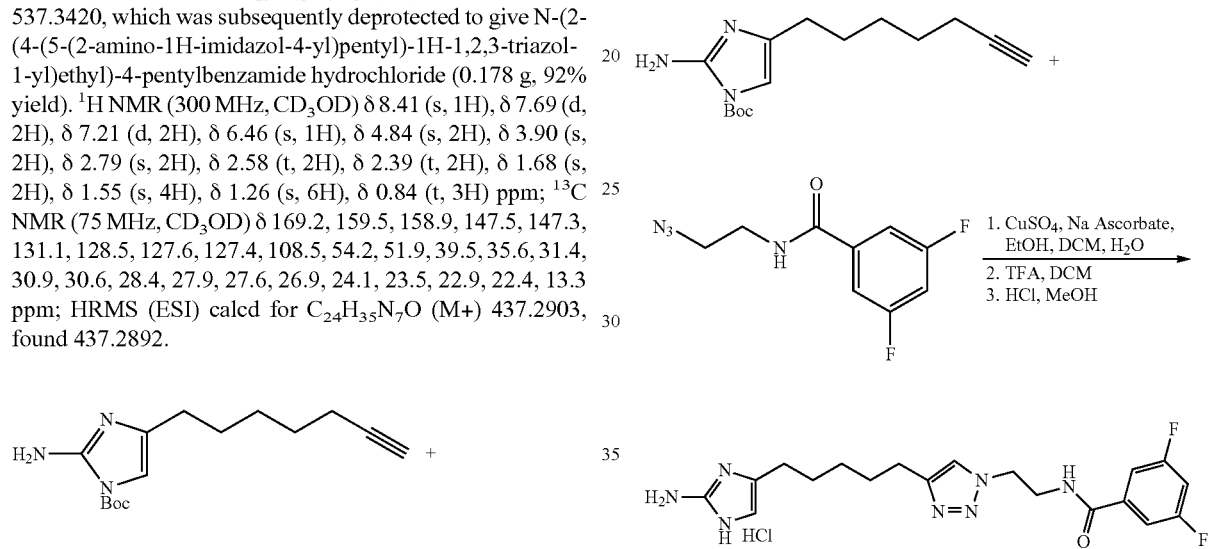

N-(2-(4-(5-(2-amino-1H-imidazol-4-yl)pentyl)-1H-1,2,3-triazol-1-yl)ethyl)-3,5-difluorobenzamide hydrochloride: tert-butyl 2-amino-4-(hept-6-ynyl)-1H-imidazole-1-carboxylate (0.123 g, 0.442 mmol) was reacted with N-(2-azidoethyl)-3,5-difluorobenzamide (0.100 g, 0.442 mmol) following the general click procedure to give tert-butyl 2-amino-4-(5-(1-(2-(3,5-difluorobenzamido)ethyl)-1H-1,2,3-triazol-4-yl)pentyl)-1H-imidazole-1-carboxylate $^1$H NMR (300 MHz, CDCl$_3$) δ 8.25 (s, 1H), δ 7.39 (m, 3H), δ 6.88 (t, 1H), δ 6.43 (s, 1H), δ 6.38 (bs, 2H), δ 4.55 (s, 2H), δ 3.93 (s, 2H), δ 2.56 (t, 2H), δ 2.24 (s, 2H), δ 1.55 (m, 14H), δ 1.23 (s, 2H) ppm; $^{13}$C NMR (75 MHz, CDCl$_3$) δ 165.9, 164.3, 164.2, 161.9, 150.3, 149.3, 148.2, 137.6, 122.4, 111.0, 110.8, 107.3, 107.1, 106.8, 106.6, 85.5, 49.3, 40.4, 29.9, 29.5, 29.1, 28.7, 28.2, 27.9, 27.5, 25.4 ppm; HRMS (ESI) calcd for C$_{24}$H$_{31}$F$_2$N$_7$O$_3$ (M+) 503.2456, found 503.2458, which was subsequently deprotected to give N-(2-(4-(5-(2-amino-1H-imidazol-4-yl)pentyl)-1H-1,2,3-triazol-1-yl)ethyl)-3,5-difluorobenzamide hydrochloride (0.115 g, 59% yield). $^1$H NMR (400 MHz, CD$_3$OD) δ 8.55 (s, 1H), δ 7.42 (d, 2H), δ 7.29 (t, 1H), δ 6.51 (s, 1H), δ 4.84 (t, 2H), δ 3.96 (q, 2H), δ 2.89 (t, 2H), δ 2.49 (t, 2H), δ 1.79 (m, 2H), δ 1.75 (m, 2H), δ 1.44 (m, 2H) ppm; $^{13}$C NMR (75 MHz, CD$_3$OD) δ 164.5, 164.4, 127.6, 126.9, 110.6, 110.6, 110.3, 108.5, 107.1, 106.8, 106.6, 52.5, 39.5, 30.4, 27.9, 27.8, 27.6, 24.0, 23.8, 23.1 ppm; HRMS (ESI) calcd for C$_{19}$H$_{23}$F$_2$N$_7$O (M+) 403.1932, found 403.1926.

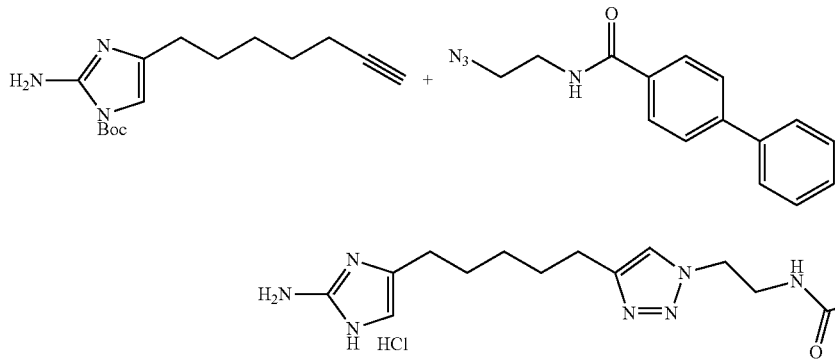

N-(2-(4-(5-(2-amino-1H-imidazol-4-yl)pentyl)-1H-1,2,3-triazol-1-yl)ethyl)biphenyl-4-carboxamide hydrochloride: tert-butyl 2-amino-4-(hept-6-ynyl)-1H-imidazole-1-carboxylate (0.093 g, 0.334 mmol) was reacted with N-(2-azidoethyl)biphenyl-4-carboxamide (0.089 g, 0.334 mmol) following the general click procedure to give tert-butyl 2-amino-4-(5-(1-(2-biphenyl-4-ylcarboxamidoethyl)-1H-1,2,3-triazol-4-yl)pentyl)-1H-imidazole-1-carboxylate $^1$H NMR (300 MHz, CDCl$_3$) δ 7.91 (d, 3H), δ 7.57 (t, 4H), δ 7.44 (t, 3H), δ 7.34 (1H), δ 4.60 (t, 2H), δ 3.96 (q, 2H), δ 2.63 (t, 2H), δ 2.27 (t, 2H), 61.62 (m, 13H), δ 1.33 (m, 2H) ppm; $^{13}$C NMR (75 MHz, CDCl$_3$) δ 168.0, 149.6, 148.3, 144.6, 140.1, 138.8, 132.8, 129.1, 128.2, 128.0, 127.4, 127.3, 122.2, 84.9, 49.4, 40.3, 29.3, 28.9, 28.3, 28.2, 28.1, 25.6 ppm; HRMS (ESI) calcd for C$_{30}$H$_{37}$N$_7$O$_3$ (M+) 543.2958, found 543.2949, which was subsequently deprotected to give N-(2-(4-(5-(2-amino-1H-imidazol-4-yl)pentyl)-1H-1,2,3-triazol-1-yl)ethyl)biphenyl-4-carboxamide hydrochloride (0.093 g, 58% yield). $^1$H NMR (300 MHz, CD$_3$OD) δ 8.35 (s, 1H), δ 7.88 (d, 2H), δ 7.65 (d, 2H), δ 7.57 (d, 2H), δ 7.39 (t, 2H), δ 7.34 (t, 1H), δ 6.39 (s, 1H), δ 4.81 (s, 2H), δ 3.96 (s, 2H), δ 2.78 (s, 2H), δ 2.37 (t, 2H), δ 1.67 (s, 2H), δ 1.56 (t, 2H), δ 1.33 (s, 2H) ppm; $^{13}$C NMR (75 MHz, CD$_3$OD) δ 203.6, 158.9, 160.1, 159.5, 159.1, 159.0, 158.5, 149.8, 147.2, 144.6, 132.4, 128.9, 127.9, 127.6, 126.9, 126.4, 108.4, 51.7, 39.5, 27.9, 27.6, 24.0, 23.5, 7.2 ppm; HRMS (ESI) calcd for C$_{25}$H$_{29}$N$_7$O (M+) 443.2434, found 443.2423.

was reacted with N-(2-azidoethyl)-2',4'-difluoro-3-hydroxybiphenyl-4-carboxamide (0.097 g, 0.306 mmol) following the general click procedure to give tert-butyl 2-amino-4-(5-(1-(2-(2',4'-difluoro-3-hydroxybiphenyl-4-ylcarboxamido)ethyl)-1H-1,2,3-triazol-4-yl)pentyl)-1H-imidazole-1-carboxylate $^1$H NMR (300 MHz, CDCl$_3$) δ 8.54 (S, 1H), δ 7.83 (s, 1H), δ 7.37 (d, 1H), δ 7.28 (s, 1H), δ 7.18 (s, 1H), δ 6.89 (d, 1H), δ 6.72 (s, 2H), δ 6.39 (s, 1H), δ 4.57 (s, 2H), δ 3.81 (s, 2H), δ 3.34 (s, 1H), δ 2.47 (s, 2H), δ 2.07 (s, 2H), δ 1.49 (m, 13H), δ 1.17 (s, 2H) ppm; $^{13}$C NMR (75 MHz, CDCl$_3$) δ 169.5, 163.7, 161.3, 160.5, 159.9, 150.5, 149.2, 148.2, 137.1, 136.3, 134.5, 131.4, 12.8, 126.8, 124.4, 122.3, 117.9, 116.1, 111.9, 111.6, 106.7, 104.8, 104.4, 104.1, 85.8, 50.5, 49.4, 46.6, 50.0, 37.9, 29.9, 28.9, 28.5, 28.3, 28.1, 27.4, 25.3, 25.0 ppm; HRMS (ESI) calcd for C$_{30}$H$_{35}$F$_2$N$_4$O$_4$(M+) 595.2729, found 595.2717, which was subsequently deprotected to give (0.137 g, 84% yield). $^1$H NMR (400 MHz, CD$_3$OD) δ 8.60 (s, 1H), δ 7.89 (s, 1H), δ 7.52 (s, 2H), δ 6.97 (t, 3H), δ 6.45 (s, 1H), δ 4.81 (s, 2H), δ 2.78 (s, 2H), δ 2.42 (s, 2H), δ 1.72 (s, 2H), δ 1.61 (d, 2H), δ 1.38 (s, 2H) ppm; $^{13}$C NMR (100 MHz, CD$_3$OD) δ 172.9, 169.8, 161.6, 159.5, 147.2, 134.4, 131.7, 128.4, 127.6, 126.0, 117.5, 115.6, 111.7, 111.5, 108.5, 104.2, 104.0, 103.7, 94.6, 51.9, 39.0, 27.9, 27.6, 26.8, 24.1, 23.8 ppm; HRMS (ESI) calcd for C$_{25}$H$_{27}$F$_2$N$_7$O$_2$(M+) 459.2194, found 459.2190.

Procedure to Determine the Inhibitory Effect of Test Compounds on E. faecium, MRSA, S. epidermidis, PAO1, PA14,

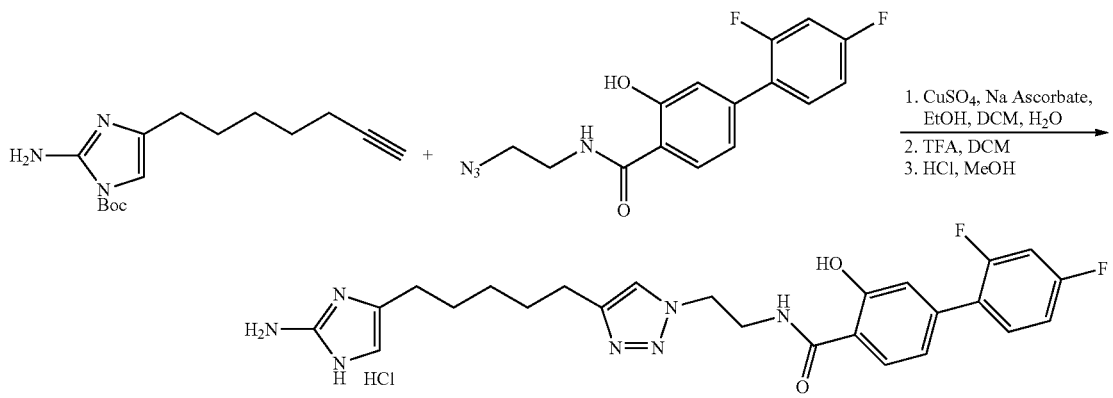

N-(2-(4-(5-(2-amino-1H-imidazol-4-yl)pentyl)-1H-1,2,3-triazol-1-yl)ethyl)-2',4'-difluoro-3-hydroxybiphenyl-4-carboxamide hydrochloride: tert-butyl 2-amino-4-(hept-6-ynyl)-1H-imidazole-1-carboxylate (0.085 g, 0.306 mmol)

E. Coli and MDRAB Biofilm Formation: Inhibition assays were performed by taking an overnight culture of bacterial strain and subculturing it at an OD$_{600}$ of 0.01 into the necessary media (brain heart infusion for E. faecium, tryptic soy broth with a 0.5% glucose supplement (TSBG) for MRSA, Luria-Bertani (LB) media for MDRAB, Luria-Bertani media without NaCl (LBNS) for PAO1 and PA14, Luria-Bertani (LB) media for *E. coli* and tryptic soy broth with a 0.5% glucose supplement and a 3.0% NaCl supplement (TGN) for *S. epidermidis*. Stock solutions of predetermined concentrations of the test compound were then made in the necessary media. These stock solutions were aliquoted (100 μL) into the wells of the 96-well PVC microtiter plate. Sample plates were then wrapped in GLAD Press n' Seal® followed by an incubation under stationary conditions for 24 h at 37° C. After incubation, the media was discarded from the wells and the plates were washed thoroughly with water. Plates were then stained with 100 μL of 0.1% solution of crystal violet (CV) and then incubated at ambient temperature for 30 min. Plates were washed with water again and the remaining stain was solubilized with 200 μL of 95% ethanol. A sample of 125 μL of solubilized CV stain from each well was transferred to the corresponding wells of a polystyrene microtiter dish. Biofilm inhibition was quantitated by measuring the $OD_{540}$ of each well in which a negative control lane wherein no biofilm was formed served as a background and was subtracted out.

Procedure to Determine the Dispersal Effect of Compounds on *E. faecium*, MRSA, *S. epidermidis*, PAO1, PA14, *E. Coli* and MDRAB Preformed Biofilms: Dispersion assays were performed by taking an overnight culture of bacterial strain and subculturing it at an $OD_{600}$ of 0.01 into the necessary media (brain heart infusion for *E. faecium*, tryptic soy broth with a 0.5% glucose supplement (TSBG) for MRSA, Luria-Bertani (LB) media for MDRAB, Luria-Bertani media without NaCl (LBNS) for PAO1 and PA14, Luria-Bertani (LB) media for *E. coli* and tryptic soy broth with a 0.5% glucose supplement and a 3.0% NaCl supplement (TGN) for *S. epidermidis*. The resulting bacterial suspension was aliquoted (100 μL) into the wells of a 96-well PVC microtiter plate. Plates were then wrapped in GLAD Press n' Seal® followed by an incubation under stationary conditions at ambient temperature to establish the biofilms. After 24 h, the media was discarded from the wells and the plates were washed thoroughly with water. Stock solutions of predetermined concentrations of the test compound were then made in the necessary media. These stock solutions were aliquoted (100 μL) into the wells of the 96-well PVC microtiter plate with the established biofilms. Media alone was added to a subset of the wells to serve as a control. Sample Plates were then incubated for 24 h at 37° C. After incubation, the media was discarded from the wells and the plates were washed thoroughly with water. Plates were then stained with 100 μl of 0.1% solution of crystal violet (CV) and then incubated at ambient temperature for 30 min. Plates were washed with water again and the remaining stain was solubilized with 200 μL of 95% ethanol. A sample of 125 μL of solubilized CV stain from each well was transferred to the corresponding wells of a polystyrene microtiter dish. Biofilm dispersion was quantitated by measuring the $OD_{540}$ of each well in which a negative control lane wherein no biofilm was formed served as a background and was subtracted out.

Procedure to Determine the Effect of Leading Test Compounds on *E. faecium*, MRSA, *S. epidermidis*, PAO1, PA14, *E. Coli* and MDRAB Planktonic Viability via Growth Curve Analysis Growth curves were performed by taking an overnight culture of bacterial strain and subculturing it at an $M_{oo}$ of 0.01 into the necessary media (brain heart infusion for *E. faecium*, tryptic soy broth with a 0.5% glucose supplement (TSBG) for MRSA, Luria-Bertani (LB) media for MDRAB, Luria-Bertani media without NaCl (LBNS) for PAO1 and PA14, Luria-Bertani (LB) media for *E. coli* and nutrient broth for *S. epidermidis*. The resulting bacterial suspension was then aliquoted (3.0 mL) into culture tubes. The test compound was then added at a predetermined concentration to the media of the test samples. Controls were employed in which no test compound was added to the bacterial suspension. Samples were then placed in an incubator at 37° C. and shaken at 200 rpm. The $OD_{600}$ of the samples was measured at time intervals starting at 2 hours and ending at 24 hours.

Procedure to Determine the Effect of Leading Test Compounds on *C. albicans* and *C. neoformans* Planktonic Viability via Growth Curve Analysis: Growth curves were performed by taking an overnight culture of yeast strain and subculturing it at an $OD_{600}$ of 0.01 into YPD (Yeast extract, peptone and dextrose (BD 242820)) media. The resulting bacterial suspension was then aliquoted (3.0 mL) into culture tubes. The test compound was then added at a predetermined concentration to the media of the test samples. Controls were employed in which no test compound was added to the bacterial suspension. Samples were then placed in an incubator at 37° C. and shaken at 200 rpm. The $OD_{600}$ of the samples was measured at time intervals starting at 2 hours and ending at 24 hours.

Colony Count Procedure to Determine the Effect of Leading Test Compounds on *E. faecium*, MRSA and *S. epidermidis* planktonic viability: Colony counts were performed by taking an overnight culture of bacterial strain and subculturing it at an $OD_{600}$ of 0.01 into the necessary media (brain heart infusion for *E. faecium*, tryptic soy broth (TSB) for MRSA and nutrient broth (NB) for *S. epidermidis*). The resulting bacterial suspension was then aliquoted (3.0 mL) into culture tubes. A test compound was then added to the media of the test samples at a predetermined concentration to the media of the test samples. Controls were employed in which no test compound was added to the bacterial suspension. Samples were then placed in an incubator at 37° C. and shaken at 200 rpm until the $OD_{600}$ of the control samples reached approximately 1.2. At this point, 100 μL was taken from each culture tube and then diluted serially into LB media. Then, 10 μL was removed from each serial dilution and plated out on a square gridded Petri dish followed by 16 h of incubation at 37° C. to grow viable colonies, which were quantified through employment of the track-dilution method.

Figure 7A:
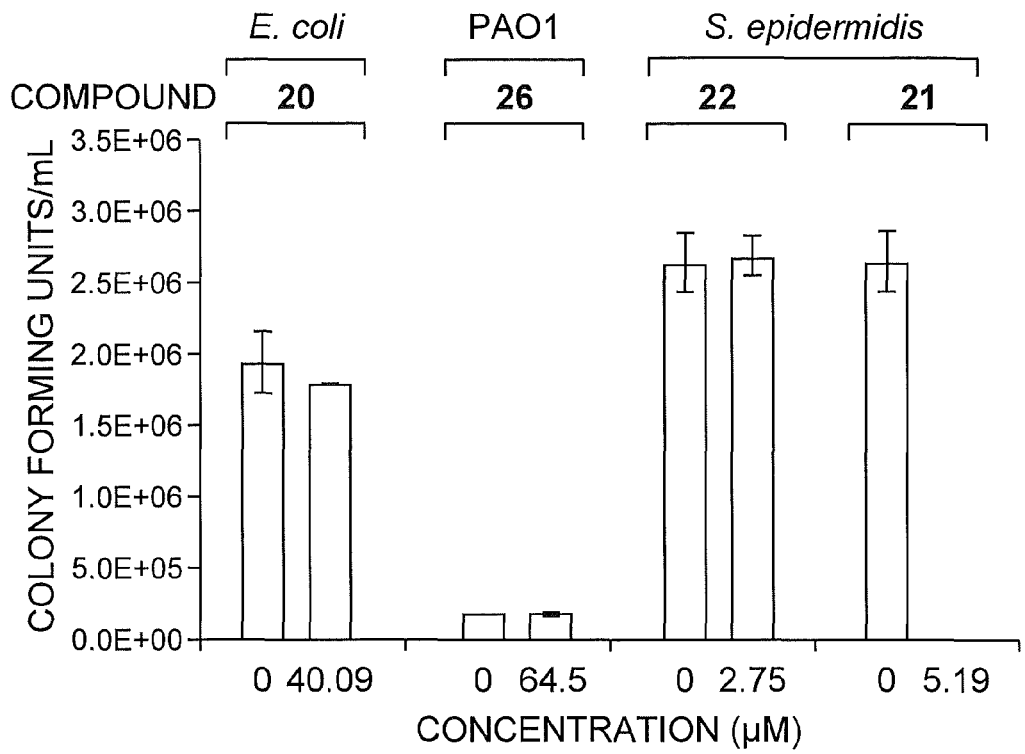
FIG. 7A-7C. Colony counts for bacteria grown in the presence or absence of compounds 20-26. 7A: Colony counts for *E. coli* in the presence or absence of 20 (40.09 µM), for PAO1 in the presence or absence of 26 (64.5 µM), and for *S. epidermidis* in the presence or absence of 22 (2.75 µM) and 21 (5.19 µM). 7B: Colony counts for PA14 in the presence or absence of 24 (38.14 µM), PAO1 in the presence or absence of 24 (1.09 µM), MRSA in the presence or absence of 23 (4.33 µM), and PA14 in the presence or absence of 23 (34.38 µM). 7C: In the presence or absence of 25, colony counts for *S. epidermidis* (0.61 µM), *E. coli* (11.19 µM), MDRAB (1.94 µM) and MRSA (1.88 µM).
Figure 7B:
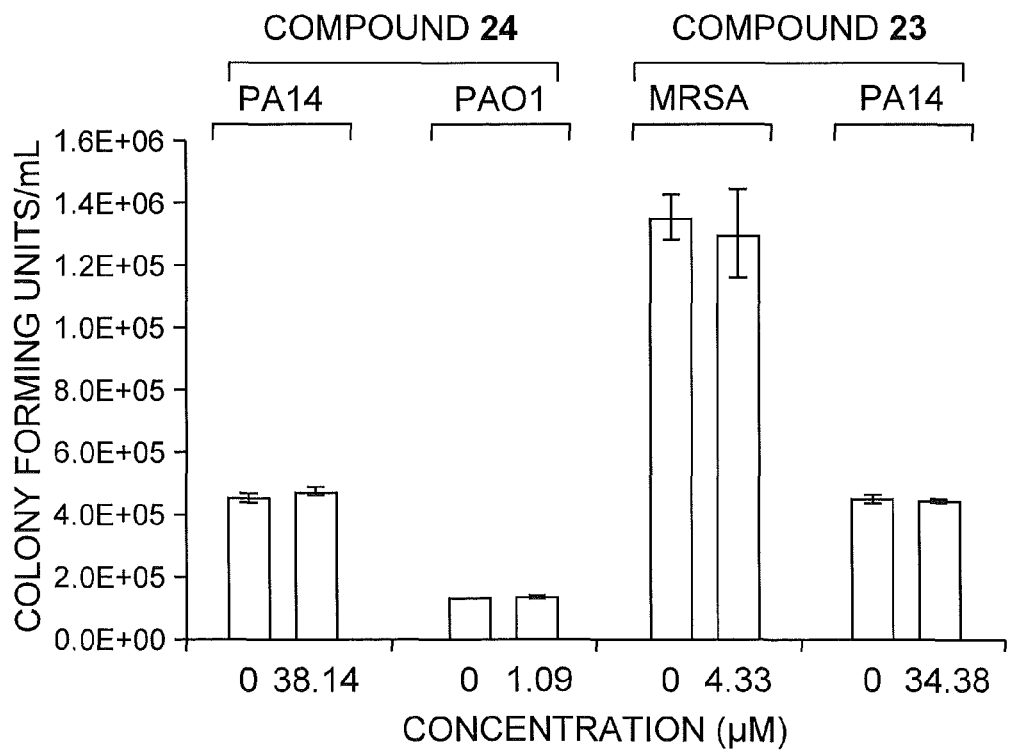
Figure 7C:
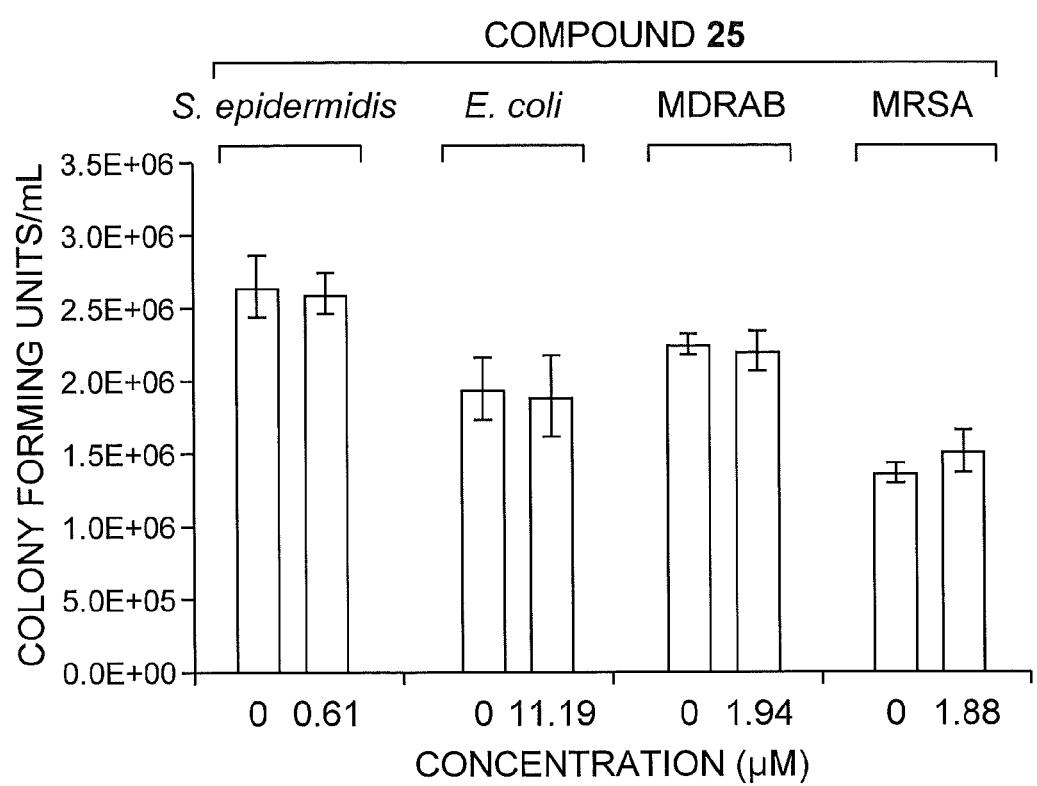

Results. Inhibition and dispersion testing, growth curves and colony counts were performed as detailed above for compounds 20-26. Results are shown in FIG. 5-7.

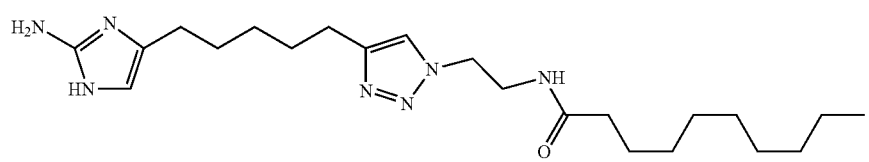

20

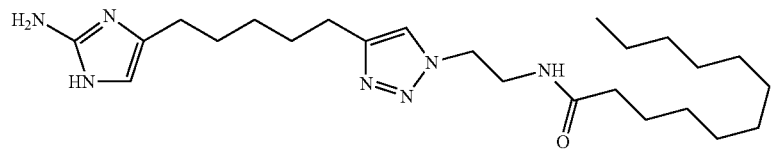
21
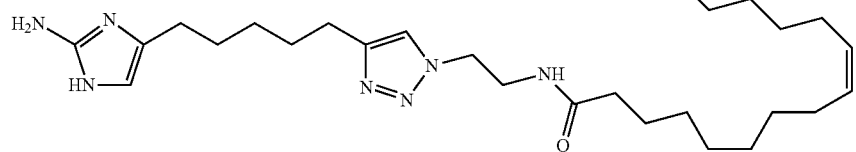
22
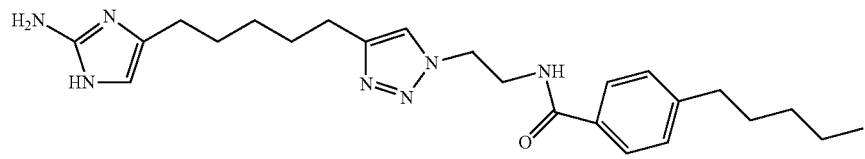
23
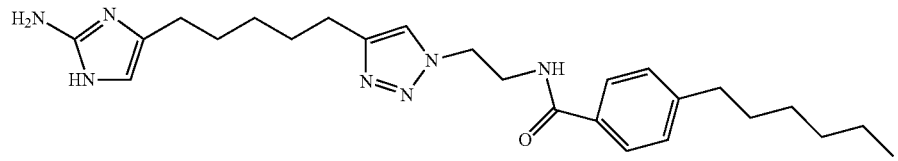
24
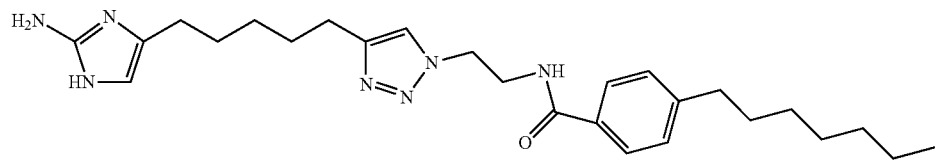
25
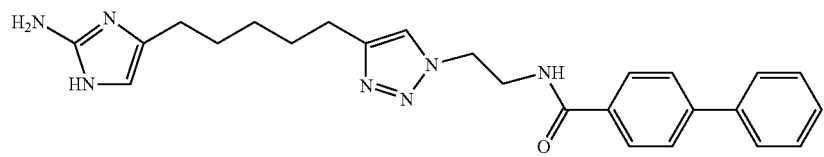
26
Example 7
Synthesis of Additional Compounds
The following compounds have been synthesized, as detailed below:
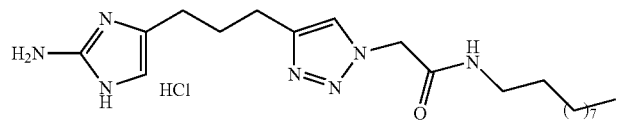
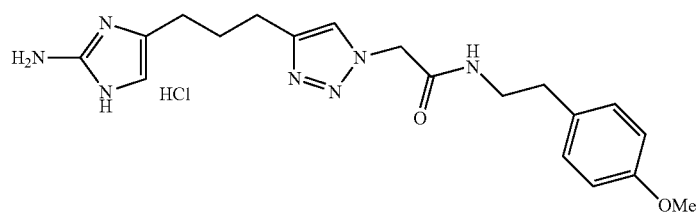 [SMILES: COc1ccc(CCNC(=O)Cn2cc(CCCc3c[nH]c(N)n3)nn2)cc1 ; Cl]

-continued
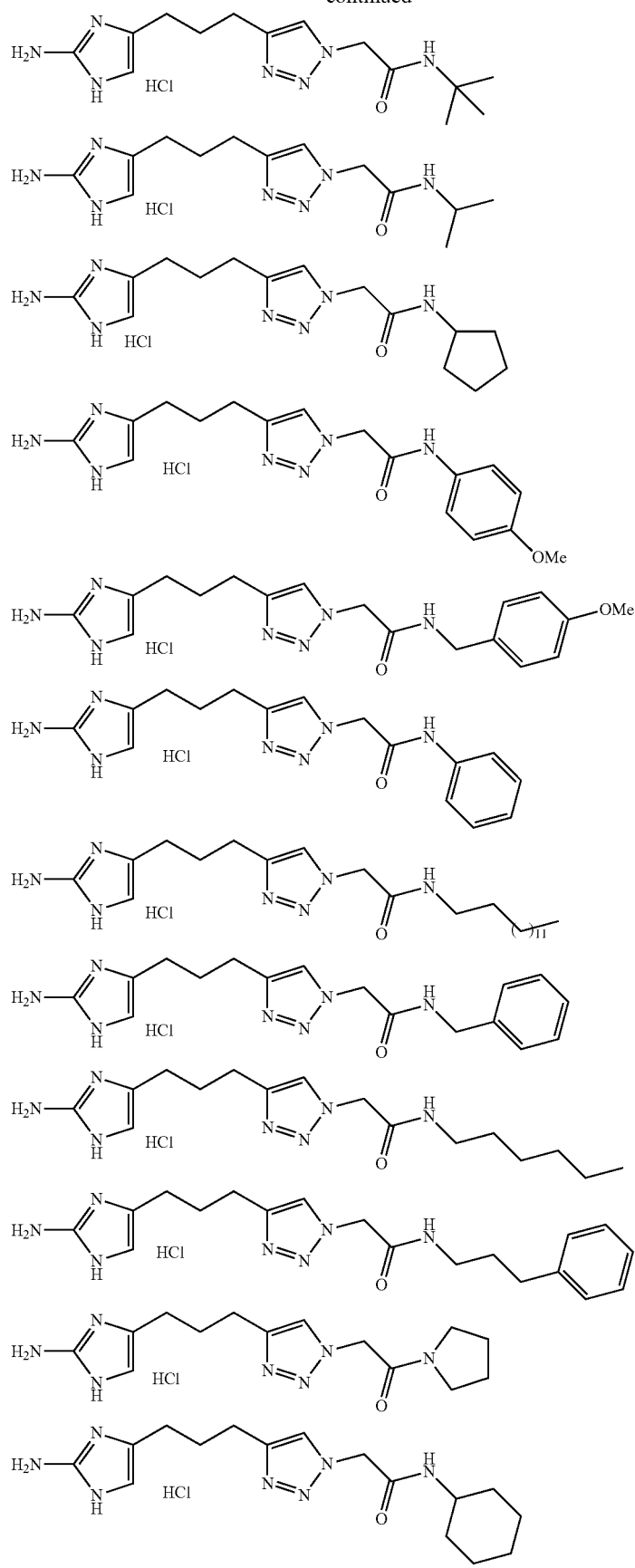

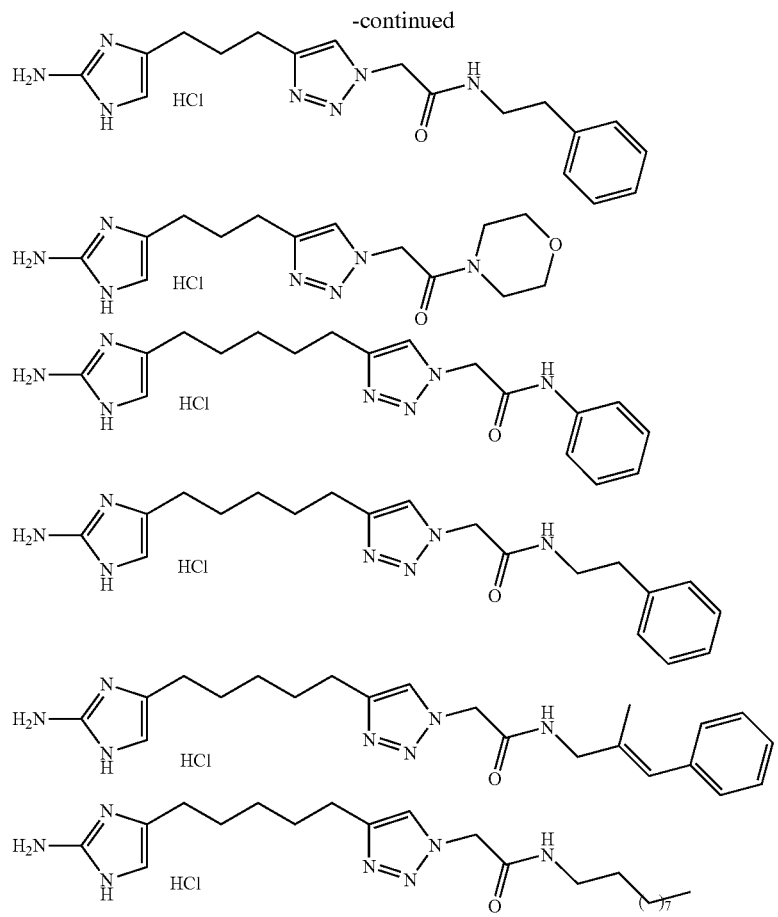

General procedure for click reactions and subsequent Boc deprotection: The terminal alkyne (1.0 equiv.) and the appropriate azide (3.0 equiv.) were dissolved in a 1:1:1 mixture of ethanol, water, and dichloromethane (ca. 3.6 mL per 0.100 g of terminal alkyne). To this solution sodium ascorbate (60 mol %) and Copper (II) sulfate pentahydrate (30 mol %) were added while stirring at room temperature. Reaction mixtures were allowed to stir until completion via TLC analysis (12-24 hrs). The solvents were then removed de vacuo in which the resulting residue was dissolved in dichloromethane and purified via silica gel column chromatography (1:40 methanol:dichloromethane to 1:10 methanol:dichloromethane). To remove the Boc protecting group, the resulting product was then dissolved in a 1:4 trifluoroacetic acid:dichloromethane mixture and allowed to stir for 1.5 hours. Upon completion, the reaction mixture was concentrated de vacuo and then left on a high vacuum overnight. Then, methanol supplemented with HCl was added to the product forming the HCl salt of the deprotected product and then concentrated de vacuo. The resulting residue was washed with diethyl ether and then placed on a high vacuum overnight.

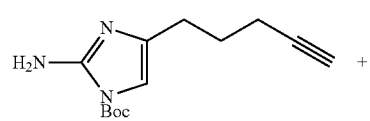

2-{4-[3-(2-amino-1H-imidazol-4-yl)-propyl]-[1,2,3]triazol-1-yl}-N-decyl-acetamide hydrochloride: Following the general procedure, 2-amino-4-pent-4-ynyl-imidazole-1-carboxylic acid tert-butyl ester (0.101 g, 0.405 mmol) was reacted with 2-Azido-N-decyl-acetamide (0.288 g, 1.198 mmol) and afforded 0.055 g (59% yield) of 2-{4-[3-(2-amino-1H-imidazol-4-yl)-propyl]-[1,2,3]triazol-1-yl}-N-decyl-acetamide hydrochloride (1). $^1$H NMR (400 MHz, CD$_3$OD) δ 8.26 (s, 1H), 6.56 (s, 1H), 5.30 (s, 2H), 3.23 (t, J=7.6, 2H), 2.87 (bs, 2H), 2.59 (bs, 2H), 2.03 (bs, 2H), 1.54 (t, J=6.8, 2H), 1.32-1.29 (m, 16H), 0.89 (t, J=6.8, 3H); $^{13}$C NMR (100 MHz, CD$_3$OD) δ 184.1, 166.9, 148.9, 148.6, 128.0, 110.3, 54.4, 40.9, 33.2, 30.8, 30.6, 30.5, 30.4, 28.5, 28.1, 24.8, 24.6, 23.8, 14.6; HRMS (ESI) calculated for C$_{20}$H$_{35}$N$_7$O (MH$^+$) 389.2903, found 389.29.

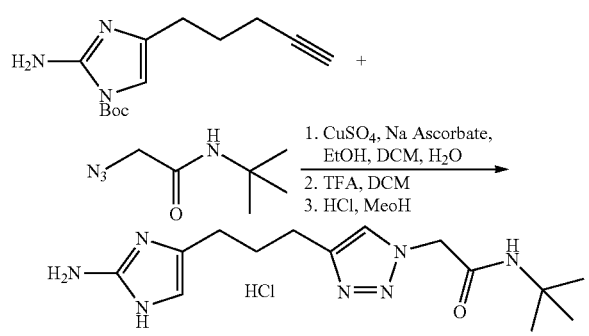

2-{4-[3-(2-amino-1H-imidazol-4-yl)-propyl]-[1,2,3]triazol-1-yl}-N-tert-butyl-acetamide hydrochloride: Following the general procedure, 2-amino-4-pent-4-ynyl-imidazole-1-carboxylic acid tert-butyl ester (0.100 g, 0.401 mmol) was reacted with 2-azido-N-tert-butyl-acetamide (0.187 g, 1.201 mmol) and afforded 0.052 g (79% yield) of 2-{4-[3-(2-amino-1H-imidazol-4-yl)-propyl]-[1,2,3]triazol-1-yl}-N-tert-butyl-acetamide hydrochloride (2). $^1$H NMR (400 MHz, CD$_3$OD) δ 6.57 (s, 1H), 5.23 (s, 2H), 2.85 (bs, 2H), 2.59 (bs, 2H), 2.04 (bs, 2H), 1.35 (s, 9H); $^{13}$C NMR (100 MHz, CD$_3$OD) δ 166.1, 148.6, 128.1, 110.3, 66.1, 54.8, 52.8, 28.9, 28.5, 24.8, 15.6; HRMS (ESI), calculated for C$_{14}$H$_{23}$N$_7$O (MH$^+$) 305.1964, found 305.1959.

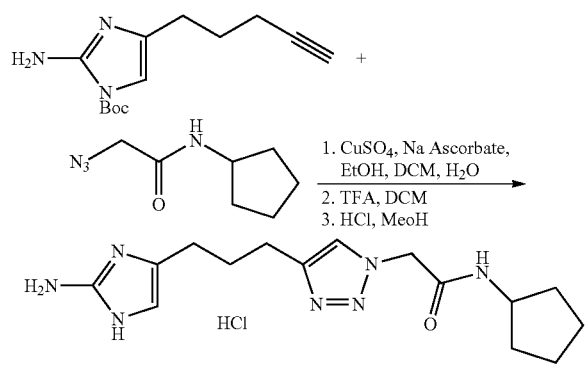

2-{4-[3-(2-amino-1H-imidazol-4-yl)-propyl]-1,2,31-triazol-1-yl}-N-cyclopentyl-acetamide hydrochloride: Following the general procedure, 2-amino-4-pent-4-ynyl-imidazole-1-carboxylic acid tert-butyl ester (0.100 g, 0.401 mmol) was reacted with 2-azido-N-cyclopentyl-acetamide (0.202 g, 1.202 mmol) and afforded 0.045 g (58% yield) of 2-{4-[3-(2-amino-1H-imidazol-4-yl)-propyl]-[1,2,3]triazol-1-yl}-N-cyclopentyl-acetamide hydrochloride (3). $^1$H NMR (400 MHz, CD$_3$OD) δ 8.23 (s, 1H), 6.57 (s, 1H), 5.29 (s, 2H), 3.98 (s, 1H), 3.35 (s, 1H), 2.87 (t, J=6.4, 2H), 2.59 (t, J=6.8, 2H), 2.02 (t, J=6.8, 2H), 1.94-1.89 (m, 2H), 1.75 (bs, 2H), 1.61 (t, J=6.8, 2H), 1.57-1.51 (m, 2H); $^{13}$C NMR (100 MHz, CD$_3$OD) δ 166.3, 148.6, 128.0, 110.3, 55.4, 54.4, 52.9, 33.6, 28.4, 24.9, 24.7, 24.5; HRMS (ESI), calculated for C$_{15}$H$_{23}$N$_7$O (MH$^+$) 317.1964, found 317.1961.

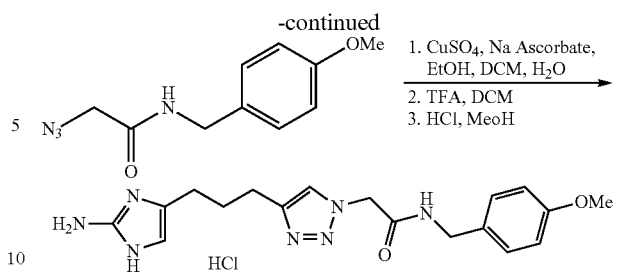

2-{4-[3-(2-amino-1H-imidazol-4-yl)-propyl]-[1,2,3]-triazol-1-yl}-N-(4-methoxy-benzyl)-acetamide hydrochloride: Following the general procedure, 2-amino-4-pent-4-ynyl-imidazole-1-carboxylic acid tert-butyl ester (0.050 g, 0.200 mmol) was reacted with 2-azido-N-(4-methoxy-benzyl)-acetamide (0.066 g, 0.300 mmol) and afforded 0.054 g (71% yield) of 2-{4-[3-(2-amino-1H-imidazol-4-yl)-propyl]-[1,2,3]triazol-1-yl}-N-(4-methoxy-benzyl)-acetamide hydrochloride (4). $^1$H NMR (400 MHz, CD$_3$OD) δ 8.52 (s, 1H), 7.24 (d, J=8.4, 2H), 6.87 (d, J=8.4, 2H), 6.59 (s, 1H), 5.47 (s, 2H), 4.35 (s, 2H), 3.76 (s, 3H), 3.35 (s, 1H), 2.95 (t, J=7.2, 2H), 2.62 (t, J=7.2, 2H), 2.06 (t, J=6.8, 2H); $^{13}$C NMR (100 MHz, CD$_3$OD) δ 165.9, 160.7, 148.6, 145.6, 131.2, 130.3, 129.5, 127.7, 115.1, 110.4, 55.9, 55.3, 44.1, 28.0, 24.7, 23.8; HRMS (ESI), calculated for C$_{18}$H$_{23}$N$_7$O$_2$ (MH$^+$) 369.1913, found 369.1911.

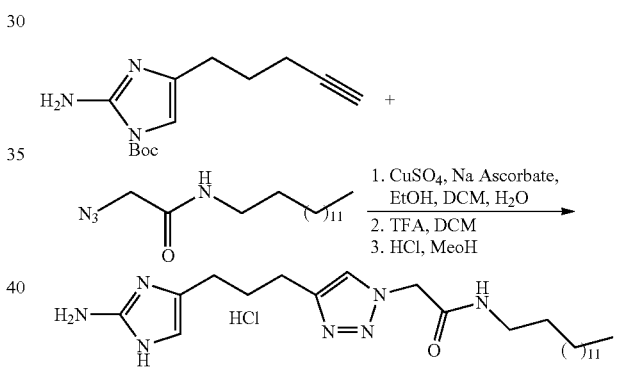

2-{4-[3-(2-amino-4H-imidazol-4-yl)-propyl]-[1,2,3]triazol-1-yl}-N-tetradecyl-acetamide hydrochloride: Following the general procedure, 2-amino-4-pent-4-ynyl-imidazole-1-carboxylic acid tert-butyl ester (0.100 g, 0.401 mmol) was reacted with 2-azido-N-tetradecyl-acetamide (0.356 g, 1.201 mmol) and afforded 0.059 g (70% yield) of 2-{4-[3-(2-amino-1H-imidazol-4-yl)-propyl]-[1,2,3]triazol-1-yl}-N-tetradecyl-acetamide hydrochloride (5). $^1$H NMR (400 MHz, CD$_3$OD) δ 8.40 (s, 1H), 6.59 (s, 1H), 5.37 (s, 2H), 3.23 (t, J=6.8, 1H), 2.92 (bs, 2H), 2.613 (t, J=6.8, 2H), 2.05 (bs, 2H), 1.54 (t, J=6.4, 2H), 1.28 (s, 24H), 0.89 (t, J=6.8, 3H); $^{13}$C NMR (100 MHz, CD$_3$OD) δ 181.1, 166.3, 148.6, 140.1, 127.8, 110.4, 54.9, 40.9, 33.2, 30.9, 30.8, 30.6, 30.5, 30.4, 28.2, 28.1, 24.7, 24.1, 23.8, 14.6; HRMS (ESI), calculated for C$_{24}$H$_{43}$N$_7$O (MH$^+$) 445.3529, found 445.3519.

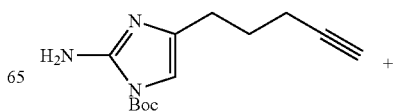

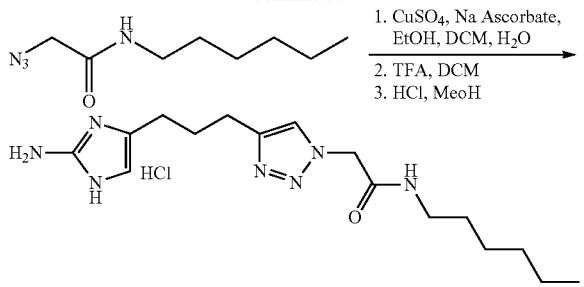
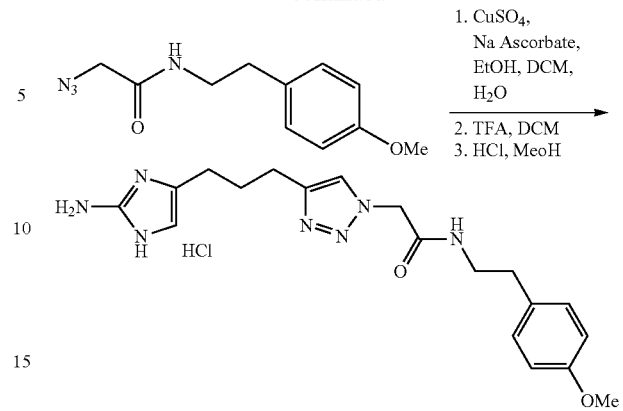

2-{4-[3-(2-amino-1H-imidazol-4-yl)-propyl]-[1,2,3]triazol-1-yl}-N-hexyl-acetamide hydrochloride: Following the general procedure, 2-amino-4-pent-4-ynyl-imidazole-1-carboxylic acid tert-butyl ester (0.101 g, 0.401 mmol) was reacted with 2-azido-N-hexyl-acetamide (0.221 g, 1.20 mmol) and afforded 0.061 mg (77% yield) of 2-{4-[3-(2-amino-1H-imidazol-4-yl)-propyl]-[1,2,3]triazol-1-yl}-N-hexyl-acetamide hydrochloride (6). $^1$H NMR (400 MHz, CD$_3$OD) δ 8.46 (s, 1H), 6.59 (s, 1H), 5.25 (s, 2H), 3.23 (s, 1H), 2.84 (bs, 2H), 2.58 (bs, 2H), 2.03 (bs, 2H), 1.53 (t, J=11.2, 2H), 1.30 (m, 8H), 0.89 (t, J=6.0, 3H); $^{13}$C NMR (100 MHz, CD$_3$OD) δ 175.8, 167.2, 148.6, 128.2, 110.3, 54.2, 40.9, 32.7, 30.3, 28.6, 27.8, 25.0, 24.8, 23.7, 14.5; HRMS (ESI), calculated for C$_{16}$H$_{27}$N$_7$O (MH$^+$) 333.2277, found 333.2271.

2-{4-[3-(2-amino-4H-imidazol-4-yl)-propyl]-1,2,31-triazol-1-yl}-N-[2-(4-methoxy-phenyl)-ethyl]-acetamide hydrochloride: Following the general procedure, 2-amino-4-pent-4-ynyl-imidazole-1-carboxylic acid tert-butyl ester (0.101 g, 0.401 mmol) was reacted with 2-azido-N-[2-(4-methoxy-phenyl)-ethyl]-acetamide (0.281 g, 1.198 mmol) and afforded 0.057 g (61% yield) of 2-{4-[3-(2-amino-1H-imidazol-4-yl)-propyl]-[1,2,3]triazol-1-yl}-N-[2-(4-methoxy-phenyl)-ethyl]-acetamide hydrochloride (8). $^1$H NMR (400 MHz, CD$_3$OD) δ 8.29 (s, 1H), 7.12 (d, J=8.0, 2H), 6.83 (d, J=8.4, 2H), 6.56 (s, 1H), 5.27 (s, 2H), 3.74 (s, 3H), 3.42 (t, J=7.2, 2H), 2.86 (bs, 2H), 2.76 (t, J=6.8, 2H), 2.59 (bs, 2H), 2.03 (bs, 2H); $^{13}$C NMR (100 MHz, CD$_3$OD) δ 167.1, 159.9, 148.6, 132.2, 130.9, 128.2, 115.1, 110.3, 67.0, 55.9, 54.3, 42.6, 35.6, 28.5, 24.8, 15.6; HRMS (ESI), calculated for C$_{19}$H$_{25}$N$_7$O$_2$ (MH$^+$) 383.2069, found 383.2069.

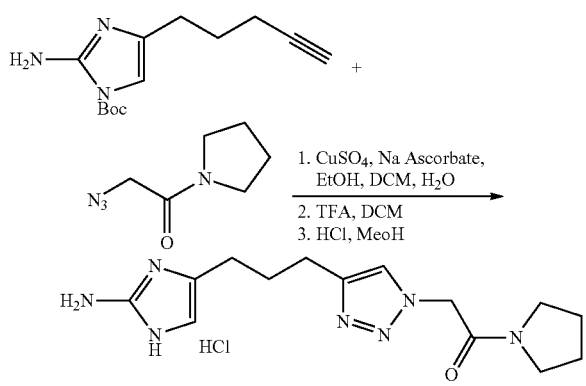

2-{4-[3-(2-amino-1H-imidazol-4-yl)-propyl]-[1,2,3]triazol-1-yl}-1-pyrrolidin-1-yl-ethanone hydrochloride: Following the general procedure, 2-amino-4-pent-4-ynyl-imidazole-1-carboxylic acid tert-butyl ester (0.050 g, 0.200 mmol) was reacted with 2-azido-1-pyrrolidin-1-yl-ethanone (0.093 g, 0.600 mmol) and afforded 0.036 g (54% yield) of 2-{4-[3-(2-amino-1H-imidazol-4-yl)-propyl]-[1,2,3]triazol-1-yl}-1-pyrrolidin-1-yl-ethanone hydrochloride (7). $^1$H NMR (400 MHz, CD$_3$OD) δ 8.54 (s, 11-1), 6.60 (s, 1H), 5.69 (s, 2H), 3.64 (t, J=6.4, 2H), 3.45 (t, J=6.8, 2H), 3.35 (s, 1H), 2.97 (bs, 2H), 2.63 (bs, 2H), 2.07 (t, J=6.8, 4H), 1.97-1.92 (m, 2H); $^{13}$C NMR (100 MHz, CD$_3$OD) δ 164.4, 148.7, 127.7, 110.5, 55.3, 47.7, 47.3, 28.0, 27.1, 25.2, 24.7, 23.8; HRMS (ESI), calculated for C$_{14}$H$_{21}$N$_7$O (MH$^+$) 303.1807, found 303.1809.

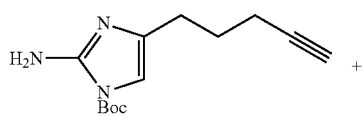

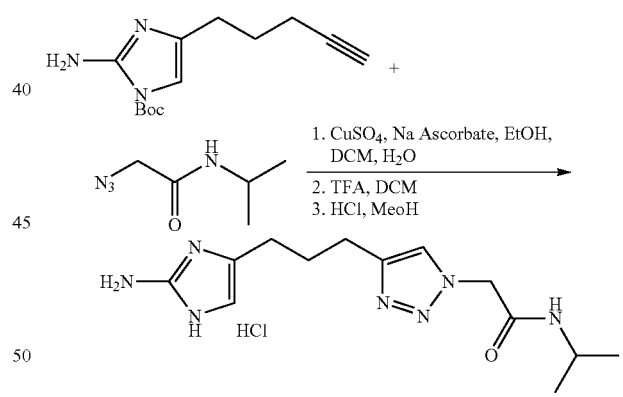

2-{4-[3-(2-amino-1H-imidazol-4-yl)-propyl]-[1,2,3]-triazol-1-yl}-N-isopropyl-acetamide hydrochloride: Following the general procedure, 2-amino-4-pent-4-ynyl-imidazole-1-carboxylic acid tert-butyl ester (0.100 g, 0.401 mmol) was reacted with 2-azido-N-isopropyl-acetamide (0.170 g, 1.201 mmol) and afforded 0.074 g (56% yield) of 2-{4-[3-(2-amino-1H-imidazol-4-yl)-propyl]-[1,2,3]triazol-1-yl}-N-isopropyl-acetamide hydrochloride (9). $^1$H NMR (400 MHz, CD$_3$OD) δ 8.27 (s, 1H), 6.58 (s, 1H), 5.30 (s, 2H), 3.99 (s, 1H), 3.35 (s, 1H), 2.88 (t, J=6.4, 2H), 2.59 (t, J=7.2, 2H), 2.05-2.01 (m, 2H), 1.18 (d, J=6.8, 6H); $^{13}$C NMR (100 MHz, CD$_3$OD) δ 165.8, 148.6, 127.9, 110.3, 54.5, 43.5, 28.4, 24.8, 24.4, 22.6; HRMS (ESI), calculated for C$_{13}$H$_{21}$N$_7$O (MH) 291.1807, found 291.1804.

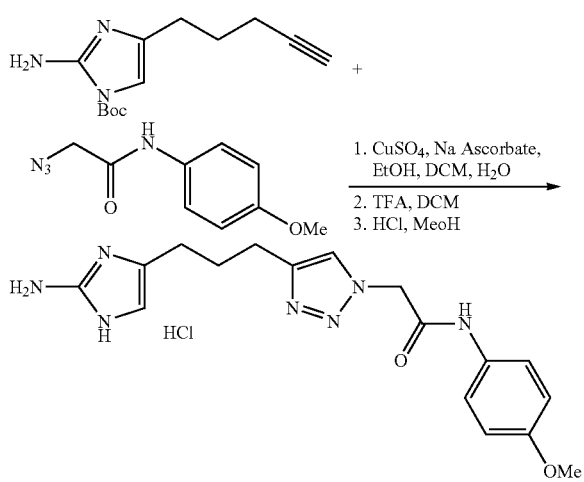

2-{4-[3-(2-amino-1H-imidazol-4-yl)-propyl]-[1,2,3]-triazol-1-yl}-N-(4-methoxy-phenyl)-acetamide hydrochloride: Following the general procedure, 2-amino-4-pent-4-ynyl-imidazole-1-carboxylic acid tert-butyl ester (0.050 g, 0.200 mmol) was reacted with 2-azido-N-(4-methoxy-phenyl)-acetamide (0.124 g, 0.600 mmol) and afforded 0.051 g (66% yield) of 2-{4-[3-(2-amino-1H-imidazol-4-yl)-propyl]-[1,2,3]triazol-1-yl}-N-(4-methoxy-phenyl)-acetamide hydrochloride (10). $^1$H NMR (400 MHz, CD$_3$OD) δ 8.30 (s, 1H), 7.48 (d, J=8.8, 2H), 6.86 (d, J=8.8, 2H), 6.55 (s, 1H), 5.48 (s, 1H), 3.75 (s, 3H), 3.34 (s, 1H), 2.86 (bs, 2H), 2.57 (bs, 2H), 2.01 (bs, 2H); $^{13}$C NMR (100 MHz, CD$_3$OD) δ 164.8, 158.3, 148.6, 132.1, 128.0, 123.0, 115.2, 110.3, 56.0, 54.9, 28.4, 24.7, 24.6; HRMS (ESI), calculated for C$_{17}$H$_{21}$N$_7$O$_2$ (MH$^+$) 355.1756, found 355.1756.

125.9, 121.3, 110.6, 56.2, 27.9, 24.3, 23.9; HRMS (ESI), calculated for C$_{16}$H$_{19}$N$_7$O (MO 325.1651, found 325.1644.

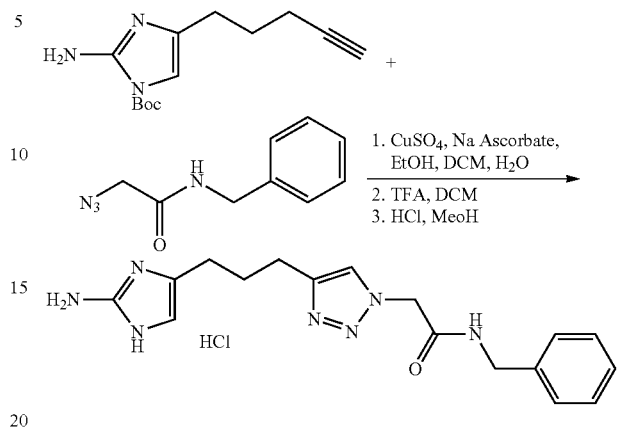

2-{4-[3-(2-amino-1H-imidazol-4-yl)-propyl]-[1,2,3]triazol-1-yl}-N-benzyl-acetamide hydrochloride: Following the general procedure, 2-amino-4-pent-4-ynyl-imidazole-1-carboxylic acid tert-butyl ester (0.100 g, 0.401 mmol) was reacted with 2-Azido-N-benzyl-acetamide (0.228 g, 1.198 mmol) and afforded 0.060 g (71% yield) of 2-{4-[3-(2-amino-1H-imidazol-4-yl)-propyl]-[1,2,3]triazol-1-yl}-N-benzyl-acetamide hydrochloride (12). $^1$H NMR (400 MHz, CD$_3$OD) δ 8.52 (s, 1H), 7.32-7.25 (m, 5H), 6.59 (s, 1H), 5.48 (s, 2H), 4.43 (s, 2H), 3.34 (s, 1H), 2.94 (bs, 2H), 2.61 (bs, 2H), 2.06 (bs, 2H); $^{13}$C NMR (100 MHz, CD$_3$OD) δ 166.1, 148.6, 139.3, 129.7, 128.9, 128.6, 127.7, 110.5, 55.2, 44.6, 28.0, 24.7, 23.9; HRMS (ESI) calculated for C$_{17}$H$_{21}$N$_7$O (MH$^+$) 339.1807, found 339.1800.

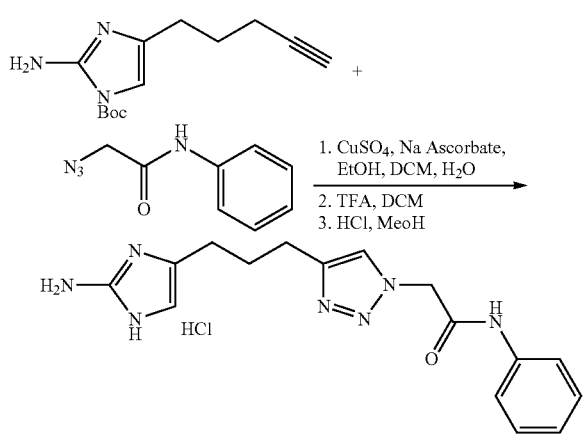

2-{4-[3-(2-amino-1H-imidazol-4-yl)-propyl]-[1,2,3]triazol-1-yl}-N-phenyl-acetamide hydrochloride: Following the general procedure, 2-amino-4-pent-4-ynyl-imidazole-1-carboxylic acid tert-butyl ester (0.100 g, 0.401 mmol) was reacted with 2-azido-N-phenyl-acetamide (0.211 g, 1.201 mmol) and afforded 0.064 g (53% yield) of 2-{4-[3-(2-amino-1H-imidazol-4-yl)-propyl]-[1,2,3]triazol-1-yl}-N-phenyl-acetamide hydrochloride (11). $^1$H NMR (400 MHz, CD$_3$OD) δ 8.76 (s, 1H), 7.58 (d, J=6.8, 2H), 7.29 (t, J=6.8, 2H), 7.09 (t, J=7.2, 1H), 6.59 (s, 1H), 5.67 (s, 2H), 3.34 (s, 1H), 2.98 (bs, 2H), 2.62 (bs, 2H), 2.09 (bs, 2H); $^{13}$C NMR (100 MHz, CD$_3$OD) δ 163.9, 148.6, 139.1, 130.1, 127.6,

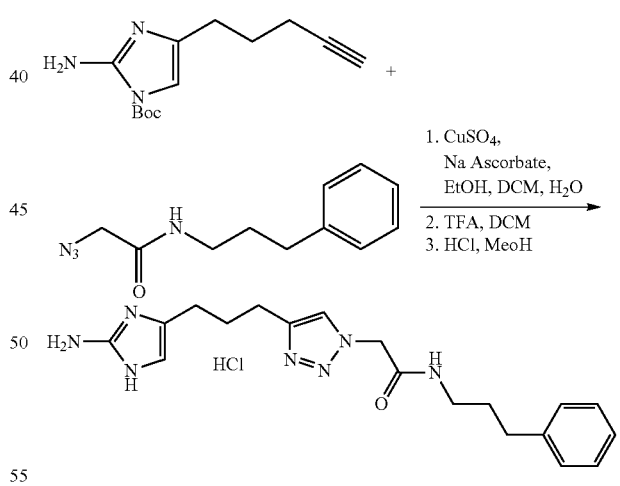

2-{4-[3-(2-amino-1H-imidazol-4-yl)-propyl]-[1,2,3]-triazol-1-yl}-N-(3-phenyl-propyl)-acetamide hydrochloride: Following the general procedure, 2-amino-4-pent-4-ynyl-imidazole-1-carboxylic acid tert-butyl ester (0.100 g, 0.401 mmol) was reacted with 2-azido-N-(3-phenyl-propyl)-acetamide (0.261 g, 1.201 mmol) and afforded 0.062 g (49% yield) of 2-{4-[3-(2-amino-1H-imidazol-4-yl)-propyl]-[1,2,3]triazol-1-yl}-N-(3-phenyl-propyl)-acetamide hydrochloride (13). $^1$H NMR (400 MHz, CD$_3$OD) δ 8.50 (s, 1H), 7.26-7.12 (m, 5H), 6.58 (s, 1H), 5.41 (s, 2H), 3.35 (s, 1H), 3.28 (bs, 2H), 2.93 (bs, 2H), 2.65 (t, J=7.6, 2H), 2.05 (bs, 2H), 1.85 (t, J=6.8, 2H); $^{13}$C NMR (100 MHz, CD$_3$OD) δ 166.2, 142.9, 129.6, 129.5, 127.7, 127.1, 110.4, 55.2, 40.5, 34.2, 32.1, 28.1, 24.7, 23.9; HRMS (ESI), calculated for C$_{19}$H$_{25}$N$_7$O (MH$^+$) 367.2120, found 367.2112.

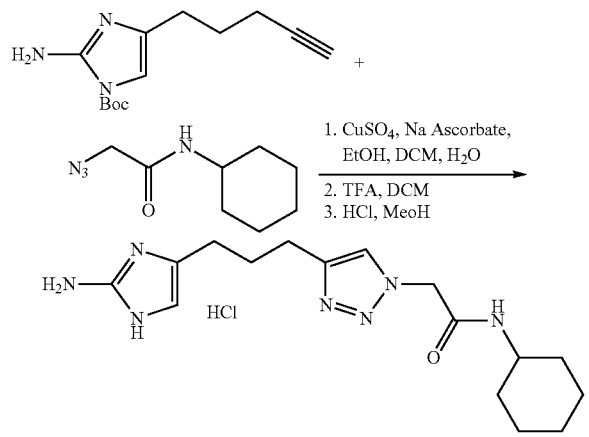

2-{4-[3-(2-amino-1H-imidazol-4-yl)-propyl][1,2,3]triazol-1-yl}-N-cyclohexyl-acetamide hydrochloride: Following the general procedure, 2-amino-4-pent-4-ynyl-imidazole-1-carboxylic acid tert-butyl ester (0.100 g, 0.401 mmol) was reacted with 2-azido-N-cyclohexyl-acetamide (0.219 g, 1.201 mmol) and afforded 0.060 g (69% yield) of 2-{4-[3-(2-amino-1H-imidazol-4-yl)-propyl]-[1,2,3]triazol-1-yl}-N-cyclohexyl-acetamide hydrochloride (14). $^1$H NMR (400 MHz, CD$_3$OD) δ 8.59 (s, 1H), 6.61 (s, 1H), 5.42 (s, 2H), 3.65 (s, 1H), 3.26 (s, 2H), 2.97 (bs, 2H), 2.63 (bs, 2H), 2.08 (bs, 2H), 1.87 (bs, 2H), 1.75 (bs, 2H), 1.38-1.18 (m, 6H); $^{13}$C NMR (100 MHz, CD$_3$OD) δ 164.9, 148.6, 130.4, 127.7, 110.5, 55.4, 50.5, 33.6, 28.0, 26.6, 26.0, 24.7, 23.8; HRMS (ESI), calculated for C$_{16}$H$_{26}$N$_7$O (MH$^+$) 331.2120, found 331.2114.

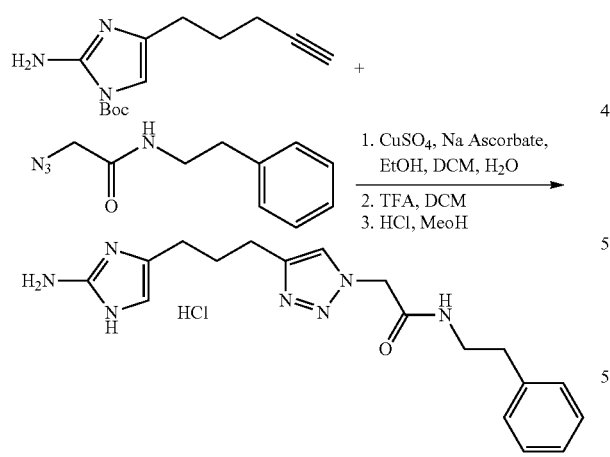

2-{4-[3-(2-amino-1H-imidazol-4-yl)-propyl]-[1,2,3]triazol-1-yl}-N-phenethyl-acetamide hydrochloride: Following the general procedure, 2-amino-4-pent-4-ynyl-imidazole-1-carboxylic acid tert-butyl ester (0.100 g, 0.401 mmol) was reacted with 2-azido-N-phenethyl-acetamide (0.240 g, 1.201 mmol) and afforded 0.060 g (41% yield) of 2-{4-[3-(2-amino-1H-imidazol-4-yl)-propyl]-[1,2,3]triazol-1-yl}-N-phenethyl-acetamide hydrochloride. $^1$H NMR (400 MHz, CD$_3$OD) δ 8.67 (s, 1H), 7.34-7.18 (m, 5H), 6.61 (s, 1H), 3.47 (bs, 2H), 3.35 (s, 1H), 3.17 (bs, 2H), 2.99 (t, J=8.4, 2H), 2.84 (t, J=6.8, 2H), 2.63 (bs, 2H), 2.08 (bs, 2H); $^{13}$C NMR (100 MHz, CD$_3$OD) 167.3, 165.5, 140.2, 138.1, 130.0, 129.9, 129.6, 128.2, 127.5, 110.5, 55.7, 42.5, 36.4, 34.5, 27.9, 24.7; HRMS (ESI) calculated for C$_{18}$H$_{23}$N$_7$O (MH$^+$) 353.1964, found 353.1965.

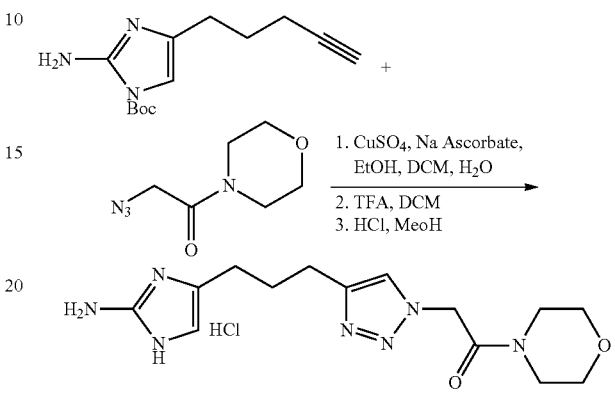

2-{4-[3-(2-amino-1H-imidazol-4-yl)-propyl]-[1,2,3]triazol-1-yl}-N-morpholin-4-yl-acetamide hydrochloride: Following the general procedure, 2-amino-4-pent-4-ynyl-imidazole-1-carboxylic acid tert-butyl ester (0.100 g, 0.401 mmol) was reacted with 2-azido-1-morpholin-4-yl-ethanone (0.204, 1.20 mmol) and afforded 0.050 g (76% yield) of 2-{4-[3-(2-amino-1H-imidazol-4-yl)-propyl]-[1,2,3]triazol-1-yl}-N-morpholin-4-yl-acetamide hydrochloride. $^1$H NMR (400 MHz, CD$_3$OD) δ 8.58 (s, 1H), 6.61 (s, 1H), 5.85 (s, 2H), 3.76 (bs, 2H), 3.7 (bs, 2H), 3.61 (bs, 4H), 3.34 (s, 1H), 2.89 (bs, 2H), 2.64 (bs, 2H), 2.09 (bs, 2H); $^{13}$C NMR (100 MHz, CD$_3$OD) δ 164.7, 148.7, 127.6, 110.5, 67.5, 55.1, 46.7, 43.9, 36.6, 27.9, 24.7, 23.7; HRMS (ESI), calculated for C$_{14}$H$_{21}$N$_7$O$_2$ (MH$^+$) 319.1756, found 319.1756.

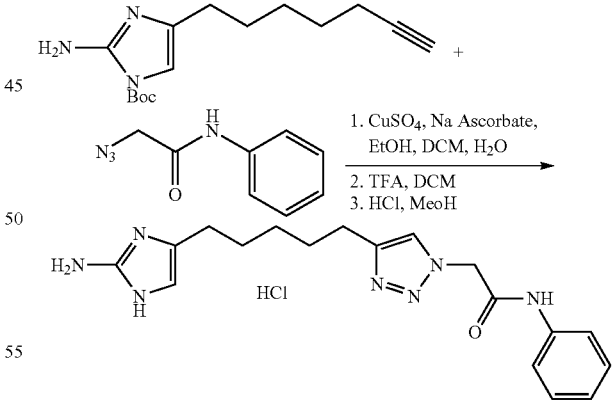

2-{4-[5-(2-amino-1H-imidazol-4-yl)-pentyl]-[1,2,3]triazol-1-yl}-N-phenyl-acetamide hydrchloride: Following the general procedure, 2-amino-4-hept-6-ynyl-imidazole-1-carboxylic acid tert-butyl ester (0.075 g, 0.270 mmol) was reacted with 2-azido-N-phenyl-acetamide (0.072 g, 0.410 mmol) and afforded 0.050 g (51% yield) of 2-{4-[5-(2-amino-1H-imidazol-4-yl)-pentyl]-[1,2,3]triazol-1-yl}-N-phenyl-acetamide hydrochloride. $^1$H NMR (400 MHz, CD$_3$OD) δ 8.53 (s, 1H), 7.59 (d, J=7.6, 2H), 7.31 (t, J=7.2, 2H), 7.11 (t, J=7.2, 1H), 6.50 (s, 1H), 5.62 (s, 2H), 3.96 (s, 1H), 2.89 (bs, 2H), 2.50 (t, J=6.8, 2H), 1.79 (bs, 2H), 1.66 (bs, 2H), 1.45 (bs, 2H); $^{13}$C NMR (100 MHz, CD$_3$OD) δ 164.3, 148.6, 139.2, 130.1, 128.9, 125.9, 121.2, 109.8, 55.7, 28.9, 25.3, 24.7; HRMS (ESI), calculated for C$_{18}$H$_{23}$N$_7$O (MH$^+$) 353.1964, found 353.1968.

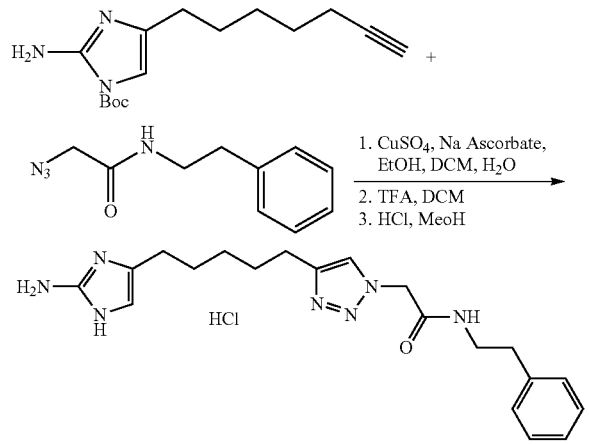

2-{4-[5-(2-amino-1H-imidazol-4-yl)-pentyl]-[1,2,3]triazol-1-yl}-N-phenethyl-acetamide hydrochloride: Following the general procedure, 2-amino-4-hept-6-ynyl-imidazole-1-carboxylic acid tert-butyl ester (0.075 g, 0.270 mmol) was reacted with 2-azido-N-phenethyl-acetamide (0.054 g, 0.270 mmol) and afforded 0.059 g (74% yield) of 2-{4-[5-(2-amino-1H-imidazol-4-yl)-pentyl]-[1,2,3]triazol-1-yl}-N-phenethyl-acetamide hydrochloride. $^1$H NMR (400 MHz, CD$_3$OD) δ 8.23 (s, 2H), 7.23-7.19 (m, 5H), 6.51 (s, 1H), 5.32 (s, 2H), 3.48 (t, J=7.6, 1H), 2.84 (m, 4H), 2.51 (t, J=7.6, 2H), 1.77 (bs, 2H), 1.66 (t, J=7.2, 2H), 1.45 (bs, 2H); $^{13}$C NMR (100 MHz, CD$_3$OD) δ 167.8, 148.5, 147.0, 129.9, 129.7, 128.8, 128.3, 127.6, 109.8, 54.8, 42.4, 36.4, 29.3, 28.9, 25.3, 24.8; HRMS (ESI) calculated for C$_{20}$H$_{27}$N$_7$O (MH$^+$) 381.2277, found 381.2275.

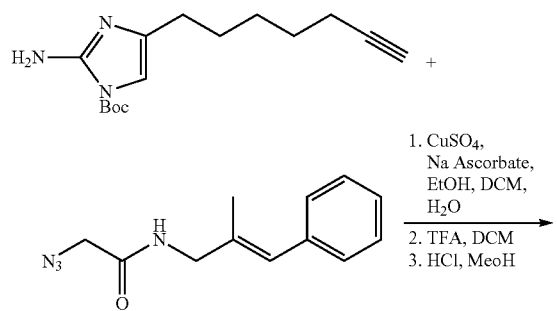

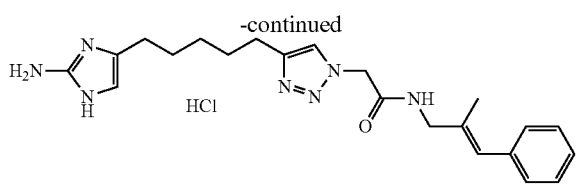

2-{4-[5-(2-amino-1H-imidazol-4-yl)-pentyl]-[1,2,3]triazol-1-yl}-N-(2-methyl-3-phenyl-allyl)-acetamide hydrochloride: Following the general procedure, 2-amino-4-hept-6-ynyl-imidazole-1-carboxylic acid tert-butyl ester (0.075 g, 0.270 mmol) was reacted with 2-azido-N-(2-methyl-3-phenyl-allyl)-acetamide (0.069 g, 0.300 mmol) and afforded 0.046 g (47% yield) of 2-{4-[5-(2-amino-1H-imidazol-4-yl)-pentyl]-[1,2,3]triazol-1-yl}-N-(2-methyl-3-phenyl-allyl)-acetamide hydrochloride. $^1$H NMR (400 MHz, CD$_3$OD) δ 8.49 (s, 1H), 7.29-7.18 (m, 5H), 6.49 (s, 1H), 6.46 (s, 1H), 5.47 (s, 2H), 3.97 (s, 2H), 2.87 (bs, 2H), 2.51 (bs, 2H), 1.89 (s, 3H), 1.79 (bs, 2H), 1.66 (bs, 2H), 1.45 (bs, 2H); $^{13}$C NMR (100 MHz, CD$_3$OD) δ 166.5, 148.5, 138.9, 135.4, 130.0, 129.3, 128.9, 127.7, 127.6, 109.8, 55.1, 29.3, 29.2, 28.9, 25.3, 24.8, 16.5; HRMS (ESI), calculated for C$_{22}$H$_{29}$N$_7$O (MH$^+$) 407.2434, found 407.2432.

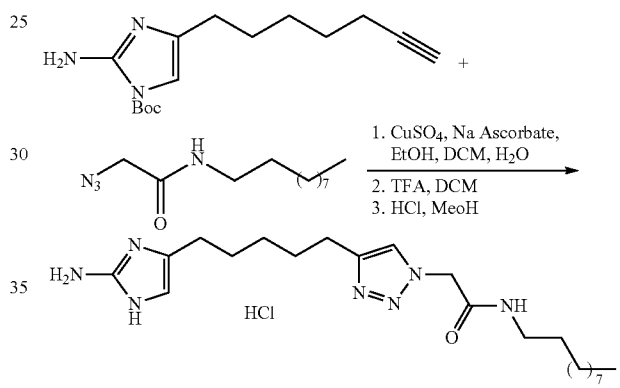

2-{4-[5-(2-amino-1H-imidazol-4-yl)-pentyl]-[1,2,3]triazol-1-yl}-N-decyl-acetamide hydrochloride: Following the general procedure, 2-amino-4-hept-6-ynyl-imidazole-1-carboxylic acid tert-butyl ester (0.075 g, 0.270 mmol) was reacted with 2-azido-N-decyl-acetamide (0.097 g, 0.405 mmol) and afforded 0.090 g (85% yield) of 2-{4-[5-(2-amino-1H-imidazol-4-yl)-pentyl]-[1,2,3]triazol-1-yl}-N-decyl-acetamide hydrochloride. $^1$H NMR (400 MHz, CD$_3$OD) δ 6.51 (s, 1H), 5.40 (s, 2H), 3.21 (s, 1H), 2.51 (s, 2H), 1.74 (m, 4H), 1.51 (bs, 4H), 1.26 (s, 18H), 0.86 (t, J=6.8, 3H); $^{13}$C NMR (100 MHz, CD$_3$OD) δ 176.5, 165.8, 156.5, 128.7, 109.9, 54.9, 40.7, 37.8, 32.9, 30.5, 30.3, 30.1, 29.1, 28.8, 28.4, 27.9, 25.3, 24.8, 23.6, 14.3; HRMS (ESI) calculated for C$_{22}$H$_{39}$N$_7$O (MH$^+$) 417.3216, found 417.3211.

Biofilm inhibition has been tested for the following compounds, each of which was tested at a concentration of 100 μM.

| Compound | MRSA % Inhibition | E. coli % Inhibition |
|---|---|---|
| | 99.0 ± 1 | 62.7 ± 0.4 |

-continued

| Compound | MRSA % Inhibition | E. coli % Inhibition |
|---|---|---|
| 2-aminoimidazole-propyl-triazole-CH₂C(O)NH-tBu · HCl | 28.2 ± 15 | — |
| 2-aminoimidazole-propyl-triazole-CH₂C(O)NH-cyclopentyl · HCl | 64.0 ± 4 | — |
| 2-aminoimidazole-propyl-triazole-CH₂C(O)NH-CH₂-(4-MeO-C₆H₄) · HCl | 71.0 ± 3 | — |
| 2-aminoimidazole-propyl-triazole-CH₂C(O)NH-(CH₂)₁₁CH₃ · HCl | 90.8 ± 8 | 35.6 ± 0.6 |
| 2-aminoimidazole-propyl-triazole-CH₂C(O)NH-hexyl · HCl | 83.1 ± 16 | — |
| 2-aminoimidazole-propyl-triazole-CH₂C(O)-pyrrolidine · HCl | 35.4 ± 5 | — |
| 2-aminoimidazole-propyl-triazole-CH₂C(O)NH-CH₂CH₂-(4-MeO-C₆H₄) · HCl | 18.3 ± 5 | — |
| 2-aminoimidazole-propyl-triazole-CH₂C(O)NH-iPr · HCl | 36.4 ± 3 | — |
| 2-aminoimidazole-propyl-triazole-CH₂C(O)NH-(4-MeO-C₆H₄) · HCl | 41.1 ± 2 | — |

-continued

| Compound | MRSA % Inhibition | E. coli % Inhibition |
|---|---|---|
| | 41.9 ± 2 | — |
| | 58.1 ± 2 | — |
| | 64.8 ± 2 | — |
| | 40.5 ± 4 | — |

The foregoing is illustrative of the present invention, and is not to be construed as limiting thereof. The invention is defined by the following claims, with equivalents of the claims to be included therein.

That which is claimed is:

1. A compound of Formula (IV)(a):

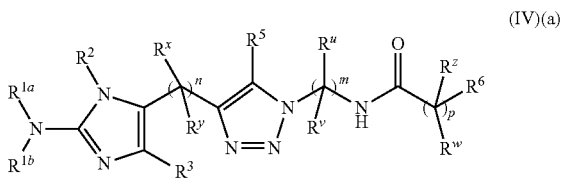

(IV)(a)

wherein:
R$^{1a}$ and R$^{1b}$ are each H;
R$^2$, R$^3$, R$^5$ and are each independently H or alkyl;
each occurrence of R$^x$, R$^y$, R$^u$, R$^v$, R$^z$ and R$^w$ is present or absent (depending upon chain saturation), and are each independently H or alkyl;
R$^6$ is independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;
n=0 to 10;
m=0 to 10; and
p=0 to 20
or a pharmaceutically acceptable salt or prodrug thereof.

2. The compound of claim 1, wherein R$^6$ is H.
3. The compound of claim 1, wherein R$^6$ is aryl.
4. The compound of claim 1, wherein p=0 and R$^6$ is substituted aryl or heteroaryl.
5. The compound of claim 1, wherein R$^6$ is a group:

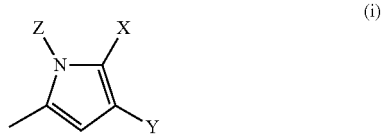

(i)

wherein:
X, Y and Z are each independently selected from the group consisting of: H, methyl, Br and Cl.

6. The compound of claim 1, wherein R$^6$ is a group:

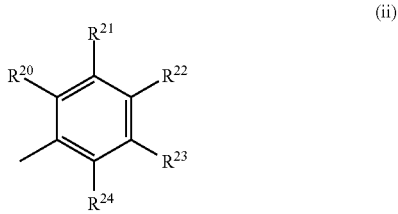

(ii)

wherein:
R$^{20}$, R$^{21}$, R$^{22}$, R$^{23}$ and R$^{24}$ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

7. The compound of claim 6, wherein said compound has the formula:

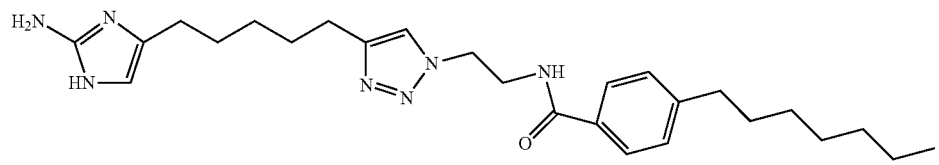 [SMILES: CCCCCCCc1ccc(C(=O)NCCn2cc(CCCCCc3c[nH]c(N)n3)nn2)cc1]

or a pharmaceutically acceptable salt or prodrug thereof.

8. A compound of Formula (V)(a):

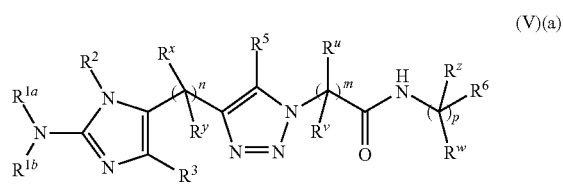

wherein:

$R^{1a}$ and $R^{1b}$ are each H;

$R^2$, $R^3$, $R^5$ and are each independently H or alkyl;

each occurrence of $R^x$, $R^y$, $R^u$, $R^v$, $R^z$ and $R^w$ is present or absent (depending upon chain saturation), and are each independently H or alkyl;

$R^6$ is independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

n=0 to 10;

m=0 to 10; and p=0 to 20 or a pharmaceutically acceptable salt or prodrug thereof.

9. The compound of claim 8, wherein $R^6$ is aryl.

10. The compound of claim 8, wherein $R^6$ is H.

11. The compound of claim 10, wherein said compound has the formula:

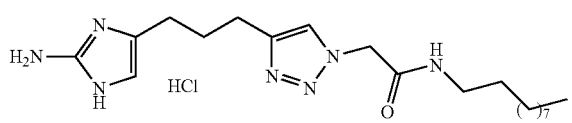

or a pharmaceutically acceptable salt or prodrug thereof.

12. A composition comprising the compound of claim 1 and a biocide.

13. A composition comprising the compound of claim 1 in a pharmaceutically acceptable carrier.

14. A composition comprising:
a compound of Formula (IV)(a):

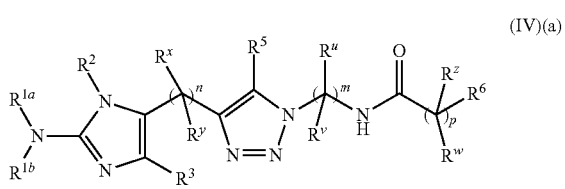

wherein:

$R^{1a}$ and $R^{1b}$ are each H;

$R^2$, $R^3$, $R^5$ and are each independently H or alkyl;

each occurrence of $R^x$, $R^y$, $R^u$, $R^v$, $R^z$ and $R^w$ is present or absent (depending upon chain saturation), and are each independently H or alkyl;

$R^6$ is independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

n=0 to 10;

m=0 to 10; and p=0 to 20 covalently coupled to a substrate.

15. A biofilm removing or inhibiting coating composition, comprising:
(a) a film-forming resin;
(b) a solvent that disperses said resin;
(c) an effective amount of the compound of claim 1, wherein said effective amount of said compound removes or inhibits the growth of a biofilm thereon; and
(d) optionally, at least one pigment.

16. A biofilm removing or inhibiting coating composition, comprising:
(a) a film-forming resin;
(b) a solvent that disperses said resin;
(c) an effective amount of:
a compound of Formula (IV)(a):

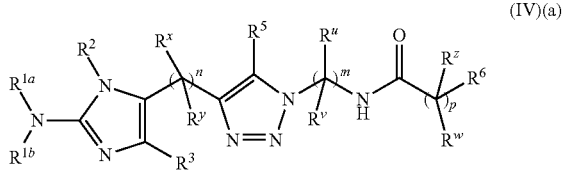

wherein:

R$^{1a}$ and R$^{1b}$ are each H;

R$^2$, R$^3$, R$^5$ and are each independently H or alkyl;

each occurrence of R$^x$, R$^y$, R$^u$, R$^v$, R$^z$ and R$^w$ is present or absent (depending upon chain saturation), and are each independently H or alkyl;

R$^6$ is independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

n=0 to 10;

m=0 to 10; and p=0 to 20 wherein said effective amount of said compound removes or inhibits the growth of a biofilm thereon; and (d) optionally, at least one pigment, wherein said compound is covalently coupled to said resin.

17. The coating composition of claim 15, wherein said resin comprises a polymeric material.

18. A substrate coated with the coating composition of claim 15.

19. The compound of claim 1, wherein n=1 to 6.

20. The compound of claim 1, wherein n=1 to 6 and m=1 to 3.

21. The compound of claim 1, wherein n=1 to 6, m=1 to 3, p=0, and R$^6$ is a substituted aryl.

22. The compound of claim 1, wherein n=1 to 6, m=1 to 3, p=0, and R$^6$ is an aryl substituted with an alkyl having from 1 to 10 carbon atoms.

23. The compound of claim 1, wherein n=1 to 6, m=1 to 3, p=0, and R$^6$ is a group:

(ii)

wherein:

R$^{20}$, R$^{21}$, R$^{22}$, R$^{23}$ and R$^{24}$ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

24. The compound of claim 23, wherein R$^{20}$, R$^{21}$, R$^{23}$ and R$^{24}$ are each H, and wherein R$^{22}$ is an alkyl having from 1 to 20 carbon atoms.

25. The compound of claim 23, wherein R$^{20}$, R$^{21}$, R$^{23}$ and R$^{24}$ are each H, and wherein R$^{22}$ is an alkyl having from 1 to 10 carbon atoms.

26. The compound of claim 23, wherein R$^{20}$, R$^{21}$, R$^{23}$ and R$^{24}$ are each H, and wherein R$^{22}$ is an alkyl having from 4 to 7 carbon atoms.

27. The compound of claim 6, wherein said compound has the formula:

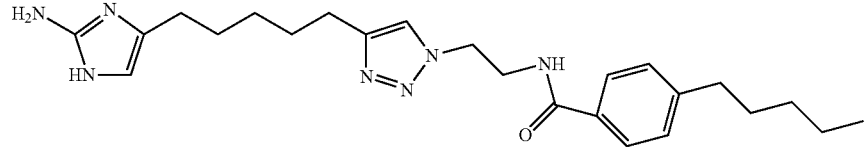 [SMILES: CCCCCc1ccc(C(=O)NCCn2cc(CCCCCc3c[nH]c(N)n3)nn2)cc1]

or a pharmaceutically acceptable salt thereof.

* * * * *

UNITED STATES PATENT AND TRADEMARK OFFICE
CERTIFICATE OF CORRECTION

PATENT NO. : 8,367,713 B2
APPLICATION NO. : 13/011532
DATED : February 5, 2013
INVENTOR(S) : Melander et al.

Page 1 of 2

It is certified that error appears in the above-identified patent and that said Letters Patent is hereby corrected as shown below:

In the Specification:
Column 3, Lines 5-15, (I): Please correct the compound below:

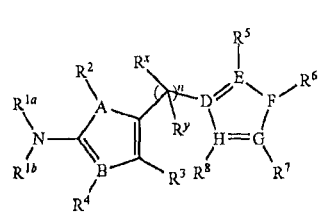

to read as:

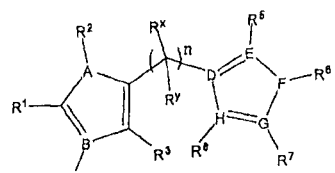

Column 43, Lines 35-43, (V): Please correct the compound below:

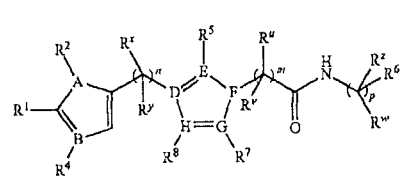

to read as:

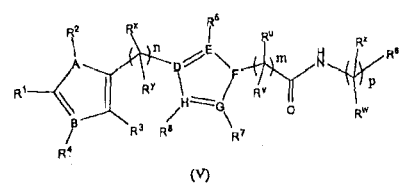

Column 48, third compound, please correct the compound below:

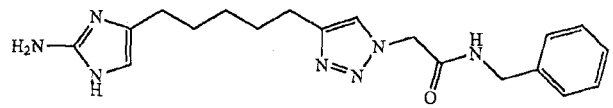

to read as:

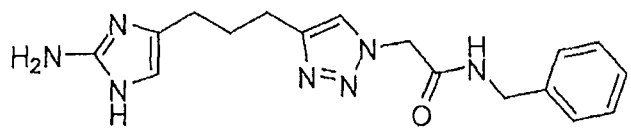

Column 64, Line 45: Please correct "at 800 M (highest"
to read -- at 800 μM (highest --

Signed and Sealed this
Twenty-ninth Day of July, 2014

Michelle K. Lee
*Deputy Director of the United States Patent and Trademark Office*

CERTIFICATE OF CORRECTION (continued)

U.S. Pat. No. 8,367,713 B2

Column 91, Line 65: Please correct "supplemented with 104/mL of 100×"
to read -- supplemented with 10 μL/mL of 100× --

Column 123, second bond, please replace the bond below:

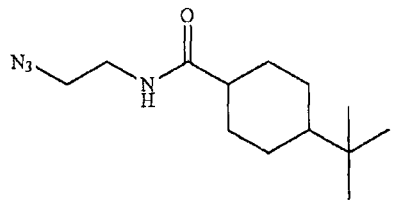   to read as:   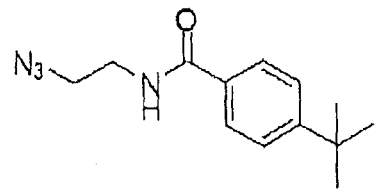

Column 134, Line 5: Please correct "subculturing it at an $M_{00}$"
to read -- subculturing it at an $OD_{600}$ --

Column 144, Line 66: Please correct "(MH)"
to read -- $(MH^+)$ --

Column 146, Line 2: Please correct "(MO 325.1651,"
to read -- $(MH^+)$ 325.1651, --